(12) United States Patent
Pashine et al.

(10) Patent No.: US 11,155,618 B2
(45) Date of Patent: Oct. 26, 2021

(54) ANTI-TREM-1 ANTIBODIES AND USES THEREOF

(71) Applicant: BRISTOL-MYERS SQUIBB COMPANY, Princeton, NJ (US)

(72) Inventors: Achal Pashine, Mahwah, NJ (US); Michael L. Gosselin, Boston, MA (US); Aaron P. Yamniuk, Lawrenceville, NJ (US); Derek A. Holmes, Lawrenceville, NJ (US); Guodong Chen, East Brunswick, NJ (US); Priyanka Apurva Madia, Franklin Park, NJ (US); Richard Yu-Cheng Huang, Bridgewater, NJ (US); Stephen Michael Carl, Howell, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 16/371,964

(22) Filed: Apr. 1, 2019

(65) Prior Publication Data

US 2019/0300608 A1 Oct. 3, 2019

Related U.S. Application Data

(60) Provisional application No. 62/651,605, filed on Apr. 2, 2018.

(51) Int. Cl.
| | | |
|---|---|---|
| *A61K 39/395* | (2006.01) |
| *C07K 16/18* | (2006.01) |
| *C07K 16/28* | (2006.01) |
| *A61K 47/68* | (2017.01) |
| *C12N 15/85* | (2006.01) |
| *A61P 29/00* | (2006.01) |

(52) U.S. Cl.
CPC ...... *C07K 16/2803* (2013.01); *A61K 47/6803* (2017.08); *A61P 29/00* (2018.01); *C12N 15/85* (2013.01); *C07K 2317/32* (2013.01); *C07K 2317/565* (2013.01); *C07K 2317/90* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,439,196 A | 3/1984 | Higuchi |
| 4,444,887 A | 4/1984 | Hoffmann |
| 4,447,224 A | 5/1984 | Decant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,676,980 A | 6/1987 | Segal et al. |
| 4,683,195 A | 7/1987 | Mullis et al. |
| 4,683,202 A | 7/1987 | Mullis |
| 4,716,111 A | 12/1987 | Osband et al. |
| 4,736,866 A | 4/1988 | Leder et al. |
| 4,741,900 A | 5/1988 | Alvarez et al. |
| 4,790,824 A | 12/1988 | Morrow et al. |
| 4,816,397 A | 3/1989 | Boss et al. |
| 4,816,567 A | 3/1989 | Cabilly et al. |
| 4,870,009 A | 9/1989 | Evans et al. |
| 4,873,191 A | 10/1989 | Wagner et al. |
| 4,873,316 A | 10/1989 | Meade et al. |
| 4,881,175 A | 11/1989 | Ladner |
| 4,941,880 A | 7/1990 | Burns |
| 4,946,778 A | 8/1990 | Ladner et al. |
| 4,980,286 A | 12/1990 | Morgan et al. |
| 4,987,071 A | 1/1991 | Cech et al. |
| 5,013,653 A | 5/1991 | Huston et al. |
| 5,064,413 A | 11/1991 | McKinnon et al. |
| 5,091,513 A | 2/1992 | Huston et al. |
| 5,116,742 A | 5/1992 | Cech et al. |
| 5,132,405 A | 7/1992 | Huston et al. |
| 5,223,409 A | 6/1993 | Ladner et al. |
| 5,225,539 A | 7/1993 | Winter |
| 5,258,498 A | 11/1993 | Huston et al. |
| 5,260,203 A | 11/1993 | Ladner et al. |
| 5,272,057 A | 12/1993 | Smulson et al. |
| 5,272,071 A | 12/1993 | Chappel |

(Continued)

FOREIGN PATENT DOCUMENTS

| | | |
|---|---|---|
| EP | 0264166 A1 | 4/1988 |
| EP | 0439095 A2 | 7/1991 |

(Continued)

OTHER PUBLICATIONS

MacCallum et al. (1996). J. Mol. Biol. 262:732-745.*

(Continued)

*Primary Examiner* — Christine J Saoud
*Assistant Examiner* — Jon M Lockard
(74) *Attorney, Agent, or Firm* — Morgan, Lewis & Bockius LLP

(57) ABSTRACT

Provided herein are antibodies, or antigen-binding portions thereof, that specifically bind and inhibit TREM-1 signaling, wherein the antibodies do not bind to one or more FcγRs and do not induce the myeloid cells to produce inflammatory cytokines. Also provided are uses of such antibodies, or antigen-binding portions thereof, in therapeutic applications, such as treatment of autoimmune diseases.

35 Claims, 29 Drawing Sheets

Figure 3:
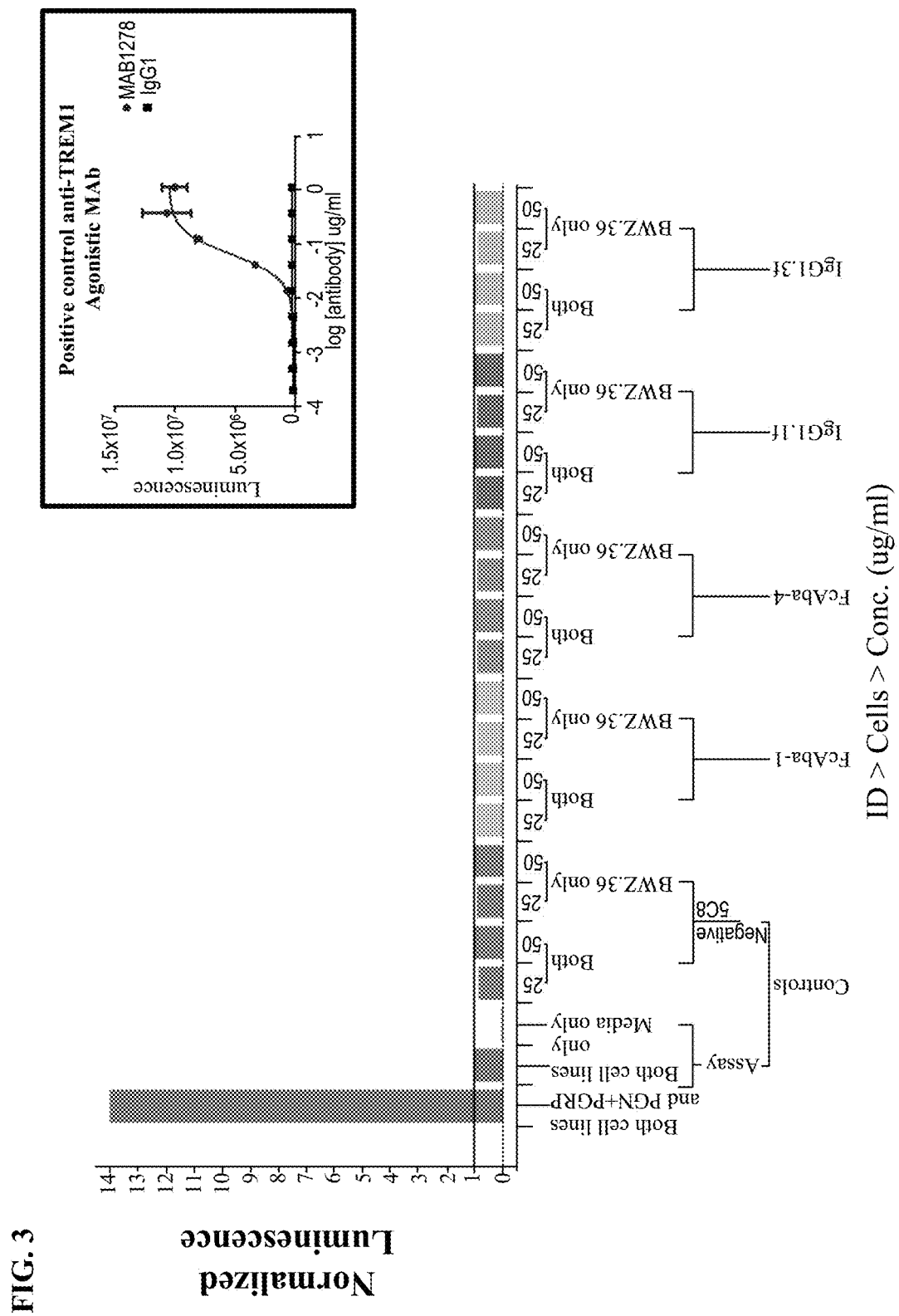

Specification includes a Sequence Listing.

(56) References Cited

U.S. PATENT DOCUMENTS

| | | |
|---|---|---|
| 5,283,317 A | 2/1994 | Saifer et al. |
| 5,312,335 A | 5/1994 | McKinnon et al. |
| 5,328,470 A | 7/1994 | Nabel et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,403,484 A | 4/1995 | Ladner et al. |
| 5,413,923 A | 5/1995 | Kucherlapati et al. |
| 5,416,016 A | 5/1995 | Low et al. |
| 5,420,526 A | 5/1995 | Fensch |
| 5,424,286 A | 6/1995 | Eng |
| 5,427,908 A | 6/1995 | Dower et al. |
| 5,436,146 A | 7/1995 | Shenk et al. |
| 5,455,030 A | 10/1995 | Ladner et al. |
| 5,459,039 A | 10/1995 | Modrich et al. |
| 5,474,981 A | 12/1995 | Leder et al. |
| 5,476,786 A | 12/1995 | Huston |
| 5,482,858 A | 1/1996 | Huston et al. |
| 5,498,531 A | 3/1996 | Jarrell |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,677,425 A | 10/1997 | Bodmer et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,807,715 A | 9/1998 | Morrison et al. |
| 5,814,318 A | 9/1998 | Lonberg et al. |
| 5,821,047 A | 10/1998 | Garrard et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 6,165,745 A | 12/2000 | Ward et al. |
| 6,194,551 B1 | 2/2001 | Idusogie et al. |
| 6,277,375 B1 | 8/2001 | Ward |
| 6,420,526 B1 | 7/2002 | Ruben et al. |
| 6,437,095 B1 | 8/2002 | Lilie et al. |
| 6,504,010 B1 | 1/2003 | Wang et al. |
| 6,509,448 B2 | 1/2003 | Wang et al. |
| 6,638,768 B1 | 10/2003 | Mouellic et al. |
| 6,737,056 B1 | 5/2004 | Presta |
| 6,858,204 B2 | 2/2005 | Henderson et al. |
| 6,878,687 B1 | 4/2005 | Ruben et al. |
| 6,989,452 B2 | 1/2006 | Ng et al. |
| 7,087,600 B2 | 8/2006 | Ng et al. |
| 7,129,261 B2 | 10/2006 | Ng et al. |
| 7,317,091 B2 | 1/2008 | Lazar et al. |
| 8,013,116 B2 | 9/2011 | Faure et al. |
| 8,101,720 B2 | 1/2012 | Lazar et al. |
| 8,231,878 B2 | 7/2012 | Colonna et al. |
| 8,981,061 B2 | 3/2015 | Colonna et al. |
| 9,000,127 B2 | 4/2015 | Stennicke et al. |
| 9,550,830 B2 | 1/2017 | Stennicke et al. |
| 2002/0128444 A1 | 9/2002 | Gingras et al. |
| 2002/0161201 A1 | 10/2002 | Filpula et al. |
| 2002/0172952 A1 | 11/2002 | Henderson et al. |
| 2002/0197669 A1 | 12/2002 | Bangur et al. |
| 2003/0049618 A1 | 3/2003 | Ruben et al. |
| 2003/0054363 A1 | 3/2003 | Henderson et al. |
| 2003/0077282 A1 | 4/2003 | Bigler et al. |
| 2003/0134283 A1 | 7/2003 | Peterson et al. |
| 2003/0165875 A1 | 9/2003 | Colonna et al. |
| 2003/0166068 A1 | 9/2003 | Ashida et al. |
| 2003/0170255 A1 | 9/2003 | Watanabe et al. |
| 2003/0175858 A1 | 9/2003 | Ruben et al. |
| 2003/0211510 A1 | 11/2003 | Henderson et al. |
| 2004/0236092 A1 | 11/2004 | Dziarski et al. |
| 2005/0238646 A1 | 10/2005 | Ledbetter et al. |
| 2005/0255114 A1 | 11/2005 | Labat et al. |
| 2006/0004081 A1 | 1/2006 | Chen et al. |
| 2006/0024317 A1 | 2/2006 | Boyd et al. |
| 2006/0183125 A1 | 8/2006 | Mariani et al. |
| 2006/0247295 A1 | 11/2006 | Gangwar et al. |
| 2009/0092582 A1 | 4/2009 | Bogin et al. |
| 2010/0310560 A1 | 12/2010 | Colonna et al. |
| 2015/0274825 A1 | 10/2015 | Stennicke et al. |
| 2016/0251434 A1 | 9/2016 | Colonna et al. |
| 2017/0183406 A1 | 6/2017 | Gurney et al. |
| 2017/0190775 A1 | 7/2017 | Stennicke et al. |
| 2017/0320946 A1 | 11/2017 | Colonna et al. |

FOREIGN PATENT DOCUMENTS

| | | |
|---|---|---|
| EP | 0439098 A2 | 7/1991 |
| EP | 0592106 A1 | 4/1994 |
| EP | 0239400 B1 | 8/1994 |
| EP | 1022286 A1 | 7/2000 |
| EP | 0592106 B1 | 11/2004 |
| EP | 1498424 A2 | 1/2005 |
| EP | 0519596 B1 | 2/2005 |
| TW | 201431878 A | 8/2014 |
| WO | WO-8809810 A1 | 12/1988 |
| WO | WO-8910134 A1 | 11/1989 |
| WO | WO-9002809 A1 | 3/1990 |
| WO | WO-9011354 A1 | 10/1990 |
| WO | WO-9109967 A1 | 7/1991 |
| WO | WO-9110737 A1 | 7/1991 |
| WO | WO-9110741 A1 | 7/1991 |
| WO | WO-9200968 A1 | 1/1992 |
| WO | WO-9201047 A1 | 1/1992 |
| WO | WO-9206180 A1 | 4/1992 |
| WO | WO-9218619 A1 | 10/1992 |
| WO | WO-9220316 A2 | 11/1992 |
| WO | WO-9222324 A1 | 12/1992 |
| WO | WO-9222635 A1 | 12/1992 |
| WO | WO-9304169 A1 | 3/1993 |
| WO | WO-9311236 A1 | 6/1993 |
| WO | WO-9314188 A1 | 7/1993 |
| WO | WO-9320221 A1 | 10/1993 |
| WO | WO-9321232 A1 | 10/1993 |
| WO | WO-9408598 A1 | 4/1994 |
| WO | WO-9410300 A1 | 5/1994 |
| WO | WO-9412649 A2 | 6/1994 |
| WO | WO-9416101 A2 | 7/1994 |
| WO | WO-9429351 A2 | 12/1994 |
| WO | WO-9515982 A2 | 6/1995 |
| WO | WO-9517886 A1 | 7/1995 |
| WO | WO-9520401 A1 | 8/1995 |
| WO | WO-9632478 A1 | 10/1996 |
| WO | WO-9633735 A1 | 10/1996 |
| WO | WO-9634096 A1 | 10/1996 |
| WO | WO-9707668 A1 | 3/1997 |
| WO | WO-9707669 A1 | 3/1997 |
| WO | WO-9734631 A1 | 9/1997 |
| WO | WO-9808871 A1 | 3/1998 |
| WO | WO-9816654 A1 | 4/1998 |
| WO | WO-9839446 A2 | 9/1998 |
| WO | WO-9839448 A2 | 9/1998 |
| WO | WO-9846645 A2 | 10/1998 |
| WO | WO-9850433 A2 | 11/1998 |
| WO | WO-9902686 A1 | 1/1999 |
| WO | WO-0000610 A2 | 1/2000 |
| WO | WO-0042072 A2 | 7/2000 |
| WO | WO-0153312 A1 | 7/2001 |
| WO | WO-0158957 A2 | 8/2001 |
| WO | WO-0190304 A1 | 11/2001 |
| WO | WO-0206919 A2 | 1/2002 |
| WO | WO-02096910 A1 | 12/2002 |
| WO | WO-03025138 A2 | 3/2003 |
| WO | WO-03029401 A2 | 4/2003 |

(56) References Cited

FOREIGN PATENT DOCUMENTS

| | | |
|---|---|---|
| WO | WO-03030835 A2 | 4/2003 |
| WO | WO-03037267 A2 | 5/2003 |
| WO | WO-03060071 A2 | 7/2003 |
| WO | WO-03061712 A1 | 7/2003 |
| WO | WO-03080667 A2 | 10/2003 |
| WO | WO-2004016750 A2 | 2/2004 |
| WO | WO-2004020591 A2 | 3/2004 |
| WO | WO-2004029207 A2 | 4/2004 |
| WO | WO-2004035752 A2 | 4/2004 |
| WO | WO-2004063351 A2 | 7/2004 |
| WO | WO-2004074455 A2 | 9/2004 |
| WO | WO-2004081233 A1 | 9/2004 |
| WO | WO-2004099249 A2 | 11/2004 |
| WO | WO-2005005601 A2 | 1/2005 |
| WO | WO-2005040217 A2 | 5/2005 |
| WO | WO-2005040219 A1 | 5/2005 |
| WO | WO-2005048823 A2 | 6/2005 |
| WO | WO-2005070963 A1 | 8/2005 |
| WO | WO-2005071408 A1 | 8/2005 |
| WO | WO-2005091944 A2 | 10/2005 |
| WO | WO-2005092925 A2 | 10/2005 |
| WO | WO-2005113606 A2 | 12/2005 |
| WO | WO-2006020114 A2 | 2/2006 |
| WO | WO-2006028595 A2 | 3/2006 |
| WO | WO-2006028714 A2 | 3/2006 |
| WO | WO-2006056492 A1 | 6/2006 |
| WO | WO-2006065582 A2 | 6/2006 |
| WO | WO-2006078463 A2 | 7/2006 |
| WO | WO-2006097537 A2 | 9/2006 |
| WO | WO-2006135886 A2 | 12/2006 |
| WO | WO-2006138275 A2 | 12/2006 |
| WO | WO-2007038658 A2 | 4/2007 |
| WO | WO-2007051081 A1 | 5/2007 |
| WO | WO-2007059404 A2 | 5/2007 |
| WO | WO-2007146968 A2 | 12/2007 |
| WO | WO-2008049113 A2 | 4/2008 |
| WO | WO-2008083312 A2 | 7/2008 |
| WO | WO-2008088849 A2 | 7/2008 |
| WO | WO-2008103693 A2 | 8/2008 |
| WO | WO-2008121563 A2 | 10/2008 |
| WO | WO-2009018386 A1 | 2/2009 |
| WO | WO-2009020802 A2 | 2/2009 |
| WO | WO-2009030771 A1 | 3/2009 |
| WO | WO-2009059278 A1 | 5/2009 |
| WO | WO-2009117033 A2 | 9/2009 |
| WO | WO-2009126380 A2 | 10/2009 |
| WO | WO-2009141359 A1 | 11/2009 |
| WO | WO-2010006060 A2 | 1/2010 |
| WO | WO-2010042747 A2 | 4/2010 |
| WO | WO-2010044952 A2 | 4/2010 |
| WO | WO-2010065439 A1 | 6/2010 |
| WO | WO-2010084169 A2 | 7/2010 |
| WO | WO-2010132370 A2 | 11/2010 |
| WO | WO-2010141469 A2 | 12/2010 |
| WO | WO-2010142665 A1 | 12/2010 |
| WO | WO-2011005481 A1 | 1/2011 |
| WO | WO-2011028952 A1 | 3/2011 |
| WO | WO-2011047097 A2 | 4/2011 |
| WO | WO-2011055968 A2 | 5/2011 |
| WO | WO-2011069104 A2 | 6/2011 |
| WO | WO-2011091078 A2 | 7/2011 |
| WO | WO-2011137362 A1 | 11/2011 |
| WO | WO-2012064733 A2 | 5/2012 |
| WO | WO-2012088290 A2 | 6/2012 |
| WO | WO-2012088302 A2 | 6/2012 |
| WO | WO-2012109624 A2 | 8/2012 |
| WO | WO-2013120553 A1 | 8/2013 |
| WO | WO-2014072876 A2 | 5/2014 |
| WO | WO-2015187835 A2 | 12/2015 |
| WO | WO-2016009086 A1 | 1/2016 |
| WO | WO-2016106302 A1 | 6/2016 |
| WO | WO-2017087678 A2 | 5/2017 |
| WO | WO-2017152102 A2 | 9/2017 |
| WO | WO-2018013818 A2 | 1/2018 |
| WO | 2018217976 A1 | 11/2018 |
| WO | 2018217988 A1 | 11/2018 |
| WO | 2018218056 A1 | 11/2018 |
| WO | WO-2019195126 A1 | 10/2019 |

OTHER PUBLICATIONS

De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
International Search Report and Written Opinion for International Application No. PCT/US2019/025100, dated Jul. 24, 2019, Netherlands, 18 pages.
Bouchon, A., et al., "Cutting Edge: Inflammatory Responses Can Be Triggered by TREM-1, A Novel Receptor Expressed on Neutrophils and Monocytes," Journal of Immunology 164(10):4991-4995, American Association of Immunologists, United States (2000).
Bouchon, A., et al., "TREM-1 Amplifies Inflammation and is a Crucial Mediator of Septic Shock," Nature 410(6832):1103-1107, Nature Publishing Group, England (2001).
GenBank, "*Homo sapiens* Triggering Receptor Expressed on Myeloid Cells 1 (TREM1), mRNA," Accession No. NM_018643.2, accessed at https://www.ncbi.nlm.nih.gov/nuccore/NM_018643.2, May 15, 2011.
Genbank, "*Homo sapiens* Triggering Receptor Expressed on Myeloid Cells 1 (TREM1), Transcript Variant 2, mRNA," accession No. NM_001242589.2, accessed at https://www.ncbi.nlm.nih.gov/nuccore/NM_001242589, Jun. 2018.
Genbank, "*Homo sapiens* Triggering Receptor Expressed on Myeloid Cells 1 (TREM1), Transcript Variant 3, mRNA," accession No. NM_001242590.2, accessed at https://www.ncbi.nlm.nih.gov/nuccore/NM_001242590, Jun. 2018.
Genbank, "Peptidoglycan Recognition Protein 1 Precursor [*Homo sapiens*]," accession No. NP_005082.1, accessed at https://www.ncbi.nlm.nih.gov/protein/NP_005082.1, Jul. 2018.
Genbank, "PREDICTED: Triggering Receptor Expressed on Myeloid Cells 1 [macaca Mulatta]," accession No. XP_001082517, accessed at https://www.ncbi.nlm.nih.gov/protein/XP_001082517.1, Dec. 2015.
GenBank, "Triggering Receptor Expressed on Myeloid Cells 1 Isoform 1 Precursor [*Homo sapiens*]," Accession No. NP_061113.1, accessed at https://www.ncbi.nlm.nih.gov/protein/8924262/, Jul. 31, 2017.
Genbank, "Triggering Receptor Expressed on Myeloid Cells 1 Isoform 2 Precursor [*Homo sapiens*]," accession No. NP_001229518.1, accessed at https://www.ncbi.nlm.nih.gov/protein/NP_001229518.1, Jun. 2018.
Genbank, "Triggering Receptor Expressed on Myeloid Cells 1 Isoform 3 Precursor [*Homo sapiens*]," accession No. NP_001229519, accessed at https://www.ncbi.nlm.nih.gov/protein/NP_001229519, Jun. 2018.
Warncke, M., et al., "Different Adaptations of IgG Effector Function in Human and Nonhuman Primates and Implications for Therapeutic Antibody Treatment," Journal of Immunology 188(9):4405-4411, American Association of Immunologists, United States (2012).
Karpovsky, B., et al., "Production of Target-specific Effector Cells Using Hetero-cross-linked Aggregates Containing Anti-target Cell and Anti-fc Gamma Receptor Antibodies," The Journal of Experimental Medicine 160(6):1686-1701, Rockefeller University Press, United States (1984).
Kuai, J., et al., "TREM-1 Expression Is Increased in the Synovium of Rheumatoid Arthritis Patients and Induces the Expression of Pro-inflammatory Cytokines," Rheumatology 48(11):1352-1358, Mercury International, England (2009).
Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (1985).
Schenk, M., et al., "TREM-1-expressing Intestinal Macrophages Crucially Amplify Chronic Inflammation in Experimental Colitis

(56) References Cited

OTHER PUBLICATIONS and Inflammatory Bowel Diseases," The Journal of Clinical Investigation 117(10):3097-3106, American Society for Clinical Investigation, United States (2007).
Shire, S.J., et al., "Challenges in the Development of High Protein Concentration Formulations," Journal of Pharmaceutical Sciences 93(6):1390-1402, Elsevier, United States (2004).
Strohl, W.R., "Optimization of Fc-mediated Effector Functions of Monoclonal Antibodies," Current Opinion in Biotechnology 20(6):685-691, Elsevier, England (2009).
ABCAM., Anti-PGRPS antibody [188C424] (ab13903), accessed at http://www.abcam.com/PGRPS-antibody-188C424-ab13903.html accessed on Jun. 12, 2014.
ABCAM., Atlas Antibodies, PGRP Antibodies, United States Biological, List of Anti-PGRP Abs, accessed at http://www.antibodyresource.com/search/Antibodies/ffb4623f-177 d-13a0-16e2-11 05223fb311/PG RP accessed on Jan. 8, 2014.
ABCAM., Atlas Antibodies, United States Biological Peptidoglycan recognition protein short Antibodies, List of Anti-PGRP Abs accessed on http://www.antibodyresource.com/search/Antibodies/3a8d5b63-12d8-12d6-1 b99-11 fb615758f5/Peptidoglycan- recognition-protein-short accessed on Jan. 8, 2014.
ABCAM., Atlas Antibodies, United States Biological, 075594 Antibodies, List of Anti-PGRP Abs, accessed at http://www.antibodyresource, com/search/Anti bod ies/125bfebf-0922-1605-3416-8213e4 73b271/07 5594 accessed on Jan. 8, 2014.
ABCAM., Atlas Antibodies, United States Biological, Cytokine tag7 Antibodies, List of Anti-PGRP Abs, accessed at http://www.antibodyresource .com/search/Antibodies/17 a31750-abb9-1 c85-b872-c3a2e 796189c/Cytokine-tag 7 accessed on Jan. 8, 2014.
ABCAM., Atlas Antibodies, United States Biological, Peptidoglycan recognition protein 1 Antibodies, List of Anti-PGRP Abs, accessed at http://www.antibodyresource, com/search/a nti bod ies/ede383a0-138e-c073-1710-f9db 1294bc02/Peptidoglycan- recognition-protein-1 accessed on Jan. 8, 2014.
ABCAM., Atlas Antibodies, United States Biological, Peptidoglycan recognition protein 1 Antibodies, List of Anti-PGRP Abs, accessed at http://www.antibodyresource.com/search/Antibodies/1208015d-1757 -26ad-1 f04-6c9171376236/Peptidoglycan- recognition-protein-1 accessed on Jan. 8, 2014.
ABCAM., Atlas Antibodies, United States Biological,Tag7 Antibodies, List of Anti-PGRP Abs accessed at http://www.antibodyresource. com/search/Anti bod ies/04 1 07168-8402-51 df-bb36-4dd2bf8e 16d 1/Tag accessed on Jan. 8, 2014.
ABCAM., Atlas Antibodies, United States Biological,TNFSF3L Antibodies, List of Anti-PGRP Abs accessed at http://www.antibodyresource.com/search/Antibodies/f33a5126-45cd-5220-878c- -Ofd9aa63ba35/TNFSF3L accessed on Jan. 8, 2014.
Abravaya, K., et al., "Detection of Point Mutations with a Modified Ligase Chain Reaction (Gap-LCR)," Nucleic Acids Research 23(4):675-682, Oxford University Press, England (Feb. 1995).
Adams, P.D., et al., "PHENIX: A Comprehensive Python-based System for Macromolecular Structure Solution," Acta Crystallographica. Section D, Biological Crystallography 66(Pt 2):213-221, Wiley-Blackwell, United States (2010).
Aderem, A. and Ulevitch, R.J., "Toll-like Receptors in the Induction of the Innate Immune Response," Nature 406(6797):782-787, Nature Publishing Group, England (Aug. 2000).
Adrie, C., et al., "Postresuscitation Disease After Cardiac Arrest: A Sepsis-like Syndrome?," Current Opinion in Critical Care 10(3):208-212, Lippincott Williams & Wilkins, United States (Jun. 2004).
Alexander, H.R., et al., "A Recombinant Human Receptor Antagonist to Interleukin 1 Improves Survival After Lethal Endotoxemia in Mice," The Journal of Experimental Medicine 173(4):1029-1032, Rockefeller University Press, United States (Apr. 1991).
Allahham, A., et al., "Flow and Injection Characteristics of Pharmaceutical Parenteral Formulations Using a Micro-capillary Rheometer," International Journal of Pharmaceutics 270(1-2):139-148, Elsevier/North-Holland Biomedical Press, Netherlands (2004).

Amann, E., et al., "Tightly Regulated Tac Promoter Vectors Useful for the Expression of Unfused and Fused Proteins in *Escherichia coli*," Gene 69(2):301-315, Elsevier/North-Holland, Netherlands (1988).
Amatngalim, G.D., et al., "Cathelicidin Peptide LL-37 Modulates TREM-1 Expression and Inflammatory Responses to Microbial Compounds," Inflammation 34(5)412-425, Kluwer Academic/Plenum Publishers, United States (Oct. 2011).
Ames, R.S., et al., "Conversion of Murine Fabs Isolated From a Combinatorial Phage Display Library to Full Length Immunoglobulins," Journal of Immunological Methods 184(2): 177-186, Elsevier, Netherlands (1995).
Andersen, M.D. and Faber, J.H., "Structural Characterization of Both the Non-proteolytic and Proteolytic Activation Pathways of Coagulation Factor XIII Studied by Hydrogen-deuterium Exchange Mass Spectrometry," International Journal of Mass Spectrometry 302(1-3):139-148, (2011).
Angal, S., et al., "A Single Amino Acid Substitution Abolishes the Heterogeneity of Chimeric Mouse/Human (IgG4) Antibody," Molecular Immunology 30(1):105-108, Pergamon Press, England (Jan. 1993).
Anti-TREM1 antibody produced in rabbit | Sigma-Aldrich HPA005563 product information, accessed at, https://www.laborne.com/product/Sigma-Aldrich/HPA005563.html, last accessed on Jun. 12, 2018, 3 pages.
Appelmelk, B.J., et al., "Use of Mucin and Hemoglobin in Experimental Murine Gram-negative Bacteremia Enhances the Immunoprotective Action of Antibodies Reactive With the Lipopolysaccharide Core Region," Antonie van Leeuwenhoek 52(6):537-542, Springer, Netherlands (1986).
Arnon, et al., "Monoclonal Antibodies for Immunotargeting of Drugs in Cancer Therapy," in Monoclonal Antibodies and Cancer Therapy, Reisfeld et al., eds., Alan R. Liss, Inc., (1985), pp. 243-256.
Arts, R.J., et al., "TREM-1 Interaction with the LPS/TLR4 Receptor Complex," European Cytokine Network 22(1):11-14, John Libbey Eurotext Ltd, France (2011).
Attwood, T.K., "Genomics. The Babel of Bioinformatics," Science 290(5491):471-473, American Association for the Advancement of Science, United States (Oct. 2000).
Ausubel, et al., Current Protocols in Molecular Biology, John Wiley & Sons (1992).
Bakker, A.B., et al., "DAP12-deficient Mice Fail to Develop Autoimmunity Due to Impaired Antigen Priming," Immunity 13(3):345-353, Cell Press, United States (Sep. 2000).
Bakker, A.B., et al., "Myeloid DAP12-associating Lectin (MDL)-1 is a Cell Surface Receptor Involved in the Activation of Myeloid Cells," Proceedings of the National Academy of Sciences 96(17):9792-9796, National Academy of Sciences, United States (Aug. 1999).
Bakker, A.B., et al., "NK Cell Activation: Distinct Stimulatory Pathways Counterbalancing Inhibitory Signals," Human lmmunology61(1):18-27, Elsevier/North-Holland, United States (Jan. 2000).
Baldari, C., et al., "A Novel Leader Peptide Which Allows Efficient Secretion of a Fragment of Human Interleukin 1 Beta in Saccharomyces cerevisiae,"The EMBO Journal 6(1):229-234, Wiley Blackwell, England (Jan. 1987).
Baldwin, et al., "Analysis Results, and Future Prospective of the Therapeutic Use of the Radiolabeled Antibody in Cancer Therapy," In Monoclonal Antibodies for Cancer Detection and Therapy, eds. Adacemic Press, pp. 303-316 (1985).
Banerji, J., et al., "A Lymphocyte-specific Cellular Enhancer Is Located Downstream of the Joining Region in Immunoglobulin Heavy Chain Genes," Cell 33(3)729-740, Cell Press, United States (Jul. 1983).
Barany, F., "Genetic Disease Detection and Dna Amplification Using Cloned Thermostable Ligase," Proceedings of the National Academy of Sciences 88(1):189-193, National Academy of Sciences, United States (Jan. 1991).
Bartel, D.P. and Szostak, J.W., "Isolation of New Ribozymes From a Large Pool of Random Sequences," Science 261 (5127):1411-1418, American Association for the Advancement of Science, United States (Sep. 1993).

(56) References Cited

OTHER PUBLICATIONS

Bartel, P. "Elimination of false positives that arise in using the two-hybrid system," Biotechniques 14(6):920-924, (1993).
Bauer, S., et al., "Activation of NK Cells and T Cells by NKG2D, a Receptor for Stress-inducible MICA," Science 285(5428)727-729, American Association for the Advancement of Science, United States (Jul. 1999).
Begum, N.A., et al., "Mycobacterium bovis Bcg Cell Wall-specific Differentially Expressed Genes Identified by Differential Display and cDNA Subtraction in Human Macrophages," Infection and Immunity 72(2):937-948, American Society for Microbiology, United States (Feb. 2004).
Benda, P., et al., "Differentiated Rat Glial Cell Strain in Tissue Culture," Science 161(3839):370-371, American Association for the Advancement of Science, United States (Jul. 1968).
Bethea, Deidra, et al., "Mechanisms of self-association of a human monoclonal antibody CNTO607", Protein Engineering, Design & Selection, 2012, vol. 25, No. 10, pp. 531-537.
Better, M., et al., "*Escherichia coli* Secretion of an Active Chimeric Antibody Fragment," Science 240(4855): 1041-1043, Association for the Advancement of Science, United States (May 1988).
Beutler, B., "Endotoxin, Toll-like Receptor 4, and the Afferent Limb of Innate Immunity," Current opinion in microbiology 3(1):23-28, Current Biology, England (Feb. 2000).
Beutler, B., et al., "Passive Immunization Against Cachectin/tumor Necrosis Factor Protects Mice From Lethal Effect of Endotoxin," Science 229(4716):869-871, American Association for the Advancement of Science, United States (Aug. 1985).
Bird, R.E., et al., "Single-chain Antigen-binding Proteins," Science 242(4877):423-426, Association for the Advancement of Science, United States (Oct. 1988).
Bleharski, J.R., et al., "A Role for Triggering Receptor Expressed on Myeloid Cells-1 in Host Defense During the Early-induced and Adaptive Phases of the Immune Response," Journal of Immunology 170(7):3812-3818, American Association of Immunologists, United States (Apr. 2003).
Boesen, J.J., et al., "Circumvention of Chemotherapy-induced Myelosuppression by Transfer of the mdr1 Gene," Biotherapy 6(4):291-302, Kluwer Academic Publishers, Netherlands (1993).
Bolin, S.R., et al., "Survey of Cell Lines in the American Type Culture Collection for Bovine Viral Diarrhea Virus," Journal of Virological Methods 48(2-3)211-221, Elsevier/North-Holland Biomedical Press, Netherlands (Jul. 1994).
Bone, R.C., "The Pathogenesis of Sepsis," Annals of Internal Medicine 115(6):457-469, American College of Physicians, United States (Sep. 1991).
Bone, R.C., et al., "Definitions for Sepsis and Organ Failure and Guidelines for the Use of Innovative Therapies in Sepsis. The ACCP/SCCM Consensus Conference Committee. American College of Chest Physicians/Society of Critical Care Medicine," Chest 101 (6):1644-1655, Elsevier, United States (Jun. 1992).
Bordelon-Riser, M.E., "Necessity for Two Human Chromosomes for Human Chorionic Gonadotropin Production in Human-mouse Hybrids," Somatic Cell Genetics 5(5):597-613, Plenum, United States (Sep. 1979).
Bork, P. and Bairoch, A., "Go Hunting in Sequence Databases but Watch out for the Traps," Trends in Genetics 12(10)425-427, Elsevier Trends Journals, England (Oct. 1996).
Bork, P., "Powers and Pitfalls in Sequence Analysis: The 70% Hurdle," Genome Research 10(4):398-400, Cold Spring Harbor Laboratory Press, United States (Apr. 2000).
Bostanci, N., et al., "Involvement of the TREM-1/DAP12 Pathway in the Innate Immune Responses to Porphyromonas Gingivalis," Molecular Immunology 49(1-2):387-394, Pergamon Press, England (Oct. 2011).
Bout, A., et al., "Lung Gene Therapy: In Vivo Adenovirus-mediated Gene Transfer to Rhesus Monkey Airway Epithelium," Human Gene Therapy 5(1):3-10, Liebert, United States (Jan. 1994).
Bradley, "Teratocarcinomas and Embryonic Stem Cells: A Practical Approach," Robertson, ed., IRL, Oxford, pp. 113-152(1987).

Bradley, A., "Modifying the Mammalian Genome by Gene Targeting," Current Opinion in Biotechnology 2(6):823-829, Elsevier, England (Dec. 1991).
Brenner, S.E., "Errors in Genome Annotation," Trends in Genetics 15(4):132-133, Elsevier Trends Journals, England (Apr. 1999).
Brinkmann, U., et al., "Phage Display of Disulfide-stabilized Fv Fragments," Journal of Immunological Methods 182(1):41-50, Elsevier, Netherlands (1995).
Brown, M., et al., "Tolerance to Single, but not Multiple, Amino Acid Replacements in Antibody VH CDR2: A Means of Minimizing B Cell Wastage from Somatic Hypermutation?," Journal of Immunology 156(9):3285-3291, American Association of Immunologists, United States (May 1996).
Burton, D.R. and Barbas, C.F. 3rd., "Human Antibodies From Combinatorial Libraries," Advances in Immunology 57:191-280, Academic Press, United States (1994).
Byrne, G.W. and Ruddle, F.H., "Multiplex Gene Regulation: a Two-tiered Approach to Transgene Regulation in Transgenic Mice," Proceedings of the National Academy of Sciences USA 86(14):5473-5477 (Jul. 1989).
Calame, K., et al., "Transcriptional Controlling Elements in the Immunoglobulin and T Cell Receptor Loci," Advances in Immunology 43:235-275 (1988).
Calandra, T., et al., "Protection From Septic Shock by Neutralization of Macrophage Migration Inhibitory Factor," Nature Medicine 6(2):164-170, Nature Publishing Company, United States (2000).
Camper, S.A. and Tilghman, S.M., "Postnatal Repression of the Alpha-fetoprotein Gene Is Enhancer Independent," Genes & Development 3:537-546 (1989).
Cantoni, C., et al., "Nkp44, a Triggering Receptor Involved in Tumor Cell Lysis by Activated Human Natural Killer Cells, Is a Novel Member of the Immunoglobulin Superfamily," Journal of Experimental Medicine 189(5)787-796, Rockefeller University Press, United States (Mar. 1999).
Carrell., et al., "A Novel Procedure for the Synthesis of Libraries Containing Small Organic Molecules," Angewandte Chemie International Edition in English 33:2059-2061, (1994).
Celia, M., et al., "A Novel Inhibitory Receptor (ILT3) Expressed on Monocytes, Macrophages, and Dendritic Cells Involved in Antigen Processing," Journal of Experimental Medicine 185(10):1743-1751, Rockefeller University Press, United States (May 1997).
Chaudhri, Anuj, et al., "The Role of Amino Acid Sequence in the Self-Association of Therapeutic Monoclonal Antibodies: Insights from Coarse-Grained Modeling", The Journal of Physical Chemistry, 2013, vol. 117, pp. 1269-1279.
Chen, S.H., et al., "Gene Therapy for Brain Tumors: Regression of Experimental Gliomas by Adenovirus-mediated Gene Transfer in Vivo," Proceedings of the National Academy of Sciences 91 (8):3054-3057, National Academy of Sciences, United States (Apr. 1994).
Cho, C.Y., et al., "An unnatural biopolymer," Science 261 (5126):1303-1305, American Association for the Advancement of Science, United States (1993).
Chomel, B.B., et al., "Bartonella Henselae Prevalence in Domestic Cats in California: Risk Factors and Association Between Bacteremia and Antibody Titers," Journal of Clinical Microbiology 33(9)2445-2450, American Society for Microbiology, United States (Sep. 1995).
Chothia, C. and Lesk, A.M., "Canonical Structures for the Hypervariable Regions of Immunoglobulins," Journal of Molecular Biology 196(4):901-917, Elsevier Science, United States (Aug. 1987).
Clowes, M.M., et al., "Long-term Biological Response of Injured Rat Carotid Artery Seeded With Smooth Muscle Cells Expressing Retrovirally Introduced Human Genes," The Journal of Clinical Investigation 93(2):644-651, American Society for Clinical Investigation, United States (Feb. 1994).
Cohen, A.S., et al., "Emerging Technologies for Sequencing Antisense Oligonucleotides: Capillary Electrophoresis and Mass Spectrometry," Advances in Chromatography 36:127-162, CRC Press, United States (1996).
Cohen, J., "The Immunopathogenesis of Sepsis," Nature 420(6917)1885-891, Nature Publishing Group, England (Dec. 2002).
Cohen, J., "TREM-1 in Sepsis," Lancet 358(9284):776-778, Elsevier, England (Sep. 2001).

(56) References Cited

OTHER PUBLICATIONS

Colbere-Garapin, F., et al., "A New Dominant Hybrid Selective Marker for Higher Eukaryotic Cells," Journal of Molecular Biology 150(1):1-14, Elsevier, England (Jul. 1981).
Collart, M.A., et al., "Regulation of Tumor Necrosis Factor Alpha Transcription in Macrophages: Involvement of Four Kappa B-like Motifs and of Constitutive and Inducible Forms of NF-kappa B," Molecular and Cellular Biology 10(4):1498-1506, American Society for Microbiology, United States (Apr. 1990).
Colonna, M. and Facchetti, F., "TREM-1 (Triggering Receptor Expressed on Myeloid Cells): A New Player in Acute Inflammatory Responses," The Journal of Infectious Diseases 187(2):5397-5401, Oxford University Press, United States (Jun. 2003).
Colonna, M., "TREMS in the Immune System and Beyond," Nature Reviews. Immunology 3(6):445-453, Nature Pub. Group, England (Jun. 2003).
Connolly, B.D., et al., "Weak Interactions Govern the Viscosity of Concentrated Antibody Solutions: High-throughput Analysis Using the Diffusion Interaction Parameter," Biophysical Journal 103(1):69-78, Cell Press, United States (2012).
Coskun, T., et al., "Fibroblast Growth Factor 21 Corrects Obesity in Mice," Endocrinology 149(12):6018-6027, Oxford University Press, United States (Dec. 2008).
Cotten, M., et al., "Receptor-mediated Transport of DNA Into Eukaryotic Cells," Methods in Enzymology 217:618-644, Academic Press, United States (1993).
Cotton, R.G., "Current Methods of Mutation Detection," Mutation Research 285(1):125-144, Elsevier, Netherlands (Jan. 1993).
Cotton, R.G., et al., "Reactivity of Cytosine and Thymine in Single-base-pair Mismatches With Hydroxylamine and Osmium Tetroxide and Its Application to the Study of Mutations," Proceedings of the National Academy of Sciences 85(12):4397-4401, National Academy of Sciences, United States (Jun. 1988).
Cox, G., et al., "IL-10 Enhances Resolution of Pulmonary Inflammation in Vivo by Promoting Apoptosis of Neutrophils," The American Journal of Physiology 271(4 Pt 1):L566-L571, American Physiological Society, United States (Oct. 1996).
Cronin, M.T., et al., "Cystic Fibrosis Mutation Detection by Hybridization to Light-generated DNA Probe Arrays," Human Mutation 7(3):244-255, Wiley-Liss, United States (1996).
Cruickshank, D.W., "Remarks About Protein Structure Precision," Acta Crystallographica. Section D, Biological Crystallography 55(Pt 3):583-601, Wiley-Blackwell, United States (1999).
Cruikshank, W.W., et al., "A Lipidated Anti-Tat Antibody Enters Living Cells and Blocks HIV-1 Viral Replication," Journal of Acquired Immune Deficiency Syndromes and Human Retrovirology 14(3):193-203, Lippincott Williams & Wilkins, United States (Mar. 1997).
Cull, M.G., et al., "Screening for Receptor Ligands Using Large Libraries of Peptides Linked to the C Terminus of the Lac Repressor," Proceedings of the National Academy of Sciences 89(5):1865-1869, National Academy of Sciences, United States (Mar. 1992).
Cwirla, S.E., et al., "Peptides on phage: a vast library of peptides for identifying ligands," Proceedings of the National Academy of Sciences 87(16):6378-6382, National Academy of Sciences, United States, (1990).
Database EMBL, Sequence from Patent WO200283856-A2, Sep. 17, 2003 "Human G-protein Coupled Receptor Phosphorylation Site Peptide SEQ ID 131," retrieved from EBI Database accession No. ABJ38803.
Database EMBL, Sequence Information from JP2000116377-A, Oct. 10, 2000 "N-terminus of Porcine Trypsin," retrieved from EBI Database accession No. AAB03087.
Davenport, C.M., et al., "Inhibition of Pro-inflammatory Cytokine Generation by CTLA4-Ig in the Skin and Colon of Mice Adoptively Transplanted with CD45RBhi CD4+ T Cells Correlates with Suppression of Psoriasis and Colitis," International Immunopharmacology 2(5):653-672, Elsevier Science, Netherlands (2002).

Daws, M.R., et al., "Cloning and Characterization of a Novel Mouse Myeloid DAP12-associated Receptor Family," European Journal of Immunology 31 (3):783-791, Wiley-VCH, Germany (Mar. 2001).
Devlin, J.J., et al., "Random peptide libraries: a source of specific protein binding molecules," Science 249(4967):404-406, American Association for the Advancement of Science, United States (1990).
Dewitt, S.H., et al., "Diversomers: an approach to nonpeptide, nonoligomeric chemical diversity," Proceedings of the National Academy of Sciences 90(15):6909-6913, National Academy of Sciences, United States (1993).
Dietrich, J., et al., "Cutting Edge: Signal-regulatory Protein Beta 1 is a DAP12-associated Activating Receptor Expressed in Myeloid Cells," Journal of Immunology 164(1):9-12, American Association of Immunologists, United States (Jan. 2000).
Dinarello, C.A., "Proinflammatory and Anti-inflammatory Cytokines as Mediators in the Pathogenesis of Septic Shock," Chest 112(6):3215-3295, Elsevier, United States (Dec. 1997).
Doerks T., et al., "Protein Annotation: Detective Work for Function Prediction," Trends in Genetics 14(6):248-250, Elsevier Trends Journals, England (Jun. 1998).
Downey, G.P., et al., "Intracellular Signaling in Neutrophil Priming and Activation," Seminars in Cell Biology 6(6):345-356, Academic Press, England (Dec. 1995).
Dziarski, R., "Peptidoglycan Recognition Proteins (PGRPS)," Molecular Immunology 40(12):877-886, Pergamon Press, England (Feb. 2004).
Dziarski, R., et al., "Peptidoglycan Recognition in Innate Immunity," Endotoxin Research 11 (5):304-310, Sage Publications, United States (2005).
Dziarski, R., et al., "Review: Mammalian Peptidoglycan Recognition Proteins (PGRPs) in Innate Immunity," Innate Immunity 16(3):168-174, Sage Publications, United States (Jun. 2010).
Dziarski, R Gupta, D., "The Peptidoglycan Recognition Proteins (PGRPs)," Genome Biology 7(8):232.1-232.13, BioMed Central Ltd, England (2006).
Echtenacher, B., et al., "Critical Protective Role of Mast Cells in a Model of Acute Septic Peritonitis," Nature 381(6577):75-77, Nature Publishing Group, England (May 1996).
Echtenacher, B., et al., "Requirement of Endogenous Tumor Necrosis Factor/cachectin for Recovery From Experimental Peritonitis," Journal of Immunology 145(11):3762-3766, American Association of Immunologists, United States (Dec. 1990).
Echtenacher, B., et al., "Tumor Necrosis Factor-dependent Adhesions as a Major Protective Mechanism Early in Septic Peritonitis in Mice," Infection and Immunity 69(6):3550-3555, American Society for Microbiology, United States (Jun. 2001).
Edlund, T., et al., "Cell-specific Expression of the Rat Insulin Gene: Evidence for Role of Two Distinct 5' Flanking Elements," Science 230(4728):912-916, American Association for the Advancement of Science, United States (Nov. 1985).
Emsley, P., et al., "Features and Development of Coot," Acta Crystallographica. Section D, Biological Crystallography 66(Pt 4):486-501, Wiley-Blackwell, United States (2010).
Engh, R.A. and Huber, R., "Accurate Bond and Angle Parameters for X-ray Protein Structure Refinement," Acta Crystallographica Section A 47(4):392-400, (1991).
Erb, E., et al., "Recursive deconvolution of combinatorial chemical libraries," Proceedings of the National Academy of Sciences 91 (24): 11422-11426, National Academy of Sciences, United States (1994).
Erickson, S.K., "Nonalcoholic Fatty Liver Disease," Journal of Lipid Research 50:S412-S416, American Society for Biochemistry and Molecular Biology, United States (Apr. 2009).
Eskandari, M.K., et al., "Anti-tumor Necrosis Factor Antibody Therapy Fails to Prevent Lethality After Cecal Ligation and Puncture or Endotoxemia," Journal of Immunology 148(9):2724-2730, American Association of Immunologists, United States (May 1992).
European Search Report for EP Application No. 14177547.8, European Patent Office, Munich, Germany, dated Feb. 2, 2015, 10 pages.
European Search Report for EP Application No. 14194893.5, European Patent Office, Munich, Germany, dated Jan. 14, 2016, 12 pages.

(56) References Cited

OTHER PUBLICATIONS

Facchetti, F., et al., "Suppurative Granulomatous Lymphadenitis. Immunohistochemical Evidence fora B-cell-associated Granuloma," The American Journal of Surgical Pathology 16(10):955-961, Wolters Kluwer Health, Inc., United States (Oct. 1992).

Felici, F., et al., "Selection of Antibody Ligands from a Large Library of Oligopeptides Expressed on a Multivalent Exposition Vector," Journal of Molecular Biology 222(2):301 -310, Elsevier Science, United States (Nov. 1991).

Fell, H.P., et al., "Genetic Construction and Characterization of a Fusion Protein Consisting of a Chimeric F(ab') With Specificity for Carcinomas and Human IL-2," Journal of Immunology 146(7)2446-2452, American Association of Immunologists, United States (Apr. 1991).

Fiering, S., et al., "Single Cell Assay of a Transcription Factor Reveals a Threshold in Transcription Activated by Signals Emanating From the T-cell Antigen Receptor," Genes & Development 4(10):1823-1834, Cold Spring Harbor Laboratory Press, United States (1990).

Finn, P.J., et al. , "Synthesis and Properties of DNA-PNA Chimeric Oligomers," Nucleic Acids Research 24(17):3357-3363, Oxford University Press, England (Sep. 1996).

Fisher, C.J., et al., "Treatment of Septic Shock with the Tumor Necrosis Factor Receptor: Fc Fusion Protein the Soluble TNF Receptor Sepsis Study Group," The New England Journal of Medicine 334(26):1697-1702, Massachusetts Medical Society, United States (Jun. 1996).

Fodor, S.P., et al., "Multiplexed biochemical assays with biological chips," Nature 364(6437):555-556, Nature Publishing Group, United States (1993).

Forster, R., et al., "CCR7 Coordinates the Primary Immune Response by Establishing Functional Microenvironments in Secondary Lymphoid Organs," Cell 99(1)23-33, Cell Press, United States (Oct. 1999).

Gallop, M.A., et al., "Applications of combinatorial technologies to drug discovery. 1. Background and peptide combinatorial libraries," Journal of Medicinal Chemistry 37(9):1233-1251, (1994).

Garcia, R.A., et al., "Hydrogen/deuterium Exchange Mass Spectrometry for Investigating Proteinligand Interactions," Assay and Drug Development Technologies 2(1):81-91, Mary Ann Liebert, Inc., United States (2004).

Gasparini, P., et al., "Restriction Site Generating-polymerase Chain Reaction (RG-PCR) for the Probeless Detection of Hidden Genetic Variation: Application to the Study of Some Common Cystic Fibrosis Mutations," Molecular and Cellular Probes 6(1):1-7, Academic Press, England (Feb. 1992).

Gautier, C., et al., "alpha-DNA Iv: alpha-anomeric and beta-anomeric Tetrathymidylates Covalently Linked to Intercalating Oxazolopyridocarbazole Synthesis, Physicochemical Properties and Poly," Nucleic Acids Research 15(16):6625-6641 , Oxford University Press, England (Aug. 1987).

GenBank, "AL681 036 XGC-gastrula Xenopus tropicalis cDNA clone TGas068103 5-, mRNA sequence," Accession No. AL681036. 2, accessed at https://www.ncbi.nlm.nih.gov/nucest/AI681036, Nov. 10, 2003.

GenBank, "AL962750 XGC-gastrula Xenopus tropicalis cDNA clone TGas109m03 5-, mRNA sequence," Accession No. AL962750. 2, accessed at https://www.ncbi.nlm.nih.gov/nucest/AI962750, Dec. 5, 2003.

GenBank, "AL968134 XGC-gastrula Xenopus tropicalis cDNA clone TGas113h24 5-, mRNA sequence," Accession No. AL968134. 2, accessed at https://www.ncbi.nlm.nih.gov/nucest/AI968134, Dec. 5, 2003.

GenBank, "Cloning Vector pIRESIhyg, Complete Plasmid Sequence," Accession No. U89672.1, accessed at https://www.ncbi.nlm.nih.gov/nuccore/U89672, Mar. 21, 1997.

GenBank, "CMO-TT0011 -251099-080f05 TT0011 Homo sapiens cDNA, mRNA sequence," Accession No. AW394041.1, accessed at https://www.ncbi.nlm.nih.gov/nucest/AW394041, Feb. 4, 2000.

GenBank, "Homo sapiens triggering receptor expressed on monocytes 1 mRNA, complete cds," Accession No. AF196329.1, accessed at https://www.ncbi.nlm.nih.gov/nuccore/AF196329, May 24, 2000.

GenBank, "Homo sapiens triggering receptor expressed on myeloid cells 2 mRNA, complete cds," Accession No. AF213457.1, accessed at https://www.ncbi.nlm.nih.gov/nuccore/AF213457, May 23, 2000.

GenBank, "HUM517F10B Human placenta polyA+ (TFujiwara) Homo sapiens cDNA clone Gen-517F10 5-, mRNA sequence," Accession No. D78812.1, accessed at https://www.ncbi.nlm.nih.gov/nucest/D78812, Jul. 20, 2006.

Genbank, "ne55f09.s1 NCI_CGAP_Co3 Homo sapiens cDNA clone lmage:901289 3-, mRNA sequence," Accession No. AA494171.1, accessed at https://www.ncbi.nlm.nih.gov/nucest/AA494171, Jan. 6, 2011.

Genbank, "T3 end of clone 024CH09 of library SmBAC1 from strain Puerto-Rican of Schistosoma mansoni, genomic survey sequence," Accession No. AL621023.1, accessed at https://www.ncbi.nlm.nih.gov/nucgss/AI621023, Oct. 11, 2001.

GenBank, "T3 end of clone AR0AA015A03 of library AR0AA from strain CBS 732 of Zygosaccharomyces rouxii, genomic survey sequence," Accession No. AL394092.1, accessed at https://www.ncbi.nlm.nih.gov/nucgss/AI394092, Feb. 16, 2014.

GenBank, "tb95h04.x1 NCI_CGAP_Co16 Homo sapiens cDNA clone lmage:2062135 3-, mRNA sequence," Accession No. AI337247.1, accessed at https://www.ncbi.nlm.nih.gov/nucest/A1337247, Jan. 8, 2011.

Genbank, "Tetraodon nigroviridis genome survey sequence T7 end of clone 245F13 of library G from Tetraodon nigroviridis, genomic survey sequence," Accession No. AL186456, accessed at https://www.ncbi.nlm.nih.gov/nucgss/AI186456, May 19, 2010.

GenBank, "Triggering Receptor Expressed on Myeloid Cells 1 Isoform 1 Precursor [Mus musculus]," Accession No. NP_067381.1, accessed at https://www.ncbi.nlm.nih.gov/protein/NP 067381, Jun. 3, 2017.

GenBank, "Triggering Receptor Expressed on Myeloid Cells," Accession No. Q9NP99, accessed at http://www.uniprot.org/uniprot/Q9NP99, Jun. 7, 2017.

GenBank, "UI-H-BI1-acf-g-10-0-Ul.s1 NCI_CGAP_Sub3 Homo sapiens cDNA clone lmage:2714299 3-, mRNA sequence," Accession No. AW135801.1, accessed at https://www.ncbi.nlm.nih.gov/nucest/AW135801, Jan. 6, 2011.

GenBank, "UI-H-BI1-ada-h-08-0-Ul.s1 NCI_CGAP_Sub3 Homo sapiens cDNA clone lmage:2716286 3-, mRNA sequence," Accession No. AW139363.1, accessed at https://www.ncbi.nlm.nih.gov/nucest/AW139363, Jan. 7, 2011.

GenBank, "UI-H-BI1-aea-d-11-0-Ul.s1 NCI_CGAP_Sub3 Homo sapiens cDNA clone lmage:2718764 3-, mRNA sequence," Accession No. AW139572.1, accessed at https://www.ncbi.nlm.nih.gov/nucest/AW139572, Jan. 7, 2011.

GenBank, "UI-H-BI1-aea-d-12-0-Ul.s1 NCI_CGAP_Sub3 Homo sapiens cDNA clone lmage:2718766 3-, mRNA sequence," Accession No. AW139573.1, accessed at https://www.ncbi.nlm.nih.gov/nucest/AW139573, Oct. 30, 1999.

GenBank, "xm62e07.x1 NCI_CGAP_GC6 Homo sapiens cDNA clone lmage:2688804 3-, mRNA sequence," Accession No. AW274906.1, accessed at https://www.ncbi.nlm.nih.gov/nucest/AW274906, Jan. 3, 2000.

GenBank, "yw70g03.r1 Soares_placenta_8to9weeks_2NbHP8to9W Homo sapiens cDNA clone lmage:257620 5-, mRNA sequence," Accession No. N41388.1, accessed at https://www.ncbi.nlm.nih.gov/nucest/N41388, Jan. 24, 1996.

GenBank, "zk87c02.r1 Soares_pregnant_uterus_NbHPU Homo sapiens cDNA clone lmage:489794 5-, mRNA sequence," Accession No. AA099288.1, accessed at https://www.ncbi.nlm.nih.gov/nucest/AA099288, Jan. 28, 2011.

GenBank, "zk87c02.s1 Soares_pregnant_uterus_NbHPU Homo sapiens cDNA clone lmage:489794 3-, mRNA sequence," Accession No. AA101983.1, accessed at https://www.ncbi.nlm.nih.gov/nucest/AA101983, Jan. 28, 2011.

Gencic, S. and Hudson, L.D., "Conservative Amino Acid Substitution in the Myelin Proteolipid Protein of Jimpymsd Mice," The Journal of Neuroscience 10(1):117-124, Society for Neuroscience, United States (Jan. 1990).

(56) References Cited

OTHER PUBLICATIONS

Gentz, R., et al., "Bioassay for Trans-activation using Purified Human Immunodeficiency Virus Tat-encoded Protein: Trans-activation Requires mRNA Synthesis," Proceedings of the National Academy of Sciences USA 86(3):821-824, National Academy of Sciences, United States (Feb. 1989).
Ghosh, A., et al., "A Novel Antimicrobial Peptidoglycan Recognition Protein in the Cornea," Investigative Ophthalmology & Visual Science 50(9):4185-4191, Association for Research in Vision and Ophthalmology, United States (Sep. 2009).
Gibbs, R.A., et al., "Detection of Single DNA Base Differences by Competitive Oligonucleotide Priming," Nucleic Acids Research 17(7):2437-2448, Oxford University Press, England (Apr. 1989).
Gibot, S., et al., "A Soluble Form of the Triggering Receptor Expressed on Myeloid Cells-1 Modulates the Inflammatory Response in Murine Sepsis," The Journal of Experimental Medicine 200(11):1419-1426, Rockefeller University Press, United States (Dec. 2004).
Gibot, S., et al., "Modulation of the Triggering Receptor Expressed on the Myeloid Cell Type 1 Pathway in Murine Septic Shock," Infection and immunity 74(5):2823-2830, American Society for Microbiology, United States (May 2006).
Gibot, S., et al., "Plasma Level of a Triggering Receptor Expressed on Myeloid Cells-1: its Diagnostic Accuracy in Patients with Suspected Sepsis," Annals of Internal Medicine 141 (1):9-15, American College of Physicians-American Society of Internal Medicine, United States (Jul. 2004).
Gibot, S., et al., "Soluble Triggering Receptor Expressed on Myeloid Cells and the Diagnosis of Pneumonia," The New England Journal of Medicine 350(5):451-458, Massachusetts Medical Society, United States (Jan. 2004).
Gillies, S.D., et al., "Antibody-targeted Interleukin 2 Stimulates T-cell Killing of Autologous Tumor Cells," Proceedings of the National Academy of Sciences of the United States of America 89(4):1428-1432, National Academy of Sciences, United States (1992).
Gillies, S.D., et al., "High-level Expression of Chimeric Antibodies Using Adapted cDNA Variable Region Cassettes," Journal of Immunological Methods 125(1-2):191-202, Elsevier, Netherlands (1989).
Gingras, M.C., et al., "TREM-1, MDL-1, and DAP12 Expression is Associated with a Mature Stage of Myeloid Development," Molecular Immunology 38(11):817-824, Pergamon Press, England (Mar. 2002).
Glauser, M.P., et al., "Septic Shock: Pathogenesis," Lancet 338(8769)732-736, Elsevier, England (Sep. 1991).
Goldspiel, B.R., et al., "Human Gene Therapy," Clinical Pharmacy 12(7):488-505, American Society of Hospital Pharmacists, United States (1993).
Gon, S., et al., "Involvement of Two Types of TNF Receptor in TNF-alpha Induced Neutrophil Apoptosis," Microbiology and Immunology 40(6):463-465, Wiley-Blackwell, Australia (1996).
Griffin, H.G. and Griffin, A.M., "Dna Sequencing. Recent Innovations and Future Trends," Applied Biochemistry and Biotechnology 38(1-2):147-159, Humana Press, United States (Jan.-Feb. 1993).
Griffin, M.P., et al., "Abnormal Heart Rate Characteristics Preceding Neonatal Sepsis and Sepsislike Illness," Pediatric Research 53(6):920-926, Nature Publishing Group, United States (Jun. 2003).
Grossman, M. and Wilson, J.M., "Retroviruses: Delivery Vehicle to the Liver," Current Opinion in Genetics & Development 3(1):110-114, Elsevier, England (Feb. 1993).
Grundy, S.M., et al., "Definition of Metabolic Syndrome: Report of the National Heart, Lung, and Blood Institute/American Heart Association Conference on Scientific Issues Related to Definition," Circulation 109(3):433-438, Lippincott Williams & Wilkins, United States (Jan. 2004).
Guan, R., et al., "Crystal Structure of Human Peptidoglycan Recognition Protein S (PGRP-S) at 1.70 A Resolution," Molecular Biology 347(4):683-691, Elsevier, England (Apr. 2005).
Guatelli, J.C., et al., "Isothermal, in Vitro Amplification of Nucleic Acids by a Multienzyme Reaction Modeled After Retroviral Replication," Proceedings of the National Academy of Sciences 87(5):1874-1878, National Academy of Sciences, United States (Mar. 1990).
Haapala, D.K., et al., "Isolation From Cats of an Endogenous Type C Virus With a Novel Envelope Glycoprotein," Journal of Virology 53(3):827-833, American Society for Microbiology, United States (Mar. 1985).
Hammerling, G.J., et al., "Monoclonal Antibodies and T-Cell Hybridomas," pp. 563-681, Elsevier, Newyork (1981).
Harlow, E. and Lane, D., Antibodies: A Laboratory Manual, 2nd Edition, Cold Spring Harbor Press (1988).
Haselmayer, P., et al., "TREM-1 Ligand Expression on Platelets Enhances Neutrophil Activation," Blood 110(3):1029-1035, American Society of Hematology, United States (Aug. 2007).
Haseloff, J., et al., "Simple RNA Enzymes with New and Highly Specific Endoribonuclease Activities," Nature 334(6183):585-591, Nature Publishing Group, England (Aug. 1988).
Hayashi, K., "PCR-SSCP: A Method for Detection of Mutations," Genetic Analysis, Techniques and Applications 9(3):73-79, Elsevier, Netherlands (Jun. 1992).
He, F., et al., "High-throughput Dynamic Light Scattering Method for Measuring Viscosity of Concentrated Protein Solutions," Analytical Biochemistry 399(1):141-143, Elsevier, United States (2010).
He, X.M., et al., "Expression of 06-methylguanine-DNA Methyltransferase in Six Human Medulloblastoma Cell Lines," Cancer Research 52(5):1144-1148, American Association for Cancer Research, United States (Mar. 1992).
Hebert, M.J., et al., "Sequential Morphologic Events During Apoptosis of Human Neutrophils. Modulation by Lipoxygenase-derived Eicosanoids," Journal of Immunology 157(7):31 05-3115, American Association of Immunologists, United States (Oct. 1996).
Helene, C., "The Anti-gene Strategy: Control of Gene Expression by Triplex-forming-oligonucleotides," Anti-cancer Drug Design 6(6):569-584, Oxford University Press, United States (1991).
Helene, C., et al., "Control of Gene Expression by Triple Helix-forming Oligonucleotides. The Antigene Strategy," Annals of the New York Academy of Sciences 660:27-36, Blackwell, United States (Oct. 1992).
Hellstrom, et al., "Antibodies for Drug Delivery" in Controlled Drug Delivery, 2nd edition, Robinson et al., eds., Marcel Dekker, Inc., (1987), pp. 623-653.
Hiscott, J., et al., "Characterization of a Functional NF-kappa B Site in the Human Interleukin 1 Beta Promoter: Evidence for a Positive Autoregulatory Loop," Molecular and Cellular Biology 13(10):6231-6240, American Society for Microbiology, United States (Oct. 1993).
Hoffmann, J.A., et al., "Phylogenetic Perspectives in Innate Immunity," Science 284(5418):1313-1318, American Association forthe Advancement of Science, United States (May 1999).
Holliger, P, and Hudson, P.J., "Engineered Antibody Fragments and the Rise of Single Domains," Nature Biotechnology 23(9):1126-1136, Nature America Publishing, United States (2005).
Hotchkiss, R.S. and Karl, I.E., "The Pathophysiology and Treatment of Sepsis," The New England Journal of Medicine 348(2):138-150, Massachusetts Medical Society, United States (Jan. 2003).
Houghten, R.A., et al., "The Use of Synthetic Peptide Combinatorial Libraries forthe Identification of Bioactive Peptides," Biotechniques 13(3):412-421, Informa Healthcare USA, England (Sep. 1992).
Hsu, I.C., et al., "Detection of DNA Point Mutations with DNA Mismatch Repair Enzymes," Carcinogenesis 15(8):1657-1662, Irl Press, England (Aug. 1994).
Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).
Huston, J.S., et al., "Protein Engineering of Single-chain Fv Analogs and Fusion Proteins," Methods in Enzymology 203:46-88, Academic Press, United States (1991).
Hybridization with Radioactive Probes, Current Protocols in Molecular Biology, John Wiley & Sons, N.Y. 6.3.1-6.3.6 (1989).
Hyrup, B. and Nielsen, P.E., "Peptide Nucleic Acids (PNA): Synthesis, Properties and Potential Applications," Bioorganic& Medicinal Chemistry 4(1):5-23, Elsevier Science, England (Jan. 1996).

(56) References Cited

OTHER PUBLICATIONS

Ill, C.R., et al., "Design and Construction of a Hybrid Immunoglobulin Domain With Properties of Both Heavy and Light Chain Variable Regions," Protein Engineering 10(8):949-957, IRL Press, England (1997).
Inoue, H., et al., "Sequence-dependent Hydrolysis of RNA using Modified Oligonucleotide Splints and RNase H," FEBS letters 215(2):327-330, Elsevier Science B.V, Netherlands (May 1987).
Inoue, H., et al., "Synthesis and Hybridization Studies on Two Complementary Nona(2'-0-Methyl)Ribonucleotides," Nucleic Acids Research 15(15):6131-6148, Oxford University Press, England (Aug. 1987).
International Search Report for International Application No. PCT/EP2012/074092, European Patent Office, Rijswijk, dated Jun. 20, 2013, 5 pages.
International Search Report for International Application No. PCT/EP2015/066501, European Patent Office, Rijswijk, dated Oct. 12, 2015, 6 pages.
Iwabuchi, K., et al., "Use of the two-hybrid system to identify the domain of p53 involved in oligomerization," Oncogene 8(6):1693-1696, (1993).
Jespers, L.S., et al., "Guiding the Selection of Human Antibodies from Phage Display Repertoires to a Single Epitope of an Antigen," Bio/technology 12(9):899-903, Wiley-Blackwell, United States (1994).
Jezek, Jan, et al., "Viscosity of concentrated therapeutic protein compositions", Advanced Drug Delivery Reviews, 2011, vol. 63, pp. 1107-1117.
Jobling, M.G. and Holmes, R.K., "Analysis of Structure and Function of the B Subunit of Cholera Toxin by the Use of Site-directed Mutagenesis," Molecular Microbiology 5(7):1755-1767, Blackwell Scientific Publications, England (Jul. 1991).
Kabat, E.A., et al., "Sequences of Proteins of Immunological Interest," 5th Edition, U.S. Department of Public Health and Human Services, Public Health Service, National Institutes of Health, Bethesda (1991).
Kabsch, W., "Integration, Scaling, Space-group Assignment and Post-refinement," Acta Crystallographica. Section D, Biological Crystallography 66(Pt2):133-144, Wiley-Blackwell, United States (2010).
Kamerzell, Tim J., et al., "Protein-excipient interactions: Mechanisms and biophysical characterization applied to protein formulation development", Advanced Drug Delivery Reviews, 2011, vol. 63, pp. 1118-1159.
Kanai, S., et al., "Reversible Self-association of a Concentrated Monoclonal Antibody Solution Mediated by Fab-fab Interaction That Impacts Solution Viscosity," Journal of Pharmaceutical Sciences 97(10):4219-4227, Elsevier, United States (2008).
Kang, D., et al., "A Peptidoglycan Recognition Protein in Innate Immunity Conserved From Insects to Humans," Proceedings of the National Academy of Sciences of the United States of America 95(17):10078-10082, National Academy of Sciences, United States (Aug. 1998).
Karttunen, J. and Shastri, N., "Measurement of Ligand-induced Activation in Single Viable T Cells Using the lacZ Reporter Gene," Proceedings of the National Academy of Sciences of the United States of America 88(9):3972-3976, National Academy of Sciences, United States (1991).
Katsuura, M., et al., "CD48 Expression on Leukocytes in Infectious Diseases: Flow Cytometric Analysis of Surface Antigen," Acta Paediatrica Japonica 40(6):580-585, Blackwell Scientific, Australia (Dec. 1998).
Kaufman, R.J., et al., "Translational Efficiency of Polycistronic mRNAs and Their Utilization to Express Heterologous Genes in Mammalian Cells," The EMBO Journal 6(1):187-195, Wiley Blackwell, England (Jan. 1987).
Keane, J., et al., "Tuberculosis Associated With Infliximab, a Tumor Necrosis Factor Alphaneutralizing Agent," The New England Journal of Medicine 345(15):1098-1104, Massachusetts Medical Society, United States (Oct. 2001).
Keen, J., et al., "Rapid Detection of Single Base Mismatches as Heteroduplexes on Hydrolink Gels," Trends in Genetics 7(1):5, Elsevier Trends Journals, England (Jan. 1991).
Kelker, M.S., et al., "Crystal Structure of Human Triggering Receptor Expressed on Myeloid Cells 1 (TREM-1) at 1.47 A," Journal of Molecular Biology 342(4):1237-1248, Elsevier, England (2004).
Kessel, M. and Gruss, P., "Murine Developmental Control Genes," Science 249(4967):374-79, American Association for the Advancement of Science, United States (Jul. 1990).
Ketchem, Randal R., et al., "Mitigation of monoclonal antibody viscosity by modification of protein surface charge", American Chemical Society, 2012, vol. 243, p. 1.
Kettleborough, C.A., et al., "Isolation of Tumor Cell-specific Single-chain Fv From Immunized Mice Using Phage-antibody Libraries and the Re-construction of Whole Antibodies From These Antibody Fragments," European Journal of Immunology 24(4):952-958, Wiley-VCH, Germany (1994).
Kharitonenkov, A., et al., "FGF-21 as a Novel Metabolic Regulator," The Journal of Clinical Investigation 115(6):1627-1635, American Society for Clinical Investigation, United States (Jun. 2005).
Kharitonenkov, A., et al., "The Metabolic State of Diabetic Monkeys Is Regulated by Fibroblast Growth Factor-21," Endocrinology 148(2):774-781, Oxford University Press, United States (Feb. 2007).
Kiem, H.P., et al., "Retrovirus-mediated Gene Transduction Into Canine Peripheral Blood Repopulating Cells," Blood 83(6):1467-1473, American Society of Hematology, United States (Mar. 1994).
Knappik, A. and Pluckthun, A., "An Improved Affinity Tag Based on the Flag Peptide for the Detection and Purification of Recombinant Antibody Fragments," Biotechniques 17(4)754-761, Informa Healthcare USA, England (Oct. 1994).
Knudsen, L.B., "Glucagon-like Peptide-1: The Basis of a New Class of Treatment for Type 2 Diabetes," Journal of Medicinal Chemistry 47(17):4128-4134, American Chemical Society, United States (Aug. 2004).
Kohler, G., "Immunoglobulin Chain Loss in Hybridoma Lines," Proceedings of the National Academy of Sciences USA 77(4):2197-2199, National Academy of Sciences, United States (Apr. 1980).
Koller, B.H. And Smithies, O., "Inactivating the beta 2-Microglobulin Locus in Mouse Embryonic Stem Cells by Homologous Recombination," Proceedings of the National Academy of Sciences USA 86(22):8932-8935, National Academy of Sciences, United States (Nov. 1989).
Kozai, M.J., et al., "Extensive Polymorphisms Observed in HIV-1 Clade B Protease Gene Using High-density Oligonucleotide Arrays," Nature Medicine 2(7)753-759, Nature Publishing Company, United States (Jul. 1996).
Kozarsky, K.F. and Wilson, J.M., "Gene Therapy: Adenovirus Vectors," Current Opinion in Genetics & Development 3(3):499-503, Elsevier, England (Jun. 1993).
Kruse, C.A., et al., "Characterization of a Continuous Human Glioma Cell Line DBTRG-05MG: Growth Kinetics, Karyotype, Receptor Expression, and Tumor Suppressor Gene Analyses," In Vitro Cellular & Developmental Biology 28A(9-10):609-614, Tissue Culture Association, United States (Sep.-Oct. 1992).
Kubagawa, H., et al., "Biochemical Nature and Cellular Distribution of the Paired Immunoglobulin-like Receptors, PIR-A and PIR-B,"The Journal of Experimental Medicine 189(2):309-318, Rockefeller University Press, United States (Jan. 1999).
Kunkel, T.A., et al., "Rapid and Efficient Site-specific Mutagenesis Without Phenotypic Selection," Methods in Enzymology 154:367-382, Academic Press, United States (1987).
Kurjan, J. and Herskowitz, I., "Structure of a Yeast Pheromone Gene (MF Alpha): A Putative Alpha-factor Precursor Contains Four Tandem Copies of Mature Alpha-factor," Cell 30(3):933-943, Cell Press, United States (Oct. 1982).
Kwoh, D.Y., et al., "Transcription-Based Amplification System and Detection of Amplified Human Immunodeficiency Virus Type 1 with a Bead-Based Sandwich Hybridization Format," Proceedings of the National Academy of Sciences of the United States of America 86(4):11731177, National Academy of Sciences, United States (1989).
Lakso, M., et al., "Targeted Oncogene Activation by Site-specific Recombination in Transgenic Mice," Proceedings of the National

(56) References Cited

OTHER PUBLICATIONS

Academy of Sciences 89(14):6232-6236, National Academy of Sciences, United States (Jul. 1992).

Lam, K.S., "Application of Combinatorial Library Methods in Cancer Research and Drug Discovery," Anticancer Drug Design 12(3):145-67, (1997).

Lam, K.S., et al., "A New Type of Synthetic Peptide Library for Identifying Ligand-Binding Activity," Nature 354:82-84, Nature Publishing Group, United States (1991).

Landegren, U., et al., "A Ligase-mediated Gene Detection Technique," Science 241(4869):1077-1080, American Association for the Advancement of Science, United States (Aug. 1988).

Lane, P., et al., "CD40 Ligand-independent B Cell Activation Revealed by CD40 Ligand-deficient T Cell Clones: Evidence for Distinct Activation Requirements for Antibody Formation and B Cell Proliferation," European Journal of Immunology 25(6):1788-1793, Wiley-VCH, Germany (Jun. 1995).

Lanier, L.L., "NK Cell Receptors," Annual Review of Immunology 16:359-393, Annual Reviews Inc., United States (1998).

Lanier, L.L., et al., "Immunoreceptor DAP12 Bearing a Tyrosine-based Activation Motif Is Involved in Activating NK Cells," Nature 391 (6668):703-707, Nature Publishing Group, England (Feb. 1998).

Lantz, M., et al., "Characterization in Vitro of a Human Tumor Necrosis Factor-binding Protein. A Soluble Form of a Tumor Necrosis Factor Receptor," The Journal of Clinical Investigation 86(5):1396-1402, American Society for Clinical Investigation, United States (Nov. 1990).

Larin, S.S., et al., "Immunotherapy with Autologous Tumor Cells Engineered to Secrete Tag7/PGRP, an Innate Immunity Recognition Molecule," Gene Medicine 6(7):798-808, John Wiley & Sons, England (Jul. 2004).

Lemaitre, M., et al., "Specific Antiviral Activity of a Poly (L-Lysine)-Conjugated Oligodeoxyribonucleotide Sequence Complementary to Vesicular Stomatitis Virus N Protein mRNA Initiation Site," Proceedings of the National Academy of Sciences 84(3):648-652, National Academy of Science, United States (Feb. 1987).

Letsinger, R.L., et al., "Cholesteryl-conjugated Oligonucleotides: Synthesis, Properties, and activity as Inhibitors of Replication of Human Immunodeficiency Virus in Cell Culture," Proceedings of the National Academy of Sciences USA 86(17):6553-6556, National Academy of Science, United States (Sep. 1989).

Li, E., et al., "Targeted Mutation of the DNA Methyltransferase Gene Results in Embryonic Lethality," Cell 69(6):915-926, Cell Press, United States (Jun. 1992).

Liu, J., et al., "Reversible Self-association Increases the Viscosity of a Concentrated Monoclonal Antibody in Aqueous Solution," Journal of Pharmaceutical Sciences 94(9):1928-1940, Elsevier, United States (2005).

Lizard!, M.P., et al., "Exponential Amplification of Recombinant—RNA Hybridization Probes," Nature Biotechnology 6:1197-1202 (1988).

Loeffler, J.P., et al., "Gene Transfer Into Primary and Established Mammalian Cell Lines With Lipopolyamine-coated DNA," Methods in Enzymology 217:599-618, Academic Press, United States (1993).

Lolis, E. and Bucala, R., "Therapeutic Approaches to Innate Immunity: Severe Sepsis and Septic Shock," Nature Reviews. Drug Discovery 2(8):635-645, Nature Pub. Group, England (Aug. 2003).

Lonberg, N. and Huszar, D., "Human Antibodies from Transgenic Mice," International Reviews of Immunology 13(1):65-93, Informa Healthcare, England (1995).

Lowy, I., et al., "Isolation of Transforming DNA: Cloning the Hamster aprt Gene," Cell 22(3):817-823, Cell Press, United States (Dec. 1980).

LS Bio/LifeSpan BioSciences, Inc., Pglyrpl 1 pgrp antibody (Is-c38137), accessed at http://www.lsbio .com/a nti bod ies/PG LY RP 1-PG RP-Antibody-LS-C38137/37645.

LS Bio/LifeSpan BioSciences, Inc., Pglyrpl/ Pgrp antibody (Is-c579), accessed at http://www.lsbio.com/Antibodies/PGLYRP1-PGRP-Antibody-LS-0579/2801.

LS Bio/LifeSpan BioSciences, Inc., Pglyrpl/pgrp antibody (Is-b4940), accessed at http://www.lsbio.com/Antibodies/PGLYRP1-PGRP-Antibody-LS-B4940/128350.

LS Bio/LifeSpan BioSciences, Inc., Pglyrpl/pgrp antibody (Is-c578), accessed at http://www.lsbio.com/Antibodies/PGLYRP1-PGRP-Antibody-LS-C578/2800.

Lucklow, V.A., et al., "High Level Expression of Nonfused Foreign Genes With Autographa Californica Nuclear Polyhedrosis Virus Expression Vectors," Virology 170(1):31-39 (1989).

Madura, K., et al., "N-recognin/Ubc2 interactions in the N-end rule pathway," The Journal of Biological Chemistry 268(16):12046-12054, The American Society for Biochemistry and Molecular Biology, Inc., United States (1993).

Mag, M., et al., "Synthesis and Selective Cleavage of Oligodeoxyribonucleotides Containing Non-chiral Internucleotide Phosphoramidate Linkages," Nucleic Acids Research 17(15):5973-5988 (Aug. 1989).

Maher, L.J., et al., "DNA Triple-helix Formation: an Approach to Artificial Gene Repressors?," BioEssays 14(12):807-815, Wiley, United States (Dec. 1992).

Malaviya, R., et al., "Mast Cell Modulation of Neutrophil Influx and Bacterial Clearance at Sites of Infection Through TNF-alpha," Nature 381(6577):77-80, Nature Publishing Group, England (May 1996).

Mandell, J.G., et al., "Identification of Protein-protein Interfaces by Decreased Amide Proton Solvent Accessibility," Proceedings of the National Academy of Sciences of the United States of America 95(25):14705-14710, National Academy of Sciences, United States (1998).

Mansart, A., et al., "Hemodynamic Effects of Early Versus Late Glucocorticosteroid Administration in Experimental Septic Shock," Shock 19(1):38-44, Lippincott Williams & Wilkins, United states (Jan. 2003).

Mastrangeli, A., et al., "Diversity of Airway Epithelial Cell Targets for In Vivo Recombinant Adenovirus-Mediated Gene Transfer," Journal of Clinical Investigation 91 (1):225-234, American Society for Clinical Investigation, United States (Jan. 1993).

Maxam, A.M. And Gilbert, W., "A New Method for Sequencing DNA," Proceedings of the National Academy of Sciences USA 74(2):560-564, National Academy of Sciences, United States (Feb. 1977).

McNamara, M.J., et al., "Interleukin-1 Receptor Antibody (Il-1 rab) Protection and Treatment Against Lethal Endotoxemia in Mice," Journal of Surgical Research 54(4):316-321, Academic Press, United States (Apr. 1993).

Medzhitov, R., et al., "Innate Immunity," The New England Journal of Medicine 343(5):338-344, Massachusetts Medical Society, United States (Aug. 2000).

Micanovic, R., et al., "Different Roles of N- and C-Termini in the Functional Activity of FGF21 ," Journal of Cellular Physiology 219(2):227-234, Wiley-Liss, United States (May 2009).

Michael, S.F., et al., "Mutagenesis by Incorporation of a Phosphorylated Oligo During PCR Amplification," BioTechniques 16(3):410-412, Informa Healthcare USA, England (Mar. 1994).

Miller, A.D., et al., "Use of Retroviral Vectors for Gene Transfer and Expression," Methods in Enzymology 217:581-599, Academic Press, United States (1993).

Mohamadzadeh, M., et al., "Activation of Triggering Receptor Expressed on Myeloid Cells-1 on Human Neutrophils by Marburg and Ebola Viruses," Journal of Virology 80(14):7235-7244, American Society for Microbiology, United States (Jul. 2006).

Molloy, E.J., "Triggering Receptor Expressed on Myeloid Cells (TREM) Family and the Application of its Antagonists," Recent Patents on Anti-infective Drug Discovery 4(1):51-56, Bentham Science Publishers, Netherlands (2009).

Morgan, R.A. and Anderson, W.F., "Human Gene Therapy," Annual Review of Biochemistry 62:191-217, Annual Reviews, United States (1993).

Mori, S.I., et al., "A Novel Amino Acid Substitution at the Receptor-binding Site on the Hemagglutinin of H3N2 Influenza a Viruses Isolated From 6 Cases With Acute Encephalopathy During the 1997-1998 Season in Tokyo," Archives of Virology 144(1 ):147-155, Springer-Verlag, Austria (1999).

(56) References Cited

OTHER PUBLICATIONS

Morrison, D.C., et al., "Endotoxins and Disease Mechanisms," Annual Review of Medicine 38:417-432, Annual Reviews, United States (1987).

Morrison, S.L., "Transfectomas Provide Novel Chimeric Antibodies," Science 229(4719):1202-1207, Association for the Advancement of Science, United States (Sep. 1985).

Mulligan, R.C. and Berg, P., "Selection for Animal Cells that Express the Escherichia coll Gene Coding forXanthine-guanine Phosphoribosyltransferase," Proceedings of the National Academy of Sciences USA 78(4):2072-2076, National Academy of Sciences, United States (Apr. 1981).

Mulligan, R.C., "The Basic Science of Gene Therapy," Science 260(5110):926-932, American Association for the Advancement of Science, United States (1993).

Mullinax, R.L., et al., "Expression of a Heterodimeric Fab Antibody Protein in One Cloning Step," BioTechniques 12(6):864-869, Informa Healthcare, England (1992).

Murakami, Y., et al., "Intervention of an Inflammation Amplifier, Triggering Receptor Expressed on Myeloid Cells 1, for Treatment of Autoimmune Arthritis," Arthritis and Rheumatism 60(6): 1615-1623, Wiley-Blackwell, United States (Jun. 2009).

Murshudov, G.N., et al., "Refinement of Macromolecular Structures by the Maximum-likelihood Method," Acta Crystallographica. Section D, Biological Crystallography 53(Pt 3):240-255, Wiley-Blackwell, United States (1997).

Myers, R.M., et al., "Detection of Single Base Substitutions by Ribonuclease Cleavage at Mismatches in RNA:DNA Duplexes," Science 230(4731):1242-1246, American Association forthe Advancement of Science, United States (Dec. 1985).

Myers, R.M., et al., "Detection of Single Base Substitutions in Total Genomic DNA," Nature 313(6002):495-498, Nature Publishing Group, England (Feb. 1985).

Nakajima, H., et al., "2B4: an NkCell Activating Receptor With Unique Specificity and Signal Transduction Mechanism," Human Immunology 61(1):39-43, Elsevier/North-Holland, United Statesman. 2000).

Nakajima, H., et al., "Cutting Edge: Human Myeloid Cells Express an Activating lit Receptor (ILT1) That Associates With Fc Receptor Gamma-chain," Journal of Immunology 162(1):5-8, American Association of Immunologists, United States (Jan. 1999).

Nakazawa, H., et al., "UV and Skin Cancer: Specific P53 Gene Mutation in Normal Skin as a Biologically Relevant Exposure Measurement," Proceedings of the National Academy of Sciences USA 91 (1 ):360-364 (Jan. 1994).

Naramura, M., et al., "Mechanisms of Cellular Cytotoxicity Mediated by a Recombinant Antibody-IL2 Fusion Protein Against Human Melanoma Cells," Immunology Letters 39(1 ):91 -99 (Dec. 1993).

Nathan, C. and Ding, A., "TREM-1: A New Regulator of Innate Immunity in Sepsis Syndrome," Nature Medicine 7(5):530-532, Nature Publishing Company, United States (May 2001).

Nauck, MA. and Meier, J.J., "Glucagon-like Peptide 1 and Its Derivatives in the Treatment of Diabetes," Regulatory Peptides 128(2):135-148, Elsevier/North Holland, Netherlands (Jun. 2005).

Nederman, T., et al., "An in Vitro Bioassay for Quantitation of Human Interferons by Measurements of Antiproliferative Activity on a Continuous Human Lymphoma Cell Line," Biologicals 18(1):29-34, Academic Press, England (Jan. 1990).

Ngo, J.T., et al., "The Protein Folding Problem and Tertiary Structure Prediction, Chapter 14: Computational Complexity Protein Structure Prediction, and the Levinthal Paradox," 492-495 (Mar. 1995).

Nicoletti, L, et al., "A Rapid and Simple Method for Measuring Thymocyte Apoptosis by Propidium Iodide Staining and Flow Cytometry," Journal of Immunological Methods 139(2)271-279, Elsevier, Netherlands (Jun. 1991).

O'Gorman, S., et al., "Recombinase-Mediated Gene Activation and Site-specific Integration in Mammalian Cells," Science 251 (4999):1351 -1355, American Association for the Advancement of Science, United States (Mar. 1991).

O'Hare, K., et al., "Transformation of Mouse Fibroblasts to Methotrexate Resistance by a Recombinant Plasmid Expressing a Prokaryotic Dihydrofolate Reductase," Proceedings of the National Academy of Sciences USA 78(3): 1527-1531, National Academy of Sciences, United States (Mar. 1981).

Ohlsson, K., et al., "Interleukin-1 Receptor Antagonist Reduces Mortality from Endotoxin Shock," Nature 348(6301):550-552, Nature Publishing Group, England (Dec. 1990).

Qi, V.T. and Morrison, S.L., "Chimeric Antibodies," BioTechniques 4(3)214-221 (1986).

Oishi, K., et al., "Inhibition of Neutrophil Apoptosis by Antioxidants in Culture Medium," Scandinavian Journal of Immunology 45(1)21-27, Blackwell Scientific Publications, England (Jan. 1997).

Oliveira, U.S., et al., "Fungal Infections in Marrow Transplant Recipients Under Antifungal Prophylaxis With Fluconazol," Brazilian Journal of Medical and Biological Research 35(7):789-798, Brazilian Association of Scientific Dissemination, Brazil (Jul. 2002).

Olopade, O.I., et al., "Molecular Analysis of Deletions of the Short Arm of Chromosome 9 in Human Gliomas," Cancer Research 52(9)2523-2529, American Association for Cancer Research, United States (May 1992).

Orita, M., et al., "Detection of Polymorphisms of Human DNA by Gel Electrophoresis as Singlestrand Conformation Polymorphisms," Proceedings of the National Academy of Sciences USA 86(8)2766-2770, National Academy of Sciences, United States (Apr. 1989).

Osanai, A., et al., "Mouse Peptidoglycan Recognition Protein PGLYRP-1 Plays a Role in the Host Innate Immune Response Against Listeria Monocytogenes Infection," Infection and Immunity 79(2):858-866, American Society for Microbiology, United States (Feb. 2011).

Owerbach, D., et al., "Genetics of the Large, External, Transformation-sensitive(LETS) Protein: Assignment of a Gene Coding for Expression of Lets to Human Chromosome 8," Proceedings of the National Academy of Sciences USA 75(11):5640-5644, National Academy of Sciences, United States (Nov. 1978).

Padlan, E.A., "A Possible Procedure for Reducing the Immunogenicity of Antibody Variable Domains While Preserving their Ligand-binding Properties," Molecular Immunology 28(4-5):489-498, Pergamon Press., England (Apr. 1991).

Pajunen, L., et al., "Assignment of the Gene Coding for Both the Beta-subunit of Prolyl 4-hydroxylase and the Enzyme Disulfide Isomerase to Human Chromosome Region 17p11—qter," Cytogenetics and Cell Genetics 47(1-2):37-41, Karger, Switzerland (1988).

Pant, S.,D., et al. "Bovine PGLYRP1 Polymorphisms and their Association with Resistance to Mycobacterium avium ssp. Paratuberculosis," Animal Genetics 42(4):354-360, Wiley-Blackwell, England (Aug. 2011).

Perry-O'Keefe, H., et al., "Peptide Nucleic Acid Pre-gel Hybridization: an Alternative to Southern Hybridization," Proceedings of the National Academy of Sciences of the United States of America 93(25):14670-14675, National Academy of Sciences, United States (1996).

Persic, L., et al., "An Integrated Vector System for the Eukaryotic Expression of Antibodies or Their Fragments After Selection From Phage Display Libraries," Gene 187(1):9-18, Elsevier/North-Holland, Netherlands (1997).

Peschon, J.J., et al., "TNF Receptor-Deficient Mice Reveal Divergent Roles for P55 and P75 in Several Models of Inflammation," Journal of Immunology 160(2):943-952, American Association of Immunologists, United States (Jan. 1998).

Petersen, K.H., et al., "A PNA-DNA Linker Synthesis of N-((4,4'-dimethoxytrityloxy)ethyl)-N-(Thymin-1-ylacetyl)glycine," Bioorganic & Medicinal Chemistry Letters 5:1119-1124 (1995).

Pfeffer, K., et al., "Mice Deficient for the 55 Kd Tumor Necrosis Factor Receptor are Resistant to Endotoxic Shock, Yet Succumb to L. Monocytogenes Infection," Cell 73(3):457- 467, Cell Press,United States (May 1993).

Phua, J., et al., "Soluble Triggering Receptor Expressed on Myeloid Cells-1 in Acute Respiratory Infections," The European Respiratory Journal 28(4):695-702, European Respiratory Society, England (Oct. 2006).

Pinkert, C.A., et al., "An Albumin Enhancer Located 10 Kb Upstream Functions Along With Its Promoter to Direct Efficient, Liver-

(56) References Cited

OTHER PUBLICATIONS specific Expression in Transgenic Mice," Genes & Development 1(3):268-276, Cold Spring Harbor Laboratory Press, United States (May 1987).
Pittelkow, M.R. and Scott, R.E., "New Techniques for the in Vitro Culture of Human Skin Keratinocytes and Perspectives on Their Use for Grafting of Patients With Extensive Burns," Mayo Clinic Proceedings 61(10):771-777, Elsevier, England (Oct. 1986).
Potterton, E., et al., "A Graphical User Interface to the CCP4 Program Suite," Acta Crystallographica. Section D, Biological Crystallography 59(Pt 7):1131-1137, Wiley-Blackwell, United States (2003).
Poukoulidou, T., et al., "TREM-1 Expression on Neutrophilsand Monocytes of Septic Patients: Relation to the Underlying Infection and the Implicated Pathogen," BMC Infectious Diseases 11(1): 8 pages, BioMed Central, England (Nov. 2011).
Prosser, J., "Detecting Single-base Mutations," Trends in Biotechnology 11 (6):238-246, Elsevier Science Publishers, England (Jun. 1993).
Proudfoot, N.J., "Transcriptional Interference and Termination Between Duplicated Alpha-globin Gene Constructs Suggests a Novel Mechanism for Gene Regulation," Nature 322(6079):562-565, Nature Publishing Group, England (1986).
Purified anti-human CD354 TREM-1 Antibody, accessed at, https//www.biolegend.com/en-US/products/purified-anti-human-cd354-trem-1—antibody-2826, last accessed on Jun. 12, 2018, 3 pages.
Queen, C. and Baltimore, D., "Immunoglobulin Gene Transcription Is Activated by Downstream Sequence Elements," Cell 33(3):741-748, Cell Press, United States (Jul. 1983).
R&D Systems: "Human TREM-1 Antibody," Retrieved from the internet< URL: http://www.mdsystems.com/Products/MAB1278> on Oct. 26, 2010, p. 1, XP002688074.
Radaev, S., et al., "Crystal Structure of the Human Myeloid Cell Activating Receptor TREM-1," Structure 11(12):1527-1535, Cell Press, United States (Dec. 2003).
Radany, E.H., et al., "Directed Establishment of Rat Brain Cell Lines With the Phenotypic Characteristics of Type 1 Astrocytes," Proceedings of the National Academy of Sciences of the United States of America 89(14):6467-6471, National Academy of Sciences, United States (Jul. 1992).
Ramanathan, B., et al., "Cloning of Porcine Triggering Receptor Expressed on Myeloid Cells-1 (TREM-1) and its Induction by Lipopolysaccharide, Peptidoglycan, and Salmonella Enterica Serovar Typhimurium Infection," Developmental and Comparative Immunology 29(1):1-7, Elsevier Science, United States (2005).
Redl, H., et al., "Animal Models as the Basis of Pharmacologic Intervention in Trauma and Sepsis Patients," World Journal of Surgery 20(4):487-492, Springer International, United States (May 1996).
Rheinwald, J.G., "Chapter 15 Serial Cultivation of Normal Human Epidermal Keratinocytes," Methods in Cell Biology 21A:229-254, Academic Press, United States (1980).
Riechmann, L., et al., "Reshaping Human Antibodies for Therapy," Nature 332(6162):323-327, Nature Publishing Group, United States (Mar. 1988).
Riedemann, N.C., et al., "Novel Strategies for the Treatment of Sepsis," Nature Medicine 9(5):517-524, Nature Publishing Company, United States (May 2003).
Roguska, M.A., et al., "Humanization of Murine Monoclonal Antibodies through Variable Domain Resurfacing," Proceedings of the National Academy of Sciences USA91(3):969-973, National Academy of Sciences, United States (Feb. 1994).
Rosenbaum, V. and Riesner, D., "Temperature-gradient Gel Electrophoresis. Thermodynamic Analysis of Nucleic Acids and Proteins in Purified Form and in Cellular Extracts," Biophysical Chemistry 26(2-3):235-246, Elsevier Science B.V, Netherlands (May 1987).
Rosenberg, H.F, and Gallin, J.I., "Inflammation," In Fundamental Immunology, 4th Ed. W. E. Paul, ed., Chapter 32, p. 1051-1058, Lippincott-Raven Publishers, 1999.

Rosenfeld, M.A., et al., "Adenovirus-mediated Transfer of a Recombinant alpha 1-antitrypsin Gene to the Lung Epithelium in Vivo," Science 252(5004):431-434, American Association for the Advancement of Science, United States (Apr. 1991).
Rosenfeld, M.A., et al., "In Vivo Transfer of the Human Cystic Fibrosis Transmembrane Conductance Regulator Gene to the Airway Epithelium," Cell 68(1): 143-155, Cell Press, United States (Jan. 1992).
Rothe, J., et al., "Mice Lacking the Tumour Necrosis Factor Receptor 1 are Resistant to TNF-mediated Toxicity but Highly Susceptible to Infection by Listeria Monocytogenes," Nature 364(6440)798-802, Nature Publishing Group, England (Aug. 1993).
Royet, J., et al., "Peptidoglycan Recognition Proteins: Modulators of the Microbiome and Inflammation," Nature Reviews Immunology 11 (12):837-851, Nature Pub. Group, England (Nov. 2011).
Saha, S., et al., "Peptidoglycan Recognition Proteins Protect Mice from Experimental Colitis by Promoting Normal Gut Flora and Preventing Induction of Interferon-Gamma," Cell Host & Microbe 8(2):147-162, Cell Press, United States (Aug. 2010).
Saha, S., et al., "PGLYRP-2 and Nod2 are both Required for Peptidoglycan-Induced Arthritis and Local Inflammation," Cell Host& Microbe 5(2):137-150, Cell Press, United States (Feb. 2009).
Saiki, R.K., et al., "Analysis of Enzymatically Amplified Beta-globin and HLA-DQ Alpha DNA With Allele-specific Oligonucleotide Probes," Nature 324(6093):163-166, Nature Publishing Group, England (Nov. 1986).
Saiki, R.K., et al., "Genetic Analysis of Amplified DNA With Immobilized Sequence-specific Oligonucleotide Probes," Proceedings of the National Academy of Sciences of the United States of America 86(16):6230-6234, National Academy of Sciences, United States (Aug. 1989).
Saleeba, J.A. and Cotton, R.G., "Chemical Cleavage of Mismatch to Detect Mutations," Methods in Enzymology 217:286-295, Academic Press, United States (1993).
Sallusto, F., et al., "Efficient Presentation of Soluble Antigen by Cultured Human Dendritic Cells Is Maintained by Granulocyte/macrophage Colony-stimulating Factor Plus Interleukin 4 and Downregulated by Tumor Necrosis Factor Alpha," The Journal of Experimental Medicine 179(4):1109-1118, Rockefeller University Press, United States (1994).
Salmons, B. and Gunzburg, W.H., "Targeting of Retroviral Vectors for Gene Therapy," Human Gene Therapy 4(2):129-141, Liebert, United States (Apr. 1993).
Sanger, F., et al., "DNA Sequencing With Chain-terminating Inhibitors," Proceedings of the National Academy of Sciences of the United States of America 74(12):5463-5467, National Academy of Sciences, United States (Dec. 1977).
Santerre, R.F., et al., "Expression of Prokaryotic Genes for Hygromycin Band G418 Resistance as Dominant-selection Markers in Mouse L Cells," Gene 30(1 -3):147-156, Elsevier/North-Holland, Netherlands (Oct. 1984).
Sawai, H., et al., "Direct Production of the Fab Fragment Derived From the Sperm Immobilizing Antibody Using Polymerase Chain Reaction and cDNA Expression Vectors," American Journal of reproductive immunology 34(1):26-34, Wiley-Blackwell, Denmark (1995).
Schultz, L.D., et al., "Expression and Secretion in Yeast of a 400-kDa Envelope Glycoprotein Derived From Epstein-Barr Virus," Gene 54(1):113-123, Elsevier/North-Holland, Netherlands (1987).
Scott, J.K. and Smith, G.P., "Searching for peptide ligands with an epitope library," Science 249(4967):386-390, American Association for the Advancement of Science, United States (1990).
Seed, B., "An LFA-3 cDNA Encodes a Phospholipid-linked Membrane Protein Homologous to its Receptor CD2," Nature 329(6142):840-842, Nature Publishing Group, England (Oct. 1987).
Sharif, O. and Knapp, S., "From Expression to Signaling: Roles of TREM-1 and TREM-2 in Innate Immunity and Bacterial Infection," Immunobiology 213(9-10)701-713, Elsevier, Netherlands (2008).
Shu, L., et al., "Secretion of a Single-gene-encoded Immunoglobulin From Myeloma Cells," Proceedings of the National Academy of Sciences of the USA 90(17)7995-7999, National Academy of Sciences, United States (1993).

(56) References Cited

OTHER PUBLICATIONS

Skerra, A. and Pluckthun, A., "Assembly of a Functional Immunoglobulin Fv Fragment in *Escherichia coli*," Science 240(4855):1038-1041, Association for the Advancement of Science, United States (May 1988).
Skolnick, "From Genes to Protein Stucture and Function: Novel Applications of Computational Approaches in the Genomic era," Trends in Biotechnology 18:34-39, Elsevier Science Publishers, London (Jan. 2000).
Smith, D.B. and Johnson, K.S., "Single-step Purification of Polypeptides Expressed in *Escherichia coli* as Fusions with Glutathione 5-transferase," Gene 67(1):31 -40, Elsevier, Netherlands (Jul. 1988).
Smith, G.E., et al., "Production of Human Beta Interferon in Insect Cells Infected With a Baculovirus Expression Vector," Molecular and Cellular Biology 3(12):2156-2165, American Society for Microbiology, United States (Dec. 1983).
Smith, T.F. and Zhang, X., "The Challenges of Genome Sequence Annotation or "The Devil is in the Details"," Nature Biotechnology 15(12):1222-1223, Nature America Publishing, United States (Nov. 1997).
Springer, T.A., "Traffic Signals for Lymphocyte Recirculation and Leukocyte Emigration: The Multistep Paradigm," Cell 76(2):301-314, Cell Press, United States (Jan. 1994).
Standen, J. and Bihari, D., "Septic Shock," The New England Journal of Medicine 343:447-448 (Aug. 2010).
Steiner, H., "Peptidoglycan Recognition Proteins: On and Off Switches for Innate Immunity," Immunological Reviews 198:83-96, Blackwell, England (Apr. 2004).
Stemple, D.L. and Anderson, D.J., "Isolation of a Stem Cell for Neurons and Glia From the Mammalian Neural Crest," Cell 71(6):973-985, Cell Press, United States (Dec. 1992).
Stone, R., "Search for Sepsis Drugs Goes on Despite Past Failures," Science 264(5157):365-367, American Association for the Advancement of Science, United States (Apr. 1994).
Studnicka, G.M., et al., "Human-Engineered Monoclonal Antibodies Retain Full Specific Binding Activity by Preserving Non-CDR Complementarity-Modulating Residues," Protein Engineering 7(6):805-814, Oxford University Press, England (1994).
Sugimoto, T., et al., "Determination of Cell Surface Membrane Antigens Common to Both Human Neuroblastoma and Leukemia-lymphoma Cell Lines by a Panel of 38 Monoclonal Antibodies," Journal of the National Cancer Institute 73(1):51-57, Oxford University Press, United States (Jul. 1984).
Sullivan, G.W., et al., "Interaction of Tumor Necrosis Factor-alpha and Granulocyte Colonystimulating Factor on Neutrophil Apoptosis, Receptor Expression, and Bactericidal Function," Proceedings of the Association of American Physicians 108(6):455-466, Blackwell Science, Inc., United States (Nov. 1996).
Szybalska, E.H. and Szybalski, W., "Genetics of Human Cess Line IV DNA-mediated Heritable Transformation of a Biochemical Trait," Proceedings of the National Academy of Sciences USA 48:2026-2034, National Academy of Sciences, United States (Dec. 1962).
Tessarz, A.S. and Cerwenka, A., "The TREM-1/DAP12 Pathway," Immunology Letters 116(2):111-116, Elsevier/North-Holland Biomedical Press, Netherlands (Mar. 2008).
Thomas, K.R. and Capecchi, M.R., "Site-directed Mutagenesis by Gene Targeting in Mouse Embryo-derived Stem Cells," Cell 51(3):503-512, Cell Press, United States (Nov. 1987).
Thoma-Uszynski, S., et al., "Induction of Direct Antimicrobial Activity Through Mammalian Toll-like Receptors ," Science 291 (5508):1544-1547, American Association for the Advancement of Science, United States (Feb. 2001).
Thorpe, Antibody Carriers of Cytotoxic Agents in Cencer Therapy: A Review, in Monoclonal Antibodies 84: Biological and Clinical Applications, Pinchera et al., eds., pp. 475-506 (1985).
Thorpe, P.E. and Ross, W.C., "The Preparation and Cytotoxic Properties of Antibody-toxin Conjugates," Immunological Reviews 62:119-158, Blackwell, England (1982).

Tolstoshev, P., "Gene Therapy, Concepts, Current Trials and Future Directions," Annual Review of Pharmacology and Toxicology 33:573-596, Annual Reviews, United States (1993).
Tomasello, E., et al., "Combined Natural Killer Cell and Dendritic Cell Functional Deficiency in KARAP/DAP12 Loss-of-function Mutant Mice," Immunity 13(3):355-364, Cell Press, United States (Sep. 2000).
Tomic, M., et al., "A Rapid and Simple Method for Introducing Specific Mutations Into Any Position of DNA Leaving All Other Positions Unaltered," Nucleic Acids Research 18(6):1656, Oxford University Press, England (Mar. 1990).
Tracey, K.J., et al., "Shock and Tissue Injury Induced by Recombinant Human Cachectin," Science 234(4775):470-474, American Association for the Advancement of Science, United States (1986).
Traunecker, A., et al., "Myeloma Based Expression System for Production of Large Mammalian Proteins," Trends in Biotechnology 9(4):1 09-113, Elsevier Science Publisher, England (Apr. 1991).
Trowbridge, R.S., et al. , "Establishment and Characterization of Ferret Cells in Culture," In Vitro 18(11):952-960, Tissue Culture Assn, United States (Nov. 1982).
Tsuji, E., et al., "Simultaneous Onset of Acute Inflammatory Response, Sepsis-like Symptoms and Intestinal Mucosal Injury After Cancer Chemotherapy," International Journal of Cancer 107(2):303-308, Wiley-Liss, United States (Nov. 2003).
Turnbull, I.R., et al., "Cutting Edge: TREM-2 Attenuates Macrophage Activation," Journal of Immunology 177(6):3520-3524, American Association of Immunologists, United States (Sep. 2006).
Ulevitch, R.J., et al. , "Recognition of Gram-negative Bacteria and Endotoxin by the Innate Immune System," Current Opinion in Immunology 11(1):19-22, Elsevier, England (Feb. 1999).
Upender, M., et al. , "Megaprimer Method for in Vitro Mutagenesis Using Parallel Templates," Biotechniques 18(1):29-30, Informa Healthcare USA, Inc, England (Jan. 1995).
Urban, M.B., et al., "NF-kappa B Contacts DNA by a Heterodimer of the p50 and p65 Subunit," The EMBO Journal 10(7): 1817-1825, Wiley Blackwell, England (Jul. 1991).
Van DerKrol, A.R., et al., "Modulation of Eukaryotic Gene Expression by Complementary RNA or DNA Sequences," Biotechniques 6(10):958-976, Informa Healthcare, United States (Nov. 1988).
Van Keuren, M., et al. , "Regional Assignment of Human Liver-Type 6-Phosphofructokinase to Chromosome 21q22.3 by Using Somatic Cell Hybrids and a Monoclonal Anti-L Antibody," Human Genetics 74(1):34-40, Springer Verlag, Germany (Sep. 1986).
Van Zee, K.J., et al., "Tumor Necrosis Factor Soluble Receptors Circulate During Experimental and Clinical Inflammation and Can Protect Against Excessive Tumor Necrosis Factor Alpha in Vitro and in Vivo," Proceedings of the National Academy of Sciences of the United States of America 89(11)4845-4849, National Academy of Sciences, United States (Jun. 1992).
Vincent, J.L., et al., "Clinical Trials of Immunomodulatory Therapies in Severe Sepsis and Septic Shock," Clinical Infectious Diseases 34(8):1084-1093, Oxford University Press, United States (Apr. 2002).
Wada, K.N., et al., "Codon Usage Tabulated From the Genbank Genetic Sequence Data," Nucleic Acids Research 20:2111-2118, Oxford University Press, England (May 1992).
Wakayama, T., et al., "Mice Cloned From Embryonic Stem Cells," Proceedings of the National Academy of Sciences of the United States of America 96(26):14984-14989, National Academy of Sciences, United States (Dec. 1999).
Walsh, C.E., et al., "Gene Therapy for Human Hemoglobinopathies," Proceedings of the Society for Experimental Biology and Medicine 204(3):289-300, Blackwell Science, United States (Dec. 1993).
Wang, H., et al., "HMG-1 as a Late Mediator of Endotoxin Lethality in Mice," Science 285(5425)248-251, American Association for the Advancement of Science, United States (1999).
Wang, Q., et al., "A Packaging Cell Line for Propagation of Recombinant Adenovirus Vectors Containing Two Lethal Gene-region Deletions," Gene Therapy 2(10):775-783, Nature Publishing Group, England (Dec. 1995).
Warren, H.S., "Strategies for the Treatment of Sepsis," The New England Journal of Medicine 336(13):952-953, Massachusetts Medical Society, United States (Mar. 1997).

(56) References Cited

OTHER PUBLICATIONS

Wasmuth, H.E., et al., "Patients With Acute on Chronic Liver Failure Display "Sepsis-like" Immune Paralysis," Journal of Hepatology 42(2): 195-201, Elsevier, Netherlands (Feb. 2005).
Weintraub, H., et al., "Anti-sense RNA as a MolecularTool for Genetic Analysis,"Trends in Genetics 1:22-25 (1985).
Weis, D.D., et al., "Semi-automated Data Processing of Hydrogen Exchange Mass Spectra Using HX-express," Journal ofthe American Society for Mass Spectrometry 17(12):1700-1703, Springer, United States (2006).
Wells, J.A., "Additivity of Mutational Effects in Proteins," Biochemistry 29(37):8509-8517, American Chemical Society, United States (Sep. 1990).
Wheeler, A.P. and Bernard, G.R., "Treating Patients With Severe Sepsis," The New England Journal of Medicine 340(3)207-214, Massachusetts Medical Society, United States (Jan. 1999).
Wigler, M., et al., "Transfer of Purified Herpes Virus Thymidine Kinase Gene to Cultured Mouse Cells," Cell 11(1)223-232, Cell Press, United States (May 1977).
Wigler, M., et al., "Transformation of Mammalian Cells with an Amplifiable Dominant-Acting Gene," Proceedings of the National Academy of Sciences USA 77(6):3567-3570, National Academy of Sciences, United States (Jun. 1980).
Wilmut, I., et al., "Viable Offspring Derived From Fetal and Adult Mammalian Cells," Nature 385(6619):810-813, Nature Publishing Group, England (Feb. 1997).
Wilson, I.A., et al., "The Structure of an Antigenic Determinant in a Protein," Cell 37(3)767-778, Cell Press, United States (Jul. 1984).
Winoto, A. and Baltimore, D., "A Novel, Inducible and T Cell-specific Enhancer Located at the 3' End of the T Cell Receptor Alpha Locus," The EMBO Journal 8(3)729-733, Wiley Blackwell, England (Mar. 1989).
Wu, G.Y. and Wu, C.H., "Delivery Systems for Gene Therapy," Biotherapy 3(1):87-95, Kluwer Academic Publishers, Netherlands (1991).
Wu, G.Y. and Wu, C.H., "Receptor-mediated in Vitro Gene Transformation by a Soluble DNA Carrier System," The Journal of Biological Chemistry 262(10)4429-4432, American Society for Biochemistry and Molecular Biology, United States (1987).
Xu, J., et al., "Fibroblast Growth Factor 21 Reverses Hepatic Steatosis, Increases Energy Expenditure, and Improves Insulin Sensitivity in Diet-induced Obese Mice," Diabetes 58(1):250-259, American Diabetes Association, United States (2009).
Yadav, S., et al., "Specific Interactions in High Concentration Antibody Solutions Resulting in High Viscosity," Journal of Pharmaceutical Sciences 99(3):1152-1168, Elsevier, United States (2010).
Yadav, S., et al., "Viscosity Behavior of High-concentration Monoclonal Antibody Solutions: Correlation With Interaction Parameter and Electroviscous Effects," Journal of Pharmaceutical Sciences 101 (3):998-1011, Elsevier, United States (2012).
Yadav, Sandeep, et al., "Establishing a Link Between Amino Acid Sequences and SelfAssociating and Viscoelastic Behavior of Two Closely Related Monoclonal Antibodies", Pharmaceutical Research, 2011, vol. 28, pp. 1750-1764.
Yadav, Sandeep, et al., "The Influence of Charge Distribution on Self-Association and Viscosity Behavior of Monoclonal Antibody Solutions", Molecular Pharmaceutics, 2012, vol. 9, pp. 791-802.
Yamashita, Y., et al., "Inhibitory and Stimulatory Functions of Paired Ig-like Receptor (PIR) Family in RBL-2H3 Cells.," Journal of Immunology 161(8)4042-4047, American Association of Immunologists, United States (Oct. 1998).
Yie, J., et al., "FGF21 N- and C-termini Play Different Roles in Receptor Interaction and Activation," FEBS Letters 583(1):19-24, John Wiley & Sons Ltd, England (Jan. 2009).
Zervos, A.S., et al., Mxl1, a protein that specifically interacts with Maxto bind Myc-Max recognition site,Cell 72(2):223-232, Elsevier Science, United States (1993).
Zijlstra, M., et al., "Germ-line Transmission of a Disrupted beta 2-microglobulin Gene Produced by Homologous Recombination in Embryonic Stem Cells," Nature 342(6248)435-438, Nature Publishing Group, England (Nov. 1989).
Zon, G., et al., "Oligonucleotide Analogues as Potential Chemotherapeutic Agents," Pharmaceutical Research 5(9)1539-549, Kluwer Academic/Plenum Publishers, United States (Sep. 1988).
Zuckermann, R.N., et al., "Discovery of nanomolar ligands for 7-transmembrane G-protein-coupled receptors from a diverse N-(substituted)glycine peptoid librar," Journal of Medicinal Chemistry 37(17):2678-2685, ACS Publications, United Kingdom (1994).
Zwaveling, J.H., et al., "High Plasma Tumor Necrosis Factor (TNF)-alpha Concentrations and a Sepsis-like Syndrome in Patients Undergoing Hyperthermic Isolated Limb Perfusion With Recombinant TNF-alpha, Interferon-gamma, and Melphalan," Critical Care Medicine 24(5):765-770, Lippincott Williams & Wilkins, United States (May 1996).

\* cited by examiner

FIG. 1A

| Variant | Analyte | Kon (1/Ms) | koff (1/Ms) | KD (nM) |
|---|---|---|---|---|
| IgG1.3f | hu-TREM1 | 1.4E+06 | 1.3E-03 | 0.91 |
| IgG1.3f | cy-TREM1 | 4.0E+05 | 1.4E-03 | 3.4 |

FIG. 1B

| Variant | ka (1/Ms) | kd (1/s) | KD (M) | Rmax (RU) | Chi$^2$ (RU$^2$) |
|---|---|---|---|---|---|
| IgG4 A | 1.42E+06 | 1.43E-03 | 1.01E-09 | 333 | 0.234 |
| IgG4 B | 1.46E+06 | 1.43E-03 | 9.8E-10 | 334 | 0.228 |
| IgG1.1f | 1.64E+06 | 1.42E-03 | 8.66E-10 | 400 | 0.301 |
| IgG1.3f | 1.65E+06 | 1.40E-03 | 8.50E-10 | 373 | 0.282 |
| IgG4-Aba CT (mod) | 1.70E+06 | 1.51E-03 | 8.89E-10 | 374 | 0.25 |
| IgG1-Aba CT (mod) | 1.62E+06 | 1.45E-03 | 8.99E-10 | 342 | 0.255 |
| IgG1.1f (M to Q mutant) | 1.66E+06 | 1.88E-03 | 1.13E-09 | 347 | 0.277 |
| IgG4 (M to Q mutant) | 1.46E+06 | 1.85E-03 | 1.26E-09 | 376 | 0.262 |
| IgG4 (M to L mutant) | 1.29E+06 | 3.56E-03 | 2.75E-09 | 340 | 0.348 |

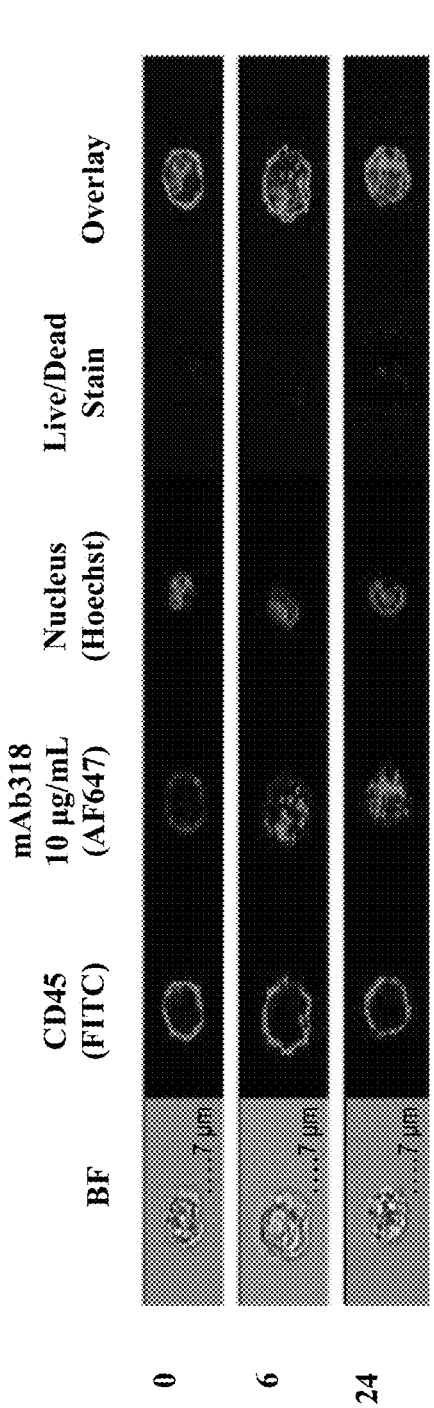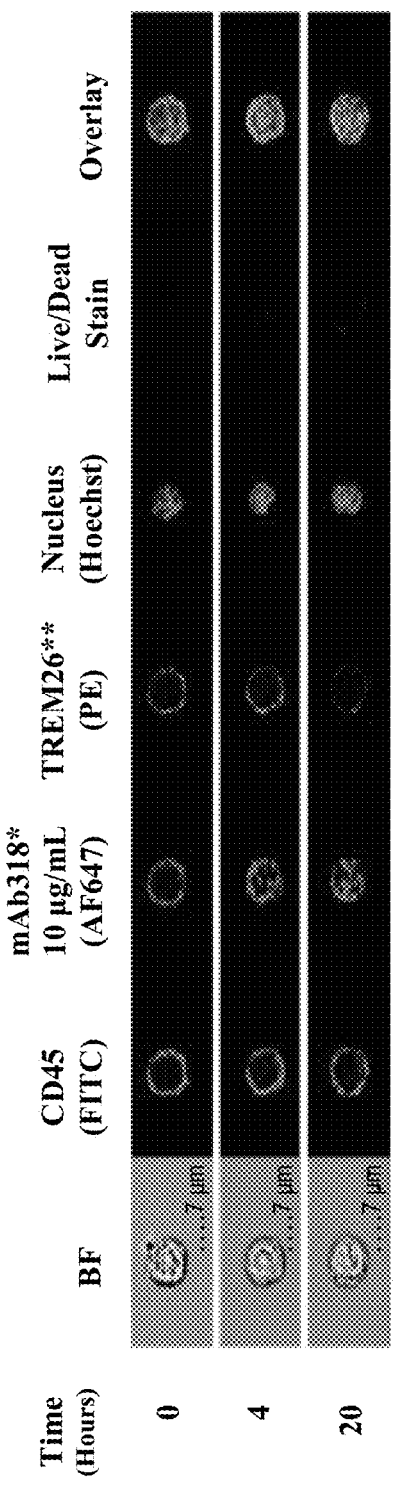
FIG. 2A
FIG. 2B

FIG. 4

| Cell Type | Assay | Stimulus | mAb 0318-IgG4 IC50 (pM) | mAb 0318-IgG1.3f IC50 (pM) | mAb 0318-IgG1.1f IC50 (pM) | mAb 0318-IgG1-Aba IC50 (pM) | mAb 0318-IgG4-Aba IC50 (pM) |
|---|---|---|---|---|---|---|---|
| PBMC | TNF-α | PGRP + PGN-Ecndss | 42 (N=3) | 25 (N=12) | 14 (N=9) | 20 (N=3) | 19 (N=3) |
| | IL-6 | | N/D | 32.26 (N=2) | N/D | N/D | N/D |
| Monocyte | TNF-α | PGRP + PGN-Ecndss | 4 (N=3) | 11 (N=9) | 9 (N=12) | 12.5 (N=3) | 15.5 (N=3) |
| Endogenous Ligand Stim Monocytes | TNF-α | PMA-Stim Neutrophil Endogenous PGRP | 44 (N=3) | 22 (N=6) | 19 (N=6) | 26 (N=6) | 17 (N=6) |
| RBC-Sedimented Whole Blood | TNF-α | PGRP + PGN-Ecndss | 55 (N=6) | 96 (N=6) | 63 (N=9) | 58 (N=3) | 94 (N=3) |
| | IL-6 | | 68.4 (N=6) | N/D | N/D | N/D | N/D |
| Neutrophils | IL-8 | PGRP + PGN-Ecndss | 37.5 (N=3) | 9 (N=3) | N/D | N/D | N/D |

FIG. 5A

|  | IL-8 Cytokine Expression (pg/mL) | | | mAb 0318-IgG1.3f Inhibition | |
|---|---|---|---|---|---|
| Donors | PGN Only | PGRP/PGN | Fold Change | Max Inhibition (%) | $IC_{50}$ (pM) |
| 298 | 518 | 4886 | 9 | 81 | 11 |
| 294 | 391 | 2319 | 6 | 81 | 14 |
| 322 | 425 | 1420 | 3 | 82 | 11 |
| 344 | 393 | 1188 | 3 | 61 | 12 |
| 351 | 388 | 1318 | 3 | 92 | 9 |
| 356 | 276 | 1377 | 5 | 62 | 12 |
|  |  |  |  | Mean $IC_{50}$ | 12 |
|  |  |  |  | Std Dev of $IC_{50}$ | 2 |

FIG. 5B

| Donors | % IL-8 +ve cells (PGN only) | % IL-8 + cells (PGRP+PGN) | $IC_{50}$ (pM) | $IC_{50}$ pM (Mean±SD) |
|---|---|---|---|---|
| A | 0.019 | 19.2 | 20.5 | 19.6±0.012 |
| B | 0.057 | 12.4 | 27.5 | |
| C | 0.043 | 21.1 | 36.0 | |
| D | 0.097 | 03.90 | ND* | |
| E | 0.025 | 29.25 | 5.2 | |
| F | 0.046 | 19.25 | 8.7 | |
| G | 0.021 | 04.04 | ND* | |

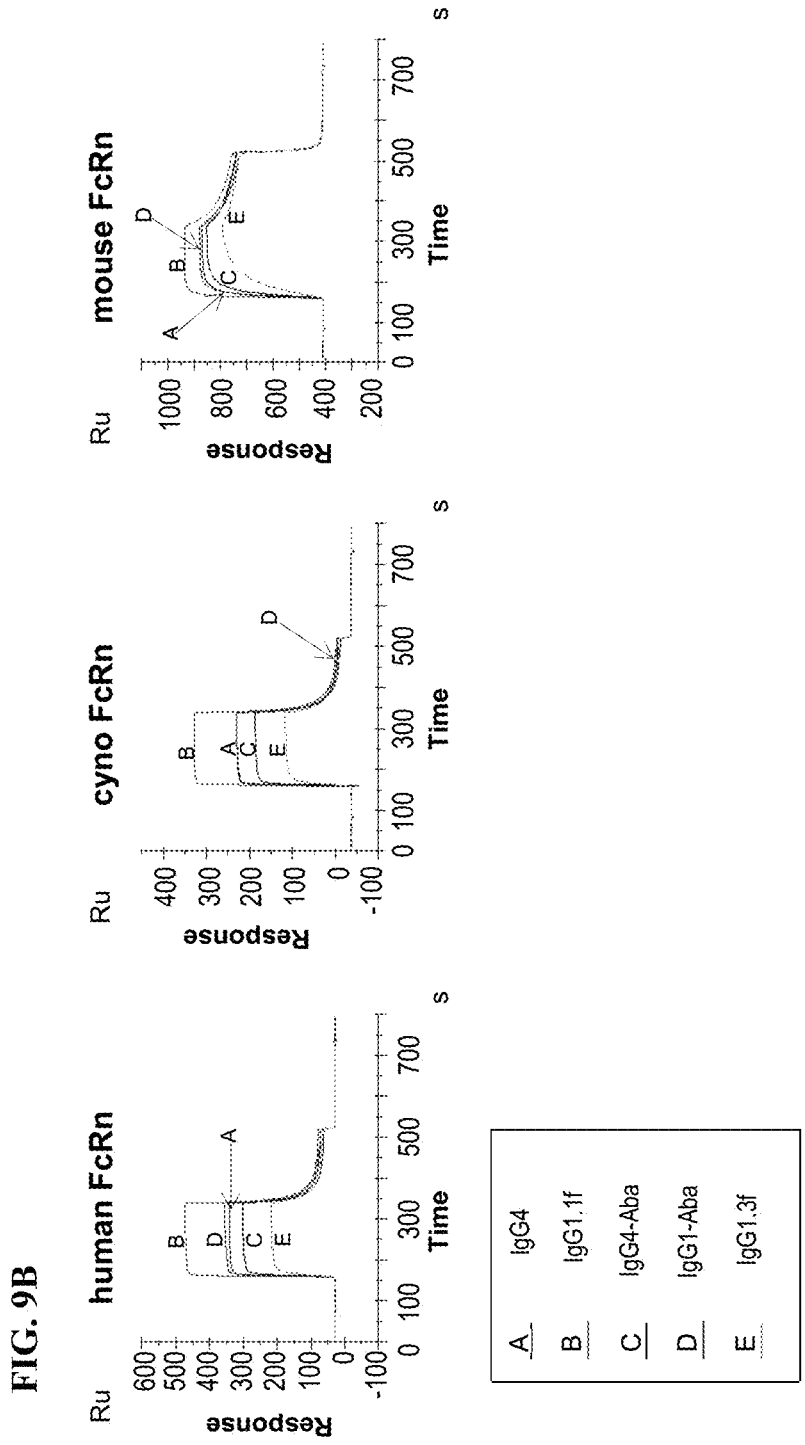

SEQUENCE LISTING

<160> NUMBER OF SEQ ID NOS: 85

<210> SEQ ID NO 1
<211> LENGTH: 234
<212> TYPE: PRT
<213> ORGANISM: homo sapiens

<400> SEQUENCE: 1

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

```
Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
        180                 185                 190

Thr Asn Val Thr Asp Ile Ile Arg Val Pro Val Phe Asn Ile Val Ile
            195                 200                 205

Leu Leu Ala Gly Gly Phe Leu Ser Lys Ser Leu Val Phe Ser Val Leu
        210                 215                 220

Phe Ala Val Thr Leu Arg Ser Phe Val Pro
225                 230
```

<210> SEQ ID NO 2
<211> LENGTH: 225
<212> TYPE: PRT
<213> ORGANISM: homo sapiens

<400> SEQUENCE: 2

```
Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Tyr Ser Phe Gln Val Pro Gly Pro
        195                 200                 205

Leu Val Trp Thr Leu Ser Pro Leu Phe Pro Ser Leu Cys Ala Glu Arg
    210                 215                 220

Met
225
```

<210> SEQ ID NO 3
<211> LENGTH: 150
<212> TYPE: PRT
<213> ORGANISM: homo sapiens

<400> SEQUENCE: 3

```
Met Arg Lys Thr Arg Leu Trp Gly Leu Leu Trp Met Leu Phe Val Ser
1               5                   10                  15
```

Glu Leu Arg Ala Ala Thr Lys Leu Thr Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Arg Cys Ser Thr Leu Ser Phe
    130                 135                 140

Ser Trp Leu Val Asp Ser
145                 150

<210> SEQ ID NO 4
<211> LENGTH: 3333
<212> TYPE: DNA
<213> ORGANISM: Homo sapiens

<400> SEQUENCE: 4
gtgcaacttt ccgaagcctc taggtcattg tggtgccttg tagctgtccc gggagccctc      60
agcagcagtt ggagctggtg cacaggaagg atgaggaaga ccaggctctg ggggctgctg     120
tggatgctct ttgtctcaga actccgagct gcaactaaat taactgagga aaagtatgaa     180
ctgaaagagg gcagaccct ggatgtgaaa tgtgactaca cgctagagaa gtttgccagc      240
agccagaaag cttggcagat aataagggac ggagagatgc caagaccct ggcatgcaca      300 gagaggcctt caaagaattc ccatccagtc aagtgggga ggatcatact agaagactac      360
catgatcatg gtttactgcg cgtccgaatg gtcaaccttc aagtggaaga ttctggactg     420
tatcagtgtg tgatctacca gcctcccaag gagcctcaca tgctgttcga tcgcatccgc     480
ttggtggtga ccaagggttt ttcagggacc cctggctcca atgagaattc tacccagaat     540
gtgtataaga ttcctcctac caccactaag gccttgtgcc cactctatac cagccccaga     600
actgtgaccc aagctccacc caagtcaact gccgatgtct ccactcctga ctctgaaatc     660
aaccttacaa atgtgacaga tatcatcagg gttccggtgt tcaacattgt cattctcctg     720
gctggtggat tcctgagtaa gagcctggtc ttctctgtcc tgtttgctgt cacgctgagg     780
tcatttgtac cctaggccca cgaacccacg agaatgtcct ctgacttcca gccacatcca     840
tctggcagtt gtgccaaggg aggagggagg aggtaaaagg cagggagtta ataacatgaa     900
ttaaatctgt aatcaccggc tatttctaaa gtcagcgtct caccttcctg cccactgccc     960
tcgttcctct aataatcttg ggtgggcatt tgtgcctcag aaaagaagtt acagccccaa    1020
acatgcttgg tccttcattc caccagccac ttggggttgg catgaaatac agacagctca    1080
atgcttttca ccgtaattct cttgtggggg ctgtgacatg cagaaggcac acctgatact    1140
tctcctgctc agttttgccc tggaccatac aattttggcc tgacctggac agagctccca    1200
ctacagaagc atcctgctcg ccccatgctg ggacttcctc tttctagcat cagacacttg    1260
ggtttcatgc ttatgtgtgg ttctttccaa cactcccaga aagggtgtt gaagattgtg     1320

```
gaacctggag aaataagaca tcgtggtgag aaagtgcatc cttctcagag aaagagttaa    1380
aactgagtat cttcttctgg ggaaatactg gcaggccgag atgggatcca taggagagca    1440
acaacagacc atgtcagaca tcctgtgtgc atttatcgct ggatcctgaa aatagccccg    1500
tgaaggcaga aatgtatgtg actagaacga ggccacatga ataagccact gcccactggc    1560
aggagtgaaa actgaagcgc tccttacctg aaggacccca aaaccatata gaatagaata    1620
accaggagtt ccgcctgtgt ctaaatgcct cttttcctgt atcacacaag gtcagggat     1680 ggtggagtaa aagctctccc cctgggaggc ttctggaggc tgtccccatg tgcttgccta    1740
gttccccact ctgccctcct cctcttctct cagtctgctc ctggaacacc tgcctcagtt    1800
tccatgctct ctccagtgcc ctccccggtg aagcaggtag gtgttcaggc caccacagag    1860
acaatctctg tgggagattg tcttgcaatc tcccacagat ttcaatcagg attttgttat    1920
ttcctacttt gagctttaaa gggaaatggg cctcatgggt ggggaaagga tggtgggtcc    1980
ttccagccca atttagtgat gcccagggca gatattatcc tcagttccca agagcaatca    2040
tacttttcca cataccgt gtgtctcatg ttaggtaaat gtattttac aatgagcacc    2100 acttctgtgg aaaagttcc ctgcacgggg aggtccagct tccagactgc tccatcgcat    2160
aaggacttcc ccattcccct aaatgctgct ctgtcagaac ctgcccaggt aatggtaatg    2220
accctagaga gatgatttct gaaccgcaat tttgagccca ttagaaggtg tgtggtgggc    2280
atttatttca tcctgatgct ctggtgagaa tctttgcaga cgcactagat ccagaagctg    2340
ttaatcttgg tgcatttatt ttcctaccta aaagaaccaa gcagctcaga ggcagtgact    2400
gtacaggatg cagtgtttat aataatgctg agcttgctgg tctggaaccc cacactttag    2460
caatcccagc attgttcctg tttatgaagt tgacaaagtg accagggcaa ggggggtatta    2520 tcattaaata cactctagga gaggcagaac acatgagggc aatgtttttc agaggtcttt    2580
aggccaccgc atcagattct cctggagcat aaagcaaatg ctttatgagt ccagggcccc    2640
tgcagaccta ctgtatacta gtatacagct ccctcttagt ggatctcaag cttgtttcca    2700
aaaagtcatt acactcctta ccaaagccca tgacacattc atacagattc atccagacat    2760
aacccactgc atggtccagt gcatgcttgt gtgcttaact tattatagat caagtgttat    2820
ttaagtccaa catattaaac gtgactgaaa tattatatgc actaaatcgg aagacaaatg    2880
gccgtgctgg atactctccc atttgcactt acaggccacg ccatgctcca tcctccccat    2940
cctgcctggg aacctgacca atgtggctaa accagcaggc tccctggctg ccagcttctg    3000
gctggttgag ccaatgggaa gcatgagagg agagccgagg gtggggagac agtcagatca    3060
gggtttctgt cctcagggct ccctccctgg caggtggtgg caggagtggc tgcattcccc    3120
tctgaaggct ccttcaagcc tctcagcaaa cagctcccat ctccaagtcc agccacctgt    3180
tccatcctct cctctgtagg cccagcagtg ggaatgaccc accactattg ccagcctcag    3240
catactgaag cacccttac tggattccct aaattctatg cacatgttta ttaaatgctc    3300
ctcaattacc cagttaaaaa aaaaaaaaaa aaa                                 3333

<210> SEQ ID NO 5
<211> LENGTH: 2102
<212> TYPE: DNA
<213> ORGANISM: homo sapiens

<400> SEQUENCE: 5
attgtggtgc cttgtagctg tcccgggagc cctcagcagc agttggagct ggtgcacagg      60
aaggatgagg aagaccaggc tctgggggct gctgtggatg ctctttgtct cagaactccg     120
```

```
agctgcaact aaattaactg aggaaaagta tgaactgaaa gaggggcaga ccctggatgt      180
gaaatgtgac tacacgctag agaagtttgc cagcagccag aaagcttggc agataataag      240
ggacggagag atgcccaaga ccctggcatg cacagagagg ccttcaaaga attcccatcc      300
agtccaagtg gggaggatca tactagaaga ctaccatgat catggtttac tgcgcgtccg      360
aatggtcaac cttcaagtgg aagattctgg actgtatcag tgtgtgatct accagcctcc      420
caaggagcct cacatgctgt tcgatcgcat ccgcttggtg gtgaccaagg ttttttcagg      480
gacccctggc tccaatgaga attctaccca gaatgtgtat aagattcctc ctaccaccac      540
taaggccttg tgcccactct ataccagccc cagaactgtg acccaagctc acccaagtc      600 aactgccgat gtctccactc ctgactctga atcaaccttt acaaatgtga cagatatcat      660
caggtatagt ttccaggtcc ctgggcccct ggtttggaca ctgagccctt gtttcccag      720 tctgtgtgct gagaggatgt gaaagtgagg aaaggggag ggtggggcag gagaagactt      780
gagtcacatt agtctgggta gaaatgtcca ggggaagaag gaagtggtga tggagaatag      840
gggaggctct cagccaggct gtccttctcc ccagttcacc ttctttgttt ccttgcaacc      900
tgagtattaa agagagggaa atggcatctt ccccaagttc cagtggagct catccaaccc      960
caggggcctg atgggcagtg ggaaagcact ctgagtgagg ggccctggat ctagtgttgg    1020
cctgactaac tgaatgtgac tttgggtgag tcaggaaccc tctctggctt tagcttcttt    1080
gacaattcag taggcatggt agaaacccaa agctggaaga cattgtccac ctaataactc    1140
tcagcaggag ctggagctgg ggctaaatgc agtattggtt tttgccttat tgttttttaa    1200
ataacattgt tgcatgtgcc caattataga taaatagaat cagaattttt gcagatgagg    1260
tccctctcag tattttaat aagatgttta ggagatttct aatgtgtagg caaacttaag    1320
aaccactaac ttagcaattt cacacctctt tacagttatt aaatgttgat ttatattaga    1380
atgtgtttat cattaaatac tgaattatca ggatggaaat actttccac atcaccacta    1440 gtctaacatg tctttttct catattctct tctagtcttt attcatgttt atacatattt    1500
taatatggca gtaagtctaa ttatacatgt ttttattctt ttccttgctg aaattattct    1560
ttgatgctgc tacctaaatt tcataaatat aatttcaatg agtgcatatt tttctatcaa    1620
ttgggaaagc cataacttac ataaccattg gcctgttctt agacattgat atagtgttga    1680
taactctgag ataacatat tcttgcagat atatttttct tctttaaat aattaactcg    1740 aaatttccat gagataattt aaacactgat atcatttgt atacaaatag catctaccaa    1800
tggtcttcca aaagattgga aacaatttgc agtgtgatcc attaagcata aataaagcag    1860
tgtcatggca ggcttacaga cacggattta gtcttttaaa tcattaaata gtgtgagtta    1920
aatcacattc ctgctaaaac aaatgtgaac tggtgcctgc tctaatttct ctatgagtgt    1980
agactccacc tccatatggg tagtggcagt gccttttttc ccattatgtt gtttggggaa    2040
caaagtgctc attaaacttc tgtggaataa atcaaacgaa tgatcaaaaa aaaaaaaaaa    2100
aa                                                                   2102
```

<210> SEQ ID NO 6
<211> LENGTH: 3140
<212> TYPE: DNA
<213> ORGANISM: homo sapiens

<400> SEQUENCE: 6

```
gtgcaacttt ccgaagcctc taggtcattg tggtgccttg tagctgtccc gggagccctc       60
```

-continued

| | | | | | |
|---|---|---|---|---|---|
| agcagcagtt | ggagctggtg | cacaggaagg | atgaggaaga | ccaggctctg | ggggctgctg | 120 |
| tggatgctct | ttgtctcaga | actccgagct | gcaactaaat | taactgagga | aaagtatgaa | 180 |
| ctgaaagagg | ggcagaccct | ggatgtgaaa | tgtgactaca | cgctagagaa | gtttgccagc | 240 |
| agccagaaag | cttggcagat | aataagggac | ggagagatgc | ccaagaccct | ggcatgcaca | 300 |
| gagaggcctt | caaagaattc | ccatccagtc | caagtgggga | ggatcatact | agaagactac | 360 |
| catgatcatg | gtttactgcg | cgtccgaatg | gtcaaccttc | aagtggaaga | ttctggactg | 420 |
| tatcagtgtg | tgatctacca | gcctcccaag | gagcctcaca | tgctgttcga | tcgcatccgc | 480 |
| ttggtggtga | ccaaggggtt | ccggtgttca | acattgtcat | tctcctggct | ggtggattcc | 540 |
| tgagtaagag | cctggtcttc | tctgtcctgt | ttgctgtcac | gctgaggtca | tttgtaccct | 600 |
| aggcccacga | acccacgaga | atgtcctctg | acttccagcc | acatccatct | ggcagttgtg | 660 |
| ccaagggagg | agggaggagg | taaaaggcag | ggagttaata | acatgaatta | aatctgtaat | 720 |
| caccggctat | ttctaaagtc | agcgtctcac | cttcctgccc | actgccctcg | ttcctctaat | 780 |
| aatcttgggt | gggcatttgt | gcctcagaaa | agaagttaca | gccccaaaca | tgcttggtcc | 840 |
| ttcattccac | cagccacttg | gggttggcat | gaaatacaga | cagctcaatg | cttttcaccg | 900 |
| taattctctt | gtggggctg  | tgacatgcag | aaggcacacc | tgatacttct | cctgctcagt | 960 |
| tttgccctgg | accatacaat | tttggcctga | cctggacaga | gctcccacta | cagaagcatc | 1020 |
| ctgctcgccc | catgctggga | cttcctcttt | ctagcatcag | acacttgggt | tcatgctta  | 1080 |
| tgtgtggttc | tttccaacac | tcccagaaaa | gggtgttgaa | gattgtggaa | cctggagaaa | 1140 |
| taagacatcg | tggtgagaaa | gtgcatcctt | ctcagagaaa | agagttaaac | tgagtatctt | 1200 |
| cttctgggga | aatactggca | ggccgagatg | ggatccatag | gagagcaaca | acagaccatg | 1260 |
| tcagacatcc | tgtgtgcatt | tatcgctgga | tcctgaaaat | agccccgtga | aggcagaaat | 1320 |
| gtatgtgact | agaacgaggc | cacatgaata | agccactgcc | cactggcagg | agtgaaaact | 1380 |
| gaagcgctcc | ttacctgaag | gaccccaaaa | ccatatagaa | tagaataacc | aggagttccg | 1440 |
| cctgtgtcta | aatgcctctt | ttcctgtatc | acacaagggt | cagggatggt | ggagtaaaag | 1500 |
| ctctccccct | gggaggcttc | tggaggctgt | ccccatgtgc | ttgcctagtt | ccccactctg | 1560 |
| ccctcctcct | cttctctcag | tctgctcctg | gaacacctgc | ctcagtttcc | atgctctctc | 1620 |
| cagtgccctc | cccggtgaag | caggtaggtg | ttcaggccac | cacagagaca | atctctgtgg | 1680 |
| gagattgtct | tgcaatctcc | cacagatttc | aatcaggatt | ttgttatttc | ctactttgag | 1740 |
| ctttaaaggg | aaatgggcct | catggtgggg | gaaaggatgg | tgggtccttc | cagcccaatt | 1800 |
| tagtgatgcc | cagggcagat | attatcctca | gttcccaaga | gcaatcatac | ttttccacac | 1860 |
| ataccgtgtg | tctcatgtta | ggtaaatgta | tttttacaat | gagcaccact | tctgtggaaa | 1920 |
| aagttccctg | cacggggagg | tccagcttcc | agactgctcc | atcgcataag | gacttcccca | 1980 |
| ttcccctaaa | tgctgctctg | tcagaacctg | cccaggtaat | ggtaatgacc | ctagagagat | 2040 |
| gatttctgaa | ccgcaatttt | gagcccatta | gaaggtgtgt | ggtgggcatt | tatttcatcc | 2100 |
| tgatgctctg | gtgagaatct | ttgcagacgc | actagatcca | gaagctgtta | atcttggtgc | 2160 |
| atttattttc | ctacctaaaa | gaaccaagca | gctcagaggc | agtgactgta | caggatgcag | 2220 |
| tgtttataat | aatgctgagc | ttgctggtct | ggaaccccac | actttagcaa | tcccagcatt | 2280 |
| gttcctgttt | atgaagttga | caaagtgacc | agggcaaggg | ggtattatca | ttaaatacac | 2340 |
| tctaggagag | gcagaacaca | tgagggcaat | gttttttcaga | ggtctttagg | ccaccgcatc | 2400 |
| agattctcct | ggagcataaa | gcaaatgctt | tatgagtcca | gggcccctgc | agacctactg | 2460 |

```
tatactagta tacagctccc tcttagtgga tctcaagctt gtttccaaaa agtcattaca    2520
ctccttacca aagcccatga cacattcata cagattcatc cagacataac ccactgcatg    2580
gtccagtgca tgcttgtgtg cttaacttat tatagatcaa gtgttattta agtccaacat    2640
attaaacgtg actgaaatat tatatgcact aaatcggaag acaaatggcc gtgctggata    2700
ctctcccatt tgcacttaca ggccacgcca tgctccatcc tccccatcct gcctgggaac    2760
ctgaccaatg tggctaaacc agcaggctcc ctggctgcca gcttctggct ggttgagcca    2820
atgggaagca tgaggagaga gccgagggtg gggagacagt cagatcaggg tttctgtcct    2880
cagggctccc tccctggcag gtggtggcag gagtggctgc attcccctct gaaggctcct    2940
tcaagcctct cagcaaacag ctcccatctc caagtccagc cacctgttcc atcctctcct    3000
ctgtaggccc agcagtggga atgacccacc actattgcca gcctcagcat actgaagcac    3060
cccttactgg attccctaaa ttctatgcac atgtttatta aatgctcctc aattacccag    3120
ttaaaaaaaa aaaaaaaaaa                                                3140
```

<210> SEQ ID NO 7
<211> LENGTH: 233
<212> TYPE: PRT
<213> ORGANISM: Macaca fascicularis

<400> SEQUENCE: 7

```
Met Arg Lys Thr Arg Leu Trp Gly Leu Leu Trp Met Leu Phe Val Ser
1               5                   10                  15

Glu Leu Arg Ala Thr Thr Glu Leu Thr Glu Glu Lys Tyr Glu Tyr Lys
            20                  25                  30

Glu Gly Gln Thr Leu Glu Val Lys Cys Asp Tyr Ala Leu Glu Lys Tyr
        35                  40                  45

Ala Asn Ser Arg Lys Ala Trp Gln Lys Met Glu Gly Lys Met Pro Lys
    50                  55                  60

Ile Leu Ala Lys Thr Glu Arg Pro Ser Glu Asn Ser His Pro Val Gln
65                  70                  75                  80

Val Gly Arg Ile Thr Leu Glu Asp Tyr Pro Asp His Gly Leu Leu Gln
                85                  90                  95

Val Gln Met Thr Asn Leu Gln Val Glu Asp Ser Gly Leu Tyr Gln Cys
            100                 105                 110

Val Ile Tyr Gln His Pro Lys Glu Ser His Val Leu Phe Asn Pro Ile
        115                 120                 125

Cys Leu Val Val Thr Lys Gly Ser Ser Gly Thr Pro Gly Ser Ser Glu
    130                 135                 140

Asn Ser Thr Gln Asn Val Tyr Arg Thr Pro Ser Thr Thr Ala Lys Ala
145                 150                 155                 160

Leu Gly Pro Arg Tyr Thr Ser Pro Arg Thr Val Thr Gln Ala Pro Pro
                165                 170                 175

Glu Ser Thr Val Val Ser Thr Pro Gly Ser Glu Ile Asn Leu Thr
            180                 185                 190

Asn Val Thr Asp Ile Ile Arg Val Pro Val Phe Asn Ile Val Ile Ile
        195                 200                 205

Val Ala Gly Gly Phe Leu Ser Lys Ser Leu Val Phe Ser Val Leu Phe
    210                 215                 220

Ala Val Thr Leu Arg Ser Phe Gly Pro
225                 230
```

```
<210> SEQ ID NO 8
<211> LENGTH: 196
<212> TYPE: PRT
<213> ORGANISM: homo sapiens

<400> SEQUENCE: 8

Met Ser Arg Arg Ser Met Leu Leu Ala Trp Ala Leu Pro Ser Leu Leu
1               5                   10                  15

Arg Leu Gly Ala Ala Gln Glu Thr Glu Asp Pro Ala Cys Cys Ser Pro
                20                  25                  30

Ile Val Pro Arg Asn Glu Trp Lys Ala Leu Ala Ser Glu Cys Ala Gln
            35                  40                  45

His Leu Ser Leu Pro Leu Arg Tyr Val Val Ser His Thr Ala Gly
    50                  55                  60

Ser Ser Cys Asn Thr Pro Ala Ser Cys Gln Gln Gln Ala Arg Asn Val
65                  70                  75                  80

Gln His Tyr His Met Lys Thr Leu Gly Trp Cys Asp Val Gly Tyr Asn
                    85                  90                  95

Phe Leu Ile Gly Glu Asp Gly Leu Val Tyr Glu Gly Arg Gly Trp Asn
                100                 105                 110

Phe Thr Gly Ala His Ser Gly His Leu Trp Asn Pro Met Ser Ile Gly
                115                 120                 125

Ile Ser Phe Met Gly Asn Tyr Met Asp Arg Val Pro Thr Pro Gln Ala
            130                 135                 140

Ile Arg Ala Ala Gln Gly Leu Leu Ala Cys Gly Val Ala Gln Gly Ala
145                 150                 155                 160

Leu Arg Ser Asn Tyr Val Leu Lys Gly His Arg Asp Val Gln Arg Thr
                    165                 170                 175

Leu Ser Pro Gly Asn Gln Leu Tyr His Leu Ile Gln Asn Trp Pro His
                180                 185                 190

Tyr Arg Ser Pro
            195

<210> SEQ ID NO 9
<211> LENGTH: 330
<212> TYPE: PRT
<213> ORGANISM: homo sapiens

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
```

-continued

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 327
<212> TYPE: PRT
<213> ORGANISM: homo sapiens

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 11
<211> LENGTH: 330
<212> TYPE: PRT
<213> ORGANISM: Artificial Sequence
<220> FEATURE:
<223> OTHER INFORMATION: IgG1-Aba Heavy Chain Constant Region

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Ser Pro Pro Ser
        100                 105                 110

Pro Ala Pro Glu Leu Leu Gly Gly Ser Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 330
<212> TYPE: PRT
<213> ORGANISM: Artificial Sequence
<220> FEATURE:
<223> OTHER INFORMATION: IgG4-Aba Heavy Chain Constant Region

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Pro Lys Ser Cys Asp Lys Thr His Thr Ser Pro Pro Ser
            100                 105                 110

Pro Ala Pro Glu Leu Leu Gly Gly Ser Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 107
<212> TYPE: PRT
<213> ORGANISM: homo sapiens

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 121
<212> TYPE: PRT
<213> ORGANISM: Artificial Sequence
<220> FEATURE:
<223> OTHER INFORMATION: mAb 0318 VH

<400> SEQUENCE: 14

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser

<210> SEQ ID NO 15
<211> LENGTH: 218
<212> TYPE: PRT
<213> ORGANISM: Artificial Sequence
<220> FEATURE:
<223> OTHER INFORMATION: mAb 0318 VL

<400> SEQUENCE: 15

```
Asp Ile Val Leu Thr Gln Ser Pro Asp Ser Leu Ala Val Ser Leu Gly
1               5                   10                  15
Glu Arg Ala Thr Ile Asn Cys Arg Ala Ser Gln Ser Val Asp Thr Phe
            20                  25                  30
Asp Tyr Ser Phe Leu His Trp Tyr Gln Gln Lys Pro Gly Gln Pro Pro
        35                  40                  45
Lys Leu Leu Ile Tyr Arg Ala Ser Asn Leu Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Ser Asn
                85                  90                  95
Gln Asp Pro Tyr Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 16
<211> LENGTH: 121
<212> TYPE: PRT
<213> ORGANISM: Artificial Sequence
<220> FEATURE:
<223> OTHER INFORMATION: 0318-IgG1.3f VH

<400> SEQUENCE: 16

```
Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser Thr Tyr
            20                  25                  30
Ala Met His Trp Val Arg Gln Ala Ser Gly Lys Gly Leu Glu Trp Val
        35                  40                  45
Gly Arg Ile Arg Thr Lys Ser Asn Tyr Ala Thr Tyr Tyr Ala Ala
    50                  55                  60
Ser Val Lys Gly Arg Phe Thr Ile Ser Arg Asp Asp Ser Lys Asn Thr
65                  70                  75                  80
```

```
Ala Tyr Leu Gln Met Asn Ser Leu Lys Thr Glu Asp Thr Ala Val Tyr
                 85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser
            115                 120

<210> SEQ ID NO 17
<211> LENGTH: 111
<212> TYPE: PRT
<213> ORGANISM: Artificial Sequence
<220> FEATURE:
<223> OTHER INFORMATION: 0318-IgG1.3f VL

<400> SEQUENCE: 17

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Gln Asp Pro Tyr Thr Phe Gly Gln Gly Thr Lys Leu Glu Ile Lys
            100                 105                 110

<210> SEQ ID NO 18
<211> LENGTH: 121
<212> TYPE: PRT
<213> ORGANISM: Artificial Sequence
<220> FEATURE:
<223> OTHER INFORMATION: 0318-IgG1.1f VH

<400> SEQUENCE: 18

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Asn Tyr Ala Thr Tyr Tyr Ala Ala
    50                  55                  60

Ser Val Lys Gly Arg Phe Thr Ile Ser Arg Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser
            115                 120

<210> SEQ ID NO 19
<211> LENGTH: 111
<212> TYPE: PRT
<213> ORGANISM: Artificial Sequence
```

<220> FEATURE:
<223> OTHER INFORMATION: 0318-IgG1.1f VL

<400> SEQUENCE: 19

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Gln Asp Pro Tyr Thr Phe Gly Gln Gly Thr Lys Leu Glu Ile Lys
            100                 105                 110

<210> SEQ ID NO 20
<211> LENGTH: 121
<212> TYPE: PRT
<213> ORGANISM: Artificial Sequence
<220> FEATURE:
<223> OTHER INFORMATION: 0318-IgG1-Aba VH

<400> SEQUENCE: 20

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser
        115                 120

<210> SEQ ID NO 21
<211> LENGTH: 111
<212> TYPE: PRT
<213> ORGANISM: Artificial Sequence
<220> FEATURE:
<223> OTHER INFORMATION: 0318-IgG1-Aba VL

<400> SEQUENCE: 21

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
            50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Gln Asp Pro Tyr Thr Phe Gly Gln Gly Thr Lys Leu Glu Ile Lys
            100                 105                 110

<210> SEQ ID NO 22
<211> LENGTH: 121
<212> TYPE: PRT
<213> ORGANISM: Artificial Sequence
<220> FEATURE:
<223> OTHER INFORMATION: 0318-IgG4-Aba VH

<400> SEQUENCE: 22

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser
        115                 120

<210> SEQ ID NO 23
<211> LENGTH: 111
<212> TYPE: PRT
<213> ORGANISM: Artificial Sequence
<220> FEATURE:
<223> OTHER INFORMATION: 0318-IgG4-Aba VL

<400> SEQUENCE: 23

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Gln Asp Pro Tyr Thr Phe Gly Gln Gly Thr Lys Leu Glu Ile Lys
            100                 105                 110

<210> SEQ ID NO 24

```
<211> LENGTH: 5
<212> TYPE: PRT
<213> ORGANISM: Artificial Sequence
<220> FEATURE:
<223> OTHER INFORMATION: 0318-IgG1.3f VH CDR1

<400> SEQUENCE: 24

Thr Tyr Ala Met His
1               5

<210> SEQ ID NO 25
<211> LENGTH: 19
<212> TYPE: PRT
<213> ORGANISM: Artificial Sequence
<220> FEATURE:
<223> OTHER INFORMATION: 0318-IgG1.3f VH CDR2

<400> SEQUENCE: 25

Arg Ile Arg Thr Lys Ser Ser Asn Tyr Ala Thr Tyr Tyr Ala Ala Ser
1               5                   10                  15

Val Lys Gly

<210> SEQ ID NO 26
<211> LENGTH: 10
<212> TYPE: PRT
<213> ORGANISM: Artificial Sequence
<220> FEATURE:
<223> OTHER INFORMATION: 0318-IgG1.3f VH CDR3

<400> SEQUENCE: 26

Asp Met Gly Ile Arg Arg Gln Phe Ala Tyr
1               5                   10

<210> SEQ ID NO 27
<211> LENGTH: 15
<212> TYPE: PRT
<213> ORGANISM: Artificial Sequence
<220> FEATURE:
<223> OTHER INFORMATION: 0318-IgG1.3f VL CDR1

<400> SEQUENCE: 27

Arg Ala Ser Gln Ser Val Asp Thr Phe Asp Tyr Ser Phe Leu His
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: 0318-IgG1.3f VL CDR2

<400> SEQUENCE: 28

Arg Ala Ser Asn Leu Glu Ser
1               5

<210> SEQ ID NO 29
<211> LENGTH: 9
<212> TYPE: PRT
<213> ORGANISM: Artificial Sequence
<220> FEATURE:
<223> OTHER INFORMATION: 0318-IgG1.3f VL CDR3

<400> SEQUENCE: 29

Gln Gln Ser Asn Gln Asp Pro Tyr Thr
1               5
```

```
<210> SEQ ID NO 30
<211> LENGTH: 5
<212> TYPE: PRT
<213> ORGANISM: Artificial Sequence
<220> FEATURE:
<223> OTHER INFORMATION: 0318-IgG1.1f VH CDR1

<400> SEQUENCE: 30

Thr Tyr Ala Met His
1               5

<210> SEQ ID NO 31
<211> LENGTH: 19
<212> TYPE: PRT
<213> ORGANISM: Artificial Sequence
<220> FEATURE:
<223> OTHER INFORMATION: 0318-IgG1.1f VH CDR2

<400> SEQUENCE: 31

Arg Ile Arg Thr Lys Ser Ser Asn Tyr Ala Thr Tyr Tyr Ala Ala Ser
1               5                   10                  15

Val Lys Gly

<210> SEQ ID NO 32
<211> LENGTH: 10
<212> TYPE: PRT
<213> ORGANISM: Artificial Sequence
<220> FEATURE:
<223> OTHER INFORMATION: 0318-IgG1.1f VH CDR3

<400> SEQUENCE: 32

Asp Met Gly Ile Arg Arg Gln Phe Ala Tyr
1               5                   10

<210> SEQ ID NO 33
<211> LENGTH: 15
<212> TYPE: PRT
<213> ORGANISM: Artificial Sequence
<220> FEATURE:
<223> OTHER INFORMATION: 0318-IgG1.1f VL CDR1

<400> SEQUENCE: 33

Arg Ala Ser Gln Ser Val Asp Thr Phe Asp Tyr Ser Phe Leu His
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: 0318-IgG1.1f VL CDR2

<400> SEQUENCE: 34

Arg Ala Ser Asn Leu Glu Ser
1               5

<210> SEQ ID NO 35
<211> LENGTH: 9
<212> TYPE: PRT
<213> ORGANISM: Artificial Sequence
<220> FEATURE:
<223> OTHER INFORMATION: 0318-IgG1.1f VL CDR3

<400> SEQUENCE: 35

Gln Gln Ser Asn Gln Asp Pro Tyr Thr
1               5
```

<210> SEQ ID NO 36
<211> LENGTH: 5
<212> TYPE: PRT
<213> ORGANISM: Artificial Sequence
<220> FEATURE:
<223> OTHER INFORMATION: 0318-IgG1-Aba VH CDR1

<400> SEQUENCE: 36

Thr Tyr Ala Met His
1               5

<210> SEQ ID NO 37
<211> LENGTH: 19
<212> TYPE: PRT
<213> ORGANISM: Artificial Sequence
<220> FEATURE:
<223> OTHER INFORMATION: 0318-IgG1-Aba VH CDR2

<400> SEQUENCE: 37

Arg Ile Arg Thr Lys Ser Ser Asn Tyr Ala Thr Tyr Tyr Ala Ala Ser
1               5                   10                  15

Val Lys Gly

<210> SEQ ID NO 38
<211> LENGTH: 10
<212> TYPE: PRT
<213> ORGANISM: Artificial Sequence
<220> FEATURE:
<223> OTHER INFORMATION: 0318-IgG1-Aba VH CDR3

<400> SEQUENCE: 38

Asp Met Gly Ile Arg Arg Gln Phe Ala Tyr
1               5                   10

<210> SEQ ID NO 39
<211> LENGTH: 15
<212> TYPE: PRT
<213> ORGANISM: Artificial Sequence
<220> FEATURE:
<223> OTHER INFORMATION: 0318-IgG1-Aba VL CDR1

<400> SEQUENCE: 39

Arg Ala Ser Gln Ser Val Asp Thr Phe Asp Tyr Ser Phe Leu His
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: 0318-IgG1-Aba VL CDR2

<400> SEQUENCE: 40

Arg Ala Ser Asn Leu Glu Ser
1               5

<210> SEQ ID NO 41
<211> LENGTH: 9
<212> TYPE: PRT
<213> ORGANISM: Artificial Sequence
<220> FEATURE:
<223> OTHER INFORMATION: 0318-IgG1-Aba VL CDR3

<400> SEQUENCE: 41

Gln Gln Ser Asn Gln Asp Pro Tyr Thr
1               5

```
<210> SEQ ID NO 42
<211> LENGTH: 5
<212> TYPE: PRT
<213> ORGANISM: Artificial Sequence
<220> FEATURE:
<223> OTHER INFORMATION: 0318-IgG4-Aba VH CDR1

<400> SEQUENCE: 42

Thr Tyr Ala Met His
1               5

<210> SEQ ID NO 43
<211> LENGTH: 19
<212> TYPE: PRT
<213> ORGANISM: Artificial Sequence
<220> FEATURE:
<223> OTHER INFORMATION: 0318-IgG4-Aba VH CDR2

<400> SEQUENCE: 43

Arg Ile Arg Thr Lys Ser Ser Asn Tyr Ala Thr Tyr Tyr Ala Ala Ser
1               5                   10                  15

Val Lys Gly

<210> SEQ ID NO 44
<211> LENGTH: 10
<212> TYPE: PRT
<213> ORGANISM: Artificial Sequence
<220> FEATURE:
<223> OTHER INFORMATION: 0318-IgG4-Aba VH CDR3

<400> SEQUENCE: 44

Asp Met Gly Ile Arg Arg Gln Phe Ala Tyr
1               5                   10

<210> SEQ ID NO 45
<211> LENGTH: 15
<212> TYPE: PRT
<213> ORGANISM: Artificial Sequence
<220> FEATURE:
<223> OTHER INFORMATION: 0318-IgG4-Aba VL CDR1

<400> SEQUENCE: 45

Arg Ala Ser Gln Ser Val Asp Thr Phe Asp Tyr Ser Phe Leu His
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: 0318-IgG4-Aba VL CDR2

<400> SEQUENCE: 46

Arg Ala Ser Asn Leu Glu Ser
1               5

<210> SEQ ID NO 47
<211> LENGTH: 9
<212> TYPE: PRT
<213> ORGANISM: Artificial Sequence
<220> FEATURE:
<223> OTHER INFORMATION: 0318-IgG4-Aba VL CDR3

<400> SEQUENCE: 47

Gln Gln Ser Asn Gln Asp Pro Tyr Thr
```

```
1               5
```

<210> SEQ ID NO 48
<211> LENGTH: 5
<212> TYPE: PRT
<213> ORGANISM: Artificial Sequence
<220> FEATURE:
<223> OTHER INFORMATION: LSPGK (C-terminal end of heavy chain)

<400> SEQUENCE: 48

```
Leu Ser Pro Gly Lys
1               5
```

<210> SEQ ID NO 49
<211> LENGTH: 4
<212> TYPE: PRT
<213> ORGANISM: Artificial Sequence
<220> FEATURE:
<223> OTHER INFORMATION: LSPG (C-terminal end of heavy chain)

<400> SEQUENCE: 49

```
Leu Ser Pro Gly
1
```

<210> SEQ ID NO 50
<211> LENGTH: 451
<212> TYPE: PRT
<213> ORGANISM: Artificial Sequence
<220> FEATURE:
<223> OTHER INFORMATION: 0318-IgG1.3f HC

<400> SEQUENCE: 50

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220
```

```
Asp Lys Thr His Thr Cys Pro Pro Cys Pro Ala Pro Glu Ala Glu Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 51
<211> LENGTH: 450
<212> TYPE: PRT
<213> ORGANISM: Artificial Sequence
<220> FEATURE:
<223> OTHER INFORMATION: 0318-IgG1.1f HC

<400> SEQUENCE: 51

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
                20                  25                  30

Ala Met His Trp Val Arg Gln Ala Ser Gly Lys Gly Leu Glu Trp Val
            35                  40                  45

Gly Arg Ile Arg Thr Lys Ser Ser Asn Tyr Ala Thr Tyr Tyr Ala Ala
        50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser Ala Ser Thr Lys Gly Pro Ser
        115                 120                 125
```

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Ala Glu Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ser Ser Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 52
<211> LENGTH: 451
<212> TYPE: PRT
<213> ORGANISM: Artificial Sequence
<220> FEATURE:
<223> OTHER INFORMATION: 0318-IgG1-Aba HC

<400> SEQUENCE: 52

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

-continued

```
Ala Met His Trp Val Arg Gln Ala Ser Gly Lys Gly Leu Glu Trp Val
         35                  40                  45
Gly Arg Ile Arg Thr Lys Ser Ser Asn Tyr Ala Thr Tyr Tyr Ala Ala
     50                  55                  60
Ser Val Lys Gly Arg Phe Thr Ile Ser Arg Asp Asp Ser Lys Asn Thr
 65                  70                  75                  80
Ala Tyr Leu Gln Met Asn Ser Leu Lys Thr Glu Asp Thr Ala Val Tyr
                     85                  90                  95
Tyr Cys Thr Arg Asp Met Gly Ile Arg Arg Gln Phe Ala Tyr Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Ser Pro Pro Ser Pro Ala Pro Glu Leu Leu Gly
225                 230                 235                 240
Gly Ser Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

Pro Gly Lys
    450

<210> SEQ ID NO 53
<211> LENGTH: 451
<212> TYPE: PRT
<213> ORGANISM: Artificial Sequence
<220> FEATURE:
<223> OTHER INFORMATION: 0318-IgG4-Aba HC

<400> SEQUENCE: 53

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Pro Lys Ser Cys
    210                 215                 220

Asp Lys Thr His Thr Ser Pro Pro Ser Pro Ala Pro Glu Leu Leu Gly
225                 230                 235                 240

Gly Ser Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 54
<211> LENGTH: 218
<212> TYPE: PRT
<213> ORGANISM: Artificial Sequence
<220> FEATURE:
<223> OTHER INFORMATION: 0318-IgG1.3f LC

<400> SEQUENCE: 54

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Gln Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 55
<211> LENGTH: 218
<212> TYPE: PRT
<213> ORGANISM: Artificial Sequence
<220> FEATURE:

<223> OTHER INFORMATION: 0318-IgG1.1f LC

<400> SEQUENCE: 55

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Gln Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 56
<211> LENGTH: 218
<212> TYPE: PRT
<213> ORGANISM: Artificial Sequence
<220> FEATURE:
<223> OTHER INFORMATION: 0318-IgG1-Aba LC

<400> SEQUENCE: 56

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Gln Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

<210> SEQ ID NO 57
<211> LENGTH: 218
<212> TYPE: PRT
<213> ORGANISM: Artificial Sequence
<220> FEATURE:
<223> OTHER INFORMATION: 0318-IgG4-Aba LC

<400> SEQUENCE: 57

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Asp Thr Phe
                20                  25                  30

Asp Tyr Ser Phe Leu His Trp Tyr Gln Gln Lys Pro Gly Gln Pro Pro
            35                  40                  45

Lys Leu Leu Ile Tyr Arg Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Gln Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

<210> SEQ ID NO 58
<211> LENGTH: 1407
<212> TYPE: DNA
<213> ORGANISM: Artificial Sequence
<220> FEATURE:
<223> OTHER INFORMATION: 0318-IgG1.3f HC

<400> SEQUENCE: 58

```
atgagggctt ggatcttctt tctgctctgc ctggccgggc gcgccttggc cgaagtgcag      60
ctcgtggagt ccggcggagg actggtccaa cctggcggct ccctgaagct gtcctgcgct     120
gcctccggct tcaccttctc cacctacgcc atgcactggg tcaggcaggc ctccggaaag     180
ggcctggaat gggtcggccg gattaggacc aagtccagca actacgctac ctactacgcc     240
gccagcgtca agggccggtt cacaatctcc cgggacgact ccaagaacac cgcctatctc     300
cagatgaaca gcctgaagac agaggacacc gccgtgtact attgcacccg ggatatgggc     360
attcggaggc agttcgccta ttggggccag ggcaccctgg tgacagtcag ctccgccagc     420
acaaaaggac ctagcgtgtt ccccctggcc cctagcagca gtccacaag cggcggcacc      480
gctgccctgg ctgtctggt gaaagactac tttcccgagc ccgtgacagt gagctggaac      540
tctggcgccc tgacatccgg agtgcacacc ttccctgccg tgctccagtc cagcggcctg     600
tacagcctga gcagcgtcgt gaccgtccct agcagcagcc tgggaaccca gacctacatc     660
tgcaacgtga accacaagcc ctccaacacc aaggtggaca gagggtgga gcccaagtcc      720
tgtgacaaga cccatacctg cccccccgt cctgctcctg aagctgaggg cgccccttcc      780
gtcttcctgt ccctcctaa gcccaaggac accctgatga tctccaggac ccccgaggtg     840
acctgtgtgg tggtggatgt gtcccacgag ccccgagg tgaagttcaa ttggtacgtc       900
gacggcgtga aggtgcacaa cgccaagacc aaacccggg aggagcagta aacagcacc      960
taccgggtgg tgtccgtgct caccgtgctg caccaggact ggctgaacgg caaggagtac    1020
aagtgtaagg tcagcaataa ggccctgcct gcccccatcg agaagaccat tagcaaggct    1080
aagggccagc ccagggaacc ccaggtgtat accctccccc ctagccggga ggagatgacc    1140
aagaaccagg tcagcctgac ctgcctggtg aaaggattct accctagcga catcgctgtg    1200
gagtgggaga gcaatggaca gcccgagaac aactacaaa ccaccccctcc cgtcctggac    1260
tccgatggca gcttctttct gtactccaag ctcaccgtcg acaagagccg gtggcagcag    1320
ggcaatgtgt ttagctgctc cgtgatgcac gaggctctgc acaaccacta cccaaaaag    1380
tccctgtccc tcagccccgg caagtga                                        1407
```

<210> SEQ ID NO 59
<211> LENGTH: 1404
<212> TYPE: DNA
<213> ORGANISM: Artificial Sequence
<220> FEATURE:
<223> OTHER INFORMATION: 0318-IgG1.1f HC

<400> SEQUENCE: 59

```
atgagggctt ggatcttctt tctgctctgc ctggccgggc gcgccttggc cgaagtgcag      60
ctggtggaaa gcggcggagg actggtgcag ccaggcggca gcctgaagct gtcttgcgcc     120
gccagcggct tcaccttcag cacctacgcc atgcactggg tccgccaggc cagcggcaag     180
ggcctggaat gggtcggacg gatccggacc aagagcagca actacgccac ctactacgcc     240
gcctccgtga agggccggtt caccatcagc cggacgaca gcaagaacac cgcctacctg      300
cagatgaaca gcctgaaaac cgaggacacc gccgtgtact actgcacccg ggacatgggc     360
atccggcggc agtttgccta ctggggccag ggcaccctgg tcacagtgtc cagcgcgtcg    420
accaagggcc catcggtctt ccccctggca ccctcctcca agagcacctc tggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
```

| | |
|---|---|
| tactccctca gcagcgtggt gaccgtgccc tccagcagct tgggcaccca gacctacatc | 660 |
| tgcaacgtga atcacaagcc cagcaacacc aaggtggaca agagagttga gcccaaatct | 720 |
| tgtgacaaaa ctcacacatg cccaccgtgc ccagcacctg aagccgaagg ggccccgtca | 780 |
| gtcttcctct tccccccaaa acccaaggac accctcatga tctcccggac ccctgaggtc | 840 |
| acatgcgtgg tggtggacgt gagccacgaa gaccctgagg tcaagttcaa ctggtacgtg | 900 |
| gacggcgtgg aggtgcataa tgccaagaca agccgcggg aggagcagta caacagcacg | 960 |
| taccgtgtgg tcagcgtcct caccgtcctg caccaggact ggctgaatgg caaggagtac | 1020 |
| aagtgcaagg tctccaacaa agccctccca agcagcatcg agaaaaccat ctccaaagcc | 1080 |
| aaagggcagc cccgagaacc acaggtgtac accctgcccc catcccggga ggagatgacc | 1140 |
| aagaaccagg tcagcctgac ctgcctggtc aaaggcttct atcccagcga catcgccgtg | 1200 |
| gagtgggaga gcaatgggca gccggagaac aactacaaga ccacgcctcc cgtgctggac | 1260 |
| tccgacggct ccttcttcct ctatagcaag ctcaccgtgg acaagagcag gtggcagcag | 1320 |
| gggaacgtct tctcatgctc cgtgatgcat gaggctctgc acaaccacta cacgcagaag | 1380 |
| agcctctccc tgtccccggg ttga | 1404 |

<210> SEQ ID NO 60
<211> LENGTH: 1407
<212> TYPE: DNA
<213> ORGANISM: Artificial Sequence
<220> FEATURE:
<223> OTHER INFORMATION: 0318-IgG1-Aba HC

<400> SEQUENCE: 60

| | |
|---|---|
| atgagggctt ggatcttctt tctgctctgc ctggccgggc gcgccttggc cgaggtccag | 60 |
| ctggtggaga gcggaggagg actcgtgcag cctggaggat ccctgaagct gtcctgcgct | 120 |
| gcctccggct ttaccttctc cacctacgcc atgcattggg tgaggcaggc ctccggcaag | 180 |
| ggcctggaat gggtgggcag gatcaggaca aagagctcca actacgccac ctactacgcc | 240 |
| gccagcgtga aggacggtt caccatctcc cgggacgatt ccaaaaacac cgcctacctc | 300 |
| cagatgaata gcctgaagac cgaggacacc gccgtctact actgcaccag ggatatgggc | 360 |
| atccggcggc agtttgccta ctggggccag ggcaccctgg tgacagtgtc cagcgctagc | 420 |
| accaaaggcc cctccgtgtt ccccctggct ccctccagca gtccacatc cggcggaacc | 480 |
| gccgctctgg gatgtctggt gaaggactac ttccccgagc ccgtgacagt gagctggaac | 540 |
| tctggcgctc tgacctccgg cgtgcacacc tttcctgctg tgctgcagtc ctccggcctc | 600 |
| tacagcctgt cctccgtcgt gacagtgccc tcctccagcc tgggcaccca gacctacatc | 660 |
| tgcaacgtga accacaagcc ttccaacacc aaggtggata gcgggtcga acccaagagc | 720 |
| tgcgacaaga cccacaccag ccccccttcc cctgctcccg agctcctggg aggcagctcc | 780 |
| gtgtttctgt tcccccccaa gcctaaggac accctgatga tcagcaggac cccgaagtg | 840 |
| acatgcgtgg tggtcgacgt gtcccacgag gaccccgagg tcaagttcaa ctggtacgtg | 900 |
| gatggagtgg aggtccataa tgccaagacc aagccccggg aggagcagta caattccacc | 960 |
| taccgggtgg tgtccgtgct gacagtcctg catcaggact ggctcaacgg caaggagtac | 1020 |
| aaatgcaagg tgtccaacaa ggctctgccc gcccccatcg agaagacaat cagcaaggct | 1080 |
| aagggccagc ctagggagcc ccaggtgtac accctgcccc cttccaggga cgagctcacc | 1140 |
| aagaaccagg tgtccctgac atgcctcgtg aagggctttt accctagcga catcgctgtg | 1200 |

| gagtgggagt ccaacggaca gcccgagaac aactacaaga caacacccccc tgtgctggac | 1260 |
| tccgacgget ccttcttcct gtacagcaag ctcaccgtgg acaaatcccg gtggcagcag | 1320 |
| ggaaacgtgt tcagctgctc cgtgatgcat gaggccctgc acaaccatta cacccagaaa | 1380 |
| tccctgtccc tgtccccegg caagtga | 1407 |

<210> SEQ ID NO 61
<211> LENGTH: 1407
<212> TYPE: DNA
<213> ORGANISM: Artificial Sequence
<220> FEATURE:
<223> OTHER INFORMATION: 0318-IgG4-Aba HC

<400> SEQUENCE: 61

| atgagggctt ggatcttctt tctgctctgc ctggccgggc gcgccttggc cgaggtccag | 60 |
| ctggtcgaga gcggcggagg actggtccag cctggaggat ccctgaagct ctcctgtgcc | 120 |
| gctagcggat ttaccttcag cacctacgct atgcattggg tgaggcaggc ttccggcaag | 180 |
| ggactggagt gggtgggacg gattcggacc aagagctcca attacgccac ctattacgcc | 240 |
| gcttccgtga agggccggtt caccatctcc agggacgact ccaagaacac cgcttacctg | 300 |
| cagatgaact ccctcaagac cgaggacacc gccgtgtatt actgcacccg gacatgggc | 360 |
| atccggaggc agttcgctta ttggggacag ggcaccctgg tgaccgtgag ctccgcctcc | 420 |
| accaagggcc cttccgtgtt ccctctggcc cctgtagca ggtccaccag cgagtccaca | 480 |
| gctgctctgg gctgtctggt gaaggattat ttccccgagc ccgtgacagt gtcctggaat | 540 |
| agcggcgccc tgacctccgg cgtgcatacc ttccctgccg tcctgcaaag cagcggcctg | 600 |
| tacagcctgt cctccgtggt gacagtccct cctccagcc tgggaaccaa gacctacacc | 660 |
| tgcaatgtgg accacaagcc tagcaacacc aaggtggaca gagggtcga gcccaagtcc | 720 |
| tgcgataaga cacacacctc ccctccttcc cctgctcctg agctgctcgg cggaagcagc | 780 |
| gtgttcctgt ccctcctaa gcctaaggac accctgatga tcagccggac ccctgaggtg | 840 |
| acctgtgtcg tggtggacgt gtcccacgaa gaccccgagg tgaaattcaa ctggtacgtg | 900 |
| gacggcgtcg aggtgcacaa cgctaagaca aaacccaggg aggagcagta caattccacc | 960 |
| taccgggtcg tgtccgtgct gaccgtgctg caccaggact ggctgaacgg caaagagtac | 1020 |
| aagtgtaagg tcagcaataa ggccctgcct gcccccattg agaagaccat ttccaaggcc | 1080 |
| aagggccagc ccagggaacc tcaggtgtac accctgcctc cctccgggga cgagctgacc | 1140 |
| aagaaccagg tcagcctgac ctgcctcgtg aagggcttct accctagcga catcgccgtg | 1200 |
| gagtgggagt ccaacggcca gcctgagaac aattacaaga ccaccccccc tgtcctggac | 1260 |
| tccgacggat ccttcttcct gtactccaag ctgacagtgg ataagtcccg gtggcagcag | 1320 |
| ggaaatgtgt tctcctgctc cgtcatgcac gaagccctgc ataaccacta cacacagaag | 1380 |
| agcctgtccc tgagcctggg caagtga | 1407 |

<210> SEQ ID NO 62
<211> LENGTH: 708
<212> TYPE: DNA
<213> ORGANISM: Artificial Sequence
<220> FEATURE:
<223> OTHER INFORMATION: 0318-IgG1.3f LC

<400> SEQUENCE: 62

| atgagggctt ggatcttctt tctgctctgc ctggccgggc gcgccttggc cgatatcgtg | 60 |
| ctgacccaga gccccgatag cctggctgtg agcctgggcg agagagccac catcaactgc | 120 |

```
agggcctccc agagcgtcga caccttcgac tacagcttcc tccactggta ccagcagaag    180
cctggccagc cccccaagct gctgatctac agggccagca acctggagag cggagtgccc    240
gataggttca gcggcagcgg ctccggaacc gactttaccc tcaccatcag ctccctgcag    300
gccgaggatg tggccgtcta ctactgccag cagagcaacc aggaccccta cacctttggc    360
cagggcacca agctggagat caagaggacc gtggccgccc cctccgtgtt catcttccct    420
cccagcgacg agcagctgaa gagcggaacc gccagcgtgg tgtgcctgct gaacaacttc    480
taccccaggg aggccaaggt gcagtggaag gtcgacaacg ccctgcagag cggcaatagc    540
caggagagcg tgaccgaaca ggacagcaag gactccacct actccctgag cagcaccctg    600
accctgagca aggccgacta cgagaagcac aaggtgtacg cctgtgaggt gacccaccag    660
ggactgagca gccccgtgac aaagagcttt aacaggggcg agtgctga             708
```

<210> SEQ ID NO 63
<211> LENGTH: 708
<212> TYPE: DNA
<213> ORGANISM: Artificial Sequence
<220> FEATURE:
<223> OTHER INFORMATION: 0318-IgG1.1f LC

<400> SEQUENCE: 63

```
atgagggctt ggatcttctt tctgctctgc ctggccgggc gcgccttggc cgatatcgtg    60
ctgacccaga gccccgatag cctggctgtg agcctgggcg agagagccac catcaactgc    120
agggcctccc agagcgtcga caccttcgac tacagcttcc tccactggta ccagcagaag    180
cctggccagc cccccaagct gctgatctac agggccagca acctggagag cggagtgccc    240
gataggttca gcggcagcgg ctccggaacc gactttaccc tcaccatcag ctccctgcag    300
gccgaggatg tggccgtcta ctactgccag cagagcaacc aggaccccta cacctttggc    360
cagggcacca agctggagat caagaggacc gtggccgccc cctccgtgtt catcttccct    420
cccagcgacg agcagctgaa gagcggaacc gccagcgtgg tgtgcctgct gaacaacttc    480
taccccaggg aggccaaggt gcagtggaag gtcgacaacg ccctgcagag cggcaatagc    540
caggagagcg tgaccgaaca ggacagcaag gactccacct actccctgag cagcaccctg    600
accctgagca aggccgacta cgagaagcac aaggtgtacg cctgtgaggt gacccaccag    660
ggactgagca gccccgtgac aaagagcttt aacaggggcg agtgctga             708
```

<210> SEQ ID NO 64
<211> LENGTH: 708
<212> TYPE: DNA
<213> ORGANISM: Artificial Sequence
<220> FEATURE:
<223> OTHER INFORMATION: 0318-IgG1-Aba LC

<400> SEQUENCE: 64

```
atgagggctt ggatcttctt tctgctctgc ctggccgggc gcgccttggc cgatatcgtg    60
ctgacccaga gccccgatag cctggctgtg agcctgggcg agagagccac catcaactgc    120
agggcctccc agagcgtcga caccttcgac tacagcttcc tccactggta ccagcagaag    180
cctggccagc cccccaagct gctgatctac agggccagca acctggagag cggagtgccc    240
gataggttca gcggcagcgg ctccggaacc gactttaccc tcaccatcag ctccctgcag    300
gccgaggatg tggccgtcta ctactgccag cagagcaacc aggaccccta cacctttggc    360
cagggcacca agctggagat caagaggacc gtggccgccc cctccgtgtt catcttccct    420
```

```
cccagcgacg agcagctgaa gagcggaacc gccagcgtgg tgtgcctgct gaacaacttc    480
taccccaggg aggccaaggt gcagtggaag gtcgacaacg ccctgcagag cggcaatagc    540
caggagagcg tgaccgaaca ggacagcaag gactccacct actccctgag cagcaccctg    600
accctgagca aggccgacta cgagaagcac aaggtgtacg cctgtgaggt gacccaccag    660
ggactgagca gccccgtgac aaagagcttt aacaggggcg agtgctga                 708
```

<210> SEQ ID NO 65
<211> LENGTH: 708
<212> TYPE: DNA
<213> ORGANISM: Artificial Sequence
<220> FEATURE:
<223> OTHER INFORMATION: 0318-IgG4-Aba LC

<400> SEQUENCE: 65

```
atgagggctt ggatcttctt tctgctctgc ctggccgggc gcgccttggc cgatatcgtg     60
ctgacccaga gccccgatag cctggctgtg agcctgggcg agagagccac catcaactgc    120
agggcctccc agagcgtcga caccttcgac tacagcttcc tccactggta ccagcagaag    180
cctggccagc cccccaagct gctgatctac agggccagca acctggagag cggagtgccc    240
gataggttca gcggcagcgg ctccggaacc gactttaccc tcaccatcag ctccctgcag    300
gccgaggatg tggccgtcta ctactgccag cagagcaacc aggacccta cacctttggc    360 cagggcacca gctggagat caagaggacc gtggccgccc cctccgtgtt catcttccct    420
cccagcgacg agcagctgaa gagcggaacc gccagcgtgg tgtgcctgct gaacaacttc    480
taccccaggg aggccaaggt gcagtggaag gtcgacaacg ccctgcagag cggcaatagc    540
caggagagcg tgaccgaaca ggacagcaag gactccacct actccctgag cagcaccctg    600
accctgagca aggccgacta cgagaagcac aaggtgtacg cctgtgaggt gacccaccag    660
ggactgagca gccccgtgac aaagagcttt aacaggggcg agtgctga                 708
```

<210> SEQ ID NO 66
<211> LENGTH: 5
<212> TYPE: PRT
<213> ORGANISM: Artificial Sequence
<220> FEATURE:
<223> OTHER INFORMATION: 0318 Ab - VH CDR1

<400> SEQUENCE: 66

Thr Tyr Ala Met His
1               5

<210> SEQ ID NO 67
<211> LENGTH: 19
<212> TYPE: PRT
<213> ORGANISM: Artificial Sequence
<220> FEATURE:
<223> OTHER INFORMATION: 0318 Ab - VH CDR2

<400> SEQUENCE: 67

Arg Ile Arg Thr Lys Ser Ser Asn Tyr Ala Thr Tyr Tyr Ala Asp Ser
1               5                   10                  15

Val Lys Asp

<210> SEQ ID NO 68
<211> LENGTH: 10
<212> TYPE: PRT
<213> ORGANISM: Artificial Sequence
<220> FEATURE:
<223> OTHER INFORMATION: 0318 Ab - VH CDR3

```
<400> SEQUENCE: 68

Asp Met Gly Gln Arg Arg Gln Phe Ala Tyr
1               5                   10

<210> SEQ ID NO 69
<211> LENGTH: 15
<212> TYPE: PRT
<213> ORGANISM: Artificial Sequence
<220> FEATURE:
<223> OTHER INFORMATION: 0318 Ab - VL CDR1

<400> SEQUENCE: 69

Arg Ala Ser Glu Ser Val Asp Thr Phe Asp Tyr Ser Phe Leu His
1               5                   10                  15

<210> SEQ ID NO 70
<211> LENGTH: 7
<212> TYPE: PRT
<213> ORGANISM: Artificial Sequence
<220> FEATURE:
<223> OTHER INFORMATION: 0318 Ab - VL CDR2

<400> SEQUENCE: 70

Arg Ala Ser Asn Leu Glu Ser
1               5

<210> SEQ ID NO 71
<211> LENGTH: 9
<212> TYPE: PRT
<213> ORGANISM: Artificial Sequence
<220> FEATURE:
<223> OTHER INFORMATION: 0318 Ab - VL CDR3

<400> SEQUENCE: 71

Gln Gln Ser Asn Glu Asp Pro Tyr Thr
1               5

<210> SEQ ID NO 72
<211> LENGTH: 10
<212> TYPE: PRT
<213> ORGANISM: Artificial Sequence
<220> FEATURE:
<223> OTHER INFORMATION: 0318 AB - VH CDR3 (mutant)

<400> SEQUENCE: 72

Asp Gln Gly Ile Arg Arg Gln Phe Ala Tyr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: 0318 AB - VH CDR3 (mutant)

<400> SEQUENCE: 73

Asp Leu Gly Ile Arg Arg Gln Phe Ala Tyr
1               5                   10

<210> SEQ ID NO 74
<211> LENGTH: 5
<212> TYPE: PRT
<213> ORGANISM: Artificial Sequence
<220> FEATURE:
<223> OTHER INFORMATION: 0318 Ab - VH CDR1 (mutant)
```

<400> SEQUENCE: 74

Thr Tyr Ala Gln His
1               5

<210> SEQ ID NO 75
<211> LENGTH: 5
<212> TYPE: PRT
<213> ORGANISM: Artificial Sequence
<220> FEATURE:
<223> OTHER INFORMATION: 0318 Ab - VH CDR1 (mutant)

<400> SEQUENCE: 75

Thr Tyr Ala Leu His
1               5

<210> SEQ ID NO 76
<211> LENGTH: 451
<212> TYPE: PRT
<213> ORGANISM: Artificial Sequence
<220> FEATURE:
<223> OTHER INFORMATION: 0318 Ab - HC (IgG4)

<400> SEQUENCE: 76

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
            85                  90                  95

Tyr Cys Thr Arg Asp Met Gly Ile Arg Arg Gln Phe Ala Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270
```

```
Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn Asp Ile Val Leu Thr Gln Ser Pro Asp Ser Leu Ala Val
            435                 440                 445

Ser Leu Gly
    450

<210> SEQ ID NO 77
<211> LENGTH: 330
<212> TYPE: PRT
<213> ORGANISM: Artificial Sequence
<220> FEATURE:
<223> OTHER INFORMATION: WT IgG1 Constant Region (Allotypic Variant)

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 78
<211> LENGTH: 330
<212> TYPE: PRT
<213> ORGANISM: Artificial Sequence
<220> FEATURE:
<223> OTHER INFORMATION: IgG1.1f HC Constant Region

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ser Ser Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 79
<211> LENGTH: 330
<212> TYPE: PRT
<213> ORGANISM: Artificial Sequence
<220> FEATURE:
<223> OTHER INFORMATION: IgG1.3f HC Constant Region

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240
```

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 80
<211> LENGTH: 5
<212> TYPE: PRT
<213> ORGANISM: Artificial Sequence
<220> FEATURE:
<223> OTHER INFORMATION: Linker

<400> SEQUENCE: 80

Pro Val Gly Val Val
1               5

<210> SEQ ID NO 81
<211> LENGTH: 121
<212> TYPE: PRT
<213> ORGANISM: Artificial Sequence
<220> FEATURE:
<223> OTHER INFORMATION: 318 Ab - Mutant

<400> SEQUENCE: 81

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Gln Gly Ile Arg Arg Gln Phe Ala Tyr Trp Gly
            100                 105                 110

Gln Gly Thr Leu Val Thr Val Ser Ser
        115                 120

<210> SEQ ID NO 82
<211> LENGTH: 121
<212> TYPE: PRT
<213> ORGANISM: Artificial Sequence
<220> FEATURE:
<223> OTHER INFORMATION: 319 Ab - Mutant

<400> SEQUENCE: 82

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr

```
            20                  25                  30
Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Leu Gly Ile Arg Arg Gln Phe Ala Tyr Trp Gly
            100                 105                 110

Gln Gly Thr Leu Val Thr Val Ser Ser
        115                 120

<210> SEQ ID NO 83
<211> LENGTH: 121
<212> TYPE: PRT
<213> ORGANISM: Artificial Sequence
<220> FEATURE:
<223> OTHER INFORMATION: 320 Ab - Mutant

<400> SEQUENCE: 83

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Gln His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser
        115                 120

<210> SEQ ID NO 84
<211> LENGTH: 121
<212> TYPE: PRT
<213> ORGANISM: Artificial Sequence
<220> FEATURE:
<223> OTHER INFORMATION: 321 Ab - Mutant

<400> SEQUENCE: 84

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Leu His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80
```

```
Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser
        115                 120
```

<210> SEQ ID NO 85
<211> LENGTH: 450
<212> TYPE: PRT
<213> ORGANISM: Artificial Sequence
<220> FEATURE:
<223> OTHER INFORMATION: 0318-IgG1.3f HC Kdel

<400> SEQUENCE: 85

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Glu Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

-continued

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450
```

ANTI-TREM-1 ANTIBODIES AND USES THEREOF

CROSS-REFERENCE TO RELATED APPLICATION

This application claims benefit of U.S. Provisional Application No. 62/651,605, filed Apr. 2, 2018, which is herein incorporated by reference in its entirety.

REFERENCE TO SEQUENCE LISTING SUBMITTED ELECTRONICALLY VIA EFS-WEB

The content of the electronically submitted sequence listing in ASCII text file (Name: 3338 0920002 SeqListing ST25.txt; Size: 110, 115 bytes; and Date of Creation: Jun. 4, 2020) incorporated by reference in its entirety.

BACKGROUND OF THE DISCLOSURE

TREM-1 is an activating receptor expressed on monocytes, macrophages, and neutrophils. These cells play a central role in chronic inflammatory diseases by releasing cytokines and other mediators that drive inflammation. TREM-1 mRNA and protein expression is up-regulated in patients with rheumatic arthritis (RA) and inflammatory bowel disease (IBD), and TREM-1-positive cells accumulate at sites of inflammation, correlating with disease severity. See Bouchon et al., *Nature* 410:1103-1107 (2001); Schenk et al., *Clin Invest* 117:3097-3106 (2007); and Kuai et al., *Rheumatology* 48:1352-1358 (2009). Peptidoglycan-recognition-protein 1 (PGLYRP1) expressed primarily by activated neutrophils is a ligand for TREM-1 and mediate TREM-1 signaling upon binding.

In vitro, engagement of TREM-1 triggers secretion of pro-inflammatory cytokines including TNF, IL-8, and monocyte chemotactic protein-1. In addition, TREM-1 signaling synergizes with multiple Toll-like Receptors (TLRs) to further boost pro-inflammatory signals. In turn, this up-regulates expression of TREM-1, leading to a vicious cycle amplifying the inflammation. See Bouchon et al., *J Immunol* 164:4991-4995 (2000). Increasing evidence indicates that TLRs contribute to the development and progression of chronic inflammatory diseases such as RA and IBD.

Humanized anti-TREM-1 mAbs that inhibit both human and cynomolgus TREM-1 function have been disclosed elsewhere. See WO 2013/120553 A1 and WO 2016/009086 A1. However, such antibodies either have viscosity profile that can hamper manufacturing process or have other issues that can limit their therapeutic potential (e.g., cytokine storm and ADCC). See Shire et al., *J. Pharm. Sci.* 93:1390-1402 (2004); and Warncke et al., *J Immunol.* 188:4405-11 (2012). Accordingly, there is a need for an anti-TREM-1 antibody that can specifically bind to and inhibit TREM-1 function but without the issues of the earlier anti-TREM-1 antibodies.

SUMMARY OF THE DISCLOSURE

Provided herein are isolated antibodies, such as monoclonal antibodies, in particular human (e.g., monoclonal) antibodies, that specifically bind triggering receptor expressed on myeloid cells-1 (TREM-1) and have desirable functional properties. In some embodiments, the antibody comprises a heavy chain variable region (VH), a light chain variable region (VL), and an IgG1 heavy chain constant region, wherein the IgG1 heavy chain constant region comprises one or more amino acid substitutions compared to a wild-type IgG1 heavy chain constant region (SEQ ID NO: 9). In some embodiments, the antibody cross-competes with mAb 0318 for binding to blocking TREM-1 and comprises a heavy chain variable region (VH), a light chain variable region (VL), and an IgG1 heavy chain constant region, wherein the IgG1 heavy chain constant region comprises one or more amino acid substitutions compared to a wild-type IgG1 heavy chain constant region (SEQ ID NO: 9).

In some embodiments, the antibody binds to the same TREM-1 eptiope as mAb 0318. In some embodiments, the antibody specifically binds to a TREM-1 epitope comprising one or more amino acid residues selected from the group consisting of the D38, V39, K40, C41, D42, Y43, T44, L45, E46, K47, F48, A49, S50, S51, Q52, K53, A54, W55, Q56, Y90, H91, D92, H93, G94, L95, and L96 of SEQ ID NO: 1. In some embodiments, the antibody specifically binds to a TREM-1 epitope comprising amino acids D38 to L45, E46 to Q56, and/or Y90 to L96 of SEQ ID NO: 1.

In some embodiments, the IgG1 heavy chain constant region of the antibody disclosed herein comprises one or more amino acid substitutions selected from the group consisting of K214R, L234A, L235E, G237A, D356E, and L358M, per EU numbering. In some embodiments, the IgG1 heavy chain constant region comprises one or more amino acid substitutions selected from the group consisting of K214R, L234A, L235E, G237A, A330S, P331S, D356E, and L358M, per EU numbering. In some embodiments, the IgG1 heavy chain constant region comprises one or more amino acid substitutions selected from the group consisting of K214R, C226S, C229S, and P238S, per EU numbering. In some embodiments, the IgG1 heavy chain constant region comprises one or more amino acid substitutions selected from the group consisting of S131C, K133R, G137E, G138S, Q196K, I199T, N203D, K214R, C226S, C229S, and P238S, per EU numbering.

In some embodiments, the antibody disclosed herein comprises a heavy chain CDR1, CDR2, and CDR3 and a light chain CDR1, CDR2, and CDR3, wherein the heavy chain CDR3 comprises DMGIRRQFAY (SEQ ID NO: 26) or DMGIRRQFAY (SEQ ID NO: 26) except one or two substitutions. In some embodiments, the heavy chain CDR3 comprises DQGIRRQFAY (SEQ ID NO: 72).

In some embodiments, the antibody disclosed herein comprises a heavy chain CDR1, CDR2, and CDR3 and a light chain CDR1, CDR2, and CDR3, wherein the heavy chain CDR2 comprises RIRTKSSNYATYYAASVKG (SEQ ID NO: 25) or RIRTKSSNYATYYAASVKG (SEQ ID NO: 25) except one or two substitutions.

In some embodiments, the antibody disclosed herein comprises a heavy chain CDR1, CDR2, and CDR3 and a light chain CDR1, CDR2, and CDR3, wherein the heavy chain CDR1 comprises TYAMH (SEQ ID NO: 24) or TYAMH (SEQ ID NO: 24) except one or two substitutions.

In some embodiments, the antibody disclosed herein comprises a heavy chain CDR1, CDR2, and CDR3 and a light chain CDR1, CDR2, and CDR3, wherein the light chain CDR1 comprises RASQSVDTFDYSFLH (SEQ ID NO: 27) or RASQSVDTFDYSFLH (SEQ ID NO: 27) except one or two substitutions. In some embodiments, the light chain CDR2 comprises RASNLES (SEQ ID NO: 28) or RASNLES (SEQ ID NO: 28) except one or two substitutions. In some embodiments, the light chain CDR3 comprises QQSNQDPYT (SEQ ID NO: 29) or QQSNQDPYT (SEQ ID NO: 29) except one or two substitutions.

In some embodiments, the VH of the antibody disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 14. In somoe embodiments, the VL of the antibody disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 15. In some embodiments, the VH and VL comprises SEQ ID NOs: 14 and 15, respectively.

In some embodiments, the antibody of the present disclosure comprises a heavy chain and a light chain, wherein the heavy chain comprises SEQ ID NO: 50, SEQ ID NO: 51, SEQ ID NO: 52, or SEQ ID NO: 53. In some embodiments, the light chain comprises SEQ ID NO: 54.

Provided herein is an isolated antibody which specifically binds to TREM-1, comprising a heavy chain CDR1, CDR2, CDR3; a light chain CDR1, CDR2, CDR3; and an IgG1 heavy chain constant region, wherein the heavy chain CDR1, CDR2, and CDR3 comprises TYAMH (SEQ ID NO: 24), RIRTKSSNYATYYAASVKG (SEQ ID NO: 25), and DMGIRRQFAY (SEQ ID NO: 26), respectively; wherein the light chain CDR1, CDR2, and CDR3 comprises RASQSVDTFDYSFLH (SEQ ID NO: 27), RASNLES (SEQ ID NO: 28), and QQSNQDPYT (SEQ ID NO: 29), respectively; and wherein the IgG1 heavy chain constant region comprises one or more amino acid substitutions selected from the group consisting of L234A, L235E, and G237A, per EU numbering.

Provided herein is an isolated antibody which specifically binds to TREM-1, comprising a heavy chain CDR1, CDR2, CDR3; a light chain CDR1, CDR2, CDR3; and an IgG1 heavy chain constant region, wherein the heavy chain CDR1, CDR2, and CDR3 comprises TYAMH (SEQ ID NO: 24), RIRTKSSNYATYYAASVKG (SEQ ID NO: 25), and DMGIRRQFAY (SEQ ID NO: 26), respectively; wherein the light chain CDR1, CDR2, and CDR3 comprises RASQSVDTFDYSFLH (SEQ ID NO: 27), RASNLES (SEQ ID NO: 28), and QQSNQDPYT (SEQ ID NO: 29), respectively; and wherein the IgG1 heavy chain constant region comprises amino acid substitutions selected from the group consisting of L234A, L235E, G237A, A330S, and P331S, per EU numbering.

Provided herein is an isolated antibody which specifically binds to TREM-1, comprising a heavy chain CDR1, CDR2, CDR3; a light chain CDR1, CDR2, CDR3; and an IgG1 heavy chain constant region, wherein the heavy chain CDR1, CDR2, and CDR3 comprises TYAMH (SEQ ID NO: 24), RIRTKSSNYATYYAASVKG (SEQ ID NO: 25), and DMGIRRQFAY (SEQ ID NO: 26), respectively; wherein the light chain CDR1, CDR2, and CDR3 comprises RASQSVDTFDYSFLH (SEQ ID NO: 27), RASNLES (SEQ ID NO: 28), and QQSNQDPYT (SEQ ID NO: 29), respectively; and wherein the IgG1 heavy chain constant region comprises one or more amino acid substitutions selected from the group consisting of K214R, C226S, C229S, and P238S, per EU numbering.

Provided herein is an isolated antibody which specifically binds to TREM-1, comprising a heavy chain CDR1, CDR2, CDR3; a light chain CDR1, CDR2, CDR3; and an IgG1 heavy chain constant region, wherein the heavy chain CDR1, CDR2, and CDR3 comprises TYAMH (SEQ ID NO: 24), RIRTKSSNYATYYAASVKG (SEQ ID NO: 25), and DMGIRRQFAY (SEQ ID NO: 26), respectively; wherein the light chain CDR1, CDR2, and CDR3 comprises RASQSVDTFDYSFLH (SEQ ID NO: 27), RASNLES (SEQ ID NO: 28), and QQSNQDPYT (SEQ ID NO: 29), respectively; and wherein the IgG1 heavy chain constant region comprises one or more amino acid substitutions selected from the group consisting of S131C, K133R, G137E, G138S, Q196K, I199T, N203D, K214R, C226S, C229S, and P238S, per EU numbering.

In some embodiments, TREM-1 comprises an amino acid sequence of SEQ ID NO: 1, SEQ ID NO: 2, SEQ ID NO: 3, or SEQ ID NO: 7.

In some embodiments, the antibody of the present disclosure has a decreased binding affinity to FcγRI (CD64), FcγRIIA (CD32), FcγRIIB (CD32), FcγRIIIA (CD16a), FcγRIIIB (CD16b), or any combination thereof compared to an antibody comprising a heavy chain consisting of the amino acid sequence as set forth in SEQ ID NO: 76 and a light chain consisting of the amino acid sequence as set forth in SEQ ID NO: 54. In some embodiments, the antibody has a decreased binding affinity to FcγRI (CD64) by at least two fold, at least three fold, at least four fold, at least five fold, at least six fold, at least seven fold, at least eight fold, at least nine fold, or at least 10 fold compared to an antibody comprising a heavy chain consisting of the amino acid sequence as set forth in SEQ ID NO: 76 and a light chain consisting of the amino acid sequence as set forth in SEQ ID NO: 54.

In some embodiments, the antibody disclosed herein is less immunogenic compared to an antibody comprising a heavy chain consisting of the amino acid sequence as set forth in SEQ ID NO: 76 and a light chain consisting of the amino acid sequence as set forth in SEQ ID NO: 54. In some embodiments, the antibody does not agonize TREM-1 signaling upon binding to TREM-1 and in the absence of a stimulator. In some embodiments, the antibody does not induce expression of an inflammatory cytokine in immature dendritic cells (iDCs) when the cells are incubated in the presence of the antibody and in the absence of a stimulator compared to an antibody comprising a heavy chain consisting of the amino acid sequence as set forth in SEQ ID NO: 76 and a light chain consisting of the amino acid sequence as set forth in SEQ ID NO: 54.

In some embodiments, the antibody disclosed herein blocks the production of an inflammatory cytokine in a cell when the cells are activated in the presence of both the antibody and a stimulator. In some embodiments, the stimulator is a TREM-1 ligand. In some embodiments, the inflammatory cytokine is selected from a group consisting of IL-6, TNF-α, IL-8, IL-1β, IL-12, chitinase-3-like protein 1 (CHI3L1), and combinations thereof.

In some embodiments, the antibody of the present disclosure binds human FcRn, cynomolgus FcRn, and/or mouse FcRn in a pH dependent manner. In some embodiments, the antibody disclosed herein is more thermally stable compared to a reference antibody comprising a heavy chain consisting of the amino acid sequence as set forth in SEQ ID NO: 76 and a light chain consisting of the amino acid sequence as set forth in SEQ ID NO: 54, as measured by a Capillary Differential scanning calorimeter (CAP-DSC). In some embodiments, about 10% to 20%, about 20% to 30% (e.g., 24%), or about 30% to 40% of the antibody is reversible when it is heated to 77° C. In some embodiments, the antibody has a higher melting temperature (Tm) compared to an antibody comprising a heavy chain consisting of the amino acid sequence as set forth in SEQ ID NO: 76 and a light chain consisting of the amino acid sequence as set forth in SEQ ID NO: 54.

In some embodiments, the antibody disclosed herein has a viscosity of less than 5 cP, less than 4 cP, less than 3 cP, less than 2.5 cP, less than 2.4 cP, less than 2.3 cP, less than 2.2 cP, less than 2.1 cP, less than 2 cP, less than 1.9 cP, less than 1.8 cP, less than 1.7 cP, less than 1.6 cP, less than 1.5 cP, less than 1.4 cP, less than 1.3 cP, less than 1.2 cP, less than 1.1 cP, less than 1.0 cP, less than 0.9 cP, less than 0.8 cP, less than 0.7 cP, less than 0.6 cP, less than 0.5 cP, less than 0.4 cP, less than 0.3 cP, less than 0.2 cP, or less than 0.1 cP at a concentration of 80 mg/mL. In some embodiments, the antibody has a viscosity of less than 10 cP (e.g., 9 cP) at a concentration of 130 mg/mL.

In some embodiments, the antibody binds to cynomolgus TREM-1 with of a $K_D$ of less than 4 nM (e.g., 3.4 nM) as measured by Biacore. In some embodiments, the antibody binds to human TREM-1 with a $K_D$ of less than 1 nM (e.g., 0.91 nM), as measured by Biacore.

In some embodiments, the antibody is monomeric as observed by size-exclusion high-performance liquid chromatography (SE-HPLC). In some embodiments, the antibody exhibits minimal risk for fragmentation as observed by two-dimensional liquid chromatography-tandem mass spectrometry (2D-LC/MS) or intact mass analysis using liquid chromatography-tandem mass spectrometry (LC/MS). In some embodiments, the antibody has an isoelectric point of 8 to 9 (e.g., 8.75).

In some embodiments, the antibody is stable in a formulation comprising histidine, sucrose, arginine, and NaCl. In some embodiments, the antibody is stable for at least 2 months in a formulation comprising 20 mM histidine, 150 mM sucrose, 25 mM arginine, and 50 mM NaCl. In some embodiments, the formulation is at a pH of 6.0 and/or wherein the formulation is stored at 4° C., 25° C., or 40° C.

Also provided herein are bispecific molecules comprising an anti-TREM-1 antibody of the present disclosure, linked to a molecule having a second binding specificity.

Provided herein are nucleic acids encoding the antibody disclosed herein, vectors comprising the nucleic acids, and cells transformed with the vectors.

Provided herein are immunoconjugates comprising the anti-TREM-1 antibodies disclosed herein, linked to an agent.

Provided herein are compositions comprising anti-TREM-1 antibodies, or antigen binding portions thereof, bispecific molecules, or immunoconjugates described herein, and a carrier. Also provided herein are kits comprising the anti-TREM-1 antibodies, or antigen binding portions thereof, bispecific molecules, or immunoconjugates described herein, and instructions for use.

Provided herein is a method of inhibiting TREM-1 activity in a subject in need thereof, comprising administering the anti-TREM-1 antibody, the bispecific molecule, the nucleic acid, the vector, the cell, or the immunoconjugate of the present disclosure.

Provided herein is a method of treating an inflammatory disease or an autoimmune disease in a subject in need thereof, comprising administering the anti-TREM-1 antibody, the bispecific molecule, the nucleic acid, the vector, the cell, or the immunoconjugate of the present disclosure. In some embodiments, the inflammatory disease or the autoimmune disease is selected from the group consisting of an inflammatory bowel disease (IBD), Crohn's disease (CD), ulcerative colitis (UC), irritable bowel syndrome, rheumatoid arthritis (RA), psoriasis, psoriatic arthritis, systemic lupus erythematosus (SLE), lupus nephritis, vasculitis, sepsis, systemic inflammatory response syndrome (SIRS), type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogrens's syndrome, autoimmune nephritis, Goodpasture's syndrome, chronic inflammatory demyelinating polyneuropathy, allergy, asthma, other autoimmune diseases that are a result of either acute or chronic inflammation, and any combinations thereof. In some embodiments, the method further comprises administering one or more additional therapeutics. In some embodiments, the additional therapeutics is an anti-IP-10 antibody or an anti-TNF-α antibody.

BRIEF DESCRIPTION OF THE DRAWINGS/FIGURES

FIGS. 1A and 1B shows that all the mAb 0318 variants bind to human and cynomolgus TREM-1 with similar affinity as the original mAb 0318 antibody (IgG4). FIG. 1A shows the binding affinity data for the 318-IgG1.3f variant to both human (top row) and cynomolgus (bottom row) TREM-1. FIG. 1B shows the binding affinity data for several different mAb 0318 variants to human TREM-1. The different variants shown include: (i) 318-IgG1.1f, (ii) 318-IgG1.3f, (iii) 318-IgG4-Aba, (iv) 318-IgG1-Aba, and (v) 318-IgG1.1f (M to Q mutant). The binding affinity data for the mAb 0318 antibody (IgG4 A and B) were provided for comparison purposes in FIG. 1B.

FIGS. 2A and 2B show the internalization of mAb 0318-IgG1.3f upon binding to TREM-1 expressed on CD14+ monocytes at various time points post-TREM-1 binding. In FIG. 2A, TREM-1 receptor expression was analyzed at 0, 6, and 24 hours post-binding. In FIG. 2B, TREM-1 receptor expression was analyzed at 0, 4, and 20 hours post-binding. FIG. 2B also provides data using the TREM26 antibody, which does not compete with the 0318 antibody variants for binding to TREM-1. The TREM26 antibody was used to assess the fate of the TREM-1 receptor once it was internalized (e.g., whether it was degraded or recycled back to the surface).

FIG. 3 shows that the mAb 0318 variants do not agonize TREM-1 signaling as measured by the BWZ/hTREM-1 Reporter Cell Assay when a reporter cell line is incubated with ("Both") or without CHO-CD32 ("BWZ 36 only"). The variant antibodies shown include: (i) 318-IgG1.1f ("IgG1.1f"), (ii) 318-IgG1.3f ("IgG1.3f"), (iii) 318-IgG4-Aba ("FcAba-4"), (iv) 318-IgG1-Aba ("FcAba-1"). The MAB1278 antibody, a known agonist of TREM-1 signaling, was used as a positive control antibody (see inserted box). The 5C8 (isotype control) antibody was used as a negative control.

FIG. 4 shows potency of the different mAb 0318 variants at blocking TREM-1 mediated production of inflammatory cytokines by different human cells. The mAb 0318 antibody variants shown in FIG. 4 inhibit TREM-1 mediated release of inflammatory cytokines (e.g., TNF-α, IL-6, or IL-8) from different human cell types: PBMC, monocytes, neutrophils, and RBC-sedimented whole blood (i.e., majority of red blood cells removed using dextran-based RBC sedimentation protocol as described in the Examples). To produce the inflammatory cytokines, the cells were stimulated with either plate-bound PGRP1 and soluble peptidoglycan that lack TLR2 activity ("PGRP+PGN-Ecndss") or phorbol 12-myristate 13-acetate (PMA) stimulated neutrophils expressing PGRP1 ("PMA-Stim Neutrophil Endogenous PGRP"). The variant antibodies shown include: (i) 0318-

IgG4, (ii) 0318-IgG1.3f, (iii) 0318-IgG1.1f, (iv) 0318-IgG1-Aba, and (v) 318-IgG4-Aba. "N/D" indicates that the expression level of the particular inflammatory cytokine was not determined.

FIGS. 5A and 5B show the potency of mAb 0318-IgG1.3f to block IL-8 production from whole blood after stimulation with PGN with or without PGRP1 in the presence of NOD2 inhibitor. FIG. 5A provides the inhibition data generated using the whole blood pharmacodynamics assay as described in the Examples. FIG. 5B provides the inhibition data generated using the whole blood intracellular cytokine assay as described in the Examples.

Figure 6A:
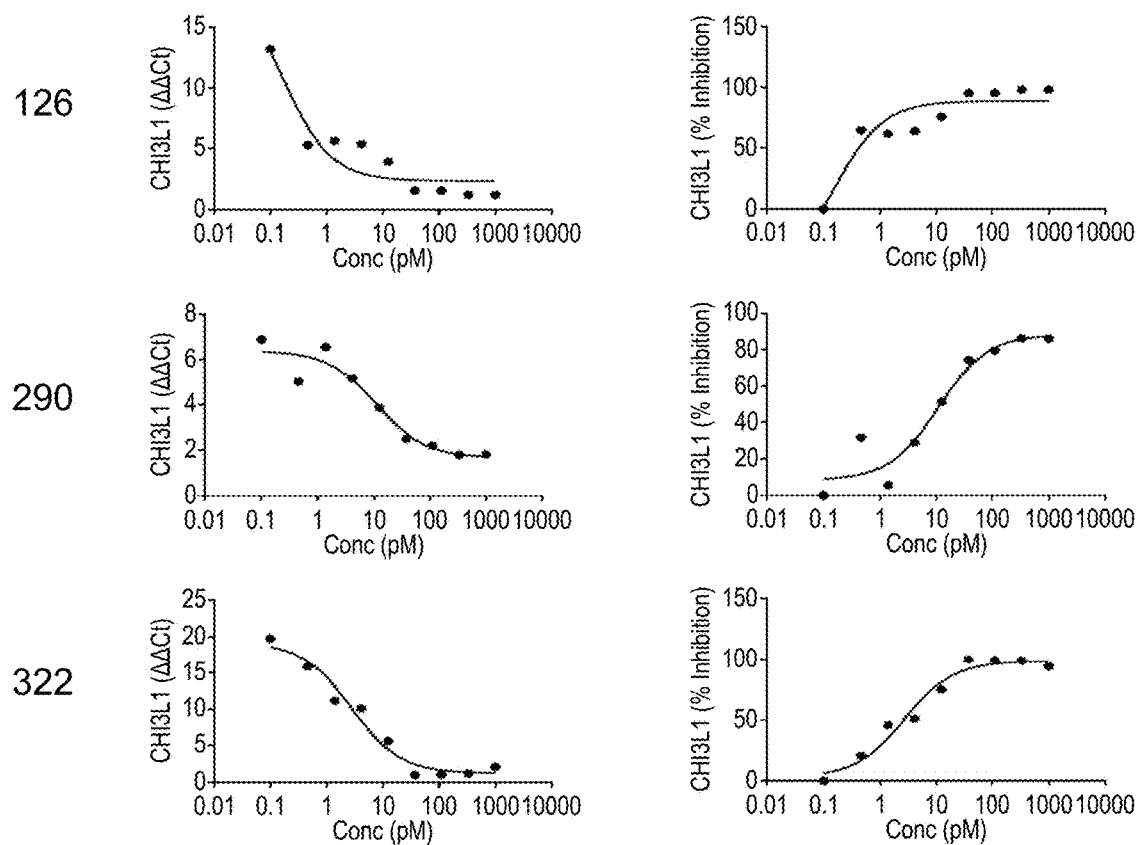
Figure 6B:
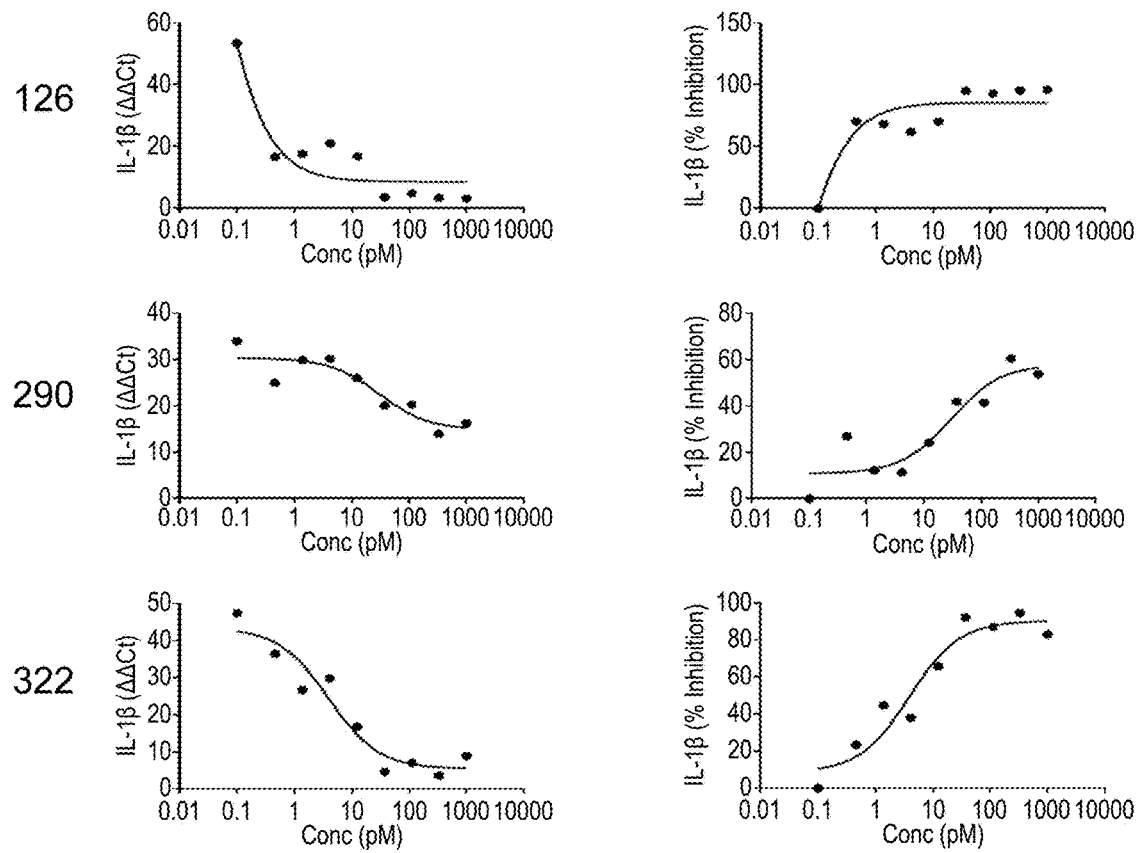
Figure 6C:
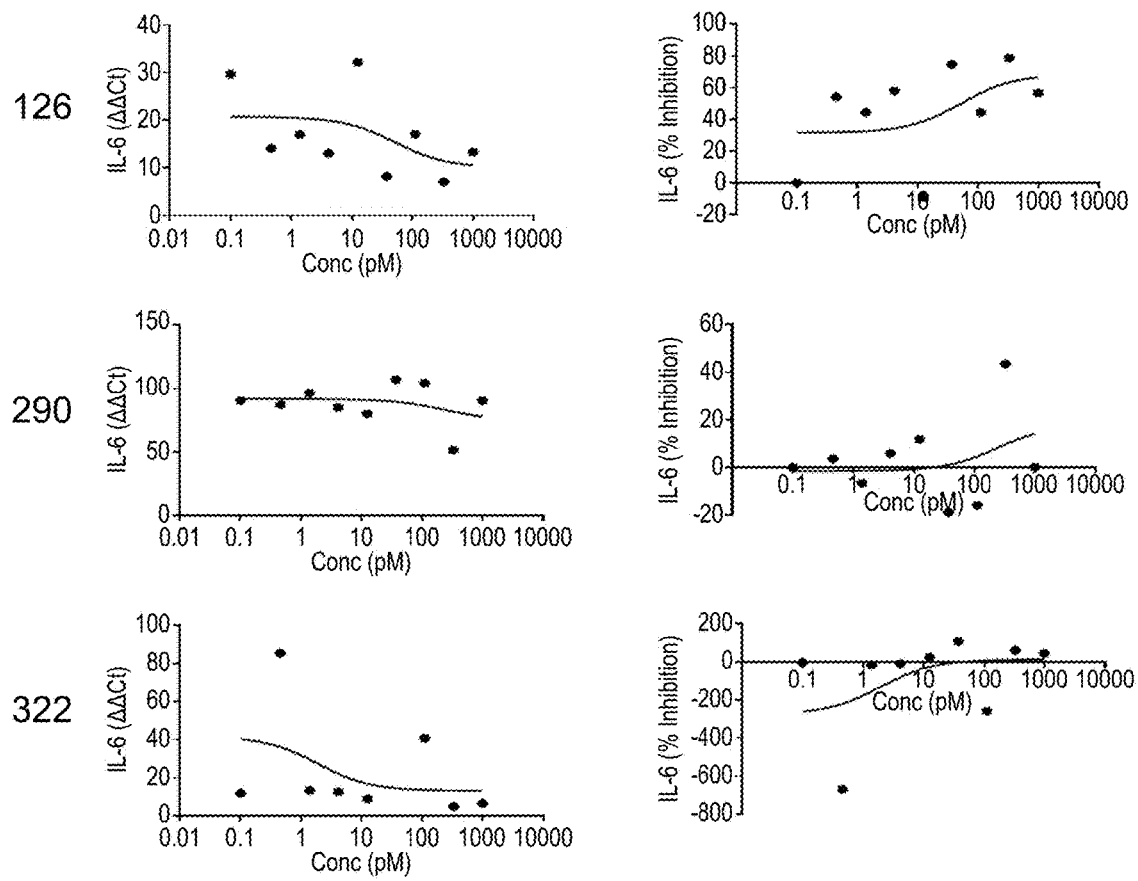

FIGS. 6A to 6C show the RNA expression levels of chitinase-3-like protein 1 ("CHI3L1") (FIG. 6A), IL-10 (FIG. 6B), and IL-6 (FIG. 6C) from whole blood stimulated in the presence of varying concentrations of mAb 0318-IgG1.3f (0-1 nM). Whole blood were collected from three different donors (#126, #290, and #322) and stimulated with soluble PGRP1 and soluble peptidoglycan that lack TLR2 activity ("Soluble PGRP+Soluble PGN-Ecndss"). In each of FIGS. 6A to 6C, the RNA expression levels (y-axis) are shown as both % inhibition (right column) and AACt (difference between the value of a reference gene and the value of the test sample) (left column). The different concentrations of the 0318-IgG1.3f antibody are shown on the x-axis.

Figure 7:
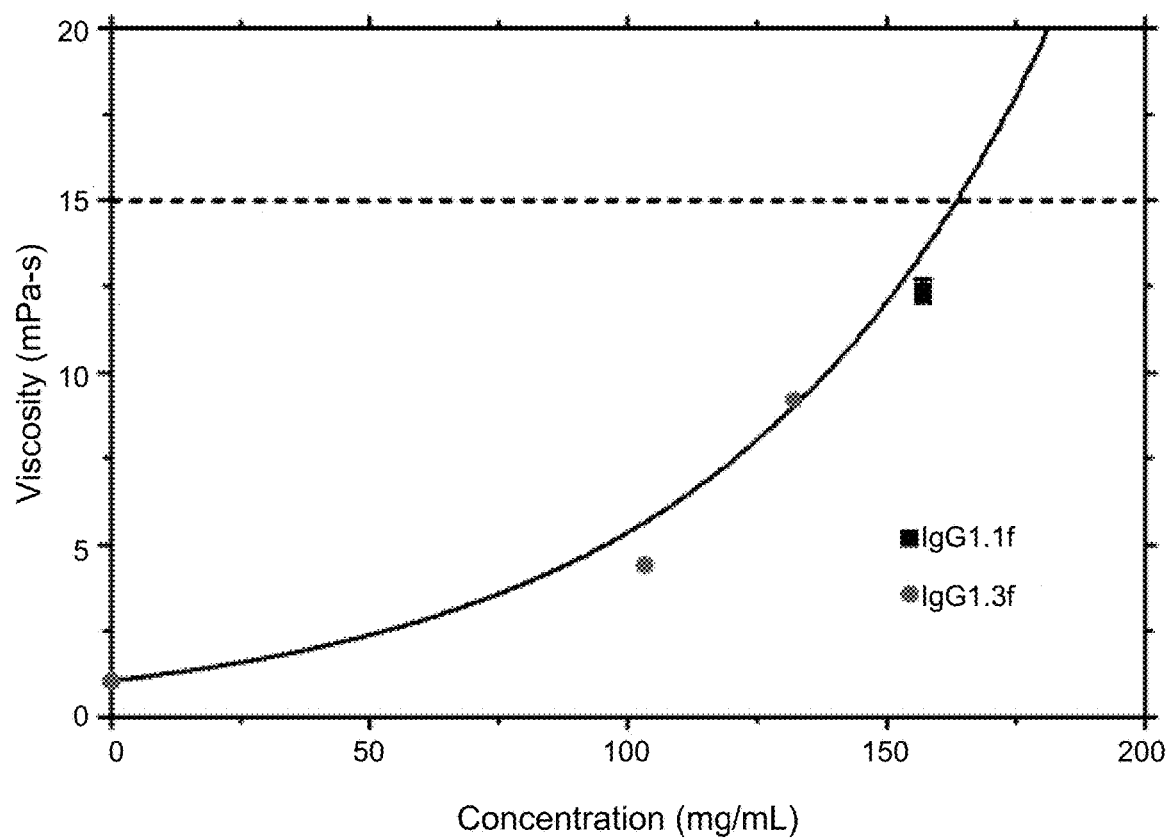

FIG. 7 shows the viscosity-concentration profile of both the 318-IgG1.1f (square) and the 318-IgG1.3f (circle) variant antibodies. The viscosity profile was generated from dilution scheme using Rheosense m-VROC dynamic viscometer using a 3 point shear sweep for each point at constant temperature. The solid line provides the best non-linear curve fit for the data shown. The dotted line shows the maximum allowable viscosity level for efficacy.

Figure 8:
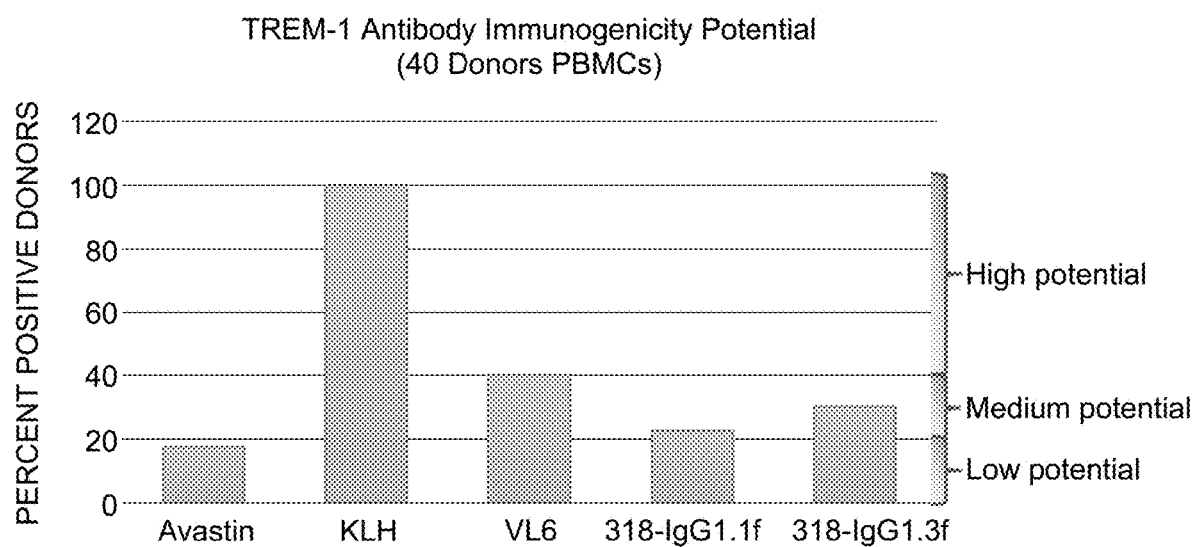

FIG. 8 shows that both the 318-IgG1.1f and the 318-IgG1.3f variant antibodies have low to medium risk for immunogenicity. VL6 (immunogenic IL-21R mAb) and KLH (keyhole limpet hemocyanin) were used as positive controls. Avastin was used as a negative control.

Figure 9A:
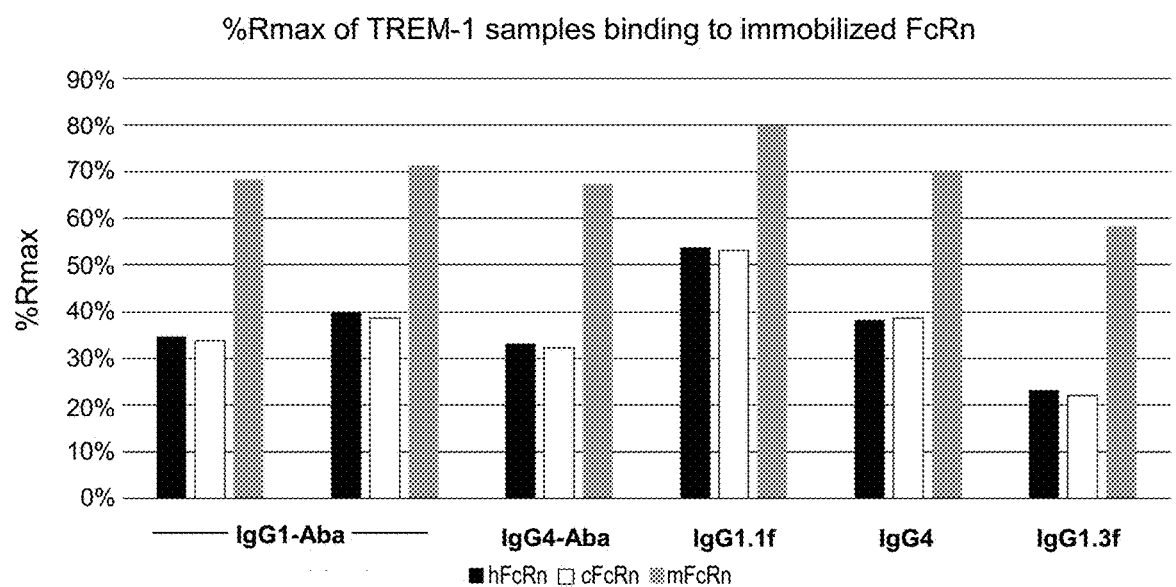
Figure 10A:
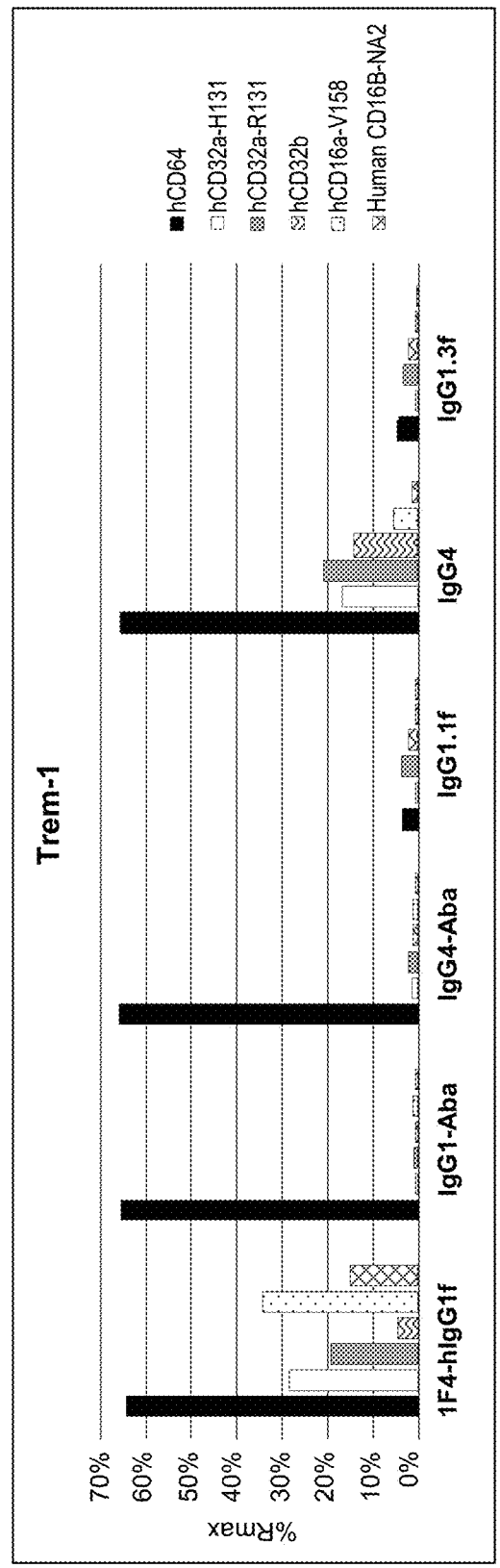
Figure 10B:
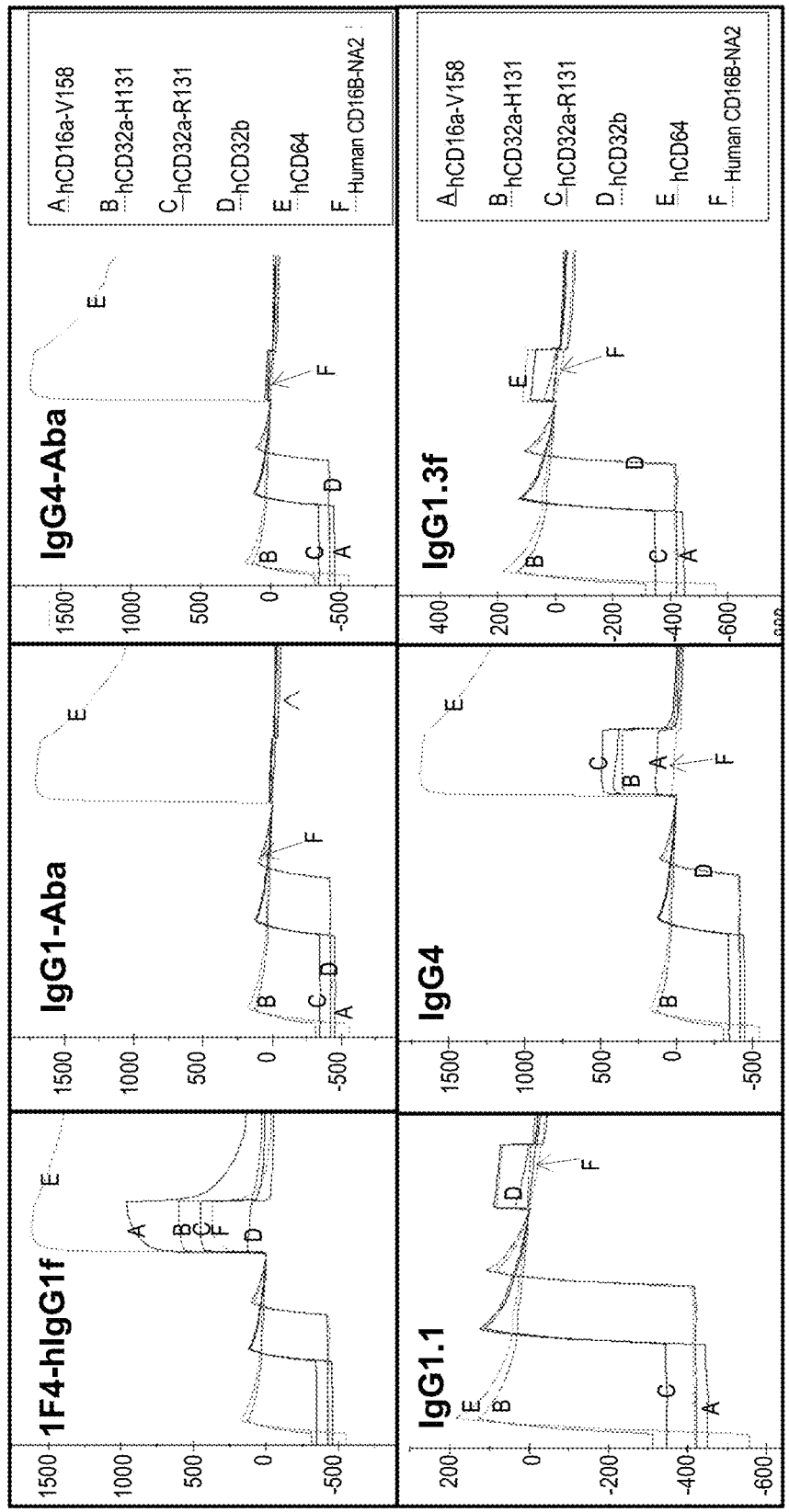

FIGS. 9A and 9B show that all the mAb 0318 variants are capable of binding to FcRn (human (black), cyno (white), and mouse (gray)) in a pH-dependent manner. FIG. 9A provides FcRn binding as % Rmax (maximum FcRn binding capacity). FIG. 9B provides the FcRn binding as sensorgrams. The 0318 antibody variants shown include: (i) IgG1-Aba, (ii) IgG4-Aba, (iii) IgG1.1f, and (iv) IgG1.3f. The mAb 0318 (IgG4) antibody is also shown for comparison purposes FIGS. 10A and 10B show that all the mAb 0318 antibody variants demonstrate decreased binding to one or more of the human FcγRs (i.e., CD64, CD32a-H131 variant, CD32a-R131 variant, CD32b, CD16a-V158 variant, and CD16B-NA2 variant). FIG. 10A shows the binding affinity as % Rmax (maximum FcγR capacity). FIG. 10B shows the sensorgrams. The 0318 antibody variants shown include: (i) IgG1-Aba, (ii) IgG4-Aba, (iii) IgG1.1f, and (iv) IgG1.3f. The mAb 0318 (IgG4) antibody is shown for comparison purposes. 1F4-hIgG1f antibody, which is known to bind to multiple FcγRs, was used as a control.

Figure 11A:
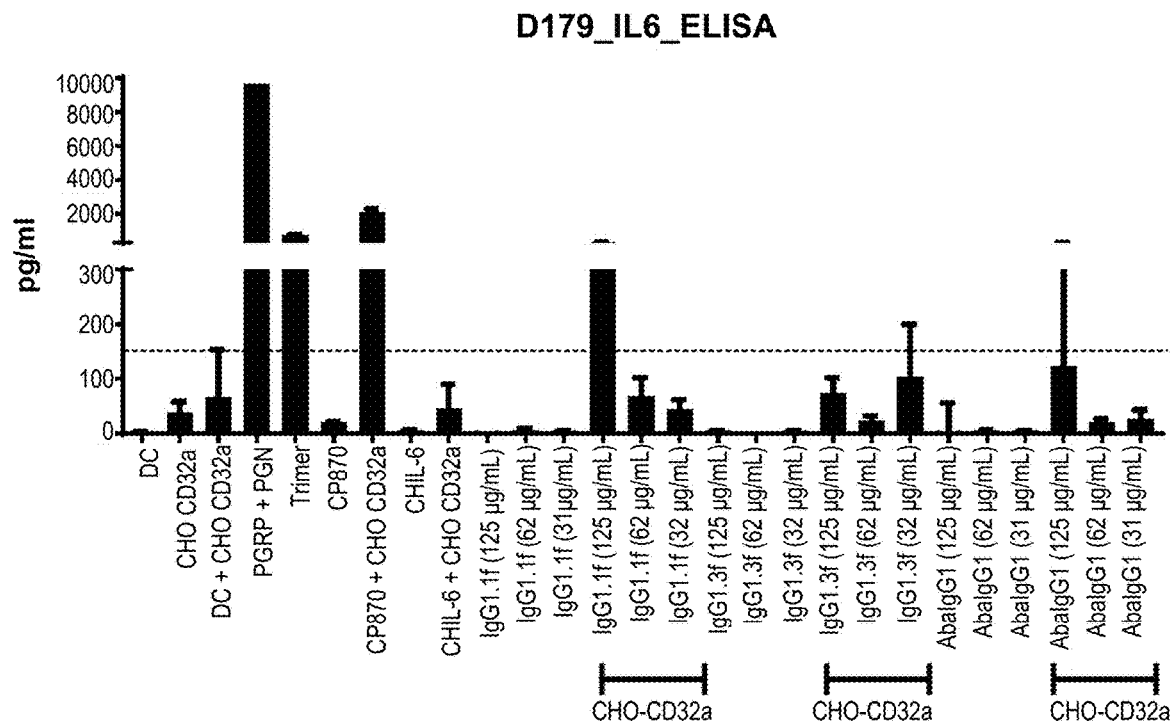
Figure 11B:
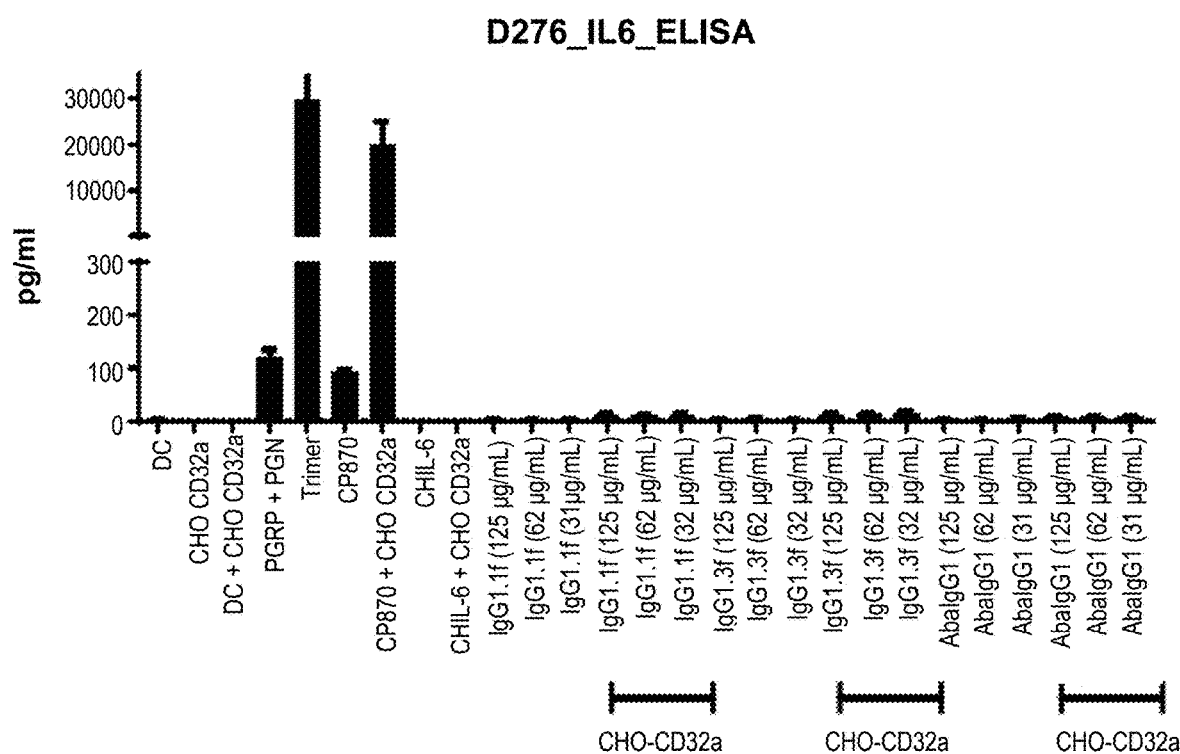
Figure 11C:
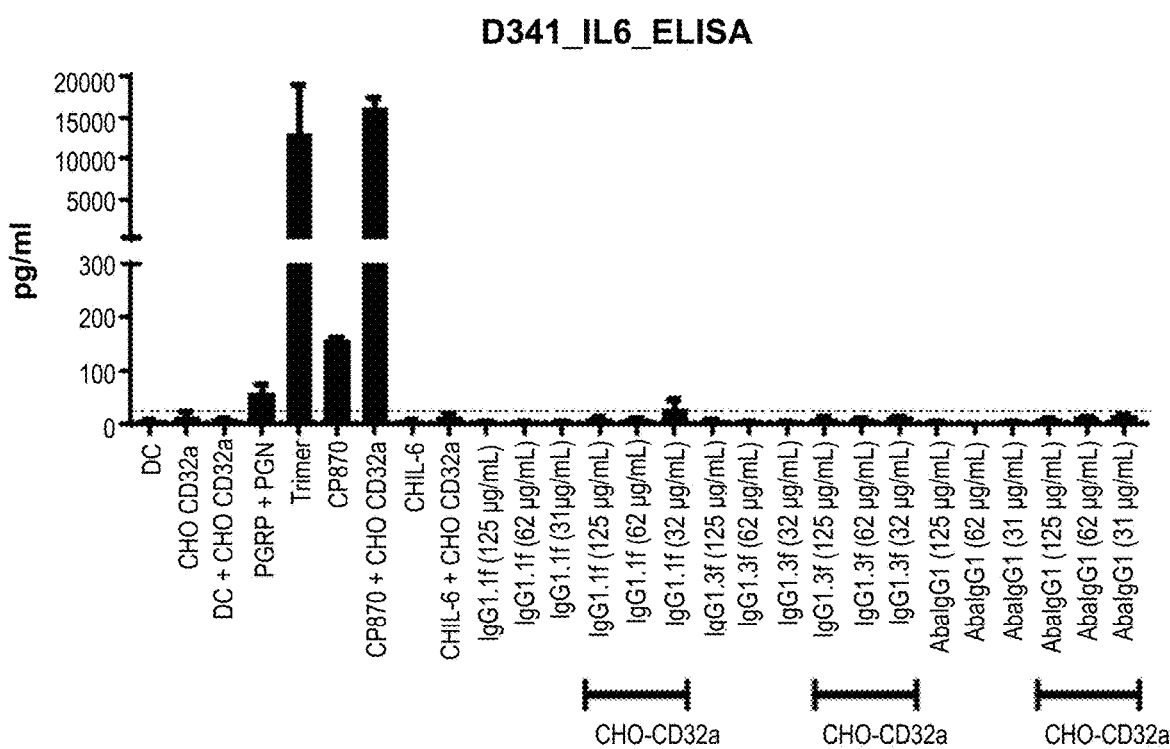
Figure 11D:
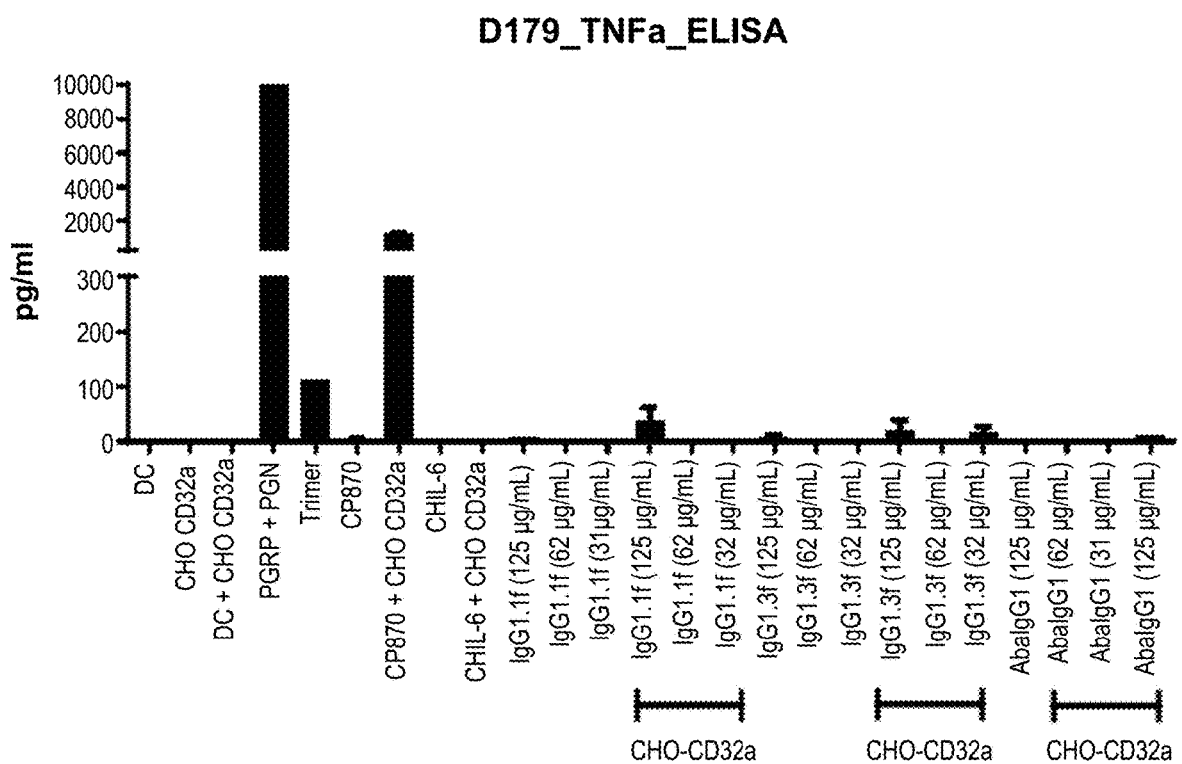
Figure 11E:
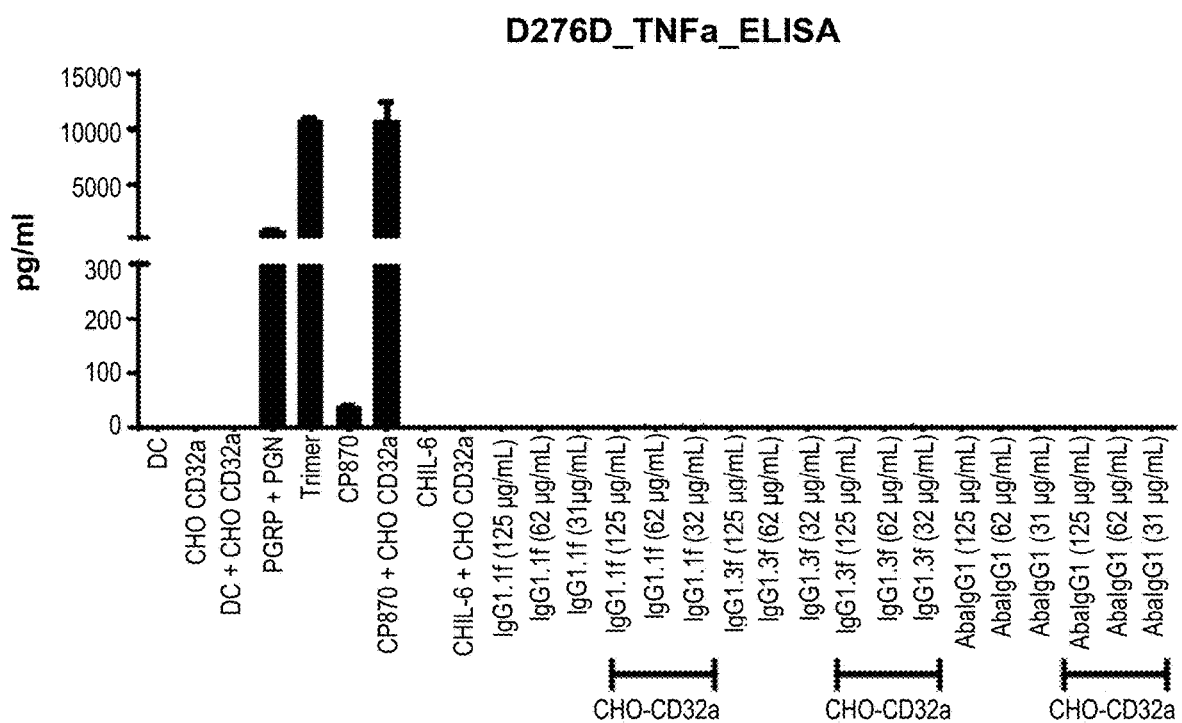
Figure 11F:
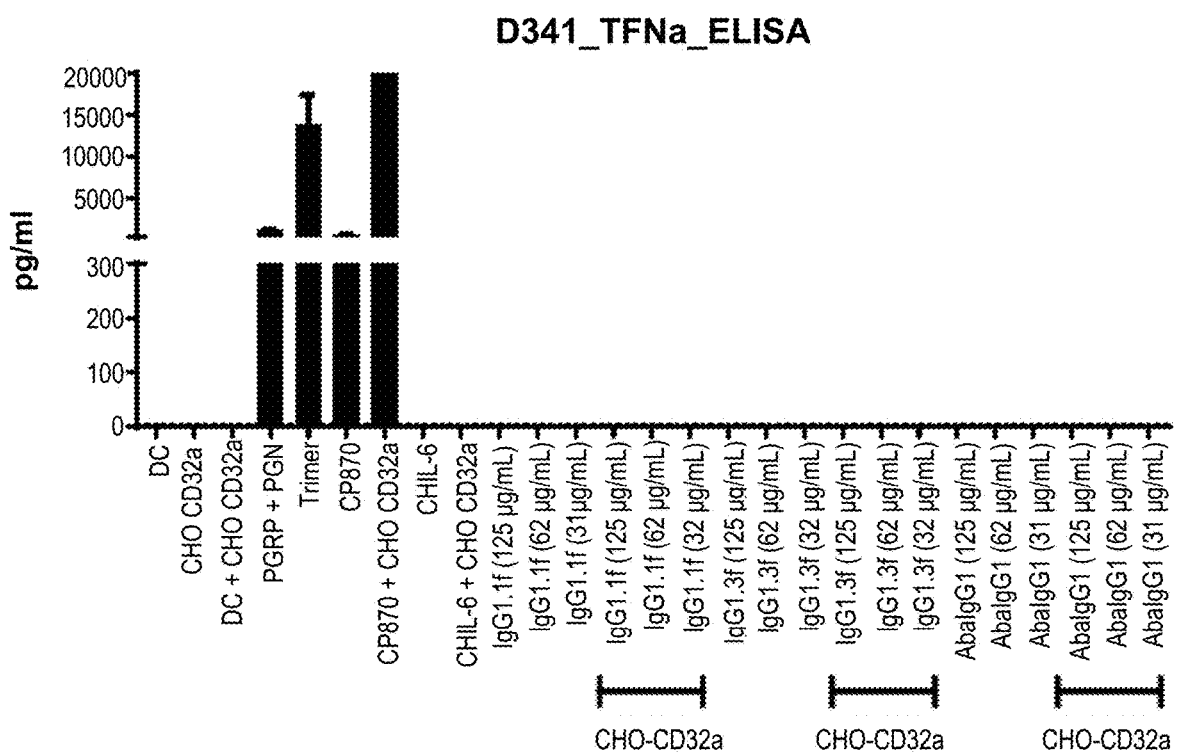
Figure 11G:
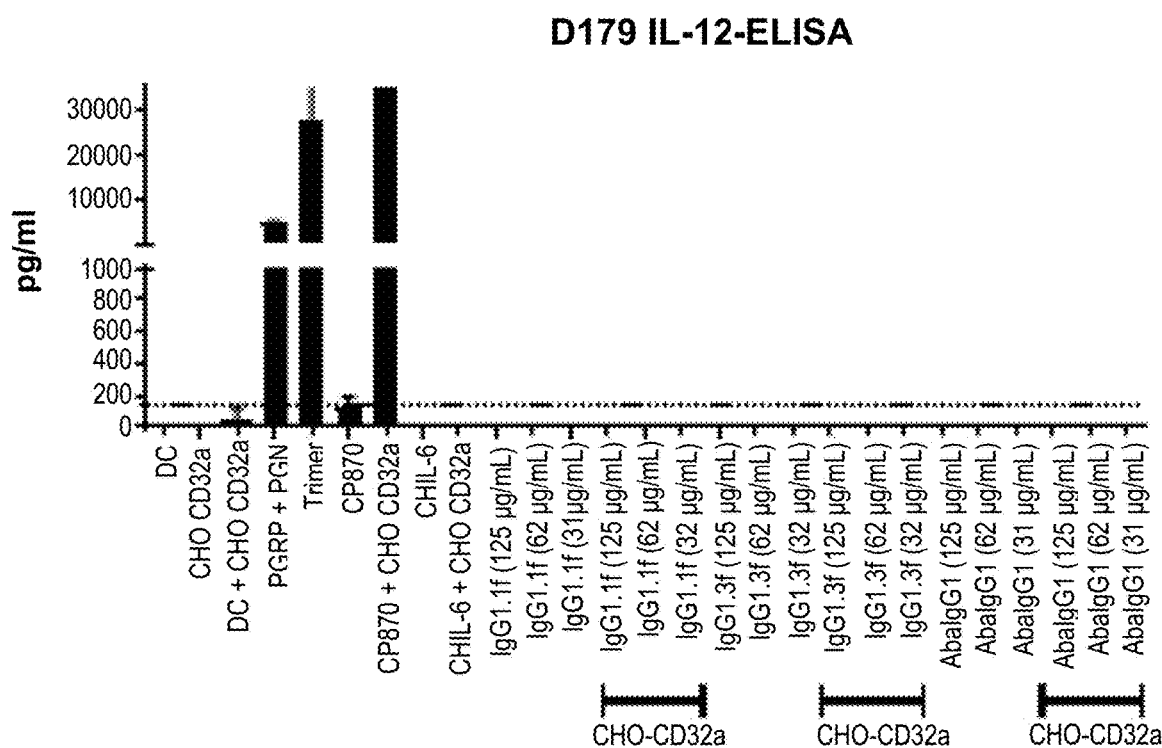
Figure 11H:
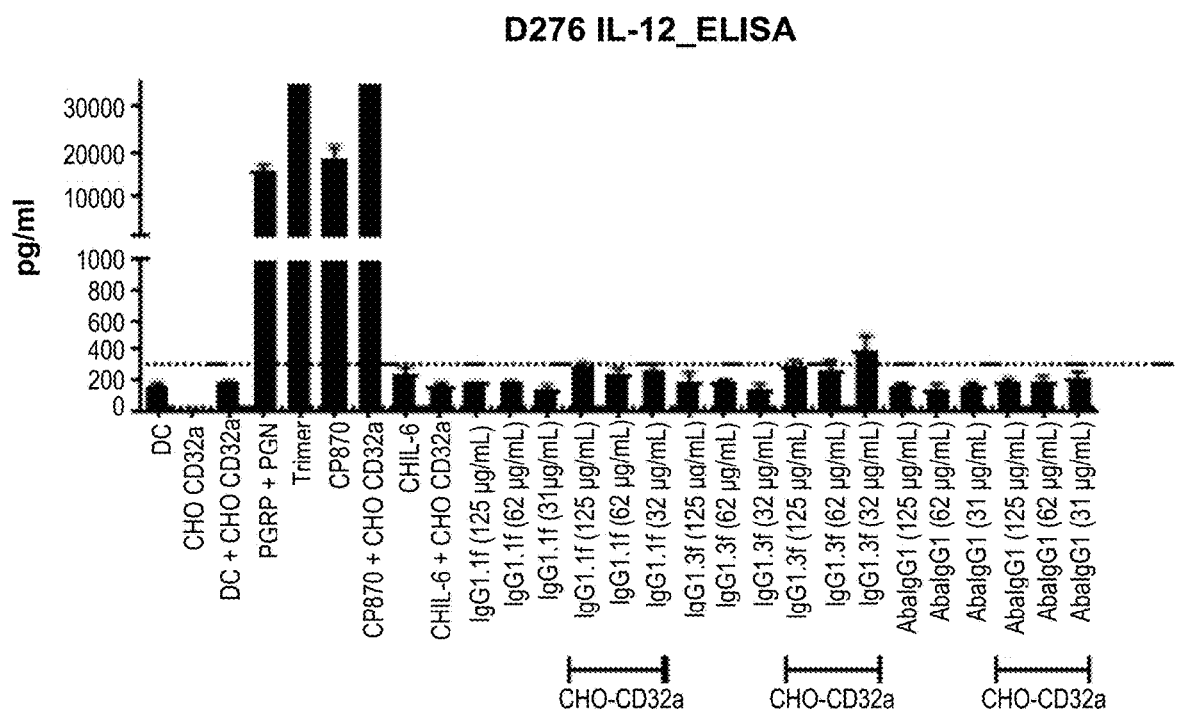
Figure 11I:
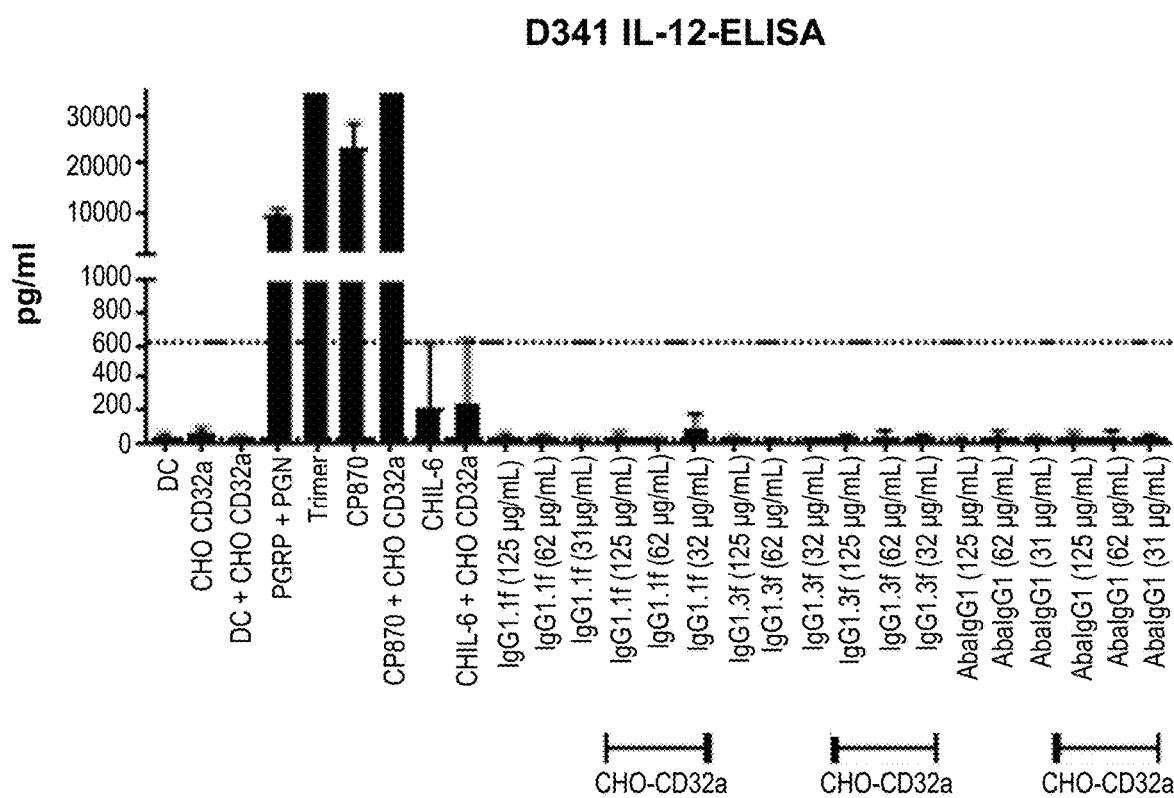

FIGS. 11A to 11I show that the 0318 variant antibodies are not agonistic on their own (i.e., in the absence of a stimulus), as measured by the release of different inflammatory cytokines (e.g., IL-6, TNF-α, and IL-12) when cultured with immature-dendritic cells. FIGS. 11A, 11B, and 11C provide the amount of IL-6 produced for immature-dendritic cells isolated from donors D179, D276, and D341, respectively. FIGS. 11D, 11E, and 11F provide the amount of TNF-α produced for immature-dendritic cells isolated from donors D179, D276, and D341, respectively. FIGS. 11G, 11H, and 11I provide the amount of IL-12 produced for immature-dendritic cells isolated from donors D179, D276, and D341, respectively. The 0318 antibody variants shown include: (i) IgG1.1f, (ii) IgG1.3f, and (iii) IgG1-Aba. The dosages (μg/mL) of the antibodies used are shown in parentheses. The immature-dendritic cells were cultured with the anti-TREM-1 antibody variants with and without CHO cells expressing membrane CD32a (to stimulate Fc cross-linking). PGRP+PGN, CD40L trimer ("Trimer"), and Pfizer's anti-CD40 agonist antibody ("CP870") were used as positive controls. The isotype antibody ("CHIL-6") was used as a negative control. The dotted line shows the lowest limit of detection for the assay.

Figure 12:
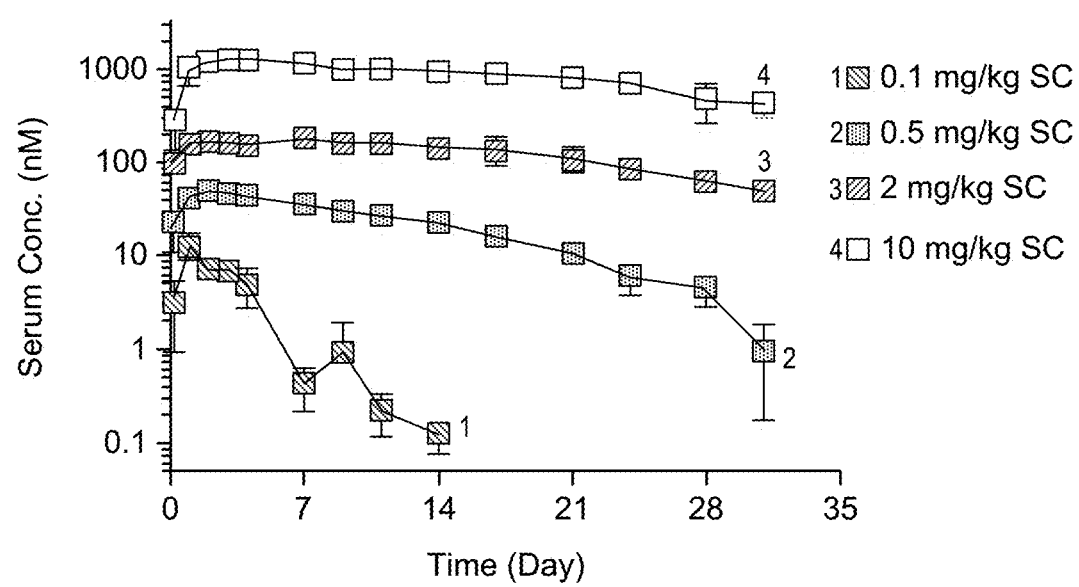

FIG. 12 shows the pharmacokinetics of single dose mAb 0318-IgG1.3f variant in cynomolgus monkey following subcutaneous administration. Each of the animals received one of the following doses: (i) 0.1 mg/kg (n=4) ("1"), (ii) 0.5 mg/kg (n=4) ("2"), (iii) 2 mg/kg (n=3) ("3"), or (iv) 10 mg/kg (n=4) ("4"). Data are shown as mean±standard deviation.

Figure 13:
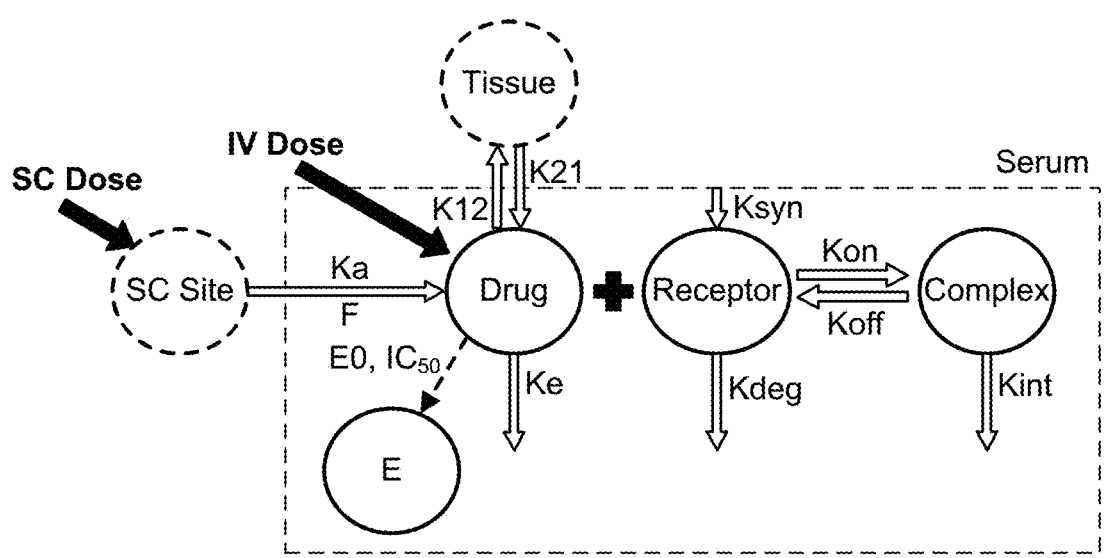

FIG. 13 shows target-mediated drug disposition schematic used to describe the pharmacokinetic (PK), pharmacodynamics (PD), and receptor occupancy (RO) data in cynomolgus monkey.

Figures 14A, 14B:
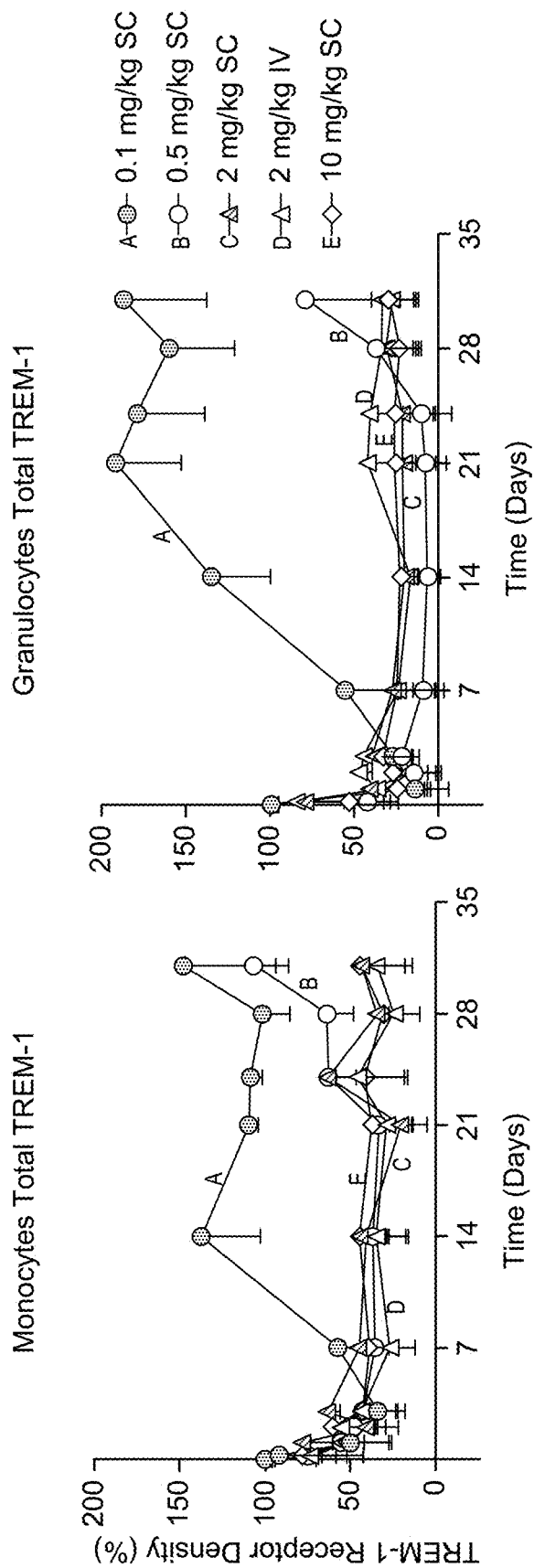

FIGS. 14A and 14B show the total TREM-1 receptor density on monocytes (FIG. 14A) and granulocytes (FIG. 14B) following single dose (subcutaneous (sc) or intravenous (iv) administration) of mAb 0318-IgG1.3f variant in cynomolgous monkey. The TREM-1 receptor density is shown as a percentage of the TREM-1 receptor density prior to administration of the antibody. Each of the animals received one of the following doses: (a) 0.1 mg/kg (sc) (n=4) ("A"), (b) 0.5 mg/kg (n=4) (sc) ("B"), (c) 2 mg/kg (n=3) (sc) ("C"), (d) 2 mg/kg (n=3) (iv) ("D"), or (e) 10 mg/kg (n=4) (sc) ("E"). Data are shown as mean±standard deviation.

Figures 15A, 15B:
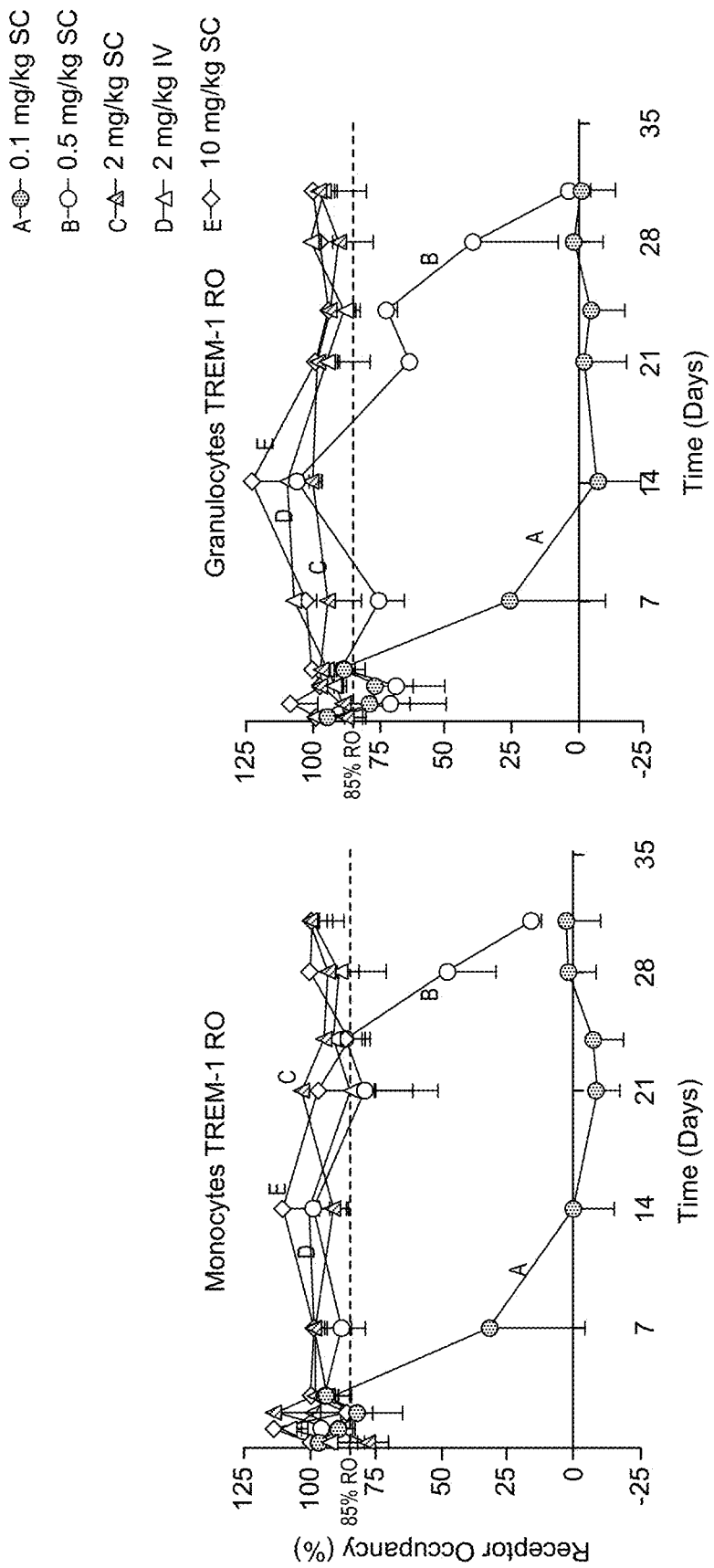

FIGS. 15A and 15B show the TREM-1 receptor occupancy on monocytes (FIG. 15A) and granulocytes (FIG. 15B) following single dose of mAb 0318-IgG1.3f variant in cynomolgous monkey. The receptor occupancy data is shown as a percentage of the total TREM-1 receptor expressed on the cells. Each of the animals received one of the following doses: (a) 0.1 mg/kg (sc) (n=4) ("A"), (b) 0.5 mg/kg (n=4) (sc) ("B"), (c) 2 mg/kg (n=3) (sc) ("C"), (d) 2 mg/kg (n=3) (iv) ("D"), or (e) 10 mg/kg (n=4) (sc) ("E"). Data are shown as mean±standard deviation. The dotted line shows 85% receptor occupancy.

Figure 16A:
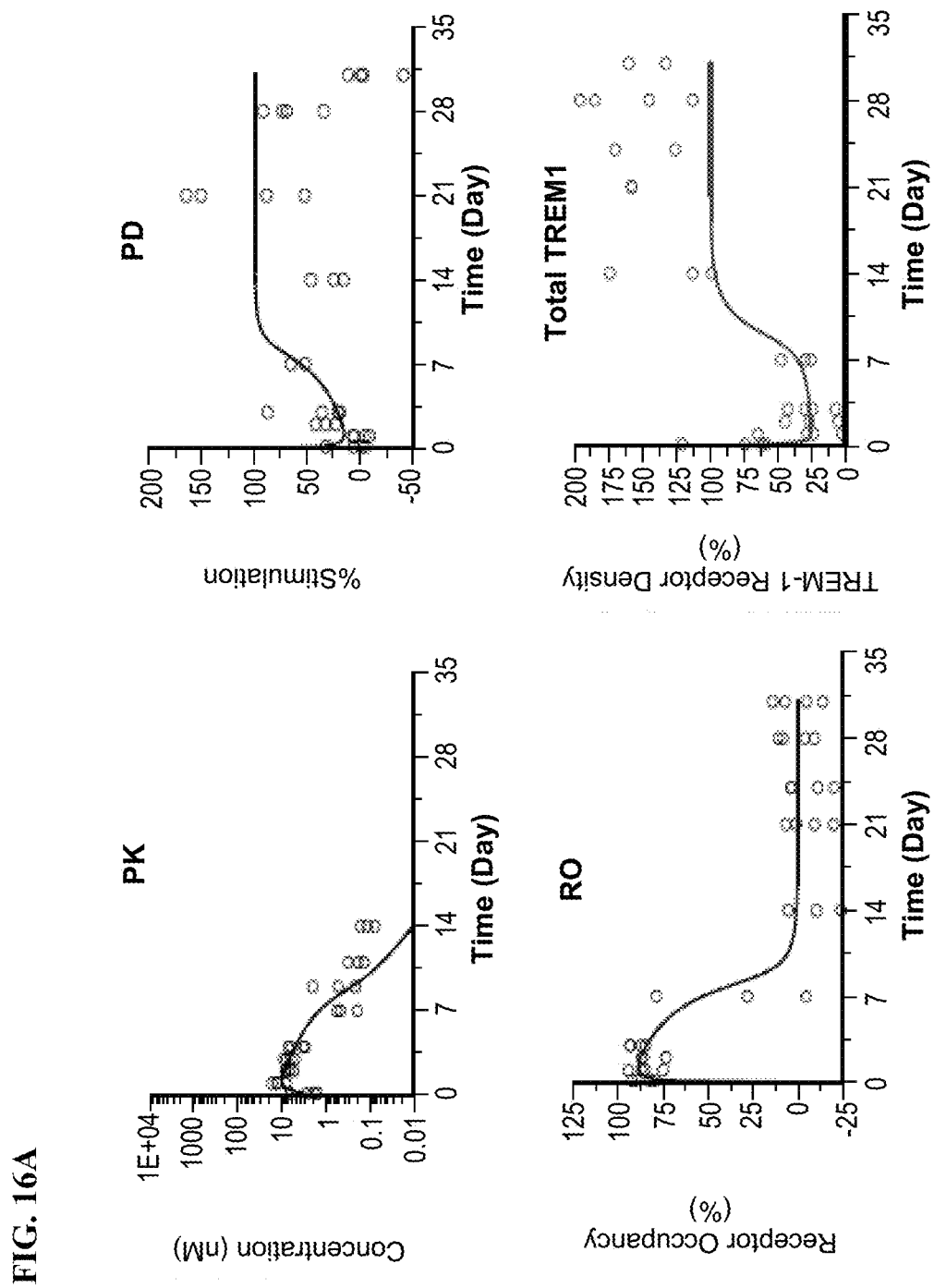
Figure 16B:
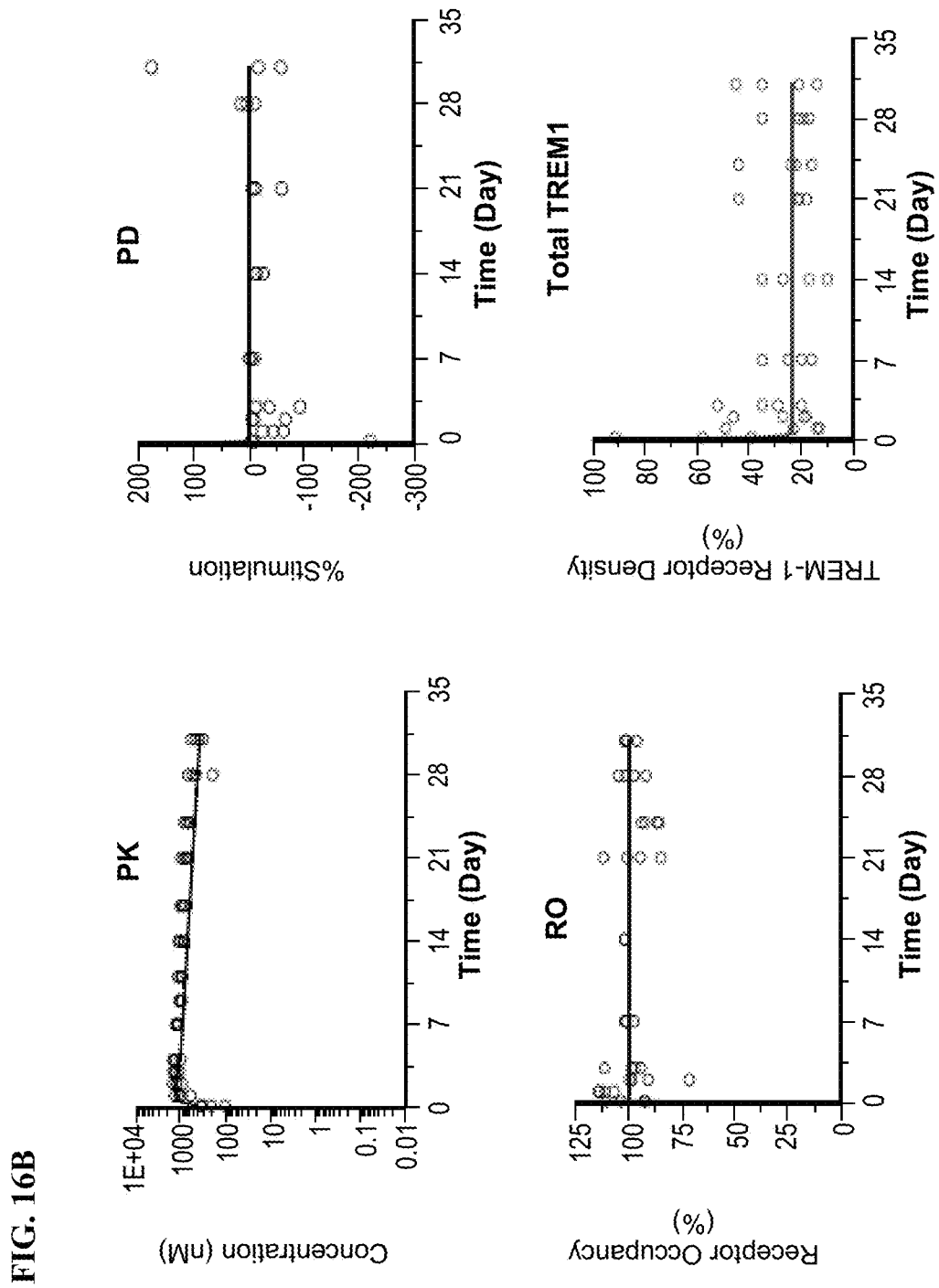

FIGS. 16A and 16B show the observed (open circle) and model-predicted (solid line) PK (upper left panel), PD (upper right panel), RO (bottom left panel), and total surface TREM-1 receptor expression (bottom right panel) following a single dose of mAb 0318-IgG1.3f variant in cynomolgus monkey described by a 2-compartment PK model with TMDD in central compartment. In FIG. 16A, each of the monkey received a single dose of 0.1 mg/kg of the antibody subcutaneously. In FIG. 16B, the animals received a single dose of 10 mg/kg of the antibody subcutaneously.

DETAILED DESCRIPTION OF DISCLOSURE

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "triggering receptor expressed on myeloid cells 1" (also known as TREM1, TREM-1, and CD354) refers to a receptor that is expressed on monocytes, macrophages, and neutrophils. Primary ligand for TREM-1 include peptidoglycan-recognition-protein 1 (PGLYRP1), which belongs to a family of peptidoglycan (PGN) binding proteins (PGRPs). When activated, TREM-1 associates with the ITAM-containing signaling adaptor protein, DAP12. Downstream signalling may include activation of the NFAT transcription factor, causing an up-regulation of pro-inflammatory cytokine production. The term "TREM-1" includes any variants or isoforms of TREM-1 which are naturally expressed by cells. Accordingly, in some embodiments, antibodies described herein can cross-react with TREM-1 from species other than human (e.g., cynomolgus TREM-1).

Three isoforms of human TREM-1 have been identified. Isoform 1 (Accession No. NP_061113.1; SEQ ID NO: 1) consists of 234 amino acids and represents the canonical sequence. Isoform 2 (Accession No. NP_001229518.1; SEQ ID NO: 2) consists of 225 amino acids and differ from the canonical sequence at amino acid residues 201-234. The amino acid residues encode part of the transmembrane domain and the cytoplasmic domain. Isoform 3 (Accession No. NP_001229519; SEQ ID NO: 3) consists of 150 amino acids, and is soluble. It lacks amino acid residues 151-234, which encode the transmembrane domain, the cytoplasmic domain, and part of the extracellular domain. The amino acid residues 138-150 also differ from the canonical sequence described above.

Below are the amino acid sequences of the three known human TREM-1 isoforms. (A) Human TREM-1 isoform 1 (Accession No. NP_061113.1; SEQ ID NO: 1; encoded by the nucleotide sequence having Accession No. NM_018643; SEQ ID NO: 4):

MRKTRLWGLLWMLFVSELRAATKLTEEKYELKEGQTLDVKCDYTLEKFAS

SQKAWQIIRDGEMPKTLACTERPSKNSHPVQVGRIILEDYHDHGLLRVRM

VNLQVEDSGLYQCVIYQPPKEPHMLFDRIRLVVTKGFSGTPGSNENSTQN

VYKIPPTTTKALCPLYTSPRTVTQAPPKSTADVSTPDSEINLTNVTDIIR

VPVFNIVILLAGGFLSKSLVFSVLFAVTLRSFVP (signal sequence is underlined);

(B) Human TREM-1 isoform 2 (Accession No. NP_001229518.1; SEQ ID NO: 2; encoded by the nucleotide sequence having Accession No. NM_001242589; SEQ ID NO: 5):

MRKTRLWGLLWMLFVSELRAATKLTEEKYELKEGQTLDVKCDYTLEKFAS

SQKAWQIIRDGEMPKTLACTERPSKNSHPVQVGRIILEDYHDHGLLRVRM

VNLQVEDSGLYQCVIYQPPKEPHMLFDRIRLVVTKGFSGTPGSNENSTQN

VYKIPPTTTKALCPLYTSPRTVTQAPPKSTADVSTPDSEINLTNVTDIIR

YSFQVPGPLVWTLSPLFPSLCAERM (signal sequence is underlined);

(C) Human TREM-1 isoform 3 (Accession No. NP_001229519; SEQ ID NO: 3; encoded by the nucleotide sequence having Accession No. NM_001242590; SEQ ID NO: 6):

MRKTRLWGLLWMLFVSELRAATKLTEEKYELKEGQTLDVKCDYTLEKFAS

SQKAWQIIRDGEMPKTLACTERPSKNSHPVQVGRIILEDYHDHGLLRVRM

VNLQVEDSGLYQCVIYQPPKEPHMLFDRIRLVVTKGFRCSTLSFSWLVDS (signal sequence is underlined).

Cynomolgus TREM-1 protein (Accession No. XP_001082517; SEQ ID NO: 7) is predicted to have the following amino acid sequence:

MRKTRLWGLLWMLFVSELRATTELTEEKYEYKEGQTLEVKCDYALEKYAN

SRKAWQKMEGKMPKILAKTERPSENSHPVQVGRITLEDYPDHGLLQVQMT

NLQVEDSGLYQCVIYQHPKESHVLFNPICLVVTKGSSGTPGSSENSTQNV

-continued

```
YRTPSTTAKALGPRYTSPRTVTQAPPESTVVVSTPGSEINLTNVTDIIRV

PVFNIVIIVAGGFLSKSLVFSVLFAVTLRSFGP (signal sequence is underlined).
```

The present disclosure relates to antibodies that specifically bind and block the function of TREM-1. The antibodies block TREM-1 function by reducing/blocking TREM-1 activation and downstream signaling.

The anti-TREM-1 antibodies of the present disclosure block TREM-1 signaling by means of one or a combination of several different mechanisms, blocking TREM-1 directly or indirectly. In one embodiment, the antibodies prevent the natural ligand of TREM-1, peptidoglycan recognition protein 1 (PGLYRP1), from creating a functional complex with TREM-1. In another embodiment, the antibodies block TREM-1 by preventing individual TREM-1 molecules from forming dimers or multimers. In some embodiments, the TREM-1 dimerization or multimerization is reduced or prevented by anti-TREM-1 antibodies that are capable of binding to a portion of TREM-1 that would otherwise reside in the interface of a TREM-1 dimer, thus preventing individual TREM-1 molecules from associating with one another. In other embodiments, the TREM-1 dimerization or multimerization is reduced or prevented by anti-TREM-1 antibodies that interfere with the interaction of TREM-1 with its ligand.

In some embodiments, the anti-TREM-1 antibodies can block PGLYRP1-induced activation of TREM-1. PGLYRP1, a highly conserved, 196 amino acid long protein consisting of a signal peptide and a peptidoglycan binding domain, is expressed in neutrophils and released upon their activation. The amino acid sequence of PGLYRP1 (Accession No. NP_005082.1; SEQ ID NO: 8) is provided below:

```
MSRRSMLLAWALPSLLRLGAAQETEDPACCSPIVPRNEWKALASECAQHL

SLPLRYVVVSHTAGSSCNTPASCQQQARNVQHYHMKTLGWCDVGYNFLIG

EDGLVYEGRGWNFTGAHSGHLWNPMSIGISFMGNYMDRVPTPQAIRAAQG

LLACGVAQGALRSNYVLKGHRDVQRTLSPGNQLYHLIQNWPHYRSP (signal sequence is underlined).
```

Accordingly, in some embodiments, the anti-TREM-1 antibodies of the present disclosure down-regulate or block the release of proinflammatory cytokines from myeloid cells (e.g., dendritic cells and monocytes). In some embodiments, the anti-TREM-1 antibodies block the release of TNF-α, MIP-Ibeta, MCP-1, IL-Ibeta, GM-CSF, IL-6 and/or IL-8 from macrophages, neutrophils, synovial tissue cells and/or a reporter cell, as disclosed herein.

While the controlled release of inflammatory cytokines in response to foreign antigens can be beneficial (e.g., mounting an effective adaptive immune response), too much inflammatory cytokine release can have dire consequences. For instance, one common and toxic clinical complication that have been observed with the in vivo administration of certain antibodies against cell surface immune receptors (e.g., anti-human CD3 antibodies such as OKT3) is the cytokine release syndrome (CRS), which is associated with the excessive release of various cytokines (e.g., TNF-alpha, IFN-gamma, and IL-2) into the circulation. CRS can occur as a result of the simultaneous binding of the antibodies to its cognate antigen (e.g., CD3 on T cells) (via the variable region of the antibody) and the Fc receptors (e.g., FcγRs) and/or complement receptors (via the constant region of the antibody) on the accessory cells (e.g., antigen presenting cells). This interaction results in the activation of the cells (e.g., T cells and/or the accessory cells) and the release of various cytokines that produce a systemic inflammatory response characterized by hypotension, pyrexia, and rigors. Other symptoms of CRS include fever, chills, nausea, vomiting, and dyspnea.

In addition to blocking the PGLYRP1-induced production of inflammatory cytokines, in one embodiment, the anti-TREM-1 antibodies of the present disclosure reduces the incidence of or results in no incidence of cytokine release syndrome when administered to a subject in need thereof. In some embodiments, the anti-TREM-1 antibodies do not induce the expression of inflammatory cytokines by cells (e.g., dendritic cells) when the cells are incubated in the presence of the antibody alone, compared to an antibody comprising a heavy chain consisting of the amino acid sequence as set forth in SEQ ID NO: 76 and a light chain consisting of the amino acid sequence as set forth in SEQ ID NO: 54. In some embodiments, the anti-TREM-1 antibodies have decreased binding to one or more FcγRs, which can help reduce the onset of CSR.

In some embodiments, the anti-TREM-1 antibodies of the present disclosure bind both human TREM-1 and TREM-1 from another species. The term "TREM-1", as used herein, thus encompasses any naturally occurring form of TREM-1 which can be derived from any suitable organism. For example, TREM-1 for use as described herein can be vertebrate TREM-1, such as mammalian TREM-1, such as TREM-1 from a primate (such as a human, a chimpanzee, a cynomolgus monkey, or a rhesus monkey); a rodent (such as a mouse or a rat), a lagomorph (such as a rabbit), or an artiodactyl (such a cow, sheep, pig or camel). In certain embodiments, TREM-1 is SEQ ID NO: 1 (human TREM-1, isoform 1). The TREM-1 can be a mature form of TREM-1, such as a TREM-1 protein that has undergone post-translational processing within a suitable cell. Such a mature TREM-1 protein can, for example, be glycosylated. The TREM-1 can be a full length TREM-1 protein.

In some embodiments, the anti-TREM-1 antibodies of the present disclosure are monoclonal antibodies, in the sense that they are directly or indirectly derived from a single clone of a B lymphocyte. In some embodiments, the anti-TREM-1 antibodies are produced, screened, and purified using, for example, the methods described in the Examples of International Publ. No. WO 2013/120553. In brief, a suitable mouse such as a TREM-1 or TREM-1/TREM-3 knock-out (KO) mouse are immunized with TREM-1, a cell expressing TREM-1, or a combination of both. In another embodiment, the anti-TREM-1 antibodies are polyclonal antibodies, in the sense that they are mixture of monoclonal antibodies as disclosed herein.

In some embodiments, the anti-TREM-1 antibodies of the current disclosure are recombinantly expressed in prokaryotic or eukaryotic cells. In some embodiments, the prokaryotic cell is *E. coli*. In certain embodiments, the eukaryotic is a yeast, insect, or mammalian cell, such as a cell derived from an organism that is a primate (such as a human, a chimpanzee, a cynomolgus monkey or a rhesus monkey), a rodent (such as a mouse or a rat), a lagomorph (such as a rabbit) or an artiodactyl (such a cow, sheep, pig or camel). Suitable mammalian cell lines include, but are not limited to, HEK293 cells, CHO cells, and HELA cells. The anti-TREM-1 antibodies as disclosed herein can also be produced by means of other methods known to the person skilled in the art, such as a phage display or a yeast display. Once produced, the antibodies can be screened for binding to, for example, full length TREM-1 or mutants thereof using the methods described in the Examples of International Publ. No. WO 2013/120553.

The term "antibody" as used herein refers to a protein, derived from a germline immunoglobulin sequence, which is capable of specifically binding to an antigen (TREM-1) or a portion thereof. The term includes full length antibodies of any class or isotype (that is, IgA, IgE, IgG, IgM and/or IgY) and any single chain or fragment thereof. An antibody that specifically binds to an antigen, or portion thereof, may bind exclusively to that antigen, or portion thereof, or it may bind to a limited number of homologous antigens, or portions thereof. Full-length antibodies usually comprise at least four polypeptide chains: two heavy (H) chains and two light (L) chains that are interconnected by disulfide bonds. One immunoglobulin sub-class of particular pharmaceutical interest is the IgG family. In humans, the IgG class may be sub-divided into 4 sub-classes: IgG1, IgG2, IgG3 and IgG4, based on the sequence of their heavy chain constant regions. The light chains can be divided into two types, kappa and lambda, based on differences in their sequence composition. IgG molecules are composed of two heavy chains, inter-linked by two or more disulfide bonds, and two light chains, each attached to a heavy chain by a disulfide bond. A heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hyper-variability, termed complementarity determining regions (CDRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The hypervariable regions of the heavy and light chains form a binding domain that is capable of interacting with an antigen, whilst the constant region of an antibody may mediate binding of the immunoglobulin to host tissues or factors, including but not limited to various cells of the immune system (effector cells), Fc receptors and the first component (C1q) of the classical complement system. Antibodies of the current invention may be isolated. The term "isolated antibody" refers to an antibody that has been separated and/or recovered from (an)other component(s) in the environment in which it was produced and/or that has been purified from a mixture of components present in the environment in which it was produced. Certain antigen-binding fragments of antibodies may be suitable in the context of the current invention, as it has been shown that the antigen-binding function of an antibody can be performed by fragments of a full-length antibody.

The term "antigen-binding portion" of an antibody refers to one or more fragment(s) of an antibody that retain the ability to specifically bind to an antigen, such as TREM-1, as described herein. Examples of antigen-binding fragments include Fab, Fab', F(ab)2, F(ab')2, F(ab)S, Fv (typically the VL and VH domains of a single arm of an antibody), single-chain Fv (scFv; see, e.g., Bird et al., *Science* 242: 42S-426 (1988); Huston et al., *PNAS* 85: 5879-5883 (1988)), dsFv, Fd (typically the VH and CH1 domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al., *Protein Eng* 10:949-57 (1997)); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, *Nat Biotechnol* 2S:1126-1136 (2005); International Publ. No. WO 2005/040219, and U.S. Publ. Nos. 2005/0238646 and 2002/0161201. These antibody fragments may be obtained using conventional techniques known to those of skill in the art, and the fragments may be screened for utility in the same manner as intact antibodies.

A "human" antibody (HuMAb) refers to an antibody having variable regions in which both the framework and CDR regions are derived from human germline immuno-globulin sequences. Furthermore, if the antibody contains a constant region, the constant region also is derived from human germline immunoglobulin sequences. The anti-TREM-1 antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to a human/non-human chimeric antibody that contains one or more sequences (CDR regions or parts thereof) that are derived from a non-human immunoglobulin. A humanised antibody is, thus, a human immunoglobulin (recipient antibody) in which at least residues from a hyper-variable region of the recipient are replaced by residues from a hyper-variable region of an antibody from a non-human species (donor antibody) such as from a mouse, rat, rabbit or non-human primate, which have the desired specificity, affinity, sequence composition and functionality. In some instances, FR residues of the human immunoglobulin are replaced by corresponding non-human residues. An example of such a modification is the introduction of one or more so-called back-mutations, which are typically amino acid residues derived from the donor antibody. Humanization of an antibody may be carried out using recombinant techniques known to the person skilled in the art (see, e.g., Antibody Engineering, Methods in Molecular Biology, vol. 248, edited by Benny K. C. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introduction (backmutation) of the amino acid residue from the donor antibody has beneficial impact on the properties of the humanized antibody. In addition to donor antibody derived backmutations, the humanized antibody can be engineered by introduction of germline residues in the CDR or framework regions, elimination of immunogenic epitopes, site-directed mutagenesis, affinity maturation, etc.

Furthermore, humanized antibodies can comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin. The term "humanised antibody derivative" refers to any modified form of the humanised antibody, such as a conjugate of the antibody and another agent or antibody.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg *Nature Biotech.* 23(9): 1117-1125 (2005)), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "chimeric antibody" refers to an antibody in which the variable regions are derived from one species and the constant regions are derived from another species, such as an antibody in which the variable regions are derived from a mouse antibody and the constant regions are derived from a human antibody.

In one embodiment, the anti-TREM-1 antibodies of the current disclosure are IgG antibodies. An "IgG antibody", e.g., a human IgG1, as used herein has, in certain embodiments, the structure of a naturally occurring IgG antibody, i.e., it has the same number of heavy and light chains and disulfide bonds as a naturally occurring IgG antibody of the same subclass. For example, the TREM-1 IgG1 antibody consists of two heavy chains (HCs) and two light chains (LCs), wherein the two heavy chains and light chains are linked by the same number and location of disulfide bridges that occur in naturally occurring IgG1 antibody (unless the antibody has been mutated to modify the disulfide bridges).

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al., mAbs 1:1 (2009)). Anti-TREM-1 antibodies described herein can be of any allotype. In some embodiments, the anti-TREM-1 antibodies are of "IgG1.3f" allotype, which comprises one or more amino acid substitutions selected from the group consisting of L234A, L235E, and G237A, per EU numbering, as compared to a wild-type IgG1 isotype (e.g., SEQ ID NO: 9). In other embodiments, the anti-TREM-1 antibodies are of "IgG1.1f" allotype, which comprises one or more amino acid substitutions selected from the group consisting of L234A, L235E, G237A, A330S, and P331S, per EU numbering, as compared to a wild-type IgG1 isotype (e.g., SEQ ID NO: 9). In certain embodiments, the anti-TREM-1 antibodies are of "IgG1-Aba" allotype, which comprises one or more amino acid substitutions selected from the group consisting of K214R, C226S, C229S, and P238S, per EU numbering, as compared to a wild-type IgG1 isotype (e.g., SEQ ID NO: 9). In further embodiments, the anti-TREM-1 antibodies are of "IgG4-Aba" allotype, which comprises the CH1 domain of a wild-type IgG4 isotype (e.g., SEQ ID NO: 10) and CH2 and CH3 domains of IgG1. In some embodiments, the IgG4-Aba allotype antibody comprises one or more amino acid substitutions selected from the group consisting of S131C, K133R, G137E, G138S, Q196K, I199T, N203D, K214R, C226S, C229S, and P238S, per EU numbering, as compared to a wild-type IgG1 isotype (e.g., SEQ ID NO: 9).

The phrases "an antibody recognizing an antigen" and "an antibody specific for an antigen" are used interchangeably herein with the term "an antibody which binds specifically to an antigen."

An "isolated antibody," as used herein, is intended to refer to an antibody that has been separated and/or recovered from (an)other component(s) in the environment in which it was produced and/or that has been purified from a mixture of components present in the environment in which it was produced.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain). In one embodiment, the anti-TREM-1 antibodies of the current disclosure comprise Fc regions that do not bind to one or more FcγRs and therefore, lack effector function (i.e., effectorless).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are known in the art. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL).

In IgG, the Fc region comprises immunoglobulin domains CH2 and CH3 and the hinge between CH1 and CH2 domains. Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3 and P224 for IgG4 to the carboxy-terminus of the heavy chain, wherein the numbering is according to the EU index as in Kabat. The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesion).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc include the various allotypes of Fcs (see, e.g., Jefferis et al., *mAbs* 1: 1 (2009)).

A "variant sequence Fc region" or "non-naturally occurring Fc" comprises a modification, typically to alter one or more of its functional properties, such as serum half-life, complement fixation, Fc-receptor binding, protein stability and/or antigen-dependent cellular cytotoxicity, or lack thereof, among others. In some embodiments, the anti-TREM-1 antibodies of the present disclosure can be chemically modified (e.g., one or more chemical moieties can be attached to the antibody) or be modified to alter its glycosylation, again to alter one or more functional properties of the antibody. In one embodiment, the anti-TREM-1 antibody is an IgG1 isotype and carries a modified Fc domain comprising one or more, and perhaps all of the following mutations that will result in decreased affinity to certain Fc receptors (L234A, L235E, and G237A) and in reduced C1q-mediated complement fixation (A330S and P331S), respectively (residue numbering according to the EU index).

The terms "hinge," "hinge domain," "hinge region," and "antibody hinge region" refer to the domain of a heavy chain constant region that joins the CH1 domain to the CH2 domain and includes the upper, middle, and lower portions of the hinge (Roux et al., *J Immunol* 161:4083 (1998)). The hinge provides varying levels of flexibility between the binding and effector regions of an antibody and also provides sites for intermolecular disulfide bonding between the two heavy chain constant regions. As used herein, a hinge starts at Glu216 and ends at Gly237 of all IgG isotypes (Roux et al., *J Immunol* 161:4083 (1998)). The sequencse of wildtype IgG1, IgG2, IgG3, and IgG4 hinges are known in the art (e.g., International PCT publication no. WO 2017/087678). In one embodiment, the hinge region of CH1 of the anti-TREM-1 antibodies is modified such that the number of cysteine residues in the hinge region is altered, e.g., increased or decreased. This approach is described further for instance in U.S. Pat. No. 5,677,425.

The constant region may be modified to stabilize the antibody, e.g., to reduce the risk of a bivalent antibody separating into two monovalent VH-VL fragments. For example, in an IgG4 constant region, residue S228 (residue numbering according to the EU index) may be mutated to a proline (P) residue to stabilize inter heavy chain disulphide bridge formation at the hinge (see, e.g., Angal et al., *Mol Immunol.* 30: 105-8(1995)). Antibodies or fragments thereof can also be defined in terms of their complementarity-determining regions (CDRs). The term "complementarity-determining region" or "hypervariable region", when used herein, refers to the regions of an antibody in which amino acid residues involved in antigen binding are situated. The region of hypervariability or CDRs can be identified as the regions with the highest variability in amino acid alignments of antibody variable domains. Databases can be used for CDR identification such as the Kabat database, the CDRs e.g., being defined as comprising amino acid residues 24-34 (CDR1), 50-59 (CDR2) and 89-97 (CDR3) of the light-chain variable domain, and 31-35 (CDR1), 50-65 (CDR2) and 95-102 (CDR3) in the heavy-chain variable domain; (Kabat et al. 1991; Sequences of Proteins of Immunological Interest, Fifth Edition, U.S. Department of Health and Human Services, NIH Publication No. 91-3242) Alternatively CDRs can be defined as those residues from a "hyper-variable loop" (residues 26-33 (L1), 50-52 (L2) and 91-96 (L3) in the light-chain variable domain and 26-32 (H1), 53-55 (H2) and 96-101 (H3) in the heavy-chain variable domain (Chothia and Lesk, *J. Mol. Biol* 196: 901-917 (1987)). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "epitope" or "antigenic determinant" refers to a site on an antigen (e.g., TREM-1) to which an immunoglobulin or antibody specifically binds, e.g., as defined by the specific method used to identify it. Epitopes can be formed both from contiguous amino acids (usually a linear epitope) or noncontiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from TREM-1) are tested for reactivity with a given antibody (e.g., anti-TREM-1 antibody). Methods of determining spatial conformation of epitopes include techniques in the art and those described herein, for example, x-ray crystallography, antigen mutational analysis, 2-dimensional nuclear magnetic resonance and HDX-MS (see, e.g., Epitope Mapping Protocols in Methods in Molecular Biology, Vol. 66, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope on TREM-1" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments, e.g., BIACORE® surface plasmon resonance (SPR) analysis. In certain embodiments, an antibody competes with, and inhibits binding of another antibody to a target by at least 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Two antibodies "cross-compete" if antibodies block each other both ways by at least 50%, i.e., regardless of whether one or the other antibody is contacted first with the antigen in the competition experiment.

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 instrument using the predetermined antigen, e.g., recombinant human TREM-1, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human TREM-1" refers to an antibody that binds to soluble or cell bound human TREM-1 with a $K_D$ of $10^{-7}$ M or less, such as approximately less than $10^{-8}$ M, $10^{-9}$ M or $10^{-10}$ M or even lower. An antibody that "cross-reacts with cynomolgus TREM-1" refers to an antibody that binds to cynomolgus TREM-1 with a $K_D$ of $10^{-7}$ M or less, such as approximately less than $10^{-8}$ M, $10^{-9}$ M or $10^{-10}$ M or even lower. In certain embodiments, such antibodies that do not cross-react with TREM-1 from a non-human species exhibit essentially undetectable binding against these proteins in standard binding assays.

The term "binding specificity" herein refers to the interaction of a molecule such as an antibody, or fragment thereof, with a single exclusive antigen, or with a limited number of highly homologous antigens (or epitopes). In contrast, antibodies that are capable of specifically binding to TREM-1 are not capable of binding dissimilar molecules. Antibodies according to the invention may not be capable of binding Nkp44, the Natural killer cell p44-related protein.

The specificity of an interaction and the value of an equilibrium binding constant can be determined directly by well-known methods. Standard assays to evaluate the ability of ligands (such as antibodies) to bind their targets are known in the art and include, for example, ELISAs, Western blots, RIAs, and flow cytometry analysis. The binding kinetics and binding affinity of the antibody also can be assessed by standard assays known in the art, such as SPR.

Competitive binding assays for determining whether two antibodies compete or cross-compete for binding include: competition for binding to myeloid cells expressing TREM-1, e.g., by flow cytometry, such as described in the Examples. Other methods include: SPR (e.g., BIACORE®), solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the term "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope. Competing antibodies, i.e., antibodies belonging to the same "bin" can have identical epitopes, overlapping epitopes, or even separate epitopes. The latter is the case if the reference antibody bound to its epitope on the antigen takes up the space required for the second antibody to contact its epitope on the antigen ("steric hindrance"). Non-competing antibodies generally have separate epitopes.

The term "binding affinity" herein refers to a measurement of the strength of a non-covalent interaction between two molecules, e.g. an antibody, or fragment thereof, and an antigen. The term "binding affinity" is used to describe monovalent interactions (intrinsic activity).

The binding affinity between two molecules, e.g. an antibody, or fragment thereof, and an antigen, through a monovalent interaction may be quantified by determination of the equilibrium dissociation constant ($K_D$). In turn, $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D=k_d/k_a$. Following the above definition, binding affinities associated with different molecular interactions, such as comparison of the binding affinity of different antibodies for a given antigen, may be compared by comparison of the $K_D$ values for the individual antibody/antigen complexes.

As used herein, the term "high affinity" for an IgG antibody refers to an antibody having a $K_D$ of $10^{-8}$ M or less, $10^{-9}$ M or less, or $10^{-10}$ M or less for a target antigen. However, "high affinity" binding can vary for other antibody isotypes. For example, "high affinity" binding for an IgM isotype refers to an antibody having a $K_D$ of $10^{-10}$ M or less, or $10^{-8}$ M or less.

The term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, a predicted nonessential amino acid residue in an anti-TREM-1 antibody is replaced with another amino acid residue from the same side chain family. Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS*, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at worldwideweb.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See worldwideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Different routes of administration for the anti-TREM-1 antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the terms "inhibits" or "blocks" (e.g., referring to inhibition/blocking of binding of TREM-1 ligand to TREM-1 on cells) are used interchangeably and encompass both partial and complete inhibition/blocking. In some embodiments, the anti-TREM-1 antibody inhibits binding of TREM-1 ligand to TREM-1 by at least about 50%, for example, about 60%, 70%, 80%, 90%, 95%, 99%, or 100%, determined, e.g., as further described herein. In some embodiments, the anti-TREM-1 antibody inhibits binding of TREM-1 ligand to TREM-1 by no more than 50%, for example, by about 40%, 30%, 20%, 10%, 5% or 1%, determined, e.g., as further described herein.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease or enhancing overall survival. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

As used herein, the terms "ug" and "uM" are used interchangeably with "μg" and "μM," respectively.

Various aspects described herein are described in further detail in the following subsections.

I. Anti-TREM-1 Antibodies

Described herein are antibodies, e.g., fully human antibodies, which are characterized by particular functional features or properties. For example, the antibodies of the present disclosure specifically bind human TREM-1, and more specifically, a particular domain (e.g., a functional domain) within the extracellular domain of human TREM-1. In one embodiment, the antibodies specifically bind to the site on TREM-1 to which the TREM-1 ligand (e.g., PGLYRP1) binds. In certain embodiments, the antibodies are antagonist antibodies, i.e., they inhibit or suppress the activity of TREM-1 (i.e., do not agonize upon binding) on cells, e.g., monocytes, macrophages, and neutrophils. In some embodiments, the anti-TREM-1 antibodies cross-react with TREM-1 from one or more non-human primates, such as cynomolgus TREM-1. In some embodiments, the anti-TREM-1 antibodies block the production of inflammatory cytokines (e.g., IL-6, TNF-α, IL-8, IL-1β, IL-12, and combinations thereof) by cells (e.g., macrophages, dendritic cells, neutrophils) upon activation. In other embodiments, the anti-TREM-1 antibodies comprise Fc regions that do not bind to one or more FcγRs. In further embodiments, the anti-TREM-1 antibodies do not induce the release of proinflammatory cytokines by myeloid cells (e.g., dendritic cells) and, thereby reduce or prevent the onset of inflammatory cytokine storm after the administration of the anti-TREM-1 antibodies to a subject in need thereof.

In some embodiments, the particular anti-TREM-1 antibodies described herein are antibodies, e.g., monoclonal, recombinant, and/or human antibodies, that cross-compete with mAb 0318 for binding to human TREM-1. In some embodiments, the anti-TREM-1 antibodies also cross-compete with mAb 0318 for binding to cynomolgus TREM-1. In other words, the anti-TREM-1 antibodies of the present disclosure belong to the same "bin" as mAb 0318 in certain embodiments.

The mAb 0318 antibody has a heavy chain variable region (VH) comprising SEQ ID NO: 14 and a light chain variable region (VL) comprising SEQ ID NO: 15. See International Publ. No. 2016/009086. The mAb 0318 also has a heavy chain CDR1, CDR2, and CDR3, which correspond to amino acids 31-35, 50-68, and 101-110 of SEQ ID NO: 14, respectively. The light chain CDR1, CDR2, and CDR3 of the mAb 0318 antibody correspond to amino acids 24-38, 54-60, and 93-101 of SEQ ID NO: 15.

Accordingly, in some embodiments, the anti-TREM-1 antibody of the present disclosure comprises a VH and VL of SEQ ID NOs: 14 and 15, respectively. In another embodiment, the VH of the anti-TREM-1 antibody comprises a CDR1 sequence of amino acids 31-35 (TYAMH) of SEQ ID NO: 14, wherein one of the amino acids can be substituted by a different amino acid. In certain embodiments, the VH of the anti-TREM-1 antibody comprises a CDR2 sequence of amino acids 50-68 (RIRTKSSNYATYYAASVKG) of SEQ ID NO: 14, wherein one, two, or three of the amino acids can be substituted by a different amino acid. In some embodiments, the VH of the anti-TREM-1 antibody comprises a CDR3 sequence of amino acids 101-110 (DM-GIRRQFAY) of SEQ ID NO: 14, wherein one, two, or three of the amino acids can be substituted by a different amino acid.

In some embodiments, the VL of the anti-TREM-1 antibody comprises a CDR1 sequence of amino acids 24-38 (QQSNQDPYT) of SEQ ID NO: 15, wherein one, two, or three of the amino acids can be substituted by a different amino acid. In other embodiments, the VL of the anti-TREM-1 antibody comprises a CDR2 sequence of amino acids 54-60 (RASNLES) of SEQ ID NO: 15, wherein one or two of the amino acids can be substituted with a different amino acid. In some embodiments, the VL of the anti-TREM-1 antibody comprises a CDR3 sequence of amino acids 93-101 (QQSNQDPYT) of SEQ ID NO: 15, wherein one or two of the amino acids can be substituted with a different amino acid.

Methionine residues in CDRs of antibodies can be oxidized, resulting in potential chemical degradation and consequent reduction in potency of the antibody. Accordingly, the anti-TREM-1 antibodies disclosed herein can have one or more methionine residues in the heavy and/or light chain CDRs replaced with amino acid residues which do not undergo oxidative degradation. In some embodiments, the methionine residues within the heavy chain CDR1 and CDR3 are replaced with amino acid residues that do not undergo oxidative degradation (e.g., glutamine or leucine). Accordingly, in one embodiment, the VH of the anti-TREM-1 antibody comprises a CDR3 sequence of amino acids 101-110 (DQGIRRQFAY) of SEQ ID NO: 81 or amino acids 101-110 (DLGIRRQFAY) of SEQ ID NO: 82. In other embodiments, the VH of the anti-TREM-1 antibody comprises a CDR1 sequence of amino acids 31-35 (TYAQH) of SEQ ID NO: 83 or amino acids 31-35 (TYALH) of SEQ ID NO: 84. Similarly, in some embodiments, deamidation sites can be removed from the anti-TREM-1 antibodies, particularly in the CDRs.

In some embodiments, the VH and VL of the anti-TREM-1 antibody comprises a VH and VL sequences of anti-TREM-1 antibodies disclosed in International Publ. No. WO 2017/152102 A2, which is hereby incorporated by reference in its entirety. In some embodiments, the VL of the anti-TREM-1 antibody comprises a CDR1 sequence selected from the group consisting of SEQ ID NOs: 9-27 from WO 2017/152102, a CDR2 sequence selected from the group consisting of SEQ ID NOs: 28-40 from WO 2017/152102, and/or a CDR3 sequence selected from the group consisting of SEQ ID NOs: 41-119 from WO 2017/152102. In one embodiment, the VH of the anti-TREM-1 antibody comprises a CDR1 sequence selected from the group consisting of SEQ ID NOs: 120-143 from WO 2017/152102, a CDR2 sequence selected from the group consisting of SEQ ID NOs: 144-172 from WO 2017/152102, and/or a CDR3 sequence selected from the group consisting of SEQ ID NOs: 173-247 from WO 2017/152102.

In some embodiments, the anti-TREM-1 antibodies of the present disclosure comprise CDR and/or variable region sequences that have at least 80% identity (e.g., at least 85%, at least 95%, at least 95%, or at least 99% identity) to the CDR and/or variable region sequences of the mAb 0318 antibody.

In some embodiments, the anti-TREM-1 antibodies comprise a heavy chain variable region (VH) and a light chain variable region (VL) comprising SEQ ID NOs: 14 and 15, respectively. In some embodiments, the anti-TREM-1 antibodies comprise a heavy chain (HC) and a light chain (LC), wherein the HC comprises SEQ ID NO: 50, SEQ ID NO: 51, SEQ ID NO: 52, or SEQ ID NO: 53. In some embodiments, the LC comprises SEQ ID NO: 54.

In some embodiments, the anti-TREM-1 antibodies of the present disclosure comprise a heavy chain variable region (VH) selected from the group consisting of SEQ ID NOs: 396-475 from WO 2017/152102 and/or a light chain variable region (VL) selected from the group consisting of SEQ ID NOs: 316-395 from WO 2017/152102.

In some embodiments, the anti-TREM-1 antibody comprises a heavy chain and a light chain, wherein the heavy chain and light chain comprises aminthe o acid sequences as shown in Table 7. In some embodiments, the anti-TREM-1 antibody comprises a heavy chain and a light chain, wherein the heavy chain comprises the amino acid sequence set forth as SEQ ID NO: 50 and the light chain comprises the amino acid sequence set forth as SEQ ID NO: 54. In some embodiments, the anti-TREM-1 antibody comprises a heavy chain and a light chain, wherein the heavy chain comprises the amino acid sequence set forth as SEQ ID NO: 51 and the light chain comprises the amino acid sequence set forth as SEQ ID NO: 54. In some embodiments, the anti-TREM-1 antibody comprises a heavy chain and a light chain, wherein the heavy chain comprises the amino acid sequence set forth as SEQ ID NO: 52 and the light chain comprises the amino acid sequence set forth as SEQ ID NO: 54. In some embodiments, the anti-TREM-1 antibody comprises a heavy chain and a light chain, wherein the heavy chain comprises the amino acid sequence set forth as SEQ ID NO: 53 and the light chain comprises the amino acid sequence set forth as SEQ ID NO: 54.

Heavy and light chains comprising an amino acid sequence that is at least 99%, 98%, 97%, 96%, 95%, 90%, 85%, or 80% identical to any of the heavy or light chains set forth herein, e.g., SEQ ID NOs: 50 to 54 can be used for forming the anti-TREM-1 antibodies having the desired characteristics, e.g., those further described herein.

In some embodiments, the anti-TREM-1 antibody of the present disclosure comprises a heavy chain and a light chain, wherein the heavy chain comprises an amino acid sequence that is at least 80%, at least 85%, at least 90%, at least 95%, at least 96%, at least 97%, at least 98%, at least 99%, or 100% identical to the amino acid sequence set forth as SEQ ID NO: 50, 51, 52, or 53 and wherein the light chain comprises an amino acid sequence that is at least 80%, at least 85%, at least 90%, at least 95%, at least 96%, at least 97%, at least 98%, at least 99%, or 100% identical to the amino acid sequence set forth as SEQ ID NO: 54.

In some embodiments, the anti-TREM1 antibody comprises a heavy chain constant region, wherein the heavy chain constant region comprises one or more amino acid substitutions selected from the group consisting of K214R, L234A, L235E, G237A, D356E, L358M, and any combination thereof per EU numbering. In some embodiments, the anti-TREM-1 antibody comprises a heavy chain constant region, wherein the heavy chain constant region comprises one or more amino acid substitutions selected from the group consisting of K214R, L234A, L235E, G237A, A330S, P331S, D356E, L358M, and any combination thereof per EU numbering. In some embodiments, the anti-TREM-1 antibody comprises a heavy chain constant region, wherein the heavy chain constant region comprises one or more amino acid substitutions selected from the group consisting of K214R, C226S, C229S, P238S, and any combination thereof per EU numbering. In some embodiments, the anti-TREM-1 antibody comprises a heavy chain constant region, wherein the heavy chain constant region comprises one or more amino acid substitutions selected from the group consisting of S131C, K133R, G137E, G138S, Q196K, I199T, N203D, K214R, C226S, C229S, P238S, and any combination thereof per EU numbering.

In one embodiment, the anti-TREM-1 antibody is capable of binding variants of human TREM-1 (e.g., TREM-1 isoforms 2 and 3, SEQ ID NOs: 2 and 3, respectively), as determined using, e.g., surface plasmon resonance. In another embodiment, the anti-TREM-1 antibody is capable of binding cynomolgus TREM-1 (SEQ ID NO: 7), as determined using, e.g., surface plasmon resonance.

In some embodiments, anti-TREM-1 antibodies described herein bind to human TREM-1 with high affinity, e.g., as determined by BIACORE™ (e.g., as described in the Examples), with a $K_D$ of $10^{-7}$ M or less, $10^{-8}$ M or less, $10^{-9}$ M (1 nM) or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M. In some embodiments, anti-TREM-1 antibodies described herein bind to cyno TREM-1, e.g., as determined by BIACORE™ (e.g., as described in the Examples), with a $K_D$ of $10^{-7}$ M or less, $10^{-8}$ M or less, $10^{-9}$ M or less, $10^{-10}$ M or less, $10^{-11}$ M or less, 10-12 M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M.

In one embodiment, the antibodies of the present disclosure bind anti-TREM-1 at one or more of the same epitopes as the mAb 0318 antibody. In some embodiments, the anti-TREM-1 antibody is capable of specifically binding (i) at least one amino acid residue selected from the group consisting of the A21, T22, K23, L24, T25, E26, and any combination thereof and (ii) at least one amino acid residue selected from the group consisting of the A49, S50, S51, Q52, K53, A54, W55, Q56, 157, 158, R59, D60, G61, E62, M63, P64, K65, T66, L67, A68, C69, T70, E71, R72, P73, S74, K75, N76, S77, H78, P79, V80, Q81, V82, G83, R84, 185, and any combination thereof and (iii) at least one amino acid residue selected from the group consisting of the C113, V114, 1115, Y116, Q117, P118, P119, and any combination thereof of human TREM-1 (e.g., Isoform 1, SEQ ID NO: 1). See WO 2016/009086.

In one embodiment, the anti-TREM-1 antibody is capable of specifically binding to amino acids D38 to F48 of SEQ ID NO: 1 (human TREM-1), as determined using, e.g., HX-MS or X-ray diffraction. In some embodiments, the anti-TREM-1 antibody has an epitope comprising one, two, three, four, five, six, seven, or all of the amino acid residues D38, V39, K40, C41, D42, Y43, T44, and L45 of SEQ ID NO: 1 (human TREM-1) and one, two, or all of the amino acid residues selected from the group consisting of the E46, K47, and F48 of SEQ ID NO: 1 (human TREM-1), as determined using, e.g., HX-MS or X-ray diffraction. In certain embodiments, the anti-TREM-1 antibody has an epitope comprising one, two, three, or all of the amino acid residues selected from the group consisting of the D42, E46, D92, and H93 of SEQ ID NO: 1 (human TREM-1), as determined using variants of TREM-1 and surface plasmon resonance.

In one embodiment, the anti-TREM-1 antibody of the present disclosure has an epitope comprising at least the amino acid residues E46 and/or D92 of SEQ ID NO: 1 (human TREM-1), as determined using variants of TREM-1 and surface plasmon resonance. In another embodiment, the anti-TREM-1 antibody comprises one, two, or all of the amino acid residues selected from the group consisting of L31, I86, and V101 of SEQ ID NO: 1 (human TREM-1). In certain embodiments, the anti-TREM-1 antibody is capable of specifically binding a polypeptide comprising amino acid residues E19 to L26 of cynomolgus monkey TREM-1 (SEQ ID NO: 7), as determined using, e.g., HX-MS or X-ray diffraction.

In one embodiment, the anti-TREM-1 antibody is capable of specifically binding human TREM-1, wherein the epitope of the antibody comprises one, two, three, four, five, six, seven, eight, nine, or all of the amino acid residues selected from the group consisting of the V39, K40, C41, D42, Y43, L45, E46, K47, F48, and A49 of SEQ ID NO: 1.

In one embodiment, the anti-TREM-1 antibody is capable of specifically binding human TREM-1, wherein the epitope of the antibody comprises the D42 of SEQ ID NO: 1. In other embodiments, the anti-TREM-1 antibody is capable of specifically binding human TREM-1, wherein the epitope of the antibody comprises the E46 of SEQ ID NO: 1. In some embodiments, the epitope of the antibody can comprise the V39, C41, D42, Y43, L45 of SEQ ID NO: 1. In further embodiments, The epitope of the antibody can comprise the E46, K47 and A49 of SEQ ID NO: 1. In a specific embodiment, the epitope of the anti-TREM-1 antibody can further comprise the F48 of SEQ ID NO: 1.

In some embodiments, the anti-TREM-1 antibody has a viscosity profile similar to that of the mAb 0318 antibody. In some embodiments, the anti-TREM-1 antibody of the present disclosure has a viscosity of less than 5 cP, less than 4 cP, less than 3 cP, less than 2.5 cP, less than 2.4 cP, less than 2.3 cP, less than 2.2 cP, less than 2.1 cP, less than 2 cP, less than 1.9 cP, less than 1.8 cP, less than 1.7 cP, less than 1.6 cP, less than 1.5 cP, less than 1.4 cP, less than 1.3 cP, less than 1.2 cP, less than 1.1 cP, less than 1.0 cP, less than 0.9 cP, less than 0.8 cP, less than 0.7 cP, less than 0.6 cP, less than 0.5 cP, less than 0.4 cP, less than 0.3 cP, less than 0.2 cP, or less than 0.1 cP at a concentration of 80 mg/mL. In some embodiments, the anti-TREM-1 antibody has a a viscosity of less than 10 cP (e.g., 9 cP) at a concentration of 130 mg/mL.

In some embodiments, the anti-TREM-1 antibody of the present disclosure comprises mutations, wherein one or more negatively charged residues in the light CDR1 and CDR3 regions of the antibody are substituted with uncharged residues. In some embodiments, the anti-TREM-1 antibody comprises a substitution at one or more of amino acid residues Dl, D30, D33, D74, D98, E27, and E97 of SEQ ID NO: 15 with an amino acid residue selected from the group consisting of glycine, alanine, serine, asparagine, glutamine, threonine, cysteine, and tyrosine. These mutations are referred to herein as "charge patch" mutations.

In some embodiments, the anti-TREM-1 antibody of the present disclosure comprises mutations in the Fab-Fab interaction area of SEQ ID NO: 14 to reduce Fab-Fab dimerization. It was previously shown with the mAb 0318 antibody that because antibodies comprise two Fabs, multimerization could impact viscosity. These mutations are referred to as "Fab-Fab interaction" mutations. In certain embodiments, the anti-TREM-1 antibody comprises a mutation at any one of residues Y32, R52, S55, S56, N57, A59, M102, I104 and R106 of SEQ ID NO: 14 or F32, D33, Y34, Y53, R54, and D98 of SEQ ID NO 15 with an amino acid residue selected from the group consisting of glycine, alanine, serine, asparagine, glutamine, threonine, cysteine, lysine, arginine, tryptophan, histidine and tyrosine.

In one embodiment, the anti-TREM-1 antibody as disclosed herein comprises a mutation at position 32 of SEQ ID NO: 15, wherein the phenylalanine is mutated to an mino acid selected from amino acid residues glycine, serine, threonine, cysteine, alanine, valine, leucine, isoleucine, and methionine. Such mutation is based on the observation that an Ala substitution in position Y90 of SEQ ID NO: 1 improved the affinity of SEQ ID NO: 3 to TREM-1. The Y90 was found to interact with a phenylalanine residue of SEQ ID NO: 15. Mutation of SEQ ID NO: 15 in order to improve the Fab-TREM-1 interaction are referred to as "Fab-TREM-1 interaction" mutations. Provided herein are anti-TREM-1 antibodies whose variable regions are linked (e.g., covalently linked or fused) to an Fc, e.g., an IgG1, IgG2, IgG3 or IgG4 Fc, which can be of any allotype or isoallotype, e.g., for IgG1: Glm, Glm1(a), Glm2(x), Glm3(f), Glm17(z); for IgG2: G2m, G2m23(n); for IgG3: G3m, G3m21(g1), G3m28(g5), G3m11(b0), G3m5(b1), G3m13 (b3), G3m14(b4), G3m10(b5), G3m15(s), G3m16(t), G3m6 (c3), G3m24(c5), G3m26(u), G3m27(v); and for K: Km, Km1, Km2, Km3 (see, e.g., Jeffries et al. (2009) mAbs 1:1). In some embodiments, the variable regions of the anti-TREM-1 antibodies disclosed herein are linked to an effectorless or mostly effectorless Fc, e.g., IgG1. In some embodiments, the variable regions of the anti-TREM-1 antibodies are linked to an Fc that has reduced binding or is incapable of binding to one or more FcγRs.

In one embodiment, the VH domain of the anti-TREM-1 antibody described herein can be fused to the constant domain of a human IgG (i.e., Fc), e.g., IgG1, IgG2, IgG3, or IgG4, which is either naturally-occurring or modified, e.g., as further described herein. For example, a VH domain can comprise the amino acid sequence of any VH domain described herein fused to a human IgG, e.g., an IgG1, constant region, such as the following wild-type human IgG1 constant domain amino acid sequence: ASTKGPSVF-PLAPSSKSTSGGTAALGCLVKDYF-PEPVTVSWNSGALTSGVHTFPAVLQSSGLYS-LSSVVTVPSSS LGTQTYICNVNHKPSNTKVDKKVEPKSCDKTH-TCPPCPAPELLGGPSVFLFPPKPKDTLMISRTPE-VTCVVVDVS HEDPE-VKFNWYVDGVEVHNAKTKPREEQYNSTYRVVSVL TVLHQDWLNGKEYKCKVSNKALPAPIEKTISKAKGQ PREPQVYTLPPSRDELTKNQVSLTCLVKGFYPSDIA-VEWESNGQPENNYKTTPPVLDSDGSFFLYSK-LTVDKSRW QQGNVFSCSVMHEALHNHYTQKSLSL-SPGK (SEQ ID NO: 9) or that of an allotypic variant of SEQ ID NO: 9 and have the following amino acid sequences:

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFELYSKLTVDKSRW

QQGNVFSCSVMHEALHNHYTQKSLSLSPGK (SEQ ID NO: 77; allotype specific amino acid residues are in bold and underlined).

In one embodiment, the VH domain of the anti-TREM-1 antibody described herein can comprise the amino acid sequence of any VH domain described herein fused to an effectorless constant region, e.g., the following effectorless human IgG1 constant domain amino acid sequences:

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDK<u>R</u>VEP

KSCDKTHTCPPCPAPE<u>AEGA</u>PSVFLFPPKPKDTLMISRTPEVTCVVVDVS

HEDPEVKFNWYVDGVEVHNAKTKPREEQYNSTYRVVSVLTVLHQDWLNGK

EYKCKVSNKALP<u>SS</u>IEKTISKAKGQPREPQVYTLPPSR<u>EEM</u>TKNQVSLTC

LVKGFYPSDIAVEWESNGQPENNYKTTPPVLDSDGSFELYSKLTVDKSRW

QQGNVFSCSVMHEALHNHYTQKSLSLSPGK (SEQ ID NO: 78; "IgG1.1f," comprising substitutions L234A, L235E, G237A, A330S and P331S, per EU numbering, which are underlined)
or

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDK<u>R</u>VEP

KSCDKTHTCPPCPAPE<u>AEGA</u>PSVFLFPPKPKDTLMISRTPEVTCVVVDVS

HEDPEVKFNWYVDGVEVHNAKTKPREEQYNSTYRVVSVLTVLHQDWLNGK

EYKCKVSNKALP<u>API</u>EKTISKAKGQPREPQVYTLPPSR<u>EEM</u>TKNQVSLTC

LVKGFYPSDIAVEWESNGQPENNYKTTPPVLDSDGSFELYSKLTVDKSRW

QQGNVFSCSVMHEALHNHYTQKSLSLSPGK (SEQ ID NO: 79; "IgG1.3f", comprising substitutions L234A, L235E and G237A, per EU numbering, which are underlined).

For example, an allotypic variant of IgG1 comprises an K97R, D239E, and/or L241M (underlined and bolded above) and numbering according to that in SEQ ID NOs: 77-79. Within the full length heavy region and according to EU numbering, these amino acid substitutions are numbered K214R, D356E, and L358M. In some embodiments, the constant region of an anti-TREM-1 antibody further comprises one or more mutations or substitutions at amino acids L117, A118, G120, A213, and P214 (underlined above) as numbered in SEQ ID NO: 77-79, or L234, A235, G237, A330 and P331, per EU numbering. In further embodiments, the constant region of the anti-TREM-1 antibody comprises one or more mutations or substitutions at amino acids L117A, A118E, G120A, A213S, and P214S of SEQ ID NO: 77-79, or L234A, L235E, G237A, A330S and P331S, per EU numbering. The constant region of the anti-TREM-1 antibody may also comprise one or more mutations or substitutions L117A, A118E and G120A of SEQ ID NO: 9, or L234A, L235E and G237A, per EU numbering.

In some embodiments, the VH domain of the anti-TREM-1 antibodies described herein comprises the amino acid sequence of any VH domain described herein fused to an IgG1 constant domain comprising the following amino acid sequences:

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDK<u>R</u>VEP

KSCDKTHT<u>SPP</u>S<u>PAPELLGGS</u>SVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFELYSKLTVDKSRW

QQGNVFSCSVMHEALHNHYTQKSLSLSPGK (SEQ ID NO: 11; "IgG1-Aba", comprising substitutions K214R, C226S, C229S, and P238S, per EU numbering, which are underlined); or ASTKGPSVFPLAP<u>CSR</u>STS<u>ES</u>TAALGCLVKDYFPEPVTVSWNSGALTSGV HTFPAVLQSSGLYSLSSVVTVPSSSLGT<u>K</u>TY<u>T</u>CNV<u>D</u>HKPSNTKVDK<u>R</u>VEP KSCDKTHT<u>SPP</u>S<u>PAPELLGGS</u>SVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFELYSKLTVDKSRW

QQGNVFSCSVMHEALHNHYTQKSLSLSPGK (SEQ ID NO: 12; "IgG4-Aba", comprising substitutions S131C, K133R, G137E, G138S, Q196K, I199T, N203D, K214R, C226S, C229S, and P238S, per EU numbering, which are underlined).

A VL domain described herein can be fused to the constant domain of a human Kappa or Lambda light chain. For example, a VL domain of a anti-TREM-1 antibody can comprise the amino acid sequence of any VL domain described herein fused to the following human IgG1 kappa light chain amino acid sequence:

(SEQ ID NO: 13)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

In certain embodiments, the heavy chain constant region comprises a lysine or another amino acid at the C-terminus, e.g., it comprises the following last amino acids: LSPGK (SEQ ID NO: 48) in the heavy chain. In certain embodiments, the heavy chain constant region is lacking one or more amino acids at the C-terminus, and has, e.g., the C-terminal sequence LSPG (SEQ ID NO: 49) or LSP.

In one embodiment, the variable region of the anti-TREM-1 antibody is linked to an effectorless or mostly effector less Fc. In certain embodiments, the variable region of the anti-TREM-1 antibody is linked to a Fc selected from the group consisting of IgG1.1f, IgG1.3f, IgG1-Aba, and IgG4-Aba, as described herein.

Generally, variable regions described herein can be linked to an Fc comprising one or more modification, typically to alter one or more functional properties of the antibody, such as Fc receptor binding, inflammatory cytokine release, serum half-life, complement fixation, and/or antigen-dependent cellular cytotoxicity. Furthermore, an antibody described herein can be chemically modified (e.g., one or more chemical moieties can be attached to the antibody) or be modified to alter its glycosylation, to alter one or more functional properties of the antibody. Each of these embodiments is described in further detail below. The numbering of residues in the Fc region is that of the EU index of Kabat.

The Fc region encompasses domains derived from the constant region of an immunoglobulin (e.g., IgG1, IgG2, IgG3, IgG4, and other classes such as IgA, IgD, IgE and IgM), including a fragment, analog, variant, mutant or derivative of the constant region. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination.

Ig molecules interact with multiple classes of cellular receptors. For example IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR).

In one embodiment, the Fc region of the anti-TREM-1 antibodies is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity.

For example, one can make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region can include two, three, four, five, etc. substitutions therein, e.g., of the specific Fc region positions identified herein.

A variant Fc region can also comprise a sequence alteration wherein amino acids involved in disulfide bond formation are removed or replaced with other amino acids. Such removal can avoid reaction with other cysteine-containing proteins present in the host cell used to produce the anti-TREM-1 antibodies described herein. Even when cysteine residues are removed, single chain Fc domains can still form a dimeric Fc domain that is held together non-covalently. In other embodiments, the Fc region can be modified to make it more compatible with a selected host cell. For example, one can remove the PA sequence near the N-terminus of a typical native Fc region, which can be recognized by a digestive enzyme in E. coli such as proline iminopeptidase. In other embodiments, one or more glycosylation sites within the Fc domain can be removed. Residues that are typically glycosylated (e.g., asparagine) can confer cytolytic response. Such residues can be deleted or substituted with unglycosylated residues (e.g., alanine). In other embodiments, sites involved in interaction with complement, such as the C1q binding site, can be removed from the Fc region. For example, one can delete or substitute the EKK sequence of human IgG1. In certain embodiments, sites that affect binding to Fc receptors can be removed, preferably sites other than salvage receptor binding sites. In other embodiments, an Fc region can be modified to remove an ADCC site. ADCC sites are known in the art; see, e.g., Sarmay et al., *Molec. Immunol.* 29 (5): 633-9 (1992) with regard to ADCC sites in IgG1. Specific examples of variant Fc domains are disclosed, for example, in WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. The number of cysteine residues in the hinge region of Fc is altered to, for example, facilitate assembly of the light and heavy chains or to increase or decrease the stability of the antibody. In one embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320, 322, 330, and/or 331 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region can be modified to decrease antibody dependent cellular cytotoxicity (ADCC) and/or to decrease the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. Other modifications for enhancing FcγR and complement interactions include but are not limited to substitutions 298 A, 333A, 334A, 326A, 247I, 339D, 339Q, 280H, 290S, 298D, 298V, 243L, 292P, 300L, 396L, 305I, and 396L. These and other modifications are reviewed in Strohl, 2009, Current Opinion in Biotechnology 20:685-691.

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, 328, 330, and/or 331 (e.g., 330 and 331), wherein numbering is according to the EU index Exemplary substitutions include but are not limited to 234A, 235E, 236R, 237A, 267R, 269R, 325L, 328R, 330S, and 331S (e.g., 330S, and 331S), wherein numbering is according to the EU index. An Fc variant can comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Optionally, the Fc region can comprise a non-naturally occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; International Publ. Nos. WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925, and WO 06/0201 14).

The affinities and binding properties of an Fc region for its ligand can be determined by a variety of in vitro assay methods (biochemical or immunological based assays) known in the art including but not limited to, equilibrium methods (e.g., enzyme-linked immunoabsorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods can utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental immunology, 4th Ed., Lippincott-Raven, Philadelphia (1999), which focuses on antibody-immunogen interactions.

In certain embodiments, the anti-TREM-1 antibodies of the present disclosure comprise an Fc that has reduced binding or is incapable of binding to FcγRs. In some embodiments, the anti-TREM-1 antibody has a decreased binding affinity to FcγRI (CD64), FcγRIIA (CD32), FcγRIIB (CD32), FcγRIIIA (CD16a), FcγRIIIB (CD16b), or any combination thereof compared to an antibody comprising a heavy chain consisting of the amino acid sequence as set forth in SEQ ID NO: 76 and a light chain consisting of the amino acid sequence as set forth in SEQ ID NO: 54. In some embodiments, the anti-TREM-1 antibody has a decreased binding affinity to FcγRI (CD64) by at least two fold, at least three fold, at least four fold, at least five fold, at least six fold, at least seven fold, at least eight fold, at least nine fold, or at least 10 fold compared to an antibody comprising a heavy chain consisting of the amino acid sequence as set forth in SEQ ID NO: 76 and a light chain consisting of the amino acid sequence as set forth in SEQ ID NO: 54.

In some embodiments, the anti-TREM-1 antibodies comprise an IgG1 Fc variant comprising: (a) one or more amino acid substitutions selected from the group consisting of L234A, L235E, G237A, and any combination thereof, per EU numbering; (b) one or more amino acid substitutions selected from the group consisting of L234A, L235E, G237A, A330S, P331S, and any combination thereof per EU numbering; (c) one or more amino acid substitutions selected from the group consisting of K214R, C226S, C229S, P238S, and any combination thereof per EU numbering; or (d) one or more amino acid substitutions selected from the group consisting of S131C, K133R, G137E, G138S, Q196K, I199T, N203D, K214R, C226S, C229S, P238S, and any combination thereof per EU numbering.

In some embodiments, the anti-TREM-1 antibody, as disclosed herein, has (a) an IgG1 isotype and comprises one or more amino acid substitutions in the Fc region at an amino acid residue selected from the group consisting of: N297A, N297Q, D270A, D265A, L234A, L235A, C226S, C229S, P238S, E233P, L234V, P238A, A327Q, A327G, P329A, K322A, L234F, L235E, P331S, T394D, A330L, M252Y, S254T, T256E, L328E, P238D, S267E, L328F, E233D, G237D, H268D, P271G, A330R, and any combination thereof, wherein the numbering of the residues is according to EU or Kabat numbering, or comprises an amino acid deletion in the Fc region at a position corresponding to glycine 236; (b) an IgG2 isotype and comprises one or more amino acid substitutions in the Fc region at an amino acid residue selected from the group consisting of: P238S, V234A, G237A, H268A, H268Q, H268E, V309L, N297A, N297Q, A330S, P331S, C232S, C233S, M252Y, S254T, T256E, and any combination thereof, wherein the numbering of the residues is according to EU or Kabat numbering; or (c) an IgG4 isotype and comprises one or more amino acid substitutions in the Fc region at an amino acid residue selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU or Kabat numbering. In some embodiments, (a) the Fc region further comprises one or more additional amino acid substitutions at an amino acid residue selected from the group consisting of A330L, L234F; L235E, P331S, and any combination thereof, wherein the numbering of the residues is according to EU or Kabat numbering; (b) the Fc region further comprises one or more additional amino acid substitutions at a position selected from the group consisting of M252Y, S254T, T256E, and any combination thereof, wherein the numbering of the residues is according to EU or Kabat numbering; or (c) the Fc region further comprises a S228P amino acid substitution according to EU or Kabat numbering. See WO 2017/152102.

In certain embodiments, an Fc is chosen that has reduced complement fixation. An exemplary Fc, e.g., IgG1 Fc, with reduced complement fixation has the following two amino acid substitutions: A330S and P331S.

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S.

II. Antibody Physical Properties

Anti-TREM-1 antibodies, e.g., those described herein, have some or all of the physical characteristics of the specific anti-TREM-1 antibodies described herein, such as the characteristics described in the Examples.

Glycosylation sites, particularly within the variable regions, can result in increased immunogenicity of the antibody or an alteration of the pK of the antibody due to altered antigen binding (Marshall et al., (1972) *Annu Rev Biochem* 41:673-702; Gala and Morrison (2004) *J. Immunol* 172:5489-94; Wallick et al., (1988) *J Exp Med* 168: 1099-109; Spiro (2002) *Glycobiology* 12:43R-56R; Parekh et al., (1985) *Nature* 316:452-7; Mimura et al., (2000) *Mol Immunol* 37:697-706). Glycosylation has been known to occur at motifs containing an N-X-S/T sequence. In some embodiments, the anti-TREM-1 antibodies of the present disclosure do not contain or have reduced variable region glycosylation. This can be achieved either by selecting antibodies that do not contain the glycosylation motif in the variable region or by mutating residues within the glycosylation region. Accordingly, in some embodiments, the anti-TREM-1 antibody as disclosed herein are less less immunogenic compared to an antibody comprising a heavy chain consisting of the amino acid sequence as set forth in SEQ ID NO: 76 and a light chain consisting of the amino acid sequence as set forth in SEQ ID NO: 54.

In some embodiments, the anti-TREM-1 antibodies do not contain asparagine isomerism sites. The deamidation of asparagine can occur on N-G or D-G sequences and result in the creation of an isoaspartic acid residue that introduces a kink into the polypeptide chain and decreases its stability (isoaspartic acid effect).

Each antibody will have a unique isoelectric point (pi), which generally falls in the pH range between 6 and 9.5. The pi for an IgG1 antibody typically falls within the pH range of 7-9.5 and the pi for an IgG4 antibody typically falls within the pH range of 6-8. There is speculation that antibodies with a pi outside the normal range can have some unfolding and instability under in vivo conditions. Thus, the anti-TREM-1 antibodies, as disclosed herein, can contain a pi value that falls in the normal range (e.g., 8-9). This can be achieved either by selecting antibodies with a pi in the normal range or by mutating charged surface residues.

Each antibody will have a characteristic melting temperature, with a higher melting temperature indicating greater overall stability in vivo (Krishnamurthy R and Manning M C (2002) *Curr Pharm Biotechnol* 3:361-71). Generally, the $T_M i$ (the temperature of initial unfolding) can be greater than 60° C., greater than 65° C., or greater than 70° C. In some embodiments, the anti-TREM-1 antibodies of the present disclosure have a higher melting temperature compared to an antibody comprising a heavy chain consisting of the amino acid sequence as set forth in SEQ ID NO: 76 and a light chain consisting of the amino acid sequence as set forth in SEQ ID NO: 54. Accordingly, in some embodiments, the anti-TREM-1 antibodies of the present disclosure are thermally stable compared to a reference antibody comprising a heavy chain consisting of the amino acid sequence as set forth in SEQ ID NO: 76 and a light chain consisting of the amino acid sequence as set forth in SEQ ID NO: 54, as measured by, e.g., a Capillary Differential scanning calorimeter (CAP-DSC). The melting point of an antibody can be measured using differential scanning calorimetry (Chen et al., (2003) *Pharm Res* 20: 1952-60; Ghirlando et al., (1999) *Immunol Lett* 68:47-52) or circular dichroism (Murray et al., (2002) *J1 Chromatogr Sci* 40:343-9). In some embodiments, about 10% to 20%, about 20% to 30% (e.g., 24%), or about 30% to 40% of the antibody is reversible when it is heated to 77° C.

In some embodiments, the anti-TREM-1 antibodies of the present disclosure do not degrade rapidly. Degradation of an antibody can be measured using capillary electrophoresis (CE) and MALDI-MS (Alexander A J and Hughes D E (1995) *Anal Chem* 67:3626-32).

In some embodiments, the anti-TREM-1 antibodies, as disclosed herein, have minimal aggregation effects, which can lead to the triggering of an unwanted immune response and/or altered or unfavorable pharmacokinetic properties. Generally, antibodies are acceptable with aggregation of 25% or less, 20% or less, 15% or less, 10% or less, or 5% or less. Aggregation can be measured by several techniques, including size-exclusion column (SEC), high performance liquid chromatography (HPLC), and dynamic light scattering (DLS). In some embodiments, the anti-TREM-1 antibodies of the present disclosure are monomeric as observed by size-exclusion high-performance liquid chromatography (SE-HPLC). In some embodiments, the anti-TREM-1 antibodies exhibit minimal risk for fragmentation as observed by two-dimensional liquid chromatography-tandem mass spectrometry (2D-LC/MS) or intact mass analysis using liquid chromatography-tandem mass spectrometry (LC/MS).

III. Nucleic Acids, Vectors, and Cells

Another aspect described herein pertains to nucleic acid molecules that encode the anti-TREM-1 antibodies described herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In some embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some embodiments, the nucleic acids described herein are those encoding the VH and VL sequences of the anti-TREM-1 antibodies of the present disclosure. Exemplary DNA sequences encoding the VH and VL sequences are set forth in SEQ ID NOs: 58-61 and 62-65, respectively.

A method for making an anti-TREM-1 antibody as disclosed herein can comprise expressing the heavy chain and the light chains in a cell line comprising the nucleotide sequences encoding the heavy and light chains with a signal peptide, e.g., SEQ ID NOs: 58-61 and 62-65, respectively. Host cells comprising these nucleotide sequences are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG2 and/or IgG 4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

Another aspect described herein pertains to cells (e.g., host cells) expressing (e.g., recombinantly) anti-TREM-1 antibodies described herein and related polynucleotides and expression vectors. Provided herein are also vectors comprising polynucleotides comprising nucleotide sequences encoding anti-TREM-1 antibodies or a fragment thereof. In some embodiments, the vectors can be used for recombinantly expressing anti-TREM-1 antibodies described herein in host cells, e.g., in mammalian cells. In some embodiments, the vectors can be used for gene therapy.

Suitable vectors for the disclosure include expression vectors, viral vectors, and plasmid vectors. In some embodiments, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the disclosure can include polynucleotides encoding the antibody or antigen binding portin thereof described herein. In some embodiments, the coding sequences for the antibody or antigen binding portin thereof is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired antibody or antigen binding portin thereof.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In some embodiments, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

IV. Immunoconjugates

The present disclosure also provides immunoconjugates comprising any of the anti-TREM-1 antibodies disclosed herein. In some embodiments, the immunoconjugate comprises an antibody or an antigen binding portion linked to an agent. In some embodiments, the immunoconjugate comprises a bispecific molecule disclosed herein linked to an agent (e.g., as therapeutic agent or a diagnostic agent).

For diagnostic purposes, appropriate agents are detectable labels that include radioisotopes, for whole body imaging, and radioisotopes, enzymes, fluorescent labels and other suitable antibody tags for sample testing. The detectable labels that can be linked to any anti-TREM-1 antibody described herein can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-STAR® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

In some embodiments, conjugation methods result in linkages which are substantially (or nearly) non-immunogenic, e.g., peptide- (i.e., amide-), sulfide-, (sterically hindered), disulfide-, hydrazone-, and ether linkages. These linkages are nearly non-immunogenic and show reasonable stability within serum (see, e.g., Senter, P. D., *Curr. Opin. Chem. Biol.* 13 (2009) 235-244; WO 2009/059278; WO 95/17886).

Depending on the biochemical nature of the moiety and the antibody, different conjugation strategies can be employed. In case the moiety is naturally-occurring or recombinant of between 50 to 500 amino acids, there are standard procedures in text books describing the chemistry for synthesis of protein conjugates, which can be easily followed by the skilled artisan (see, e.g., Hackenberger, C. P. R., and Schwarzer, D., *Angew. Chem. Int. Ed. Engl.* 47 (2008) 10030-10074). In some embodiments the reaction of a maleinimido moiety with a cysteine residue within the antibody or the moiety is used. This is an especially suited coupling chemistry in case e.g., a Fab or Fab'-fragment of an antibody is used. Alternatively, in some embodiments, coupling to the C-terminal end of the antibody or moiety is performed. C-terminal modification of a protein, e.g., of a Fab-fragment, can be performed as described (Sunbul, M. and Yin, J., *Org. Biomol. Chem.* 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., *ChemBioChem.* 10 (2009) 425-427). It is also possible to obtain a desired amino acid modification by utilizing the specific enzymatic reactivity of certain enzymes with a natural amino acid in a given sequence context (see, e.g., Taki, M. et al., *Prot. Eng. Des. Sel.* 17 (2004) 119-126; Gautier, A. et al. *Chem. Biol.* 15 (2008) 128-136; and Protease-catalyzed formation of C—N bonds is used by Bordusa, F., Highlights in Bioorganic Chemistry (2004) 389-403). Site specific reaction and covalent coupling can also be achieved by the selective reaction of terminal amino acids with appropriate modifying reagents.

The reactivity of an N-terminal cysteine with benzonitrils (see Ren, H. et al., *Angew. Chem. Int. Ed. Engl.* 48 (2009) 9658-9662) can be used to achieve a site-specific covalent coupling.

Native chemical ligation can also rely on C-terminal cysteine residues (Taylor, E. Vogel; Imperiali, B, *Nucleic Acids and Molecular Biology* (2009), 22 (Protein Engineering), 65-96).

U.S. Pat. No. 6,437,095 B1 describes a conjugation method which is based on the faster reaction of a cysteine within a stretch of negatively charged amino acids with a cysteine located in a stretch of positively charged amino acids.

The moiety can also be a synthetic peptide or peptide mimic. In case a polypeptide is chemically synthesized, amino acids with orthogonal chemical reactivity can be incorporated during such synthesis (see e.g., de Graaf, A. J. et al., *Bioconjug. Chem.* 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide, the conjugate with 1:1 stoichiometry can be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

In some embodiments, the moiety attached to an anti-TREM-1 antibody is selected from the group consisting of a binding moiety, a labeling moiety, and a biologically active moiety.

Anti-TREM-1 antibodies described herein can also be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. In some embodiments, the linker is a peptidyl linker such as Val-Cit, Ala-Val, Val-Ala-Val, Lys-Lys, Pro-Val-Gly-Val-Val (SEQ ID NO: 80), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295.

Anti-TREM-1 antibodies, e.g., those described herein, can also be used for detecting TREM-1, such as human TREM-1, e.g., human TREM-1 in tissues or tissue samples. The antibodies can be used, e.g., in an ELISA assay or in flow cytometry. In some embodiments, an anti-TREM-1 antibody is contacted with cells, e.g., cells in a tissue, for a time appropriate for specific binding to occur, and then a reagent, e.g., an antibody that detects the anti-TREM-1 antibody, is added. Exemplary assays are provided in the Examples. The anti-TREM-1 antibody can be a fully human antibody, or it can be a chimeric antibody, such as an antibody having human variable regions and murine constant regions or a portion thereof. Exemplary methods for detecting TREM-1, e.g., human TREM-1, in a sample (cell or tissue sample) comprise (i) contacting a sample with an anti-TREM-1 antibody, for a time sufficient for allowing specific binding of the anti-TREM-1 antibody to TREM-1 in the sample, and (2) contacting the sample with a detection reagent, e.g., an antibody, that specifically binds to the anti-TREM-1 antibody, such as to the Fc region of the anti-TREM-1 antibody, to thereby detect TREM-1 bound by the anti-TREM-1 antibody. Wash steps can be included after the incubation with the antibody and/or detection reagent. Anti-TREM-1 antibodies for use in these methods do not have to be linked to a label or detection agents, as a separate detection agent can be used.

Other uses for anti-TREM-1 antibodies, e.g., as monotherapy or combination therapy, are provided elsewhere herein, e.g., in the section pertaining to combination treatments.

V. Bispecific Molecules

Anti-TREM-1 antibodies described herein can be used for forming bispecific molecules. An anti-TREM-1 antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. For example, an anti-TREM-1 antibody can be linked to an antibody or scFv that binds specifically to any protein that can be used as potential targets for combination treatments, such as the proteins described herein (e.g., antibodies to IP-10 or TNF-α). The antibody described herein can in fact be derived or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for TREM-1 and a second binding specificity for a second target epitope. In some embodiments described herein in which the bispecific molecule is multispecific, the molecule can further include a third binding specificity.

In some embodiments, the bispecific molecules described herein comprise as a binding specificity at least one antibody, or an antibody fragment thereof, including, e.g., an Fab, Fab', F(ab')2, Fv, or a single chain Fv (scFv). The antibody can also be a light chain or heavy chain dimer, or any minimal fragment thereof such as a Fv or a single chain construct as described in Ladner et al. U.S. Pat. No. 4,946,778.

While human monoclonal antibodies are preferred, other antibodies which can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see, e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) *Behring Ins. Mitt. No.* 78, 118-132; Brennan et al. (1985) *Science* 229:81-83), and Glennie et al. (1987) *J. Immunol.* 139: 2367-2375). Some conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In some embodiments, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, mAb× (scFv)$_2$, Fab×F(ab')$_2$ or ligand x Fab fusion protein. A bispecific antibody can comprise an antibody comprising an scFv at the C-terminus of each heavy chain. A bispecific molecule described herein can be a single chain molecule comprising one single chain antibody and a binding determinant, or a single chain bispecific molecule comprising two binding determinants. Bispecific molecules can comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

VI. Kits

Provided herein are kits comprising one or more anti-TREM-1 antibodies described herein, or antigen-binding portions thereof, bispecific molecules, or immunoconjugates thereof. In some embodiments, provided herein is a pharmaceutical pack or kit comprising one or more containers filled with one or more of the ingredients of the pharmaceutical compositions described herein, such as one or more antibodies provided herein or an antigen-binding portion thereof, optional an instructing for use. In some embodiments, the kits contain a pharmaceutical composition described herein and any prophylactic or therapeutic agent, such as those described herein.

VII. Compositions and Formulations

Further provided herein are compositions (e.g., pharmaceutical compositions) and formulations comprising one or more of the anti-TREM-1 antibodies (including polynucleotides, vectors, and cells that encode and/or express the anti-TREM-1 antibodies) disclosed herein. For example, in one embodiment, the present disclosure provides a pharmaceutical composition comprising one or more anti-TREM-1 antibodies as disclosed herein, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, can be coated in a material to protect the compound from the action of acids and other natural conditions that can inactivate the compound.

Accordingly, one object of the present disclosure is to provide a pharmaceutical formulation, which improves the stability of the anti-TREM-1 antibodies and thus, allows for their long-term storage. In some embodiments, the pharmaceutical formulation disclosed herein comprises: (a) an anti-TREM-1 antibody; (b) a buffering agent; (c) a stabilizing agent; (d) a salt; (e) a bulking agent; and/or (f) a surfactant. In some embodiments, the pharmaceutical formulation is stable for at least 1 month, at least 2 months, at least 3 months, at least 6 months, at least 1 year, at least 2 years, at least 3 years, at least 5 years or more. In some embodiments, the formulation is stable when stored at 4° C., 25° C., or 40° C.

Buffering Agent

Buffering agents useful for the present invention can be a weak acid or base used to maintain the acidity (pH) of a solution near a chosen value after the addition of another acid or base. Suitable buffering agents can maximize the stability of the pharmaceutical formulations by maintaining pH control of the formulation. Suitable buffering agents can also ensure physiological compatibility or optimize solubility. Rheology, viscosity and other properties can also dependent on the pH of the formulation. Common buffering agents include, but are not limited to, histidine, citrate, succinate, acetate and phosphate. In some embodiments, a buffering agent comprises histidine (e.g., L-histidine) with isotonicity agents and potentially pH adjustment with an acid or a base known in the art. In certain embodiments, the buffering agent is L-histidine. In certain embodiments, the pH of the formulation is maintained between about 2 and about 10, or between about 4 and about 8.

Stabilizing Agent

Stabilizing agents are added to a pharmaceutical product in order to stabilize that product. Such agents can stabilize proteins in a number of different ways. Common stabilizing agents include, but are not limited to, amino acids such as glycine, alanine, lysine, arginine, or threonine, carbohydrates such as glucose, sucrose, trehalose, raffmose, or maltose, polyols such as glycerol, mannitol, sorbitol, cyclodextrins or destrans of any kind and molecular weight, or PEG. In one aspect of the invention, the stabilizing agent is chosen in order to maximize the stability of FIX polypeptide in lyophilized preparations. In certain embodiments, the stabilizing agent is sucrose and/or arginine.

Bulking Agent

Bulking agents can be added to a pharmaceutical product in order to add volume and mass to the product, thereby facilitating precise metering and handling thereof. Common bulking agents include, but are not limited to, lactose, sucrose, glucose, mannitol, sorbitol, calcium carbonate, or magnesium stearate.

Surfactant

Surfactants are amphipathic substances with lyophilic and lyophobic groups. A surfactant can be anionic, cationic, zwitterionic, or nonionic. Examples of nonionic surfactants include, but are not limited to, alkyl ethoxylate, nonylphenol ethoxylate, amine ethoxylate, polyethylene oxide, polypropylene oxide, fatty alcohols such as cetyl alcohol or oleyl alcohol, cocamide MEA, cocamide DEA, polysorbates, or dodecyl dimethylamine oxide. In some embodiments, the surfactant is polysorbate 20 or polysorbate 80.

In some embodiments, the pharmaceutical formulation of the present disclosure comprises:

(a) about 0.25 mg/mL to 250 mg/mL (e.g., 10 to 200 mg/mL) of an anti-TREM-1 antibody;
(b) about 20 mM histidine;
(c) about 150 mM sucrose;
(d) about 25 mM arginine; and
(e) about 50 mM NaCl.

The formulation can further comprise one or more of a buffer system, a preservative, a tonicity agent, a chelating agent, a stabilizer and/or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, $19^{th}$ edition, 1995.

In some embodiments, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In some embodiments, the pharmaceutical formulation is a freeze-dried formulation, to which the physician or the patient adds solvents and/or diluents prior to use.

Pharmaceutical compositions described herein also can be administered in combination therapy, i.e., combined with other agents. For example, the combination therapy can include a anti-anti-TREM-1 antibody described herein combined with at least one other therapeutic agent. Examples of therapeutic agents that can be used in combination therapy can include other compounds, drugs, and/or agents used for the treatment of a disease or disorder (e.g., an inflammatory disorder). Such compounds, drugs, and/or agents can include, for example, anti-inflammatory drugs or antibodies that block or reduce the production of inflammatory cytokines. In some embodiments, therapeutic agents can include an anti-IP-10 antibody, an anti-TNF-α antibody (e.g., adalimumab (HUMIRA®), golimumab (SIMPONI®), infliximab (REMICADE®), certolizumab pegol (CIMZIA®)), interferon beta-1a (e.g., AVONEX®, REBIF®), interferon beta-1b (e.g., BETASERON®, EXTAVIA®), glatiramer acetate (e.g., COPAXONE®, GLATOPA®), mitoxantrone (e.g., NOVANTRONE®), non-steroidal anti-inflammatory drugs (NSAIDs), analgesics, corticosteroids, and combinations thereof.

The pharmaceutical compounds described herein can include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein can also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that can be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition can comprise a preservative or can be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, the compositions can include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of a anti-TREM-1 antibody, e.g., described herein, the dosage ranges from about 0.0001 to 100 mg/kg, and more usually 0.01 to 5 or 10 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Exemplary dosage regimens for a anti-TREM-1 antibody described herein include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some embodiments, the anti-TREM-1 antibody is administered at a flat dose (flat dose regimen). In other embodiments, the anti-TREM-1 antibody is administered at a fixed dose with another antibody. In certain embodiments, the anti-TREM-1 antibody is administered at a dose based on body weight.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and until the patient shows partial or complete amelioration of symptoms of disease. Thereafter, the patient can be administered a prophylactic regime.

Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition described herein can be administered via one or more routes of administration using one or more of a variety of methods known in the art. As will be appreciated by the skilled artisan, the route and/or mode of administration will vary depending upon the desired results. Routes of administration for the anti-TREM-1 antibodies described herein can include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein could potentially be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a particular embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-TREM-1 antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In some embodiments, the anti-TREM-1 antibodies described herein can be formulated to ensure proper distribution in vivo. For example, the blood-brain barrier (BBB) excludes many highly hydrophilic compounds. To ensure that the therapeutic compounds described herein cross the BBB (if desired, e.g., for brain cancers), they can be formulated, for example, in liposomes. For methods of manufacturing liposomes, see, e.g., U.S. Pat. Nos. 4,522,811; 5,374,548; and 5,399,331. The liposomes can comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents Chemother.* 39: 180); surfactant protein A receptor (Briscoe et al. (1995) *Am. J. Physiol.* 1233: 134); p 120 (Schreier et al. (1994) *J. Biol. Chem.* 269:9090); see also K. Keinanen; M. L. Laukkanen (1994) *FEBS Lett.* 346: 123; J. J. Killion; I. J. Fidler (1994) *Immunomethods* 4:273.

VIII. Uses and Methods

The anti-TREM-1 antibodies of the present disclosure and the compositions comprising such antibodies (e.g., pharmaceutical composition, formulations, polynucleotides, vectors, and cells) can be used for the treatment of an inflammatory disease (e.g., by inhibiting TREM-1 activity).

Accordingly, in one aspect, the present disclosure provides methods for treating an inflammatory disease in a subject in need thereof, comprising administering a therapeutically effective dose of the anti-TREM-1 antibody to the subject. Examples of inflammatory diseases that can be treated with the present anti-TREM-1 antibodies include, but not limited to, inflammatory bowel disease (IBD), Crohn's disease (CD), ulcerative colitis (UC), irritable bowel syndrome, rheumatoid arthritis (RA), psoriasis, psoriatic arthritis, systemic lupus erythematosus (SLE), lupus nephritis, type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogrens's syndrome, autoimmune nephritis, Goodpasture's syndrome, chronic inflammatory demyelinating polyneuropathy, allergy, asthma and other autoimmune diseases that are a result of either acute or chronic inflammation.

In one embodiment, the anti-TREM-1 antibodies are suitable for use in the treatment of individuals with inflammatory bowel disease. Inflammatory Bowel Disease (IBD) is a disease that may affect any part of the gastrointestinal tract from mouth to anus, causing a wide variety of symptoms. IBD primarily causes abdominal pain, diarrhoea (which may be bloody), vomiting or weight loss, but may also cause complications outside of the gastrointestinal tract such as skin rashes, arthritis, inflammation of the eye, fatigue and lack of concentration. Patients with IBD can be divided into two major classes, those with ulcerative colitis (UC) and those with Crohn's disease (CD). CD generally involves the ileum and colon, it can affect any region of the intestine but is often discontinuous (focused areas of disease spread throughout the intestine). UC always involves the rectum (colonic) and is more continuous. In CD, the inflammation is transmural, resulting in abscesses, fistulas and strictures, whereas in UC, the inflammation is typically confined to the mucosa. There is no known pharmaceutical or surgical cure for Crohn's disease, whereas some patients with UC can be cured by surgical removal of the colon. Treatment options are restricted to controlling symptoms, maintaining remission and preventing relapse. Efficacy in inflammatory bowel disease in the clinic may be measured as a reduction in the Crohn's Disease Activity Index (CDAI) score for CD which is scoring scale based on laboratory tests and a quality of life questionnaire. In animal models, efficacy is mostly measured by increase in weight and also a disease activity index (DAI), which is a combination of stool consistency, weight and blood in stool.

In one embodiment, the anti-TREM-1 antibodies of the present disclosure are suitable for use in the treatment of individuals with rheumatoid arthritis. Rheumatoid arthritis (RA) is a systemic disease that affects nearly if not all of the body and is one of the most common forms of arthritis. It is characterized by inflammation of the joint, which causes pain, stiffness, warmth, redness and swelling. This inflammation is a consequence of inflammatory cells invading the joints, and these inflammatory cells release enzymes that may digest bone and cartilage. As a result, this inflammation can lead to severe bone and cartilage damage and to joint deterioration and severe pain, among other physiologic effects. The involved joint can lose its shape and alignment, resulting in pain and loss of movement. There are several animal models for rheumatoid arthritis known in the art. For example, in the collagen-induced arthritis (CIA) model, mice develop an inflammatory arthritis that resembles human rheumatoid arthritis. Since CIA shares similar immunological and pathological features with RA, this makes it a suitable model for screening potential human anti-inflammatory compounds. Efficacy in this model is measured by decrease in joint swelling. Efficacy in RA in the clinic is measured by the ability to reduce symptoms in patients which is measured as a combination of joint swelling, erythrocyte sedimentation rate, C-reactive protein levels and levels of serum factors, such as anti-citrullinated protein antibodies.

In one embodiment, the anti-TREM-1 antibodies as disclosed herein are suitable suitable for use in the treatment of individuals with psoriasis. Psoriasis is a T-cell mediated inflammatory disorder of the skin that can cause considerable discomfort. It is a disease for which there is currently no cure and it affects people of all ages. Although individuals with mild psoriasis can often control their disease with topical agents, more than one million patients worldwide require ultraviolet light treatments or systemic immunosuppressive therapy. Unfortunately, the inconvenience and risks of ultraviolet radiation and the toxicities of many therapies limit their long-term use. Moreover, patients usually have recurrence of psoriasis, and in some cases rebound shortly after stopping immunosuppressive therapy. A recently developed model of psoriasis based on the transfer of CD4+T cells mimics many aspects of human psoriasis and therefore can be used to identify compounds suitable for use in treatment of psoriasis (Davenport et al., *Internat. Immunopharmacol* 2: 653-672, 2002). Efficacy in this model is a measured by reduction in skin pathology using a scoring system. Similarly, efficacy in patients is measured by a decrease in skin pathology.

In one embodiment, the anti-TREM-1 antibodies are suitable for use in the treatment of individuals with psoriatic arthritis. Psoriatic arthritis (PA) is a type of inflammatory arthritis that occurs in a subset of patients with psoriasis. In these patients, the skin pathology/symptoms are accompanied by a joint swelling similar to that seen in rheumatoid arthritis. It features patchy, raised, red areas of skin inflammation with scaling. Psoriasis often affects the tips of the elbows and knees, the scalp, the navel and around the genital areas or anus. Approximately 10% of patients who have psoriasis also develop an associated inflammation of their joints.

In terms of the present disclosure, prophylactic, palliative, symptomatic and/or curative treatments may represent separate aspects of the disclosure. An antibody of the invention can be administered parenterally, such as intravenously, such as intramuscularly, such as subcutaneously. Alternatively, an antibody of the invention can be administered via a non-parenteral route, such as perorally or topically. An antibody of the invention can be administered prophylactically. An antibody of the invention can be administered therapeutically (on demand).

The following examples are offered by way of illustration and not by way of limitation. The contents of all references cited throughout this application are expressly incorporated herein by reference.

EXAMPLES

Example 1: Analysis of the Interaction Kinetics for the 318 Antibody Variants to Both Human and Cynolmogus TREM-1 by Surface Plasmon Resonance The binding kinetics of the mAb 0318 variants towards human TREM-1-Fc (hTREM-1) and cynomolgus TREM-1-Fc (cTREM-1) were determined. Binding studies were performed on a ProteOn Analyzer (BioRad) that measures molecular interactions in real time through surface plasmon resonance. Experiments were run at 25° C. and the samples were stored at 15° C. in the sample compartment. The signal (RU, response units) reported by the ProteOn is directly correlated to the mass on the individual sensor chip surfaces in the six parallel flow cells. Anti-human Fc monoclonal or anti-murine Fc polyclonal antibody from Biacore human or mouse Fc capture kits were immobilized in horizontal direction onto flow cells of a GLM sensor chip according to the manufacturer's instructions. The final immobilization level of capture antibody was approximately 2600-6000 RU in each experiment. The capture of purified monoclonal mouse or recombinantly expressed anti-hTREM-1 antibodies was conducted by diluting the antibodies to 5-10 nM into running buffer (10 mM Hepes 0.15 M NaCl, 5 mM EDTA, 0.05% surfactant P20, pH 7.4) followed by injection in vertical direction at 30 µl/min for 60 sec, creating reference interspots adjacent to all flow cells with only anti-Fc antibody immobilized. This typically resulted in final capture levels of test antibodies of approximately 100-300 RU and Rmax values of analyte of 30-90 RU. Binding of hTREM-1 or cTREM-1 proteins was conducted by injecting analyte (antigen) over all flow cells in horizontal direction to allow for comparative analyses of binding to different captured anti-TREM-1 antibodies relative to binding to the reference interspot. hTREM-1 or cTREM-1 proteins were diluted serially 1:3 to 1.2-100 nM or into running buffer, injected at 100 µl/min for 250 s and allowed to dissociate for 600s. The GLM surface was regenerated after each injection cycle of analyte via two 18 s injections of 10 mM Glycine, pH 1.7 and 50 mM NaOH at 100 µl/min. This regeneration step removed the anti-TREM-1 antibody and any bound TREM-1 protein from the immobilized capture antibody surface and allowed for the subsequent binding of the next interaction sample pair. The regeneration procedure did not remove the directly immobilized anti-Fc capture antibody from the chip surface.

Binding affinity between antibodies and the antigen was quantified by determination of the equilibrium dissociation constant ($K_D$) determined by measurement of the kinetics of complex formation and dissociation. The rate constants corresponding to the association and the dissociation of a monovalent complex such as $k_a$ (association rate) and $k_d$ (dissociation rate) were retrieved by fitting data to 1:1 Langmuir model using the ProteOn evaluation software for data analysis. $K_D$ is related to $k_a$ and $k_d$ through the equation $K_D=k_d/k_a$.

Binding curves were processed by double referencing (subtraction of reference surface signals as well as blank buffer injections over captured anti-TREM-1 antibodies) prior to data analysis. This allowed correction for instrument noise, bulk shift and drift during sample injections.

As shown in FIGS. 1A and 1B, the mAb 0318 variants (i.e., 318-IgG1.1f, 318-IgG1.3f, 318-IgG4-Aba, and 318-IgG1-Aba) were all found to have similar affinity towards human TREM-1-Fc as mAb 0318-IgG4. The 0318-IgG1.3f variant also bound to cynomolgus TREM-1, albeit with slightly reduced affinity as compared to human TREM-1. See FIG. 1A.

Example 2: Internalization Analysis of mAb 0318-IgG1.3f Upon Binding to TREM-1 Receptor The mAb 0318-IgG1.3f variant antibody was tested for its internalization in primary human monocytes using both laser scanning confocal microscopy (data not shown) and Amnis ImageStream® Imaging Flow Cytometry Analysis. As shown in FIG. 2A, at 0 hours, TREM-1 is expressed primarily on the surface of the monocytes. However, by 24 hours after antibody binding, a significant percentage (~36%) of the TREM-1 receptor (as evidenced by 0318-IgG1.3f staining) has been internalized, suggesting that upon mAb 0318-IgG1.3f antibody binding, the entire antibody-receptor complex is internalized within the cell.

Next, to determine the fate of the TREM-1 receptor once it has been internalized, the TREM26 antibody (cat. No. 314902, Biolegend; See US20150274825 at paragraph [0005]) was used for comparison. The TREM26 antibody does not compete with the 0318 antibody variants described in the present disclosure. As shown in FIG. 2B, compared to 0 hours, there was a significant reduction in TREM26+ expression (~51%) at the 20 hour time point. There was also a significant reduction (4 fold) in TREM26+ MFI (mean fluorescence index) at the 20 hour time point (post mAb 0318-IgG1.3f treatment), suggesting that the TREM-1 receptor is degraded upon internalization. This loss of TREM-1 receptor expression upon antibody exposure is reversible, however, once the antibody is removed (data not shown).

Example 3: Analysis of the mAb 0318 Variants to Efficiently Block TREM-1 Activation Using the BWZ/hTREM-1 Reporter Cell Assay The ability of the anti-TREM-1 mAb 0318 variants to inhibit human TREM-1 signaling was determined using the BWZ.36/hTREM-1DAP12:NFAT-LacZ cell line (herein also referred to as the "BWZ/hTREM-1 reporter cell") assay as described in, for example, U.S. Pat. No. 9,550,830 B2 and International Publ. No. WO 2016/009086 A1. Briefly, approximately 40,000 hTREM-1/BWZ.36 cells/well were plated in a clear bottom, black 96 well plate in the presence of 75 ng/ml PGLYRP1 (SEQ ID NO: 8) with 2.5 µg/ml PGN-ECndi (Cat. no. tlrl-kipgn, Invivogen San Diego, Calif., USA) to provide a sub-maximal positive signal, or alternatively in the presence of a sub-maximal level (1 µg/ml) of plastic adsorbed anti TREM-1 monoclonal antibody (Cat. no. MAB1278, R&D Systems, Minneapolis, Minn., USA) to provide a positive signal.

The mAb 0318 variants (i.e., 0318-IgG1.3f; 0318-IgG1.1f; 0318-IgG1-Aba; and 0318-IgG4-Aba) were titered into the assay starting at 10 µg/ml, with 5 serial 2-fold dilutions. The assay was incubated overnight at 37° C., subsequently developed with Beta Glo (Cat. no. E4740, Promega Madison, Wis., USA), as per the Beta Glo protocol, and luminescence was recorded. Data was plotted showing Beta Glo relative luminescent units vs test antibody concentration. Non-neutralizing negative control mIgG1 (Cat. no. MAB002, R&D Systems Minneapolis, Minn., USA) and neutralizing positive control polyclonal goat anti hPG-LYRP1 antibody (Cat. no. AF2590, R &D Systems, Minneapolis, Minn., USA) were run on each assay plate. The MAB1278 antibody (cat. no. MAB1278, R&D Systems; See US20150274825 at paragraph [0005]), a known agonist of TREM-1 signaling, was also used as a positive control (see inserted box).

As shown in FIG. 3, all the mAb 0318 variants were potent at inhibiting human TREM-1 signaling as observed previously with the mAb 0318 IgG4 antibody in International Publ. No. WO 2016/009086 A1.

Example 4: In Vitro Analysis of the Potency of the mAb 0318 Antibody Variants at Inhibiting TREM-1 Mediated Production of Inflammatory Cytokines by Different Primary Human Cells To further assess the antagonistic properties of the anti-TREM-1 mAb 0318 variants, their potency to block the release of various inflammatory cytokines (e.g., TNF-α, IL-6, or IL-8) from activated human primary cells was assessed. Primary monocytes, neutrophils, and peripheral blood mononuclear cells (PBMCs) were isolated from human whole blood and stimulated with plate-bound PGRP1 and soluble peptidoglycan (PGN-ECndss; a form of peptidoglycan without the TLR2 activity).

As shown in FIG. 4, all the mAb 0318 variants (i.e., IgG1.3f, IgG1.1f, IgG1-Aba, and IgG4-Aba) were all potent ($IC_{50}$ values in the ~10-20 pM range) at inhibiting TREM-1 mediated release of TNF-α from PBMC and monocytes. The potency of these mAb 0318 variants were similar to that observed with the mAb 0318-IgG4 antibody. The mAb 0318-IgG1.3f antibody was also potent in inhibiting IL-6 production ($IC_{50}$ value of ~32 pM). For neutrophils, the mAb 0318-IgG1.3f variant appeared to be better compared to the mAb 0318-IgG4 antibody at blocking TREM-1 mediated IL-8 production from neutrophils. (See FIG. 4).

As further demonstration of the antagonistic properties of the anti-TREM-1 mAb 0318 antibody variants, a monocyte-neutrophil co-culture assay was also used. Neutrophil-associated PGRP1 when co-cultured with monocytes can ligate TREM-1 receptors, resulting in monocyte-derived TNF-α production. As shown in FIG. 4, all the mAb 0318 antibody variants effectively blocked this endogenous activation ($IC_{50}$ values ranging from 19-44 pM). Similar results were observed with RBC-sedimented whole blood. (See FIG. 4).

Example 5: In Vitro Analysis of the Potency of mAb 0318-IgG1.3f to Block IL-8 Production from Stimulated Whole Blood One of the major challenges towards the development of a whole blood pharmacodynamics (PD) assay to measure the antagonistic properties of the anti-TREM-1 antibody variants is the high background resulting from the PGN stimulation. To help address this issue, whole blood was stimulated with pre-complexed PGRP1+PGN in the presence of NOD2 inhibitor (to block background cytokines produced by NOD2 stimulation by PGN). IL-8 levels were measured using the standard ligand binding pharmacodynamics assay (HTRF®) (FIG. 5A) or an intracellular cytokine staining (ICS) assay (FIG. 5B).

As shown in FIGS. 5A and 5B, the 0318-IgG1.3f antibody effectively blocked the TREM-1 mediated IL-8 production with percent inhibition ranging from about 60-90% (see FIG. 5A). The observed IC50 values (mean value of 12 pM with HTRF and 19.6 pM with ICS) were similar to that observed with other functional assays (e.g., see Example 4).

Example 6: In Vitro Analysis of the Potency of mAb 0318-IgG1.3f to Block mRNA Expression of Different Inflammatory Mediators in Stimulated Whole Blood To additionally demonstrate the antagonistic properties of mAb 0318-IgG1.3f, the expression levels of select inflammatory mediators (i.e., chitinase-3-like protein 1 ("CHI3L1"), IL1β, and IL6) were measured measured by Real-Time PCR (qPCR). Briefly, human whole blood collected in EDTA tubes from three normal healthy volunteers (donor #126, 290, and 322) was stimulated with pre-complexed hPGRP1 (50 µg/ml) and PGN-ECndss (10 µg/ml) (Invivogen tlrl-ksspgn) overnight in the presence of varying concentrations of mAb 0318-IgG1.3f (0-1 nM). Following stimulation, the plasma was removed and frozen for cytokine measurements. The mRNA was isolated from the samples using the MagMax-96 Blood Isolation Kit (ThermoFisher AM1837) according to the manufacturer's protocol. The isolated mRNA was then converted to cDNA utilizing the SuperScript VILO Master Mix (Thermo Fisher 11755250). Next, qPCR was performed using the following probes: HPRT1 (Hs99999909_m1) (Thermo Fisher 4351370), CHI3L1 (Hs01072228_m1) (Thermo Fisher 4331182), IL1β (Hs00174097_m1) (Thermo Fisher 4331182), and IL6 (Hs00985639_m1) (Thermo Fisher 4331182) and TaqMan Fast Universal Master Mix (2×) (Thermo Fisher 4366072). Gene expression values were normalized to HPRT1 and ΔΔCT values were generated. Results were then plotted and $IC_{50}$ values were determined.

As shown in FIGS. 6A-6C and in agreement with the earlier Examples, mAb 0318-IgG1.3f was able to inhibit the TREM-1 mediated expression of different inflammatory mediators in human whole blood. The inhibition appeared to be dose dependent. The IC50 values are shown in Table 1 below.

Collectively, the above results demonstrate that the mAb 0318 antibody variants described in the present disclosure are antagonistic and can effectively block TREM-1 mediated production of inflammatory cytokines from various human cells.

TABLE 1

| Cell Type | Inflammatory Mediator | Stimulus | mAb 0318-IgG1.3f IC50 (pM) |
|---|---|---|---|
| Whole Blood | CHI3L1 RNA | Soluble PGRP + Soluble PGN-Ecndss | 4.58 ± 5.60 (N = 3) |
| | IL1b RNA | | 11.15 ± 16.01 (N = 3) |
| | IL6 RNA | | 97.66 ± 125.63 (N = 3) |

Example 7: Viscosity of the mAb 0318 Variants

Sample was buffer exchanged and dialyzed into the formulation of choice (20 mM histidine, 150 mM sucrose, 25 mM arginine, 50 mM sodium chloride, pH 6.0), followed by concentration using Amicon Ultra centrifugal molecular weight cutoff filters. Aggregation state of the samples was measured to by size exclusion chromatography to control for potential changes in monomericity upon concentration, which were not observed. Concentration-dependent viscosity was determined using a RheoSense m-VROC solution viscometer using a 3 point ascending shear sweep for each concentration measured. Concentration was determined by measuring absorbance at 280 nm by nanoDrop using dilution series and extrapolation.

As shown in FIG. 7, both the 318-IgG1.1f and 318-IgG1.3f variants had similar viscosity profile. At a concentration of about 130 mg/mL, the 0318-IgG1.3f variant had a viscosity value of about 9 cP. Such viscosity profile closely mirrored that observed previously with mAb 0318-IgG4 (see International Publ. No. WO 2016/009086).

Example 8: Immunogenicity Potential of the mAb 0318 Variants

As shown in FIG. 8 and Table 2 (below), the 318-IgG1.1f and 318-IgG1.3f variants had low to medium risk for immunogenicity in human patients. Only about 22-30% of the donor had immunogenic responses (as measured by in vitro CD4$^+$ T cell proliferation) to these antibodies. The immunogenicity for the 0318-IgG1-Aba and 0318-IgG4-Aba variants was 10% and 42.5%, respectively. See Table 2 (below). In contrast, the mAb 0318-IgG4 was much more immunogenic (55%) in human patients. KLH (keyhole limpet hemocyanin) and VL6 (IL-21R mAb), which were used as positive controls, were highly immunogenic in the human patients (100% and 40%, respectively).

IgG1.3f) were all able to bind to human, mouse, and cyno FcRn in a pH dependent manner. This was also true for the mAb 0318 antibody (IgG4).

Example 10: Binding Analysis of the mAb 0318 Variants to One or More FcγRs

As discussed earlier, the in vivo administration of antibodies to certain cell surface immune receptors has the potential for inducing cytokine release, which can result in the induction of a common and toxic clinical complication known as the cytokine release syndrome (CRS). Because of the concern that FcγR engagement could lead to potential TREM-1 agonistic activity via cross-linking, mAb 0318-IgG4 was re-engineered into one of the variant formats described in the present disclosure (i.e., IgG1.1f, IgG1.3f, IgG1-Aba, or IgG4-Aba). Then, the ability of the 0318 antibody variants to bind to different FcγRs was assessed.

As shown in FIGS. 10A and 10B, the 318-IgG1.1f and 318-IgG1.3f variants had minimal binding to all of the FcγRs (i.e., FcγRI (CD64), FcγRIIA (CD32a-H131 and CD32a-R131 variants), FcγRIIB (CD32b), FcγRIIIA (CD16a-V158 variant), and FcγRIIIB (CD16b-NA2 variant)). The 318-IgG1-Aba and 318-IgG4-Aba variants did not bind to FcγRIIA, FcγRIIB, FcγRIIIA, and FcγRIIIB but did bind to FcγRI. In contrast, mAb 0318 (IgG4) showed significant binding to all of the FcγRs.

TABLE 2

| Assay | Cohort | 0318 Variant | Conc. (mg/mL) | Host Cell | EU/mg | % Monomer | Assay Conc. (ug/mL) | % Immunogenicity |
|---|---|---|---|---|---|---|---|---|
| PBMC | 40 | IgG4 | 161 | UCOE CHO | <0.001 | 97.9 | 150 | 55.0 |
| PBMC | 40 | IgG1-Aba | 145 | UCOE CHO | <0.001 | 97.3 | 150 | 10.0 |
| PBMC | 40 | IgG1.1f | 170 | UCOE CHO | <0.006 | 98.6 | 150 | 22.5 |
| PBMC | 40 | IgG4-Aba | 5 | HEK | <0.02 | 98.9 | 150 | 42.5 |
| PBMC | 40 | IgG1.3f | 4.6 | HEK | <0.02 | 99.5 | 150 | 30.0 |

Example 9: Binding Analysis of the mAb 0318 Variants to FcRn Using Surface Plasmon Resonance (SPR)

To determine whether the different mAb 0318 variants were able to bind to FcRn, the FcRn receptors (mouse, human, and cyno) were immobilized onto a BIAcore CM5-biosensor chip (GE Healthcare Bioscience, Uppsala, Sweden) via amine coupling to a level of 400 Response Unites (RU). The assay was carried out at room temperature with PBS, 0.05% Tween-20™ pH 6.0 (GE Healthcare Bioscience) as running and dilution buffer. The different mAb 0318 variants (200 nM) were injected at a flow rate of 50 μL/min at room temperature at pH 6.0. Association time was 180 seconds, dissociation phase (also at pH 6.0) took 360 seconds. Regeneration of the chip surface back to baseline was reached by a short injection of 50 mM Tris, pH 8.0, and 150 mM NaCl. Evaluation of SPR-data was performed by comparison of the biological response signal height at 180 seconds after injection and at 300 seconds after injection. The corresponding parameters are the RU max level (180 seconds after injection) and late stability (300 seconds after end of injection).

As shown in FIGS. 9A and 9B, the mAb 0318 antibody variants (IgG1-Aba mod, IgG4-Aba mod, IgG1.1f, and Example 11: Analysis of the Induction of Inflammatory Cytokines by the mAb 0318 Variants To further determine if the in vivo treatment with the mAb 0318 variants poses a risk of cytokine release syndrome, whole blood was collected from 8 human donors and the monocytes were isolated. Then, the monocytes were differentiated into immature dendritic cells by plating the monocytes (4×10$^6$ cells/well) and culturing them in a differentiation media containing IL-4 and GM-CSF (100 ng/mL). At around days 2-3 post-plating, approximately half of the differentiation media was replaced with fresh media. At day 7, the cells were harvested and the differentiation efficiency was assessed by analyzing CD14 expression on the cells using flow cytometer. Next, the immature dendritic cells were plated onto a flat bottom plate (0.8×10$^5$ cells/well) and the mAb 0318 variants were added to respective wells (with or without CHO-CD32a). Immature dendritic cells stimulated with PGRP+PGN were used as a positive control. The cells were then incubated overnight at 37° C. The next day, supernatants were harvested from the wells and the amount of TNF-α, IL-6, and IL-12 produced was assessed using an ELISA assay.

The results from representative donors are shown in FIGS. 11A to 11I. The addition of the different mAb 0318 variants (0318-IgG1.1f, 0318-IgG1.3f, and 0318-IgG1.1

Aba) resulted in minimal IL-6 (FIGS. 11A, 11B, and 11C), TNF-α (FIGS. 11D, 11E, and 11F), and IL-12 (FIGS. 11G, 11H, and 11) production by the immature dendritic cells. These results, along with those from Example 9, demonstrate that the anti-TREM-1 antibodies disclosed herein have a low risk of inducing a cytokine release syndrome when administered to patients in vivo.

Example 12: Additional Characteristics of the mAb 0318 Variants

Biophysical characteristics of the 0318-IgG1.3f variant are provided in Table 3 (below).

TABLE 3

Biophysical Characteristics of anti-TREM-1 0318-IgG1.3f Antibody

| Property | Method | Results |
| --- | --- | --- |
| Identity | LC-MS | Intact Mass confirmed |
|  | LC-MS/MS peptide map | Sequence confirmed by Lys-C peptide map (95.4% recovery; Glycosylation occupancy of 99.7%) |
| Purity/Homogeneity | SEC | 96.3% monomer, 3.6% HMW |
|  | SEC-MALS | Main Peak is 95% monomer & homogeneous (145 kDa) |
|  | LC-MS | G0F (23.3%), G1F (51.3%), G2F (17.3%), SG2F (2.1%), S2G2F (1.0%) |
|  | Capillary isoelectric focusing (cIEF) | Main Peak pI = 8.75 (55%); Acidic variants = 29.5% & Basic variants = 15.5% |
|  | SDS-PAGE | Reduced: 2 predominant bands of ~50 kDa & 25 kDa Non-Reduced: Predominant band of ~150 kDa with minor fragments of ~98 kDa, 75 kDa, 50 kDa, 25 kDa (artifacts of SDS-running conditions) |
| Affinity | SPR (Biacore) | huTREM1: $K_D$ = 0.91 nM; $k_{on}$ = 1.4E+06 (1/Ms); $k_{off}$ = 1.3E−3 (1/s) CynoTREM1: $K_D$ = 3.4 nM; $k_{on}$ = 4.0E+05 (1/Ms); $k_{off}$ = 1.4E−3 (1/s) |
| Thermal Stability | DSC | $T_m1$ = 66.2° C.; $T_m2$ = 78.4° C.; $T_m3$ = 83.2° C. Reversibility at 77° C. = 24% |
| FcγR/FcRn Interaction | SPR (Biacore) | Demonstrates decreased binding to all FcγRs Expected pH dependent FcRn binding comparable to wild-type IgG1 mAbs |

The biophysical properties of the mAb 0318-IgG1.3f variant are favorable for clinical development. The identity of the antibody was confirmed by mass spectrometry analysis (Intact Mass Analysis & Peptide Mapping). The antibody was >96% monomeric as tested by size exclusion chromatography. A single N-glycosylation site was confirmed at N301 on the heavy chain with a glycan profile matching the glycan profile of CHO-expressed monoclonal antibodies (G0F, G1F, and G2F). Thermal stability ($T_m1$=66.2° C.; $T_m2$=78.4° C.; $T_m3$=83.2° C.) and thermal reversibility (24% at 77° C.) of the mAb 0318-IgG1.3f was within the range for a typical human IgG1.3 monoclonal antibody.

Stability characteristics of the mAb 0318-IgG1.3f variant are provided in Table 4 (below).

TABLE 4

Stability of the Anti-TREM-1 0318-IgG1.3f Antibody

| Property | Method(s) | Results |
| --- | --- | --- |
| Freeze/Thaw (2 h @ −80° C., 4 h @ RT × 3) | UV, SEC, DLS, iCIEF | No freeze/thaw stability risk revealed |
| Solubility/Concentration Profile | UV, SEC | >150 mg/mL in formulation buffer (20 mM histidine, 150 mM sucrose, 50 mM sodium chloride, 25 mM arginine, pH 6.0) |
| pH Screen for Conformational and Colloidal Stability | Optim2 (Tm and Tagg onset) | Optimal conformational stability = pH 6-8 Optimal colloidal stability = pH 5-6 |
| Buffer and Excipient Screening | Optim2 (Tm and Tagg onset) | Stabilizers: sucrose, sorbitol, arginine (high concentration), glycerol |
| Accelerated Stability 150 mg/mL 12 w @ 4° C., 25° C., and 40° C. in the formulation (20 mM histidine, 150 mM sucrose, 50 mM | SEC, cIEF, HIC, LC-MS/MS (peptide mapping), LC/MS (intact | 12 w @ 40° C. = 1.2%/month increase in HMW 2.4%/month increase in LMW 12 w @ 40° C. = Increase in Rh and Pd 12 w @ 40° C. = 11%/month increase in acidic |

TABLE 4-continued

Stability of the Anti-TREM-1 0318-IgG1.3f Antibody

| Property | Method(s) | Results |
|---|---|---|
| sodium chloride, 25 mM arginine, pH 6.0) | mass), 2D-LC/MS (fragments), Biacore, bioassay, UV-Vis, DLS | variants<br>12 w @ 40° C. = 3%/month VSNK deamidation |
| Viscosity Assessment | Determine concentration-viscosity profile | Solution reaches 9 cP at ~130 mg/mL, with predicted viscosity of 12 cP at 150 mg/mL |

No physical stability issues were observed during freeze-thaw stress (3 cycles) at 150 mg/mL in the described formulation (20 mM histidine, 150 mM sucrose, 50 mM sodium chloride, 25 mM arginine, pH 6.0). Forced degradation studies in the studied formulation at 150 mg/mL were set up at 4, 25, and 40° C. (up to 3 months). CDR chemical modifications remained low throughout all temperature conditions and did not affect activity, as determined by SPR. VSNK deamidation was below expectations compared with other monoclonal antibodies on the IgG1.3f framework (3%/month increase at 40° C. storage), changes to which were time and temperature dependent. All other chemical modifications (oxidation, deamidation, isomerization) also remained low as monitored during the stability studies. Of note, storage at 40° C. indicates a formation of both HMW and LMW variants (demonstrating 1.2%/month and 2.4%/month, respectively). The observed changes were time and temperature dependent, such that HMW increased 0.25%/month, which LMW remained unchanged under 4° C. storage over the study period. The low LMW formation under 40° C. storage was characterized by 2D-LC/MS with high resolution accurate mass measurements as the cumulative species of 1 Fab loss, as well as the Fab arm, putatively at a conserved sequence in the upper hinge region.

Example 13: PK/TK/PD Study for the mAb 0318-IgG1.3f Variant in Cynomolgus Monkeys A single-dose pharmacokinetic (PK), toxicokinetic (TK), and pharmacodynamics (PD) study was conducted in Cynomolgus monkeys for the anti-TREM-1 0318-IgG1.3f antibody. Some of the animals received 2 mg/kg of the 0318-IgG1.3f antibody intravenously (n=3). Other animals received one of the following doses of the 0318-IgG1.3f antibody subcutaneously: (i) 0 mg/kg (i.e., control) (n=4), (ii) 0.1 mg/kg (n=4), (iii) 0.5 mg/kg (n=4), (iv) 2 mg/kg (n=3), or (v) 10 mg/kg (n=4). Upon antibody administration, pharmacokinetics, anti-drug antibodies (ADA), TREM-1 receptor occupancy (RO), and ex vivo pharmacodynamics responses were examined at pre-determined time points.

Pharmacokinetics (PK)

To assess the pharmacokinetics, serum concentrations of the 0318-IgG1.3f antibody were assessed in the animals with a ligand binding assay using a biotinylated recombinant TREM-1 protein as the capture reagent and a commercial polyclonal goat-anti-TREM-1 antibody as the detection reagent.

As shown in FIG. 12, the pharmacokinetics of the 0318-IgG1.3f antibody was determined to be non-linear between 0.1 and 10 mg/kg, predominantly due to target mediated clearance (i.e., internalization and degradation of the antibody upon binding to TREM-1 receptor; see Example 2).

Non-compartmental analysis based PK parameters are presented in Tables 5 (intravenous administration) and 6 (subcutaneous administration). Briefly, a 100-fold increase in dose resulted in 830-fold increase in serum exposures (AUCs). See Table 6. Clearance following 2 mg/kg IV dose was 0.1±0.02 mL/h/kg and similar to other IgG1 based mAbs in monkeys. See Table 4. The Vss at 36±5 mL/kg, was similar to plasma volume indicating limited extravascular distribution. The half-life of the 0318-IgG1.3f antibody increased from 2 days for 0.1 mg/kg dose to 10 days at 2 and 10 mg/kg (single subcutaneous dose administration). See Table 6. The bioavailability of the 0318-IgG1.3f antibody following the subcutaneous administration (2 mg/kg) was high at 84%.

TABLE 5

PK Parameters of mAb 0318-IgG1.3f in Cynomolgus Monkey after Single IV Dose
mAb 0318-IgG1.3f IV-PK Parameters in Cynomolgus Monkeys

| Dose (mg/kg) | 2 |
|---|---|
| N | 3 |
| $V_{SS}$ (mL/kg) | 36 ± 5 |
| CL (mL/h/kg) | 0.1 ± 0.02 |
| $T_{1/2}$ (days) | 10 ± 2 |
| $AUC_{last}$ (µM * h) | 116 ± 20 |
| ADA Positive/Total Examined | 3/3 (1/3)* |

*Number of monkeys out of total examined that showed persistent ADA.

TABLE 5

PK Parameters of mAb 0318-IgG1.3f in Cynomolgus Monkeys after Single SC Dose
mAb 0318-IgG1.3f SC-PK Parameters in Cynomolgus Monkeys

| Dose (mg/kg) | 0.1 | 0.5 | 2 | 10 |
|---|---|---|---|---|
| N | 4 | 4 | 3 | 4 |
| Cmax (nM) | 13 ± 4 | 50 ± 3 | 189 ± 22 | 1419 ± 93 |
| Tmax (h) | 24 | 48 | 168 ± 96 | 84 ± 24 |
| $AUC_{last}$ (µM * h) | 1 ± 0.2 | 15 ± 1 | 94 ± 13 | 649 ± 64 |
| $T_{1/2}$ (days) | 2 ± 0.4 | 4 ± 2 | 10 ± 5 | 10 ± 3 |
| SC Bioavailability | | | 84% | |
| ADA positive/Total Examined | 3/4 (2/4)* | 4/4 (2/4)* | 3/3 (2/3)* | 3/4 (1/4)* |

*Number of monkeys out of total examined that showed persistent ADA.

Anti-Drug Antibodies (ADA)

While serum ADA were detected in most monkeys (16 out of 18) following single dose (regardless of the route of administration), exposure of the 0318-IgG1.3f antibody and TREM-1 receptor occupancy (RO) was not compromised in majority of ADA positive animals. See Tables 4 and 5. Accelerated decline in terminal exposure of the 0318-IgG1.3f antibody that was accompanied with formation of ADA was observed only in two monkeys (one in 0.1 mg/kg dose-group at day 7 and one in 0.5 mg/kg dose-group at day 21). Since ADA affected exposure in these two monkeys in the terminal phase, corresponding data points were eliminated for PK analysis.

TREM-1 Receptor Occupancy (RO) and Total TREM-1 Receptor Levels

Next, the occupancy of the TREM-1 receptors expressed on peripheral blood monocytes and granulocytes were assessed. As shown in FIGS. 15A and 15B, for all doses tested, the percentage of TREM-1 receptors that were occupied (i.e., bound to the anti-TREM-1 antibodiy) were similar between the monocytes and the granulocytes. Moreover, the duration of receptor occupancy appeared to be dependent on the dose of the 0318-IgG1.3f antibody administered to the animals. At 0.5 mg/kg, there was >85% RO observed for up to 2 weeks post antibody administration. In contrast, with the 2 and 10 mg/kg, >85% of the TREM-1 receptors remained occupied for at least 1 month post administration.

Following the 0318-IgG1.3f antibody dosing, the total TREM-1 receptor levels were reduced on both monocytes and granulocytes. See FIGS. 14A and 14B. As discussed earlier, this reduction is presumably due to increased receptor turnover following antibody binding. The decrease in surface TREM-1 receptor expression was reversible and the duration of surface receptor loss was correlated with duration of receptor occupancy at least at the dose-levels examined.

Levels of soluble TREM-1 (sTREM-1) appeared to increase 10- to 50-fold following single dose of the mAb 0318 mAb-IgG1.3f variant in all dose groups tested. (Data not shown). It is unclear if the increase in sTREM-1 levels was related to the anti-TREM-1 antibody administration or to the general handling of the animals during the course of the study. In any case, since drug concentrations far exceeded (>1000 fold) sTREM-1 levels, the soluble target is not anticipated to effect binding of the mAb 0318 mAb-IgG1.3f variant to cell surface TREM-1.

Example 14: PK/TK/PD Study for the mAb 0318-IgG1.3f Variant in Cynomolgus Monkeys Described by a 2-Compartment PK Model with TMDD in Central Compartment Monkey PK, RO, total receptor levels, and PD data were described using a 2-compartment PK model with saturable target-mediated drug disposition (TMDD) in the central compartment to accommodate for the observed non-linear PK (see Example 12 and FIG. 13). A direct-effect inhibitory model was used to describe the PD response. This model was able to effectively capture the time course of PK/RO/PD observed in the monkeys. The observed (open circle) and model-predicted endpoints (solid line) are provided in FIGS. 16A (0.1 mg/kg subcutaneous dosing) and 16B (10 mg/kg subcutaneous dosing). Table 7 provides the estimated PK/PD parameters. When serum exposures of the mAb 0318-IgG1.3f variant and TREM-1 RO data were pooled from all monkeys, a concentration-dependent increase in RO was observed. See FIGS. 16A and 16B. An Emax model used to describe the concentration-RO relationship, estimated in vivo RO $EC_{50}$ to be 1.6±0.2 nM.

TABLE 7

Parameter Estimates of PK/PD Model Used to Describe Monkey PK/TK/PD Data and Projected Human Parameter Estimates

| PK Parameters | Description | Cyno-Model Estimate (CV %) | Projected Human Estimate |
| --- | --- | --- | --- |
| Ka (h−1) | Absorption rate constant | 0.049 (15) | 0.049 |
| V1 (mL/kg) | Volume of distribution of central compartment | 22 (5) | 22 |
| Ke (h−1) | Elimination rate constant from central compartment | 0.003 (10) | 0.0019 |
| K12 (h−1) | Distribution rate constants | 0.024 (14) | 0.015 |
| K21 (h−1) | | 0.022 (7) | 0.014 |
| F (%) | SC bioavailability | 80 (5) | 80 |
| Kdeg (h−1) | Target turnover rate constant | 0.09 (20) | 0.09 |
| Kint (h−1) | Target-mAb complex internalization rate constant | 0.39 (18) | 0.39 |
| R0 (nmol/kg) | Baseline target level in central compartment | 0.024 (22) | 0.024 |
| KD (nM) | mAb affinity for TREM-1 | 0.64 (12) | 0.24 |
| Koff (h−1) | mAb off-rate from TREM-1 | 0.37 (7) | 0.30 |
| IC50 (nM) | Concentration to inhibit PGN + PGRP mediated ex-vivo TREM-1 stimulation by 50% | 1.9 (92) | 0.1 |
| E0 (%) | Basal PGN + PGRP mediated ex-vivo TREM-1 stimulation (pre-dose) | 100 (fixed) | 100 |

TABLE 8

| SEQ ID | Description | Sequences |
| --- | --- | --- |
| 50 | 318-IgG1.3f Heavy Chain | EVQLVESGGGLVQPGGSLKLSCAASGFTFSTYAMHWVRQASGKGLEWVGRIRTKSSNYATYYAAS VKGRFTISRDDSKNTAYLQMNSLKTEDTAVYYCTRDMGIRRQFAYWGQGTLVTVSSASTKGPSVF PLAPSSKSTSGGTAALGCLVKDYFPEPVTVSWNSGALTSGVHTFPAVLQSSGLYSLSSVVTVPSS SLGTQTYICNVNHKPSNTKVDKRVEPKSCDKTHTCPPCPAPEAEGAPSVFLFPPKPKDTLMISRT PEVTCVVVDVSHEDPEVKFNWYVDGVEVHNAKTKPREEQYNSTYRVVSVLTVLHQDWLNGKEYKC |

TABLE 8-continued

| SEQ ID | Description | Sequences |
|---|---|---|
| | | KVSNKALPAPIEKTISKAKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHNHYTQKSLSLSPGK |
| 51 | 318-IgG1.1f<br>Heavy Chain | EVQLVESGGGLVQPGGSLKLSCAASGFTFSTYAMHWVRQASGKGLEWVGRIRTKSSNYATYYAAS<br>VKGRFTISRDDSKNTAYLQMNSLKTEDTAVYYCTRDMGIRRQFAYWGQGTLVTVSSASTKGPSVF<br>PLAPSSKSTSGGTAALGCLVKDYFPEPVTVSWNSGALTSGVHTFPAVLQSSGLYSLSSVVTVPSS<br>SLGTQTYICNVNHKPSNTKVDKRVEPKSCDKTHTCPPCPAPEAEGAPSVFLFPPKPKDTLMISRT<br>PEVTCVVVDVSHEDPEVKFNWYVDGVEVHNAKTKPREEQYNSTYRVVSVLTVLHQDWLNGKEYKC<br>KVSNKALPSSIEKTISKAKGQPREPQVYTLPPSREEMTKNQVSLTCLVKGFYPSDIAVEWESNGQ<br>PENNYKTTPPVLDSDGSFFLYSKLTVDKSRWQQGNVFSCSVMHEALHNHYTQKSLSLSPGK |
| 52 | 318-IgG1-Aba<br>Heavy Chain | EVQLVESGGGLVQPGGSLKLSCAASGFTFSTYAMHWVRQASGKGLEWVGRIRTKSSNYATYYAAS<br>VKGRFTISRDDSKNTAYLQMNSLKTEDTAVYYCTRDMGIRRQFAYWGQGTLVTVSSASTKGPSVF<br>PLAPSSKSTSGGTAALGCLVKDYFPEPVTVSWNSGALTSGVHTFPAVLQSSGLYSLSSVVTVPSS<br>SLGTQTYICNVNHKPSNTKVDKRVEPKSCDKTHTSPPSPAPELLGGSSVFLFPPKPKDTLMISRT<br>PEVTCVVVDVSHEDPEVKFNWYVDGVEVHNAKTKPREEQYNSTYRVVSVLTVLHQDWLNGKEYKC<br>KVSNKALPAPIEKTISKAKGQPREPQVYTLPPSRDELTKNQVSLTCLVKGFYPSDIAVEWESNGQ |
| 53 | 318-IgG4-Aba<br>Heavy Chain | PENNYKTTPPVLDSDGSFFLYSKLTVDKSRWQQGNVFSCSVMHEALHNHYTQKSLSLSPGK<br>EVQLVESGGGLVQPGGSLKLSCAASGFTFSTYAMHWVRQASGKGLEWVGRIRTKSSNYATYYAAS<br>VKGRFTISRDDSKNTAYLQMNSLKTEDTAVYYCTRDMGIRRQFAYWGQGTLVTVSSASTKGPSVF<br>PLAPCSRSTSESTAALGCLVKDYFPEPVTVSWNSGALTSGVHTFPAVLQSSGLYSLSSVTVPSS<br>SLGTKTYTCNVDHKPSNTKVDKRVEPKSCDKTHTSPPSPAPELLGGSSVFLFPPKPKDTLMISRT<br>PEVTCVVVDVSHEDPEVKFNWYVDGVEVHNAKTKPREEQYNSTYRVVSVLTVLHQDWLNGKEYKC<br>KVSNKALPAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGK |
| 54 | 318-IgG1.3f,<br>IgG1.1f, IgG1-<br>Aba, IgG4-Aba<br>Light Chain | DIVLTQSPDSLAVSLGERATINCRASQSVDTFDYSFLHWYQQKPGQPPKLLIYRASNLESGVPDR<br>FSGSGSGTDFTLTISSLQAEDVAVYYCQQSNQDPYTFGQGTKLEIKRTVAAPSVFIFPPSDEQLK<br>SGTASVVCLLNNFYPREAKVQWKVDNALQSGNSQESVTEQDSKDSTYSLSSTLTLSKADYEKHKV<br>YACEVTHQGLSSPVTKSFNRGEC |

What is claimed is:

1. A heavy chain comprising SEQ ID NO: 50, SEQ ID NO: 51, or SEQ ID NO: 85.

2. The heavy chain of claim 1 comprising SEQ ID NO: 50.

3. The heavy chain of claim 1 comprising SEQ ID NO: 85.

4. An isolated antibody which specifically binds to TREM-1, comprising a heavy chain and a light chain, wherein the heavy chain comprises SEQ ID NO: 85, and wherein the light chain comprises SEQ ID NO: 54.

5. An isolated antibody which specifically binds to TREM-1, comprising a heavy chain and a light chain, wherein the heavy chain comprises SEQ ID NO: 50 and wherein the light chain comprises SEQ ID NO: 54.

6. An isolated antibody which specifically binds to TREM-1, comprising a heavy chain and a light chain, wherein the heavy chain comprises SEQ ID NO: 51 and wherein the light chain comprises SEQ ID NO: 54.

7. An isolated antibody which specifically binds to TREM-1, comprising a heavy chain and a light chain, wherein the heavy chain comprises SEQ ID NO: 52 and wherein the light chain comprises SEQ ID NO: 54.

8. An isolated antibody which specifically binds to TREM-1, comprising a heavy chain CDR1, CDR2, CDR3; a light chain CDR1, CDR2, CDR3; and an IgG1 heavy chain constant region,
wherein the heavy chain CDR1, CDR2, and CDR3 comprises TYAMH (SEQ ID NO: 24), RIRTKSSNYATYYAASVKG (SEQ ID NO: 25), and DMGIRRQFAY (SEQ ID NO: 26), respectively;
wherein the light chain CDR1, CDR2, and CDR3 comprises RASQSVDTFDYSFLH (SEQ ID NO: 27), RASNLES (SEQ ID NO: 28), and QQSNQDPYT (SEQ ID NO: 29), respectively; wherein the IgG1 heavy chain constant region comprises three or more amino acid substitutions comprising L234A, L235E, and G237A, per EU numbering and wherein the heavy chain lacks a C-terminal lysine.

9. The antibody of claim 8 comprising a heavy chain variable region (VH) and a light chain variable region (VL), wherein the VH comprises SEQ ID NO: 14 and the VL comprises SEQ ID NO: 15.

10. The antibody of claim 9, wherein the antibody comprises a heavy chain and a light chain, wherein the heavy chain comprises SEQ ID NO: 85, and wherein the light chain comprises SEQ ID NO: 54.

11. An isolated antibody which specifically binds to TREM-1, comprising a heavy chain CDR1, CDR2, CDR3; a light chain CDR1, CDR2, CDR3; and an IgG1 heavy chain constant region,
wherein the heavy chain CDR1, CDR2, and CDR3 comprises TYAMH (SEQ ID NO: 24), RIRTKSSNYATYYAASVKG (SEQ ID NO: 25), and DMGIRRQFAY (SEQ ID NO: 26), respectively;
wherein the light chain CDR1, CDR2, and CDR3 comprises RASQSVDTFDYSFLH (SEQ ID NO: 27), RASNLES (SEQ ID NO: 28), and QQSNQDPYT (SEQ ID NO: 29), respectively;
wherein the IgG1 heavy chain constant region comprises three or more amino acid substitutions, wherein the substitutions comprise L234A, L235E, and G237A, per EU numbering, or
wherein the IgG1 heavy chain constant region comprises three or more amino acid substitutions and one or more amino acid deletions, wherein the substitutions comprise L234A, L235E, and G237A, per EU numbering.

12. The antibody of claim 11, comprising a heavy chain variable region (VH) and a light chain variable region (VL), wherein the VH comprises SEQ ID NO: 14 and the VL comprises SEQ ID NO: 15.

13. The antibody of claim 12, comprising a heavy chain and a light chain, wherein the heavy chain comprises SEQ ID NO: 50, SEQ ID NO: 51, or SEQ ID NO: 85; and wherein the light chain comprises SEQ ID NO: 54.

14. The antibody of claim 12, wherein the IgG1 heavy chain constant region has three substitutions, wherein the substitutions are L234A, L235E, and G237A, per EU numbering.

15. The antibody of claim 12, wherein the IgG1 heavy chain constant region has three substitutions, wherein the substitutions are L234A, L235E, and G237A, per EU numbering, and a C-terminal lysine residue of the IgG1 heavy chain constant region is present.

16. The antibody of claim 12, wherein the IgG1 heavy chain constant region has three substitutions, wherein the substitutions are L234A, L235E, and G237A, per EU numbering, and wherein the heavy chain lacks a C-terminal lysine residue.

17. The antibody of claim 11, comprising a heavy chain and a light chain, wherein the heavy chain comprises SEQ ID NO: 85, and wherein the light chain comprises SEQ ID NO: 54.

18. The antibody of claim 11, comprising a heavy chain, wherein the heavy chain lacks a C-terminal lysine residue.

19. The antibody of claim 11, wherein the IgG1 heavy chain constant region has three substitutions, wherein the substitutions are L234A, L235E, and G237A, per EU numbering.

20. The antibody of claim 11, wherein the IgG1 heavy chain constant region has three substitutions, wherein the substitutions are L234A, L235E, and G237A, per EU numbering, and a C-terminal lysine residue of the IgG1 heavy chain constant region is present.

21. The antibody of claim 11, wherein the IgG1 heavy chain constant region has three substitutions, wherein the substitutions are L234A, L235E, and G237A, per EU numbering, and wherein the heavy chain lacks a C-terminal lysine residue.

22. A bispecific molecule comprising the antibody of claim 11, linked to a molecule having a second binding specificity.

23. An immunoconjugate comprising the antibody of claim 11, linked to an agent.

24. A composition comprising the antibody of claim 11, and a carrier.

25. A kit comprising the antibody of claim 11, and an instruction for use.

26. A method of inhibiting TREM-1 activity in a human subject in need thereof, comprising administering the antibody of claim 11 to the human subject.

27. The method of claim 26, further comprising administering one or more additional therapeutics.

28. A method of treating an inflammatory disease or an autoimmune disease in a human subject in need thereof, comprising administering the antibody of claim 11 to the human subject.

29. The method of claim 28, wherein the inflammatory disease or the autoimmune disease is selected from the group consisting of an inflammatory bowel disease (IBD), Crohn's disease (CD), ulcerative colitis (UC), irritable bowel syndrome, rheumatoid arthritis (RA), psoriasis, psoriatic arthritis, systemic lupus erythematosus (SLE), lupus nephritis, vasculitis, sepsis, systemic inflammatory response syndrome (SIRS), type I diabetes, Grave's disease, multiple sclerosis (MS), autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogrens's syndrome, autoimmune nephritis, Goodpasture's syndrome, chronic inflammatory demyelinating polyneuropathy, allergy, asthma, other autoimmune diseases that are a result of either acute or chronic inflammation, and any combinations thereof.

30. The method of claim 29, wherein the inflammatory disease or autoimmune disease is Crohn's disease.

31. The method of claim 29, wherein the inflammatory disease or autoimmune disease is ulcerative colitis.

32. A method of treating Crohn's disease in a human subject in need thereof, comprising administering an isolated antibody to said human subject wherein said isolated antibody comprises a heavy chain and a light chain, wherein the heavy chain comprises SEQ ID NO: 85 and wherein the light chain comprises SEQ ID NO: 54.

33. A method of treating ulcerative colitis in a human subject in need thereof, comprising administering an isolated antibody to said human subject wherein said isolated antibody comprises a heavy chain and a light chain, wherein the heavy chain comprises SEQ ID NO: 85 and wherein the light chain comprises SEQ ID NO: 54.

34. A method of treating Crohn's disease in a human subject in need thereof, comprising administering an isolated antibody to said human subject wherein said isolated antibody comprises a heavy chain and a light chain, wherein the heavy chain comprises SEQ ID NO: 50 and wherein the light chain comprises SEQ ID NO: 54.

35. A method of treating ulcerative colitis in a human subject in need thereof, comprising administering an isolated antibody to said human subject wherein said isolated antibody comprises a heavy chain and a light chain, wherein the heavy chain comprises SEQ ID NO: 50 and wherein the light chain comprises SEQ ID NO: 54.

* * * * *